United States Patent
Perkins et al.

(10) Patent No.: US 12,312,593 B2
(45) Date of Patent: May 27, 2025

(54) LYMPHOCYTE TARGETED LENTIVIRAL VECTORS

(71) Applicant: Kelonia Therapeutics, Inc., Boston, MA (US)

(72) Inventors: Molly R. Perkins, Milton, MA (US); Kevin M. Friedman, Boston, MA (US)

(73) Assignee: Kelonia Therapeutics, Inc., Boston, MA (US)

( * ) Notice: Subject to any disclaimer, the term of this patent is extended or adjusted under 35 U.S.C. 154(b) by 0 days.

(21) Appl. No.: 18/375,868

(22) Filed: Oct. 2, 2023

(65) Prior Publication Data

US 2024/0150788 A1    May 9, 2024

Related U.S. Application Data

(63) Continuation of application No. 18/279,201, filed as application No. PCT/US2022/018027 on Feb. 25, 2022.

(60) Provisional application No. 63/154,639, filed on Feb. 26, 2021.

(51) Int. Cl.
| | |
|---|---|
| *C12N 15/86* | (2006.01) |
| *A61K 40/10* | (2025.01) |
| *A61K 40/11* | (2025.01) |
| *A61K 40/31* | (2025.01) |
| *A61K 40/42* | (2025.01) |
| *C07K 14/005* | (2006.01) |
| *C07K 14/705* | (2006.01) |
| *C07K 16/28* | (2006.01) |

(52) U.S. Cl.
CPC .............. *C12N 15/86* (2013.01); *A61K 40/10* (2025.01); *A61K 40/11* (2025.01); *A61K 40/31* (2025.01); *A61K 40/4211* (2025.01); *A61K 40/4215* (2025.01); *C07K 14/005* (2013.01); *C07K 14/70532* (2013.01); *C07K 16/2803* (2013.01); *C07K 16/2809* (2013.01); *C07K 16/2878* (2013.01); *A61K 2239/31* (2023.05); *A61K 2239/48* (2023.05); *C07K 2317/622* (2013.01); *C07K 2319/03* (2013.01); *C12N 2740/15022* (2013.01); *C12N 2740/15043* (2013.01); *C12N 2740/15051* (2013.01); *C12N 2760/20222* (2013.01)

(58) Field of Classification Search
CPC .......... C12N 15/86; C12N 2740/15022; C12N 2740/15043; C12N 2760/20222; C07K 14/005; C07K 16/2809
See application file for complete search history.

(56) References Cited

U.S. PATENT DOCUMENTS

| | | |
|---|---|---|
| 7,901,671 B2 | 3/2011 | Leboulch et al. |
| 9,994,867 B2 | 6/2018 | Baltimore et al. |
| 11,767,366 B1 | 9/2023 | Russell et al. |
| 2008/0124357 A1 | 5/2008 | Yao et al. |
| 2008/0241929 A1 | 10/2008 | Naldini et al. |
| 2014/0017766 A1 | 1/2014 | Chen et al. |
| 2015/0182617 A1 | 7/2015 | Bauche et al. |
| 2015/0316511 A1 | 11/2015 | Guo |
| 2016/0333374 A1 | 11/2016 | Anastasov et al. |
| 2017/0051252 A1 | 2/2017 | Morgan et al. |
| 2017/0176435 A1 | 6/2017 | Seidell, III et al. |
| 2017/0192011 A1 | 7/2017 | Birnbaum et al. |
| 2017/0356010 A1 | 12/2017 | Frost et al. |
| 2018/0201954 A1 | 7/2018 | Buchholz et al. |
| 2018/0362966 A1 | 12/2018 | Flechtner et al. |
| 2019/0144885 A1 | 5/2019 | Costa Fejoz et al. |
| 2020/0216502 A1 | 7/2020 | Albertini et al. |
| 2020/0371088 A1 | 11/2020 | Birnbaum et al. |
| 2022/0204946 A1 | 6/2022 | Antunes et al. |
| 2022/0340876 A1 | 10/2022 | Birnbaum et al. |
| 2023/0279363 A1 | 9/2023 | Russell et al. |
| 2024/0044873 A1 | 2/2024 | Birnbaum et al. |
| 2024/0092839 A1 | 3/2024 | Albertini et al. |
| 2024/0218390 A1 | 7/2024 | Perkins et al. |
| 2024/0317811 A1 | 9/2024 | Albertini et al. |
| 2024/0317812 A1 | 9/2024 | Albertini et al. |
| 2024/0327466 A1 | 10/2024 | Albertini et al. |
| 2024/0327467 A1 | 10/2024 | Albertini et al. |

FOREIGN PATENT DOCUMENTS

| | | |
|---|---|---|
| CA | 2344208 A1 | 10/2002 |
| CN | 108040484 A | 5/2018 |
| WO | 2001/19380 A2 | 3/2001 |
| WO | 2008/037458 A2 | 4/2008 |
| WO | 2009/013324 A1 | 1/2009 |

(Continued)

OTHER PUBLICATIONS

Zhang, N., et al., "Leucine-rich Repeat-containing G Protein-coupled Receptor 4 Facilitates Vesicular Stomatitis Virus Infection by Binding Vesicular Stomatitis Virus Glycoprotein," J Biol Chem, 292(40):16527-16538 (2017).

(Continued)

*Primary Examiner* — Fereydoun G Sajjadi
*Assistant Examiner* — Alexander W Nicol
(74) *Attorney, Agent, or Firm* — Morse, Barnes-Brown & Pendleton, P.C.; Lisa M. Warren, Esq.; Erin E. Bryan, Esq.

(57) ABSTRACT

Provided herein are lentiviral vectors comprising a mutated, heterologous envelope protein, a targeting protein, and at least one transgene for delivery to and expression by a cell characterized by the targeting protein. Also provided are methods and materials for producing the lentiviral vectors described herein, methods for transducing target cells, and cells transduced by lentiviral vectors according to the present disclosure.

10 Claims, 22 Drawing Sheets

Specification includes a Sequence Listing.

(56) References Cited

FOREIGN PATENT DOCUMENTS

| WO | 2012/088381 A2 | 6/2012 |
|---|---|---|
| WO | 2015/104376 A1 | 7/2015 |
| WO | 2015/112541 A2 | 7/2015 |
| WO | 2015/117027 A1 | 8/2015 |
| WO | 2017/182585 A1 | 10/2017 |
| WO | 2019/056015 A2 | 3/2019 |
| WO | 2019/057974 A1 | 3/2019 |
| WO | 2020/123936 A1 | 6/2020 |
| WO | 2020/236263 A1 | 11/2020 |
| WO | 2022/183072 A1 | 9/2022 |
| WO | 2022/221745 A1 | 10/2022 |

OTHER PUBLICATIONS

Bowie, J., et al., "Deciphering the Message in Progein Sequences: Tolerance to Amino Acid Substitutions," Science, 247(4948):1306-10 (1990).
Winkler, K., et al., "Changing the Antigen Binding Specificity by Single Point Mutations of an Anti-p24 (HIV-1) Antibody," J Immunol, 165(8):4505-14 (2000).
Kussie, P., et al., "A Single Engineered Amino Acid Substitution Changes Antibody Fine Specificity," J Immunol, 152(1):146-52. (1994).
Chen, Z., et al., "Human Monoclonal Antibodies Targeting the Haemagglutinin Glycoprotein can Neutralize H7N9 Influenza Virus," Nat Commun, 6:6714 (2015).
Sela-Culang, I., et al., "The Structural Basis of Antibody-Antigen Recognition," Front Immunol, 4:302 (2013).
Sirin, S., et al., "AB-Bind: Antibody Binding Mutational Database for Computational Affinity Predictions," Protein Sci, 25(2):393-409 (2015).
Höfig, I., et al., "Systematic Improvement of Lentivirus Transduction Protocols by Antibody Fragments Fused to VSV-G as Envelope Glycoprotein," Biomaterials, 35(13):4204-12 (2014).
Dreja, H., et al., "The Effects of N-terminal Insertion into VSV-G of an scFv Peptide," Viral J, 3:69, 1186 (2006).
Kameyama, Y., et al., "Antibody-dependent Gene Transduction using Gammaretroviral and Lentiviral Vectors Pseudotyped with Chimeric Vesicular Stomatitis Virus Glycoprotein," J Viral Methods, 153(1 ):49-54 (2008).
Yu, B., et al., "Engineered Cell Entry Links Receptor Biology with Single-cell Genomics," Cell, 185(26):4904-4920 (2022).
Nikolic, J., et al., "Structural Basis for the Recognition of LDL-receptor Family Members by VSV Glycoprotein," Nat Commun, 9(1):1029 (2018).
Yang, H., et al., "Cell Type-Specific Targeting with Surface-Engineered Lentiviral Vectors Co-displaying OKT3 Antibody and Fusogenic Molecule," Pharm Res, 26(6): 1432-45 (2009).
Frank, A., et al., "Surface-Engineered Lentiviral Vectors for Selective Gene Transfer into Subtypes of Lymphocytes," Mol Ther Methods Clin Dev, 12:19-31 (2018).
Milani, M., et al., "Genome Editing for Scalable Production of Alloantigen-free Lentiviral Vectors for in vivo Gene Therapy," EMBO Mol Med, 9(11):1558-1573 (2017).
Goyvaerts, C., et al., "Development of the Nanobody Display Tecnology to Target Lentiviral Vectors to Antigen-Presenting Cells," Gene Therapy, 19:1133-1140 (2012).
Chan, L., et al., "Conjugation of Lentivirus to Paramagnetic Particles via Nonviral Proteins Allows Efficient Concentration and Infection of Primary Acute Myeloid Leukemia Cells," J. of Virology, 79(20):13190-13194 (2005).
Ammayappan, et al., "Characteristics of Oncolytic Vesicular Stomatitis Virus Displaying Tumor-Targeting Ligands," Journal of Virology vol. 87(24):13543-13555 (2013).
Altschul, et al., "Basic Local Alignment Search Tool," J Mol Biol. (3):403-10 (1990).

Altschul, et al., "Gapped BLAST and PSI-BLAST: A New Generation of Protein Database Search Programs," Nucleic Acids Res, 25(17):3389-402 (1997).
Bentzen, et al., "Evolution of MHC-based Technologies Used for Detection of Antigen-responsive T Cells," Cancer Immunol Immunother, 66:657-66 (2017).
Buchholz, et al., "Retroviral Display and High Throughput Screening," Comb Chem High Throughput Screen, 11(2):99-110 (2008).
Cire, S, "Immunization of Mice with Lentiviral Vectors Targeted to MHC Class II+ Cells is Due to Preferential Transduction of Dendritic Cells in vivo," PLoS One, 9(7):e101644, (2014).
Dobson, C., et al., "Antigen Identification and High-Throughput Interaction Mapping by Reprogramming Viral Entry," Nature Methods, 19:449-460 (2022).
Finkelshtein, et al., "LDL Receptor and its Family Members Serve as the Cellular Receptors for Vesicular Stomatitis Virus," PNAS, 110(18):7306-7311 (2013).
Frank, AM, "Surface-Engineered Lentiviral Vectors for Selective Gene Transfer into Subtypes of Lymphocytes," Mol Ther Methods Clin Dev, 12:19-31, (2018).
Froelich, et al., "Targeted Gene Delivery to CD117-expressing Cells in vivo with Lentiviral Vectors Co-displaying Stem Cell Factor and a Fusogenic Molecule,", Biotechnology and Bioengineering, 104(1):206-215 (2009).
Funke, et al., Targeted Cell Entry of Lentiviral Vectors,: Mol Ther. 16(8):1427-36 (2008).
Grubaugh, et al., "Proteins as T Cell Antigens: Methods for High-throughput Identification," Vaccine 31(37) (2013).
Guideng, et al., "T Cell Antigen Discovery Via Trogocytosis," Nature Methods, 16(2):183-90 (2019).
Hastie, E, et al., "Understanding and Altering Cell Tropism of Vesicular Stomatitis Virus," Virus Res. 176(1-2):16-32 (2013).
He, et al., "Can Immunotherapy Reinforce Chemotherapy Efficacy? A New Perspective on Colorectal Cancer Treatment," Front. Immunol. 14:1237764 (2023).
Joglekar, et al., "T Cell Antigen Discovery via Signaling and Antigen-presenting Bifunctional Receptors," Nature Methods, 16(2):191-8 (2019).
Karlin, et al., "Applications and Statistics for Multiple High-scoring Segments in Molecular Sequences," Proc Natl Acad Sci US A, 90(12):5873-7 (1993).
Karlin, et al., "Methods for Assessing the Statistical Significance of Molecular Sequence Features by Using General Scoring Schemes," Proc Natl Acad Sci US A., 87(6):2264-8 (1998).
Labbe, R., et al., "Lentiviral Vectors for T Cell Engineering: Clinical Applications, Bioprocessing and Future Perspectives," Viruses 13(1528): 1-22 (2021).
Nikolic, J., et al., "Structural Basis for the Recognition of LDL-Receptor Family Members by VSV Glycoprotein," Nature Communications, 9(1029):1-12 (2018).
Ou, W, et al., "Specific Targeting of Human Interleukin ( I L)-13 Receptor A2-positive Cells with Lentiviral Vectors Dsplaying I L-13," Hum Gene Ther Methods, 2:137-47, (2012).
Peach, et al., "Both Extracellular Immunoglobin-like Domains of CD80 Contain Residues Critical for Binding T Cell Surface Receptors CTLA-4 and CD28, "J. Biol Chem, 270(36):21181-21187 (1995).
Sevier, CS, et al., "Efficient Export of the Vesicular Stomatitis Virus G Protein from the Endoplasmic Reticulum Requires a Signal in the Cytoplasmic Tail that Includes both Tyrosine-based and Di-acidic Motifs," Mol Biol Cell. 1:13-22 (2000).
Taube, et al., "Lentivirus Display: Stable Expression of Human Antibodies on the Surface of Human Cells and Virus Particles," PLoS One, 3(9):e3181 (2008).
Urban, et al., "Retroviral Display in Gene Therapy, Protein Engineering, and Vvaccine Development," ACS Chem Biol., 6(1):61-74(2011).
Urban, et al., "Selection of Functional Human Antibodies from Retroviral Display Libraries," Nucleic Acids Res., 33(4):e35 (2005).
Yang, et al., "Cell Type-specific Targeting with Surface-engineered Lentiviral Vectors Co-displaying OKT3 Antibody and Fusogenic Molecule," Pharm Res. (6):1432-45 (2009).

(56) References Cited

OTHER PUBLICATIONS

Yang, et al., "Targeting Lentiviral Vectors to Specific Cell Types in vivo," PNAS, 103(31):114 79-84 (2006).

Zhang, et al., "Cell-specific Targeting of Lentiviral Vectors Mediated by Fusion Proteins Derived from Sindbis Virus, Vesicular Stomatitis Virus, or Avian Sarcoma/Leukosis Virus," Retrovirology, Biomed Central Ltd., 7(1):3 (2010).

International Search Report from International Application No. PCT/US2022/018027, dated mailed: Jun. 21, 2022.

International Search Report from International Application No. PCT/US2020/024175, date mailed: Sep. 14, 2020.

International Search Report from International Application No. PCT/US2022/025142, dated: Apr. 10, 2022.

International Search Report from International Application No. PCT/EP2018/075824, dated: Nov. 28, 2018.

Petition for Post-Grant Review of U.S. Pat. No. 11,767,366, Before the Patent Trial and Appeal Board, *Kelonia Therapeutics, Inc.,* Petitioner v. *Interius Biotherapeutics, Inc.,* Patent Owner, 98 Pages.

Patent Owner's Preliminary Response with Exhibit 2001, in U.S. Pat. No. 11,767,366, Before the Patent Trial and Appeal Board, *Kelonia Therapeutics, Inc.,* Petitioner v. *Interius Biotherapeutics, Inc.,* Patent Owner, Case No. PGR2024-00008, 95 Pages.

Petitioner's Reply to Patent Owner's Preliminary Response in U.S. Pat. No. 11,767,366, Before the Patent Trial and Appeal Board, *Kelonia Therapeutics, Inc.,* Petitioner v. *Interius Biotherapeutics, Inc.,* Patent Owner, Case No. PGR2024-0008, 8 pages.

Patent Owner's Sur-Reply in U.S. Pat. No. 11,767,366, Before the Patent Trial and Appeal Board, *Kelonia Therapeutics, Inc.,* Petitioner v. *Interius Biotherapeutics, Inc.,* Patent Owner, Case No. PGR2024-0008, 6 pages.

Abertini, et al., "Molecular and Cellular Aspects of Rhabdovirus Entry," Viruses, 4:117-139 (2012).

Amirache, et al., "Mystery Solved: VSV-G-LVs Do Not Allow Efficient Gene Transfer into Unstimulated T Cells, B Cells, and HSCs Because They Lack the LDL Receptor," Blood, 123: 1422-1424 (2014).

Barber, G.N., "VSV-tumor Selective Replication and Protein Translation," Oncogene 24: 7710-7719 (2005).

Ferlin, et al., "Characterization of pH-sensitive Molecular Switches that Trigger the Structural Transition of Vesicular Stomatitis Virus Glycoprotein from the Postfusion State Toward the Prefusion State," J Virol, 88:13396-13409 (2014).

Roche, et al., "Crystal Structure of the Low-pH Form of the Vesicular Stomatitis Virus Glycoprotein," G. Science, 313: 187-191 (2006).

Roche, et al., "Structure of the Prefusion Form of the Vesicular Stomatitis Virus Glycoprotein G," Science 315: 843-848 (2007).

An, X., "Preliminary Study on HBV and HIV seudovirus Vector Systems," China Master's Thesis Full-text Database, Basic Science Collection: 1-121 (2007).

FIG. 2A

LYMPHOCYTE TARGETED LENTIVIRAL VECTORS

RELATED APPLICATIONS

This application is a continuation of U.S. application Ser. No. 18/279,201, filed Aug. 28, 2023, which is a national stage filing under 35 U.S.C. 371 of International Application No. PCT/US2022/018027, filed Feb. 25, 2022, which claims the benefit of U.S. Provisional Application No. 63/154,639, filed Feb. 26, 2021. The entire teachings of said applications are incorporated herein by reference. International Application No. PCT/US2022/018027 was published under PCT Article 21(2) in English.

STATEMENT REGARDING SEQUENCE LISTING

The Sequence Listing associated with this application is provided in text format in lieu of a paper copy, and is hereby incorporated by reference into the specification. The name of the text file containing the Sequence Listing is KELO-401-102X_ST26.xml. The text file is 200 KB, was created on Dec. 20, 2023, and is being submitted electronically via Patent Center.

BACKGROUND

Lentiviral vectors play a critical role in gene-modified cell therapies, particularly T cell therapies. Recently approved T cell therapies rely on retroviral vectors to transduce the therapeutic molecule (e.g., chimeric antigen receptor (CAR)) into T lymphocytes. An associated risk to CAR T cell production is the transduction of other cell types with the transgene. The use of integrating vectors with broad cell tropism, e.g., lentiviral vectors pseudotyped with a VSV-G envelope protein, can represent a serious, though rare, safety concern.

BRIEF DESCRIPTION OF THE SEVERAL VIEWS OF THE DRAWINGS

Figure 2A:
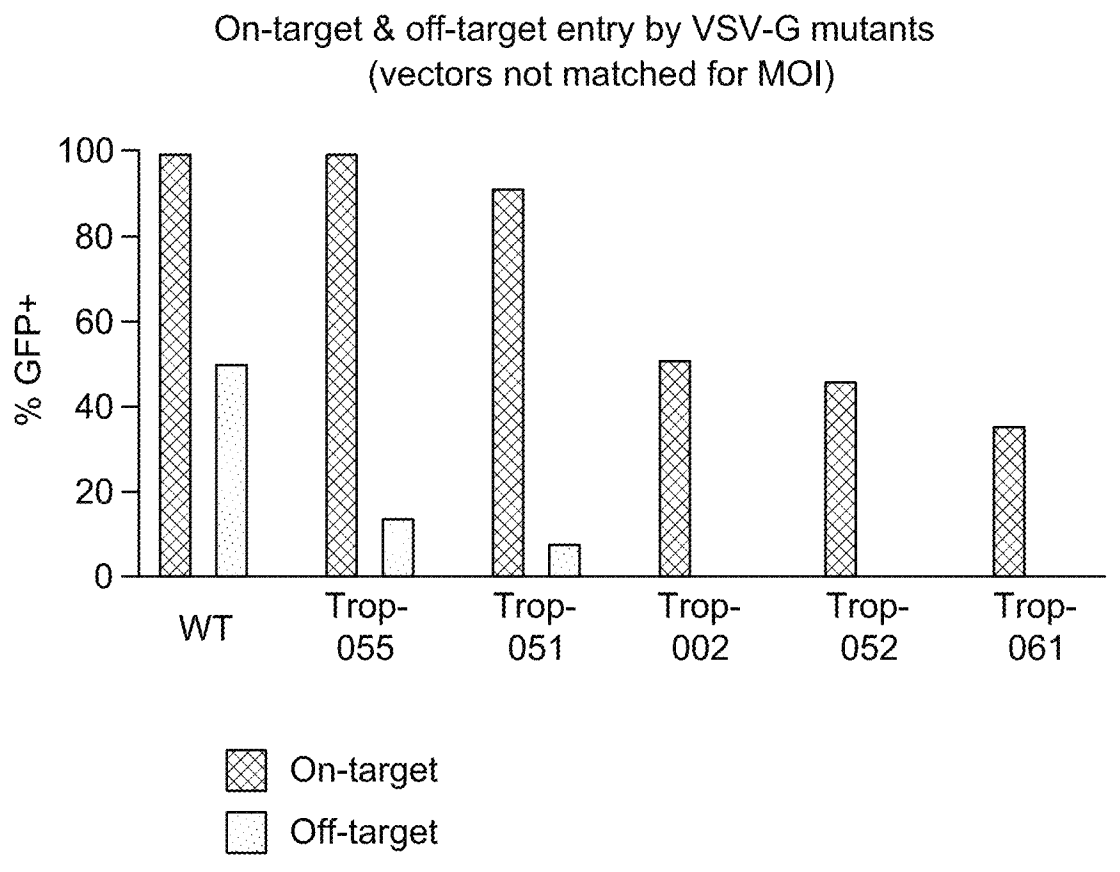

FIGS. 2A-2B depict graphs (FIG. 2A) and FACS plots (FIG. 2B) showing on-target and off-target entry of Jurkat T cells and Raji B cells by lentiviral vectors bearing mutated VSV-G envelope to abolish LDL receptor binding (Trop-002, Trop-051, Trop-052, Trop-055, and Trop-061) and T cell targeting protein CD80. In FIG. 2A, on-target entry is the left bar and off-target is the right bar of each sample. Binding of the T cell targeting protein to its cognate ligand on T cells leads to entry of the lentiviral vector, and subsequent expression of reporter green fluorescent protein (GFP) is measured.

(FIG. 3A) T cell targeting protein CD80 expressed from the VSV-G packaging plasmid is expressed at relatively equivalent levels as the mutated VSV-G on the surface of HEK293 producer cells; and (FIG. 3B) LVV generated with this approach can transduce targeted Jurkat T cells but do not transduce Raji B cells.

(FIG. 12A) T cell targeting LVV (anti-CD3 and CD80) specifically transduce human T cells (CD3+) and not human B cells (CD20+) in humanized mouse model (n=5); and (FIG. 12B) T cell targeting LVV transduce both CD8+ and CD8-(CD4) T cells compared to standard LVV which did not.

DETAILED DESCRIPTION

Figure 1:
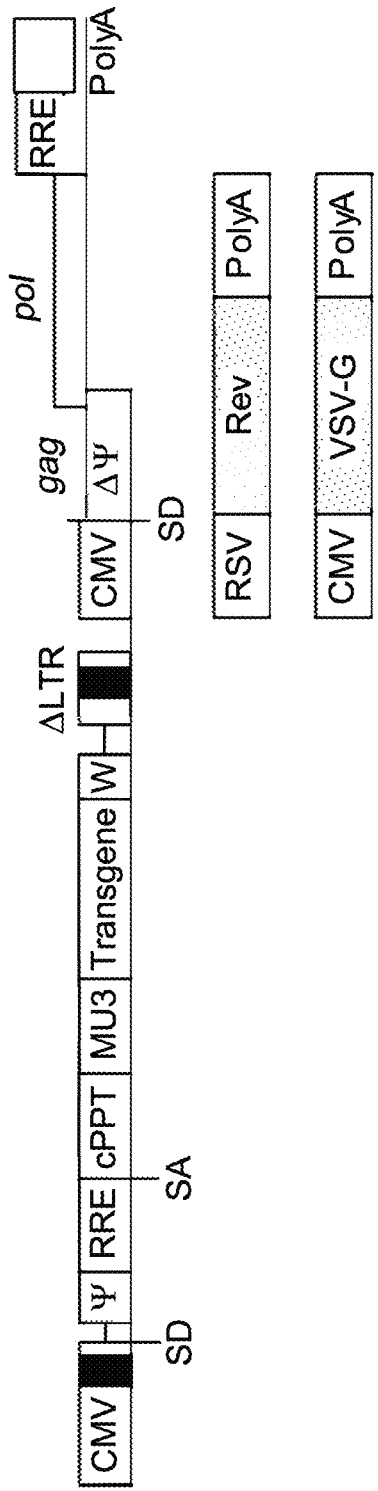
FIG. 1 is a schematic representation of helper plasmids suitable for use in a third generation LVV production system.
Figure 2B:
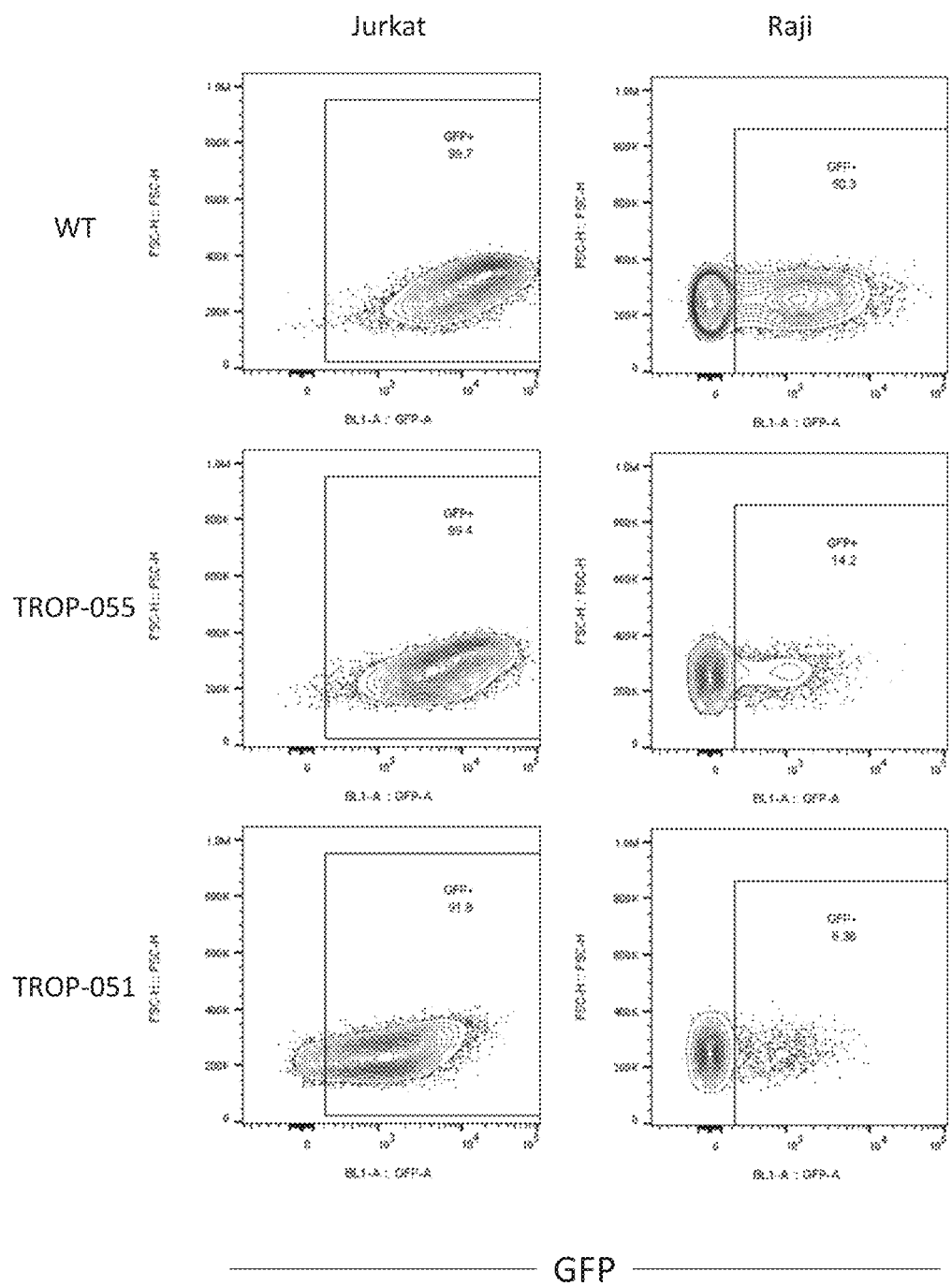
Figure 2B:
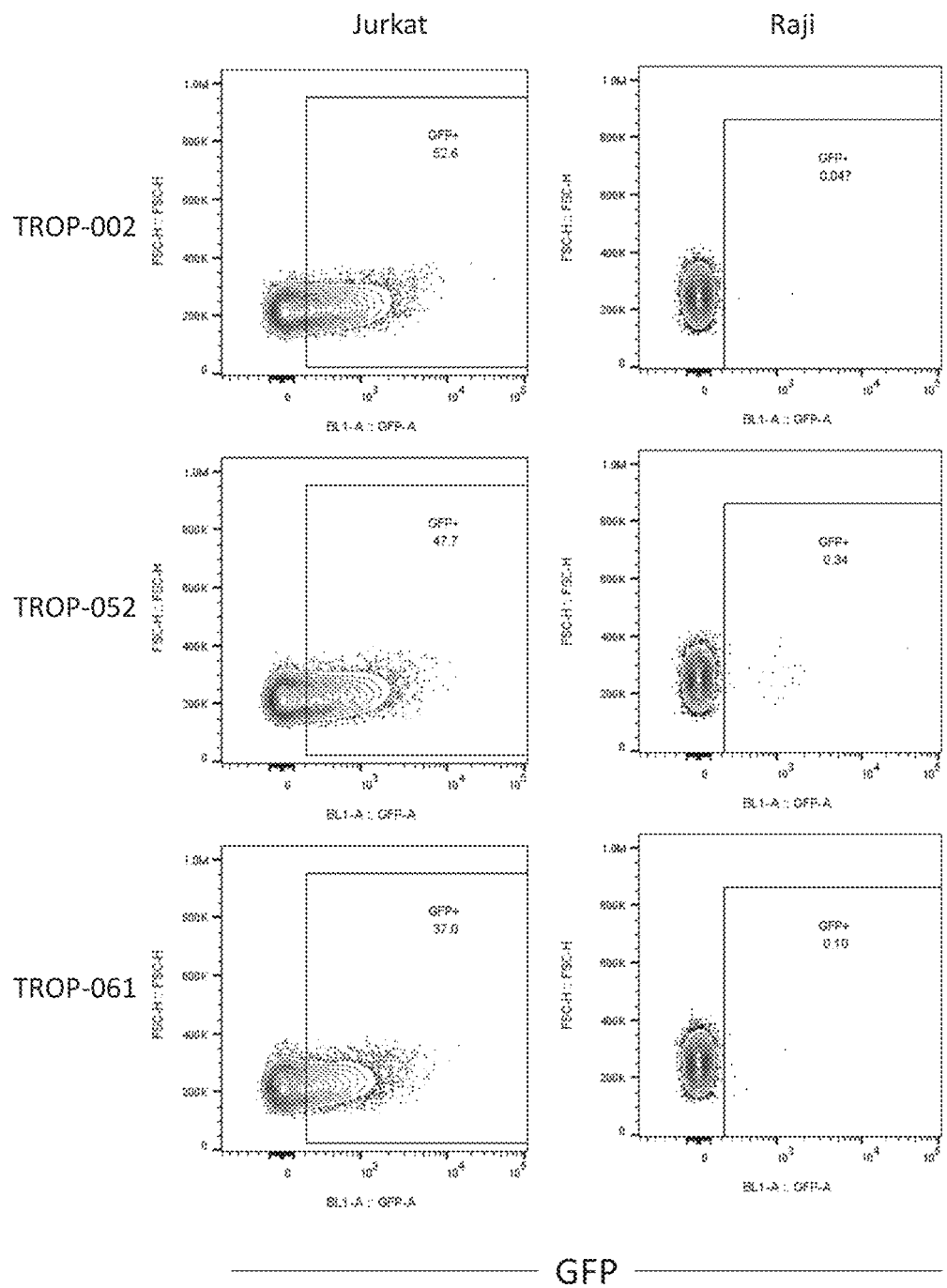
Figure 2B:
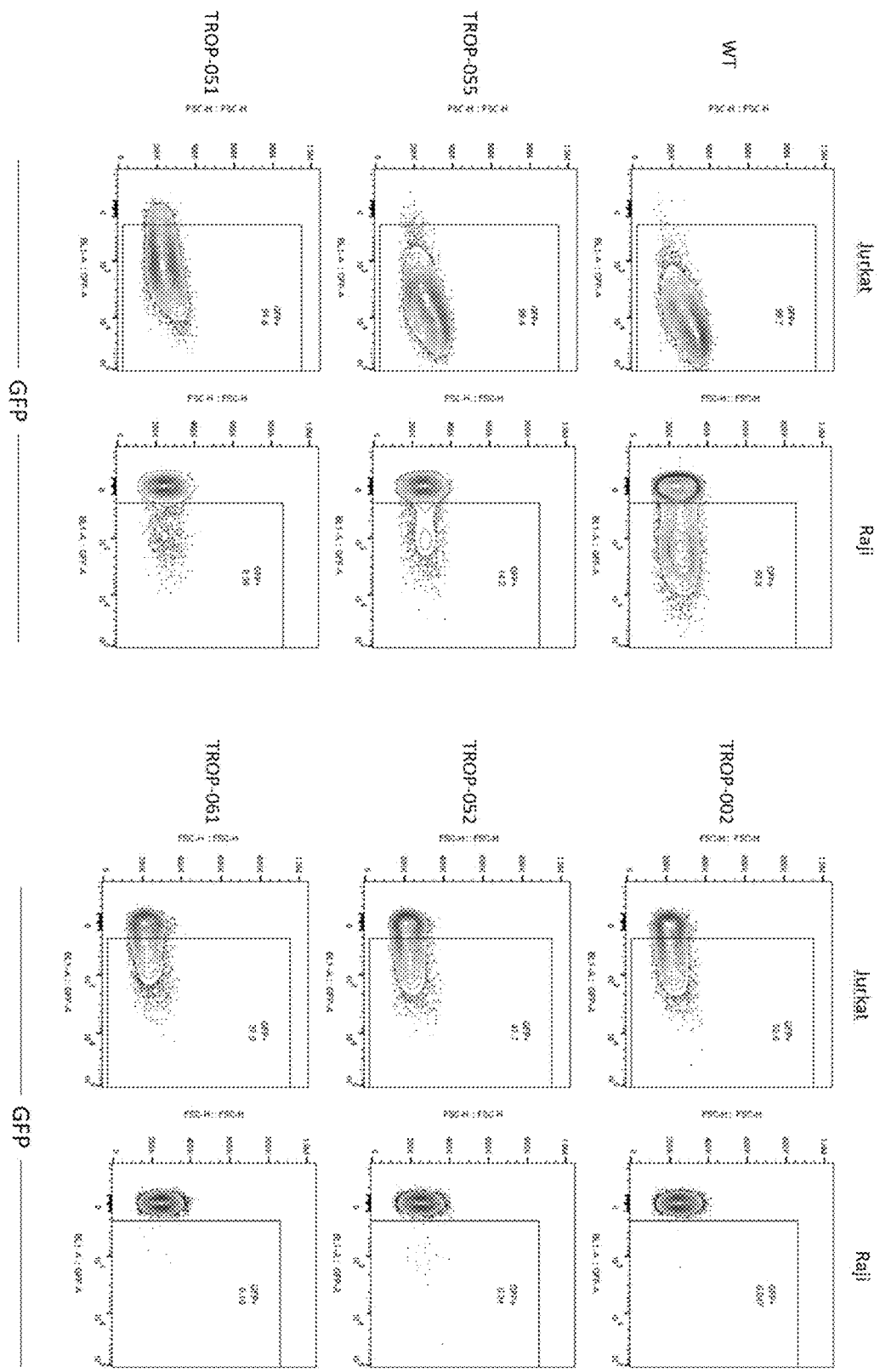
Figure 3A:
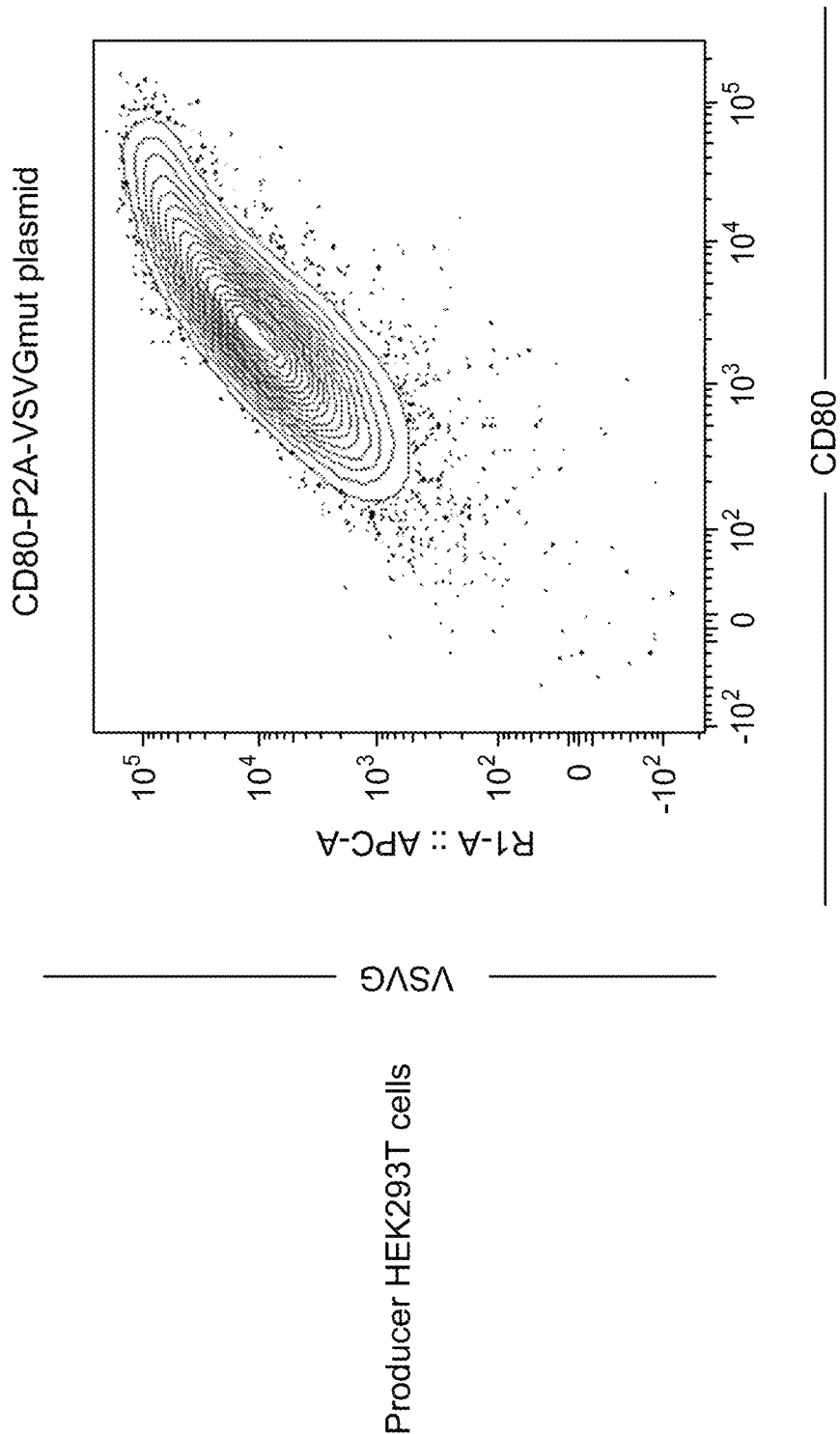
FIGS. 3A-3B depicts graphs showing.
Figure 3B:
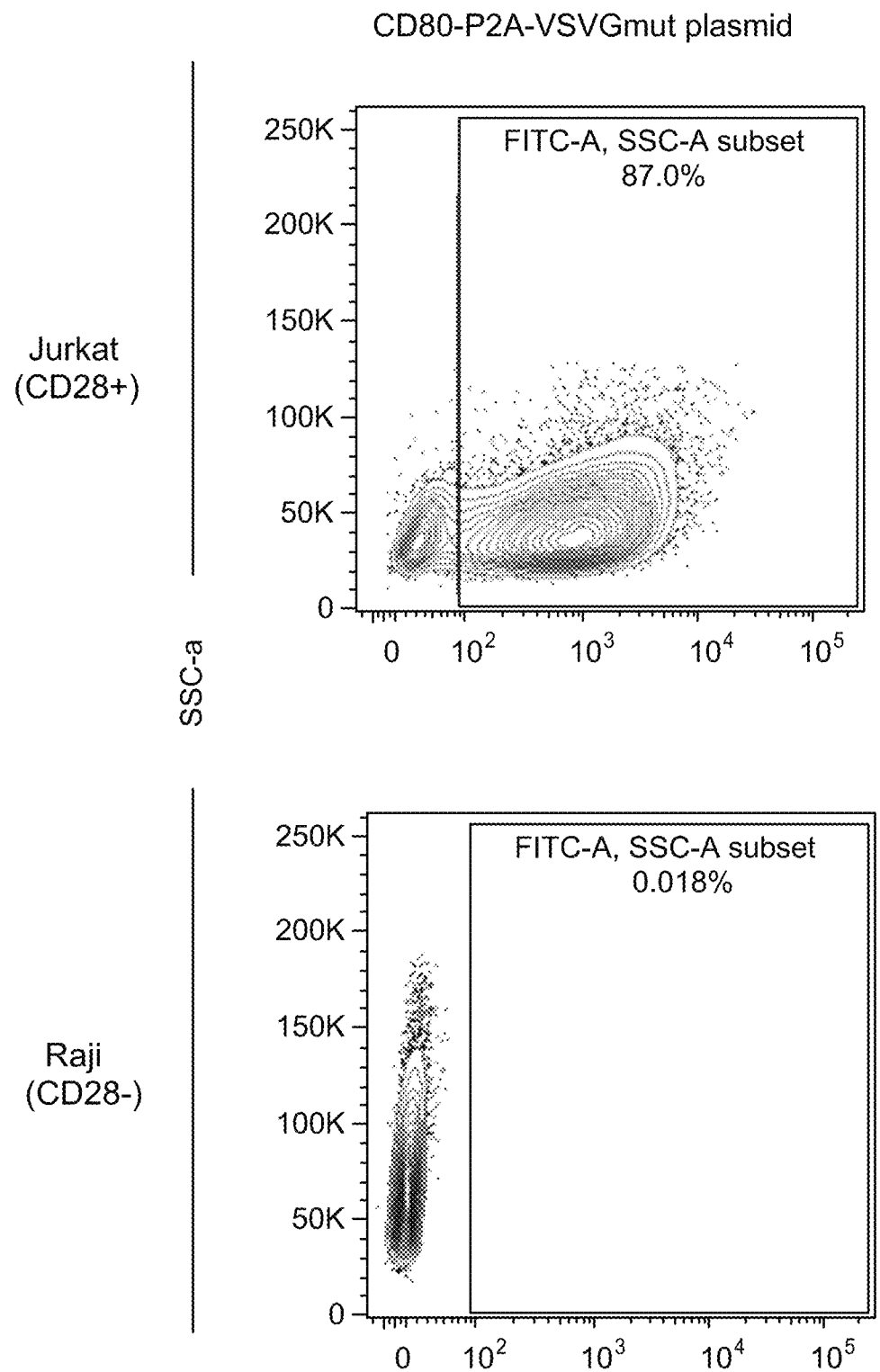
Figure 4:
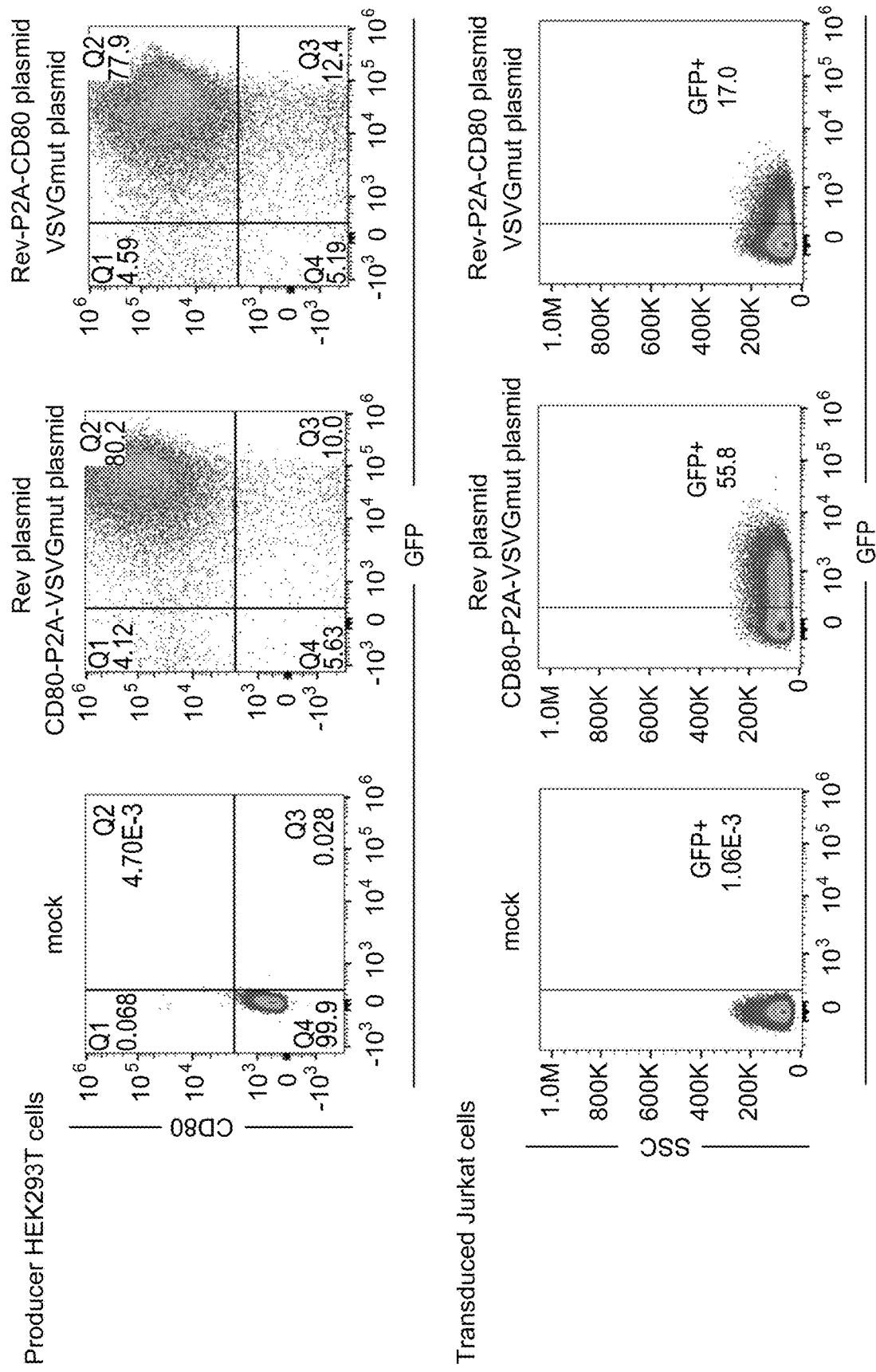
FIG. 4 depicts graphs showing: (top row) expression levels of CD80 and mutated VSV-G on the surface of HEK293T producer cells using LVV generated by cloning CD80 targeting protein into the Rev packaging plasmid or into the mutated VSV-G packaging plasmid; and (bottom) LVV generated by cloning CD80 targeting protein into the Rev packaging plasmid or into the mutated VSV-G packaging plasmid transduce targeted Jurkat T cells.
Figure 5:
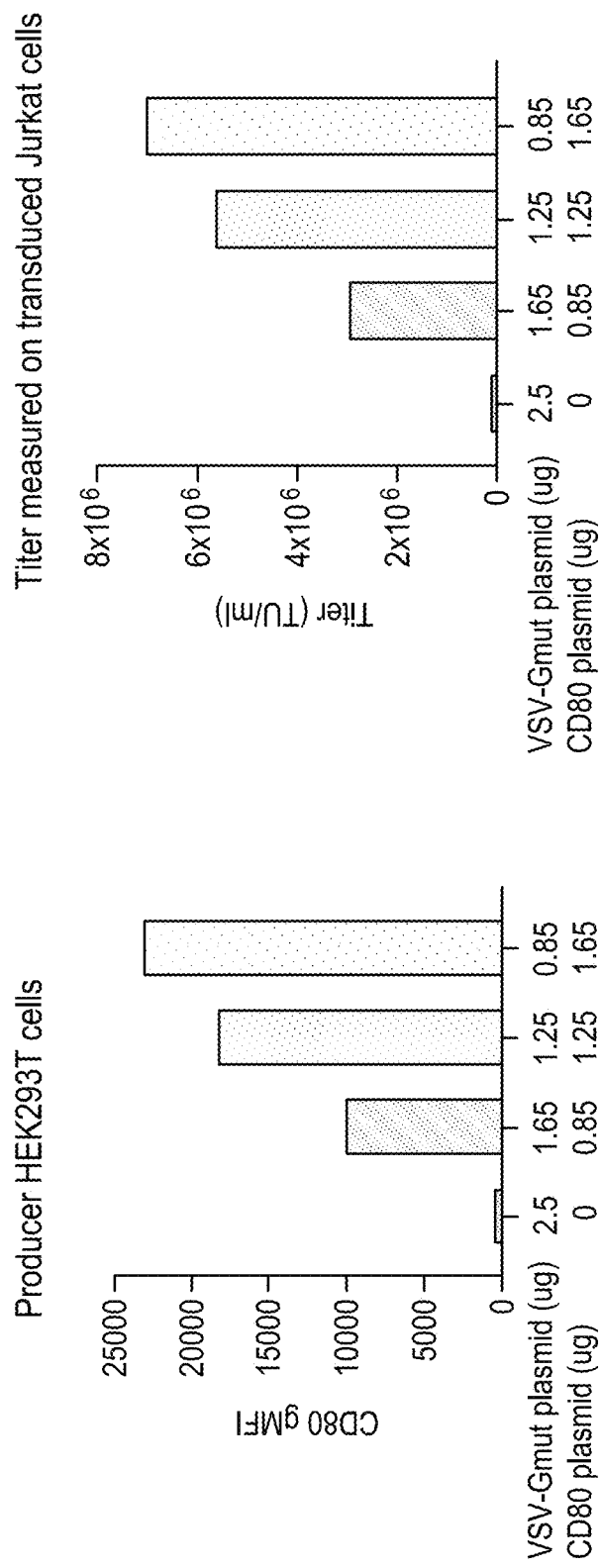
FIG. 5 depicts (left) CD80 targeting protein expression on surface of HEK293T producer cells using a five plasmid packaging system as a function of CD80 plasmid concentration; and (right) LVV generated with the five plasmid packaging system transduce targeted Jurkat T cells and transduction efficiency was associated with CD80 packaging plasmid concentration.
Figure 6A:
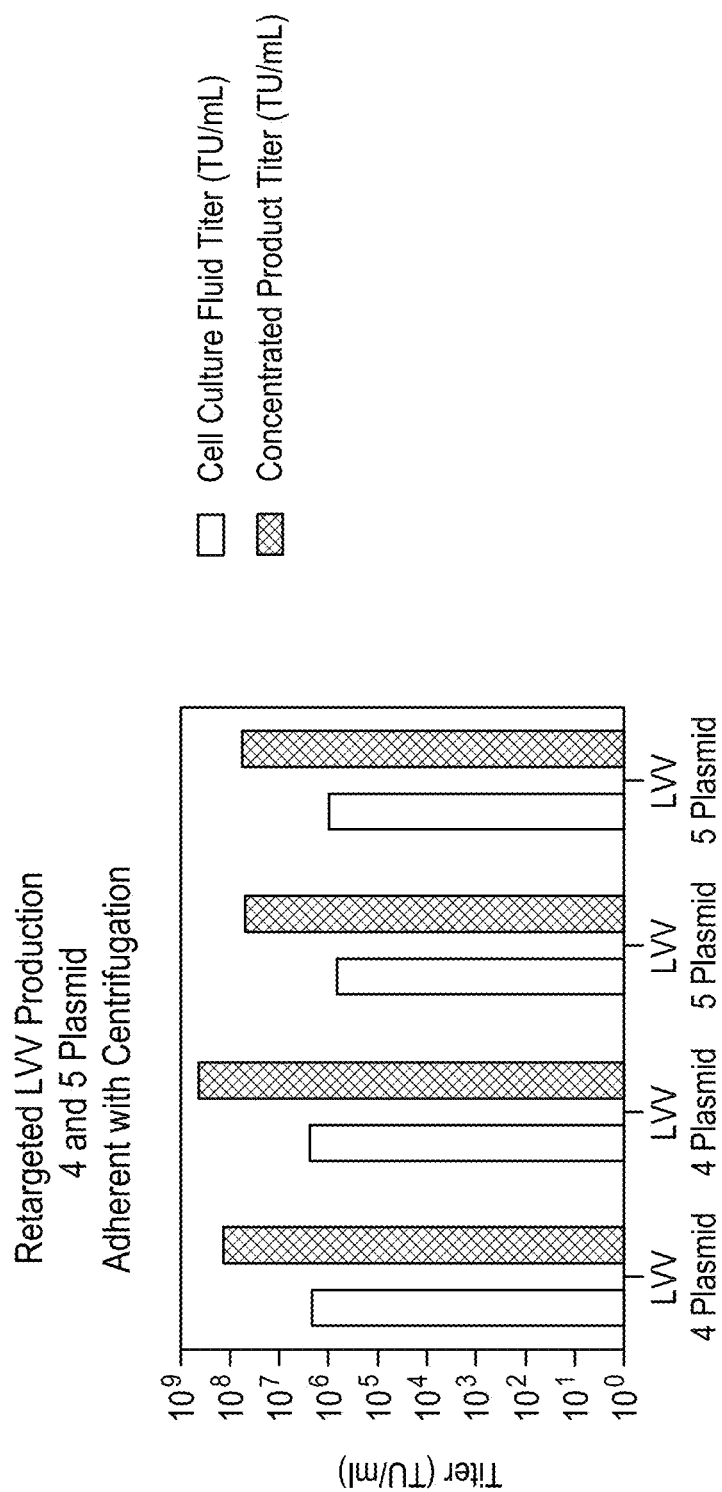
FIGS. 6A-6D depict titers of lymphocyte targeting LVV produced in adherent HEK293 or suspension HEK293 producer cells. LVV harvested from HEK293 adherent cell culture medium by centrifugation (FIG. 6A) or by anion exchange chromatography followed by tangential flow filtration (FIG. 6B). LVV harvested from HEK293 suspension cell culture medium by anion exchange chromatography (FIG. 6C). Concentration by AEX/TFF resulted in LVV preparations with a high level of purity and recovery (FIG. 6D).
Figure 6B:
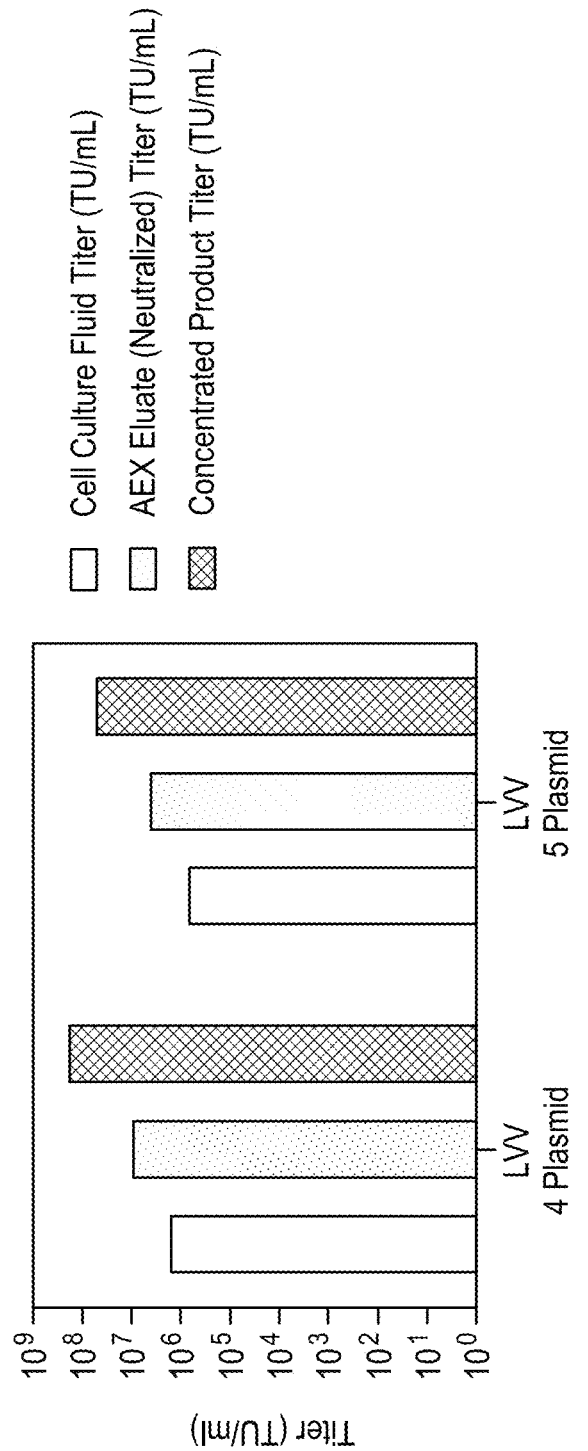
Figure 6C:
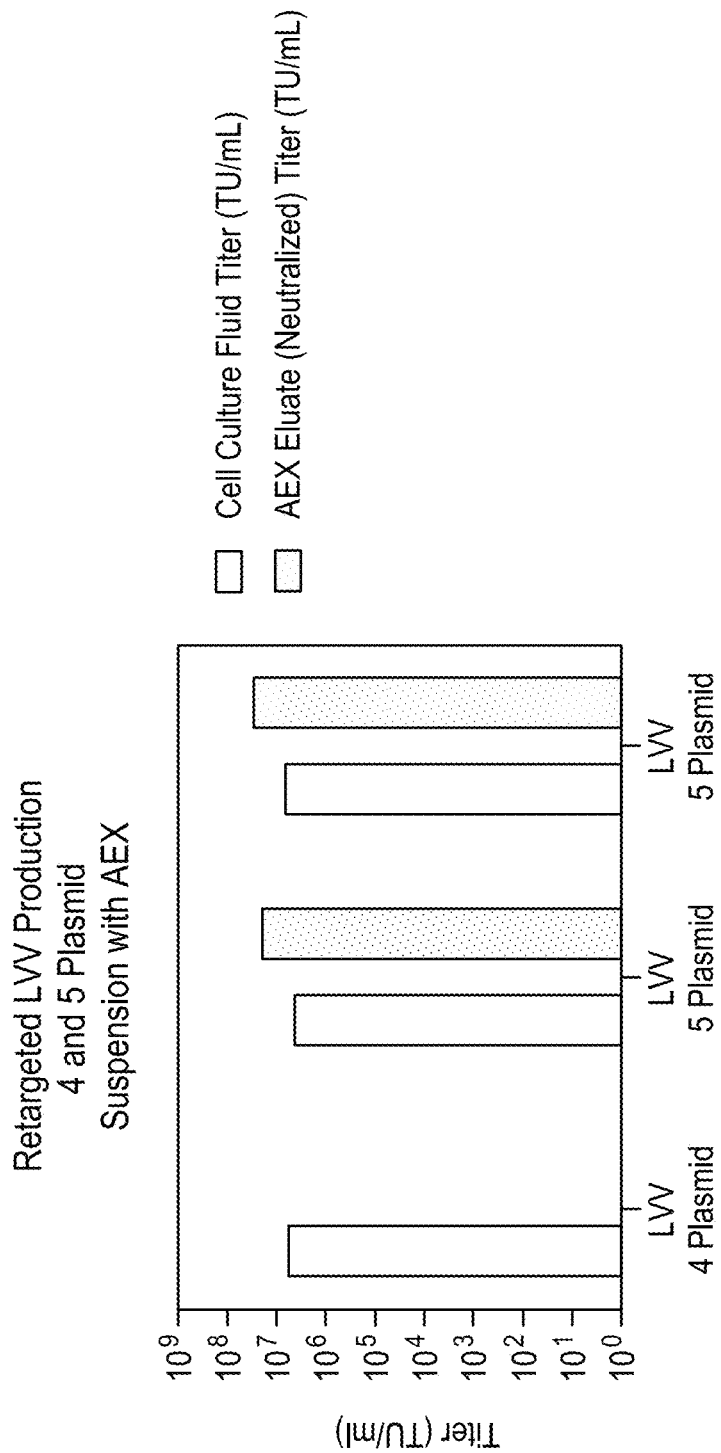
Figure 6D:
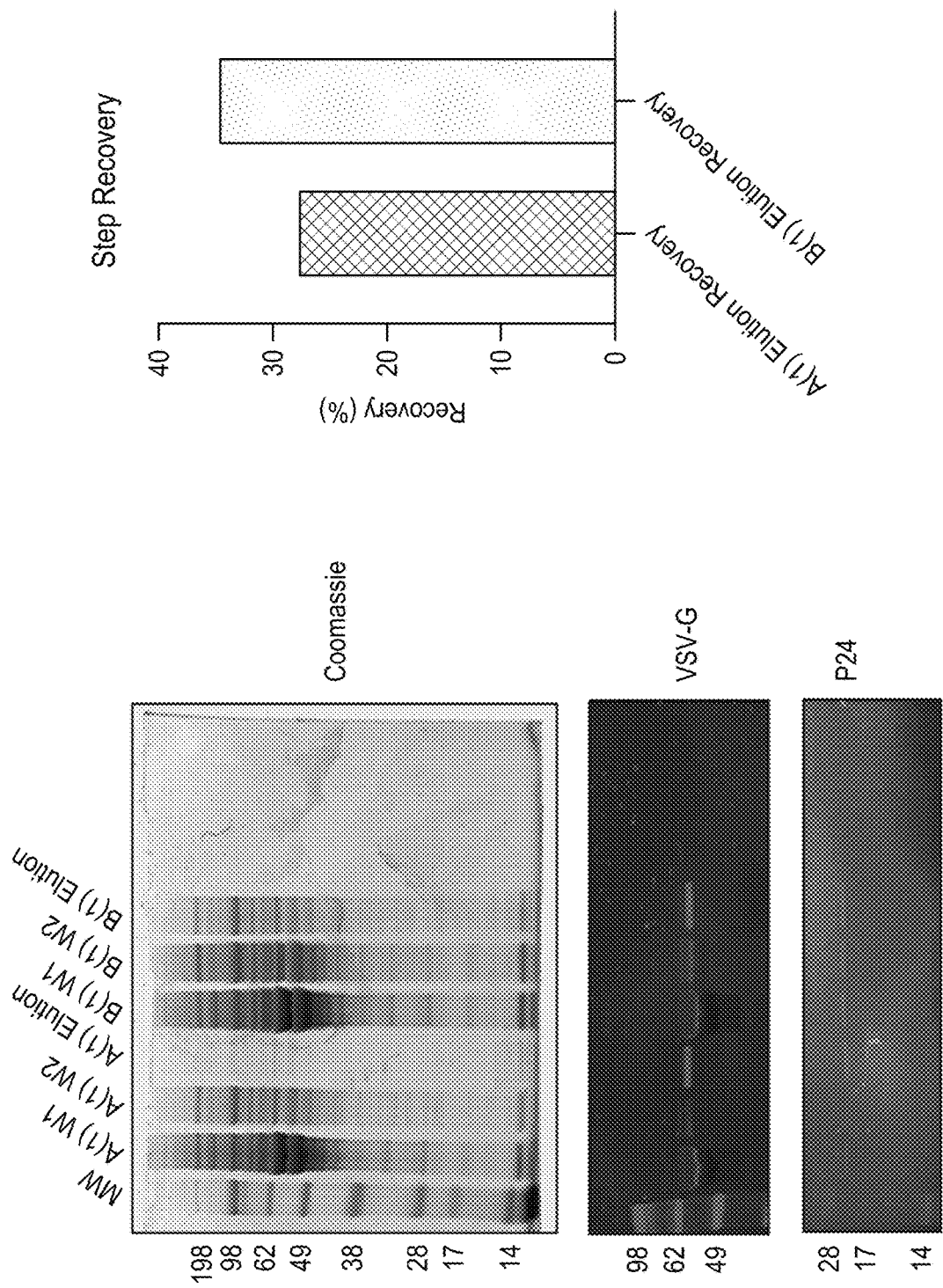

Engineered lentiviral vectors are described herein. The lentiviral vectors include a mutated, heterologous envelope protein, a targeting protein, and at least one transgene for delivery to and expression by a cell characterized by the targeting protein. In some embodiments, the targeting protein is selected to target an immune cell, including, for example a lymphocyte or a T cell. In certain such embodiments, the lentiviral vectors described herein are capable of selectively targeting and efficiently transducing resting lymphocytes, e.g., T cells. In some embodiments, lentiviral vectors described herein are capable of transducing and/or activating T cells in the absence of an exogenous T cell stimulating agent. In some embodiments, lentiviral vectors described herein enhance transduction of CD4 T cells compared to standard lentiviral vectors.

In some embodiments, the lentiviral vectors incorporating a mutated env and a targeting protein as described herein are capable of producing a high titer LVV product, as compared to standard LVV incorporating another fusogenic env protein (e.g., cocal env, paramyxovirus env, truncated VSV-G env).

Also provided are methods and materials for producing the lentiviral vectors described herein, methods for transducing target cells, and cells transduced by lentiviral vectors according to the present disclosure. In some embodiments, a lentiviral vector as described herein and/or cells transduced by such a vector may be used in treating a disease or disorder responsive to the presence of cells expressing the transgene delivered by the vector.

Definitions

Prior to setting forth this disclosure in more detail, it may be helpful to an understanding thereof to provide definitions of certain terms to be used herein.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

Terms understood by those in the art of antibody technology are each given the meaning acquired in the art, unless expressly defined differently herein. The term "antibody" is used in the broadest sense and includes polyclonal and monoclonal antibodies. An "antibody" may refer to an intact antibody comprising at least two heavy (H) chains and two light (L) chains inter-connected by disulfide bonds, as well as an antigen-binding portion (or antigen-binding domain) of an intact antibody that has or retains the capacity to bind a target molecule. An antibody may be naturally occurring, recombinantly produced, genetically engineered, or modified forms of immunoglobulins, for example intrabodies, peptibodies, nanobodies, single domain antibodies, SMIPs, multispecific antibodies (e.g., bispecific antibodies, diabodies, triabodies, tetrabodies, tandem di-scFv, tandem tri-scFv, ADAPTIR). A monoclonal antibody or antigen-binding portion thereof may be non-human, chimeric, humanized, or human, preferably humanized or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988). "Antigen-binding portion" or "antigen-binding domain" of an intact antibody is meant to encompass an "antibody fragment," which indicates a portion of an intact antibody and refers to the antigenic determining variable regions or complementary determining regions of an intact antibody. Examples of antibody fragments include, but are not limited to, Fab, Fab', F(ab')$_2$, and Fv fragments, Fab'-SH, F(ab')$_2$, diabodies, linear antibodies, scFv antibodies, VH, and multispecific antibodies formed from antibody fragments. A "Fab" (fragment antigen binding) is a portion of an antibody that binds to antigens and includes the variable region and CH1 of the heavy chain linked to the light chain via an inter-chain disulfide bond. An antibody may be of any class or subclass, including IgG and subclasses thereof (IgG$_1$, IgG$_2$, IgG$_3$, IgG$_4$), IgM, IgE, IgA, and IgD.

The term "variable region" or "variable domain" in the context of an antibody refers to the domain of an antibody heavy or light chain that is involved in binding of the antibody to antigen. The variable domains (or regions) of the heavy chain and light chain (VH and VL, respectively) of a native antibody generally have similar structures, with each domain comprising four conserved framework regions (FRs) and three complementary determining regions (CDRs). (See, e.g., Kindt et al. Kuby Immunology, 6th ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The terms "complementarity determining region" and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (HCDR1, HCDR2, HCDR3) and three CDRs in each light chain variable region (LCDR1, LCDR2, LCDR3).

As used herein, the terms "binding domain", "binding region", and "binding moiety" refer to a molecule, such as a peptide, oligopeptide, polypeptide, or protein that possesses the ability to specifically and non-covalently bind, associate, unite, recognize, or combine with a target molecule (e.g., tumor antigen). A binding domain includes any naturally occurring, synthetic, semi-synthetic, or recombinantly produced binding partner for a biological molecule or other target of interest. In some embodiments, the binding domain is an antigen-binding domain, such as an antibody or functional binding domain or antigen-binding portion thereof. Exemplary binding domains include single chain antibody variable regions (e.g., domain antibodies, sFv, scFv, Fab), receptor ectodomains (e.g., TNF-α), ligands (e.g., cytokines, chemokines), or synthetic polypeptides selected for the specific ability to bind to a biological molecule.

"Major histocompatibility complex molecule" (MHC molecule) refers to a glycoprotein that delivers a peptide antigen to a cell surface. MHC class I molecules are heterodimers composed of a membrane spanning a chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where peptide:MHC complex is recognized by $CD8^+$ T cells. MHC class II molecules deliver peptides originating in the vesicular system to the cell surface, where they are recognized by $CD4^+$ T cells. An MHC molecule may be from various animal species, including human, mouse, rat, or other mammals.

"Chimeric antigen receptor" (CAR) refers to a chimeric fusion protein comprising two or more distinct domains linked together in a way that does not occur naturally in a host cell and can function as a receptor when expressed on the surface of a cell. CARs are generally composed of an extracellular domain comprising a binding domain that binds a target antigen, an optional extracellular spacer domain, a transmembrane domain, and an intracellular signaling domain (e.g., comprising an immunoreceptor tyrosine-based activation motif (ITAM)), and optionally an intracellular costimulatory domain). In certain embodiments, an intracellular signaling domain of a CAR has an ITAM (e.g., CD3ζ) containing intracellular signaling domain and an intracellular costimulatory domain (e.g., 4-1BB). In certain embodiments, a CAR is synthesized as a single polypeptide chain or is encoded by a nucleic acid molecule as a single chain polypeptide.

A variety of assays are known for identifying binding domains of the present disclosure that specifically bind a particular target, as well as determining binding domain affinities, such as Western blot, ELISA, analytical ultracentrifugation, spectroscopy, surface plasmon resonance (BIA-CORE®) analysis, and MHC tetramer analysis (see also, e.g., Scatchard et al., *Ann. N.Y. Acad. Sci.* 51:660, 1949; Wilson, *Science* 295:2103, 2002; Wolff et al., *Cancer Res.* 53:2560, 1993; Altman et al., *Science* 274:94-96, 1996; and U.S. Pat. Nos. 5,283,173, 5,468,614, or the equivalent). As used herein, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ $M^{-1}$, while not significantly associating or uniting with any other molecules or components in a sample.

The terms "antigen" and "Ag" refer to a molecule that is capable of inducing an immune response. The immune response that is induced may involve antibody production, the activation of specific immunologically-competent cells, or both. Macromolecules, including proteins, glycoproteins, and glycolipids, can serve as an antigen. Antigens can be derived from recombinant or genomic DNA. As contemplated herein, an antigen need not be encoded (i) solely by a full-length nucleotide sequence of a gene or (ii) by a "gene" at all. An antigen can be generated or synthesized, or an antigen can be derived from a biological sample. Such a biological sample can include, but is not limited, to a tissue sample, a tumor sample, a cell, or a biological fluid.

The term "epitope" or "antigenic epitope" includes any molecule, structure, amino acid sequence or protein determinant within an antigen that is specifically bound by a cognate immune binding molecule, such as an antibody or fragment thereof (e.g., scFv), T cell receptor (TCR), CAR, or other binding molecule, domain or protein. Epitopic determinants generally contain chemically active surface groupings of molecules, such as amino acids or sugar side chains, and can have specific three-dimensional structural characteristics, as well as specific charge characteristics. An epitope may be a linear epitope or a conformational epitope.

As used herein, an "effector domain" is an intracellular portion of a fusion protein or chimeric receptor that can directly or indirectly promote a biological or physiological response in a cell expressing the effector domain when receiving the appropriate signal. In certain embodiments, an effector domain is part of a protein or protein complex that receives a signal when bound. In other embodiments, the effector domain is part of a protein or protein complex that binds directly to a target molecule, which triggers a signal from the effector domain. For example, in response to binding of a CAR to a target molecule, the effector domain may transduce a signal to the interior of the host cell, eliciting an effector function. An effector domain may directly promote a cellular response when it contains one or more signaling domains or motifs. In other embodiments, an effector domain will indirectly promote a cellular response by associating with one or more other proteins that directly promote a cellular response.

"Junction amino acids" or "junction amino acid residues" refer to one or more (e.g., about 2-20) amino acid residues between two adjacent motifs, regions or domains of a polypeptide. Junction amino acids may result from the construct design of a chimeric protein (e.g., amino acid residues resulting from the use of a restriction enzyme site during the construction of a nucleic acid molecule encoding a fusion protein).

A "disease" is a state of health of a subject wherein the subject cannot maintain homeostasis, and wherein, if the disease is not ameliorated, then the subject's health continues to deteriorate. In contrast, a "disorder" or "undesirable condition" in a subject is a state of health in which the subject is able to maintain homeostasis, but in which the subject's state of health is less favorable than it would be in the absence of the disorder or undesirable condition. Left untreated, a disorder or undesirable condition does not necessarily result in a further decrease in the subject's state of health.

"Nucleic acid molecule" and "polynucleotide" can be in the form of RNA or DNA, which includes cDNA, genomic DNA, and synthetic DNA. A nucleic acid molecule may be composed of naturally occurring nucleotides (such as deoxyribonucleotides and ribonucleotides), analogs of naturally occurring nucleotides (e.g., α-enantiomeric forms of naturally occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

"Encoding" refers to the inherent property of specific polynucleotide sequences, such as DNA, cDNA, and mRNA sequences, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a polynucleotide encodes a protein if transcription and translation of mRNA corresponding to that polynucleotide produces the protein in a cell or other biological system. Both a coding strand and a non-coding strand can be referred to as encoding a protein or other product of the polynucleotide. Unless otherwise specified, a "nucleotide sequence encoding an amino acid sequence" includes all nucleotide sequences that are degenerate versions of each other and that encode the same amino acid sequence.

As used herein, the term "endogenous" or "native" refers to a gene, protein, compound, molecule or activity that is normally present in a host or host cell, including naturally occurring variants of the gene, protein, compound, molecule, or activity.

As used herein, "homologous" or "homolog" refers to a molecule or activity from a host cell that is related by ancestry to a second gene or activity, e.g., from the same host cell, from a different host cell, from a different organism, from a different strain, from a different species. For example, a heterologous molecule or heterologous gene encoding the molecule may be homologous to a native host cell molecule or gene that encodes the molecule, respectively, and may optionally have an altered structure, sequence, expression level or any combination thereof.

As used herein, "heterologous" nucleic acid molecule, construct or sequence refers to a nucleic acid molecule or portion of a nucleic acid molecule that is not native to a host cell, but can be homologous to a nucleic acid molecule or portion of a nucleic acid molecule from the host cell. The source of the heterologous nucleic acid molecule, construct or sequence can be from a different genus or species. In some embodiments, the heterologous nucleic acid molecules are not naturally occurring. In certain embodiments, a heterologous nucleic acid molecule is added (i.e., not endogenous or native) into a host cell or host genome by, for example, conjugation, transformation, transfection, transduction, electroporation, or the like, wherein the added molecule can integrate into the host cell genome or exist as extra-chromosomal genetic material (e.g., as a plasmid or other form of self-replicating vector), and can be present in multiple copies. In addition, "heterologous" refers to a non-native enzyme, protein or other activity encoded by a non-endogenous nucleic acid molecule introduced into the host cell, even if the host cell encodes a homologous protein or activity.

As used herein, the term "engineered," "recombinant," "mutant," "modified" or "non-natural" refers to an organism, microorganism, cell, nucleic acid molecule, or vector that has been modified by introduction of a heterologous nucleic acid molecule, or refers to a cell or microorganism that has been genetically engineered by human intervention—that is, modified by introduction of a heterologous nucleic acid molecule, or refers to a cell or microorganism that has been altered such that expression of an endogenous nucleic acid molecule or gene is controlled, deregulated or constitutive, where such alterations or modifications can be introduced by genetic engineering. Human-generated genetic alterations can include, for example, modifications introducing nucleic acid molecules (which may include an expression control element, such as a promoter) encoding one or more proteins, chimeric receptors, or enzymes, or other nucleic acid molecule additions, deletions, substitutions, or other functional disruption of or addition to a cell's genetic material. Exemplary modifications include those in coding regions or functional fragments thereof heterologous or homologous polypeptides from a reference or parent molecule. Additional exemplary modifications include, for example, modifications in non-coding regulatory regions in which the modifications alter expression of a gene or operon.

As used here, the term "transgene" refers to a gene or polynucleotide encoding a protein of interest (e.g., a CAR) whose expression is desired in a host cell and that has been transferred by genetic engineering techniques into a cell. A transgene may encode proteins of therapeutic interest as well as proteins that are reporters, tags, markers, suicide proteins, etc. A transgene may be from a natural source, modification of a natural gene, or a recombinant or synthetic molecule. In certain embodiments, a transgene is a component of a vector.

The term "overexpressed" or "overexpression" of an antigen refers to an abnormally high level of antigen expression in a cell. Overexpressed antigen or overexpression of antigen is often associated with a disease state, such as in hematological malignancies and cells forming a solid tumor within a specific tissue or organ of a subject. Solid tumors or hematological malignancies characterized by overexpression of a tumor antigen can be determined by standard assays known in the art.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the term "mature polypeptide" or "mature protein" refers to a protein or polypeptide that is secreted or localized in the cell membrane or inside certain cell organelles (e.g., the endoplasmic reticulum, golgi, or endosome) and includes a partially cleaved N-terminal signal sequence (e.g., one or more amino acids of the signal sequence remaining but less than the whole signal sequence) or does not include an N-terminal signal sequence (i.e., the N-terminal signal sequence has been entirely removed, such as by an endogenous cleavage process, from the protein or polypeptide).

A "signal sequence", also referred to as "signal peptide", "leader sequence", "leader peptide", "localization signal" or "localization sequence", is a short peptide (usually 13-36 amino acids in length) present at the N-terminus of newly synthesized proteins that are destined for the plasma membrane or a secretory pathway. A signal sequence typically comprises a short stretch of hydrophilic, positively charged amino acids at the N-terminus, a central hydrophobic domain of 5-15 residues, and a C-terminal region with a cleavage site for a signal sequence. In eukaryotes, a signal sequence prompts translocation of the newly synthesized protein to the endoplasmic reticulum where it is cleaved by the signal peptidase, creating a mature protein that then proceeds to its appropriate destination. The diversity of signal sequence length and amino acid composition makes it difficult to precisely predict the cleavage site. For polypeptide sequences disclosures herein, where a signal sequence is noted, the polypeptide sequence absent the signal sequence or having a partial signal sequence is also contemplated.

The "percent identity" between two or more nucleic acid or amino acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, MA (1990), p. 8).

The term "chimeric" refers to any nucleic acid molecule or protein that is not endogenous and comprises a combination of sequences joined or linked together that are not naturally found joined or linked together in nature. For example, a chimeric nucleic acid molecule may comprise nucleic acids encoding various domains from multiple different genes. In another example, a chimeric nucleic acid molecule may comprise regulatory sequences and coding sequences that are derived from different sources, or regulatory sequences and coding sequences that are derived from the same source but arranged in a manner different than that found in nature.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may include an enhancer sequence and other regulatory elements that are required for expression of the gene product. The promoter/regulatory sequence may, for example, be one that expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The phrase "under transcriptional control" or "operatively linked" as used herein means that a promoter is in the correct location and orientation in relation to a polynucleotide to control the initiation of transcription by RNA polymerase and expression of the polynucleotide.

A "vector" is a nucleic acid molecule that is capable of transporting another nucleic acid. Vectors may be, for example, plasmids, cosmids, viruses, or phage. The term should also be construed to include non-plasmid and non-viral compounds that facilitate transfer of nucleic acid into cells. An "expression vector" is a vector that is capable of directing the expression of a protein encoded by one or more transgenes carried by the vector when it is present in the appropriate environment. The one or more transgenes to be expressed by a vector as described herein are encoded in an expression cassette.

A "lentiviral vector" is a vector derived from a lentivirus and includes one or more lentiviral packaging proteins and/or one or more lentiviral proteins necessary for expression of the one or more genes carried by the vector. The abbreviation "LVV" is used herein to refer to a lentiviral vector (singular), as well as multiple lentiviral vectors (plural).

"Lentivirus" refers to a genus of retroviruses that are capable of infecting dividing and non-dividing cells. Examples of lentiviruses include, but are not limited to HIV (human immunodeficiency virus, including HIV type 1 and HIV type 2, equine infectious anemia virus, feline immunodeficiency virus (FIV), bovine immune deficiency virus (BIV), and simian immunodeficiency virus (SIV).

"Retrovirus" refers to are RNA viruses with a single strand positive-sense RNA molecule. Retroviruses comprise a reverse transcriptase enzyme and an integrase enzyme. Upon entry into a target cell, retroviruses utilize their reverse transcriptase to transcribe their RNA molecule into a DNA molecule. Subsequently, the integrase enzyme is used to integrate the DNA molecule into the host cell genome. Upon integration into the host cell genome, the sequence from the retrovirus is referred to as a provirus (e.g., proviral sequence or provirus sequence).

As used herein, the term "expression cassette" refers to a distinct component of a vector nucleic acid comprising at least one transgene and regulatory sequences controlling its expression (e.g., promoter, 3'UTR) in a host cell. A tandem expression cassette refers to a component of a vector nucleic acid comprising at least two transgenes under the control of the same set of regulatory sequences for tandem expression of the at least two transgenes. In certain embodiments, the tandem expression cassette comprises at least two transgenes under the control of the same promoter. In certain embodiments, the first transgene and second transgene are separated by an internal ribosome entry site (IRES), furin cleavage site, or self-cleaving viral 2A peptide to allow for co-expression of two proteins from a single mRNA.

The term "immune system cell" or "immune cell" means any cell of the immune system that originates from a hematopoietic stem cell in the bone marrow. Hematopoietic stem cells give rise to two major lineages: myeloid progenitor cells (which give rise to myeloid cells such as monocytes, macrophages, dendritic cells, megakaryocytes and granulocytes) and lymphoid progenitor cells (which give rise to lymphoid cells such as T cells, B cells and natural killer (NK) cells). Exemplary immune system cells include a CD4+ T cell, a CD8+ T cell, a CD4−CD8− double negative T cell, a γδ T cell, a regulatory T cell, a natural killer cell, and a dendritic cell. Macrophages and dendritic cells may also be referred to as "antigen presenting cells" or "APCs," which are specialized cells that can activate T cells when a major histocompatibility complex (MHC) receptor on the surface of the APC complexed with a peptide interacts with a TCR on the surface of a T cell.

The term "lymphocyte" refers to immune cells of lymphoid origin, which are cells that show at least one phenotype characteristic of a lymphocyte or a precursor or progenitor thereof that distinguishes the cells from cells of erythroid or myeloid lineages. The term "lymphocytes" encompasses T cells, B cells, and natural killer (NK) cells.

The term "T cells" refers to cells of T cell lineage. "Cells of T cell lineage" refer to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., $CD3^+$, $CD4^+$, $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 linage commitment; thymocyte progenitor cells that are CD4+CD8$^+$ double positive; single positive CD4$^+$ or CD8$^+$; TCRαβ or TCR γδ; or mature and functional or activated T cells. The term "T cells" encompasses naïve T cells (CD45RA+, CCR7+, CD62L+, CD27+, CD45RO−), central memory T cells (CD45RA−, CD45RO$^+$, CD62L$^+$, CCR7+, CD27+), effector memory T cells (CD45RA−, CD45RO+, CCR7−, CD62L−, CD27−), mucosal-associated invariant T (MAIT) cells, 78 T cells, Tregs, natural killer T cells, and tissue resident T cells.

The term "natural killer cells" or "NK cells" refers to large granular lymphocytes (LGL) and constitute the third kind of cells differentiated from the common lymphoid progenitor-generating B and T lymphocytes. NK cells are known to differentiate and mature in the bone marrow, lymph nodes, spleen, tonsils, and thymus, where they then enter into the circulation. NK cells differ from natural killer T cells (NKTs) phenotypically, by origin and by respective effector functions; often, NKT cell activity promotes NK cell activity by secreting IFNγ. In contrast to NKT cells, NK cells do not express T-cell antigen receptors (TCR) or pan T marker CD3 or surface immunoglobulins (Ig) B cell receptors, but they usually express the surface markers CD16 (FcγRIII) and CD56 in humans, NK1.1 or NK1.2 in C57BL/6 mice. Up to 80% of human NK cells also express CD8.

The term "B cells" refers to cells of the B cell lineage. "Cells of B cell lineage" refers to cells that show at least one phenotypic characteristic of a B cell or a precursor or progenitor thereof that distinguishes the cells from other lymphoid cells, and cells of the erythroid or myeloid lineages. Such phenotypic characteristics can include expression of one or more proteins specific for B cells (e.g., cells positive for one or more of CD19+, CD72+, CD24+, CD20+, CD21+, CD22+, CD38+, CD40+, CD72+, CD32b+, CD268+, CD269+, CD267+, CD86+, CD80+, CD40+, CD52+, CD138+, CD27+, CD28+, CD21+, CD23+, CD84+, CD257+, CD270+, CD37+, and CD74+), or a physiological, morphological, functional, or immunological feature specific for a B cell. For example, cells of the B cell lineage may be progenitor or precursor cells committed to the B cell lineage (e.g., pre-pro-B cells, pro-B cells, and pre-B cells); immature and inactivated B cells or mature and functional or activated B cells. Thus, "B cells" encompass naïve B cells, plasma cells, regulatory B cells, marginal zone B cells, follicular B cells, lymphoplasmacytoid cells, plasmablast cells, and memory B cells (e.g., CD27+, IgD−).

The term "cytotoxic activity," also referred to as "cytolytic activity," with respect to a cell (e.g., T cell) that expresses an immune receptor (e.g., a CAR) on its surface, means that upon antigen-specific signaling (e.g., via the CAR) the cell induces a target cell to undergo apoptosis. In some embodiments, a cytotoxic cell may induce apoptosis in a target cell via the release of cytotoxins, such as perforin, granzyme, and granulysin, from granules. Perforins insert into the target cell membrane and form pores that allow water and salts to rapidly enter the target cell. Granzymes are serine proteases that induce apoptosis in the target cell. Granulysin is also capable of forming pores in the target cell membrane and is a proinflammatory molecule. In some embodiments, a cytotoxic cell may induce apoptosis in a target cell via interaction of Fas ligand, which is upregulated on T cell following antigen-specific signaling, with Fas molecules expressed on the target cell. Fas is an apoptosis-signaling receptor molecule on the surface of a number of different cells.

A "disease" is a state of health of a subject wherein the subject cannot maintain homeostasis, and wherein, if the disease is not ameliorated, then the subject's health continues to deteriorate. In contrast, a "disorder" or "undesirable condition" in a subject is a state of health in which the subject is able to maintain homeostasis, but in which the subject's state of health is less favorable than it would be in the absence of the disorder or undesirable condition. Left untreated, a disorder or undesirable condition does not necessarily result in a further decrease in the subject's state of health.

The term "cancer" as used herein is defined as disease characterized by the rapid and uncontrolled growth of aberrant cells. The aberrant cells may form solid tumors or constitute a hematological malignancy. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "subject," "patient" and "individual" are used interchangeably herein and are intended to include living organisms in which an immune response can be elicited (e.g., mammals). Examples of subjects include humans, primates, cows, horses, goats, sheep, dogs, cats, mice, rats, rabbits, guinea pigs, pigs, and transgenic species thereof.

"Adoptive cellular immunotherapy" or "adoptive immunotherapy" refers to the administration of naturally occurring or genetically engineered, disease antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

"Autologous" refers to a graft (e.g., organ, tissue, cells) derived from the same subject to which it is later to be re-introduced.

"Allogeneic" refers to a graft derived from a different subject of the same species.

A "therapeutically effective amount" or "effective amount" of a lentiviral vector or a cell transduced by a lentiviral vector as described herein (e.g., a T cell expressing a CAR as encoded by the transgene of the lentiviral vector) refers to that amount of lentiviral particles or cells sufficient to result in amelioration of one or more symptoms of the disease, disorder, or undesired condition being treated.

"Treat" or "treatment" or "ameliorate" refers to medical management of a disease, disorder, or undesired condition of a subject. In general, an appropriate dose or treatment regimen comprising a lentiviral vector or a cell expressing a CAR of this disclosure is administered in an amount sufficient to elicit a therapeutic or prophylactic benefit. Therapeutic or prophylactic/preventive benefit includes improved clinical outcome; lessening or alleviation of symptoms associated with a disease, disorder, or undesired condition; decreased occurrence of symptoms; improved quality of life; longer disease-free status; diminishment of extent of disease, disorder, or undesired condition; stabilization of disease state; delay of disease progression; remission; survival; prolonged survival; or any combination thereof.

The term "anti-tumor effect" refers to a biological effect which can be manifested by a decrease in tumor volume, a decrease in the number of tumor cells, a decrease in the number of metastases, an increase in life expectancy, or amelioration of various physiological symptoms associated with a cancerous condition. An "anti-tumor effect" can also be manifested by prevention of a hematological malignancy or tumor formation.

Additional definitions are provided throughout the present disclosure.

Lentiviral Vector

Lentivirus is a genus of retroviruses that typically gives rise to slowly developing diseases due to their ability to incorporate into a host genome. Modified lentiviral genomes are useful as viral vectors for the delivery of a nucleic acids to a host cell.

The present disclosure provides self-inactivating lentiviral vectors ("LVV") that include a viral envelope comprising a mutated, heterologous envelope protein and a tropism defining molecule (also referred to as a "targeting protein"). The LVV described herein further includes a transgene, with the LVV being capable of specifically binding to a target immune cell and transducing the target immune cell such that the transgene is expressed by the immune cell. In some embodiments, the LVV may carry more than one transgene. In further specific embodiments, the transgene encodes a chimeric antigen receptor (CAR).

Mutated Viral Envelope Protein

Lentiviral vectors as described herein are pseudotyped with a mutated heterologous viral envelope protein that, in the absence of mutation, mediates both cellular attachment and membrane fusion. In particular embodiments, the mutated envelope protein includes at least one mutation that inhibits the envelope protein's ability to bind its native target, while preserving the envelope protein's fusogenic properties. In specific embodiments, the heterologous envelope protein is a vesicular stomatitis virus G protein ("VSV-G", "VSV-G envelope protein" or "VSV-G protein") that includes one or more mutations that inhibit binding of VSV-G to the low-density lipoprotein receptor ("LDL-R"), while preserving the VSV-G protein's fusogenic function.

When referring to the envelope protein's ability to bind its native target, the terms "inhibit" and "inhibits" encompass both complete elimination of binding by the envelope protein to its native target, as well as a significant reduction in binding by the envelope protein to its native target. In particular embodiments, "significant reduction" refers to a reduction selected from a reduction of at least 95%, at least 90%, at least 85%, at least 80%, at least 75%, at least 70%, at least 65%, at least 60%, at least 55%, at least 50%, at least 45%, at least 40%, at least 35%, at least 30%, at least 25%, at least 20%, at least 15%, and at least 10% in binding to the native target.

The nucleic acid and amino acid sequences set forth in Table 10 provide references sequences for a wild type VSV-G envelope protein and examples of mutated VSV-G envelope proteins according to the present disclosure. SEQ ID NO: 77 is a reference nucleic acid sequence encoding the VSV-G envelope protein, and SEQ ID NO: 78 is an amino acid sequence of a reference VSV-G envelope protein. SEQ ID NO: 87 is a nucleic acid sequence encoding a cleavable signal peptide of the reference VSV-G envelope protein. SEQ ID NO: 88 is an amino acid sequence of the cleavable signal peptide of the reference VSV-G envelope protein. SEQ ID NO: 89 is a reference nucleic acid sequence encoding the VSV-G envelope protein, absent the signal sequence. SEQ ID NO: 90 is an amino acid sequence of a reference VSV-G envelope protein absent the sequence. The position and nature of VSV-G mutations disclosed herein are described in reference to the nucleic acid sequence and the amino acid sequence provided by SEQ ID NO: 77 absent the N-terminal signal sequence of SEQ ID NO: 87 and SEQ ID NO: 78 absent the N-terminal signal sequence of SEQ ID NO: 88, respectively. Thus, reference to a position 1 of the VSV-G env amino acid sequence for the purpose of identifying mutation position refers to position 17 of the wildtype VSV-G amino acid sequence of SEQ ID NO: 78, which is a lysine (K), or position 1 of the wildtype VSV-G amino acid sequence of SEQ ID NO: 90.

In some embodiments, the mutated VSV-G envelope protein includes a mutation at amino acid position H8, N9, Q10, K47, K50, A51, S183, S179, N180, I182, M184, Y209, I347, T350, T352, E353, R354, an insertion of TT between N9 and Q10, an insertion of GGS between H8 and N9, an insertion of GGS between N9 and Q10, an insertion of TT between N208 and Y209, an insertion of GGS between P46 and K47, an insertion of GGS between N208 and Y209, and/or a deletion of residues 1-8. In certain embodiments, the VSV-G envelope protein includes two or more mutations at amino acid positions selected from H8, N9, Q10, K47, K50, A51, S183, S179, N180, I182, M184, Y209, I347, T350, T352, E353, R354, an insertion of TT between N9 and Q10, an insertion of GGS between H8 and N9, an insertion of GGS between N9 and Q10, an insertion of TT between N208 and Y209, an insertion of GGS between P46 and K47, an insertion of GGS between N208 and Y209, and a deletion of residues 1-8. In other embodiments, the VSV-G envelope protein includes three or more mutations at amino acid positions selected from H8, N9, Q10, K47, K50, A51, S183, S179, N180, I182, M184, Y209, I347, T350, T352, E353, R354, an insertion of TT between N9 and Q10, an insertion of GGS between H8 and N9, an insertion of GGS between N9 and Q10, an insertion of TT between N208 and Y209, an insertion of GGS between P46 and K47, an insertion of GGS between N208 and Y209, and a deletion of residues 1-8. In other embodiments, the mutated VSV-G envelope protein comprises a H8A, K47A, K47Q, Y209A, R354A, and/or R354Q mutation. In still other embodiments, the VSV-G envelope protein includes one or more mutations selected from N9, Q10, K50, A51, S183, S179, N180, I182, M184, I347, T350, T352, and E353, an insertion of TT between N9 and Q10, an insertion of GGS between H8 and N9, an insertion of GGS between N9 and Q10, an insertion of TT between N208 and Y209, an insertion of GGS between P46 and K47, an insertion of GGS between N208 and Y209, and a deletion of residues 1-8. In yet other embodiments, the VSV-G envelope protein includes two or more mutations selected from a mutation at one or more of N9, Q10, K50, A51, S183, S179, N180, I182, M184, I347, T350, T352, and E353, an insertion of TT between N9 and Q10, an insertion of GGS between H8 and N9, an insertion of GGS between N9 and Q10, an insertion of TT between N208 and Y209, an insertion of GGS between P46 and K47, an insertion of GGS between N208 and Y209, and a deletion of residues 1-8. In some embodiments, a mutated VSV-G envelope protein is selected from one or more of an H8A, N9A, Q10A, K47A, K47Q, N180A, I182A, Y209A, T352A, T352W, E353A, R354A, and R354Q mutation. In some embodiments, a mutated VSV-G envelope protein is selected from one or more of an H8A, K47A, K47Q, Y209A, R354A, and R354Q mutation. In some embodiments, the mutated VSV-G envelope protein comprises a K47 mutation and a R354 mutation. In some embodiments, the mutated VSV-G envelope protein comprises a K47Q mutation and a R354A mutation. In some embodiments, the mutated VSV-G envelope protein comprises a N180 mutation, a I182 mutation, a T352 mutation, and a E353 mutation. In some embodiments, the mutated VSV-G envelope protein comprises a N180A mutation, a I182A mutation, a T352A mutation, and a E353A mutation. In some embodiments, the mutated VSV-G envelope protein comprises a T352 mutation and E353 mutation. In further embodiments, the mutated VSV-G envelope protein comprises a T352W mutation and E353A mutation. In some embodiments, the mutated VSV-G envelope protein comprises a N9 mutation, a Q10 mutation, and a N180 mutation. In some embodiments, the mutated VSV-G envelope protein comprises a N9A mutation, a Q10A mutation, and a N180A mutation. In some embodiments, the mutated VSV-G envelope protein comprises an insertion of GGS between H8 and N9 and an insertion of GGS between N9 and Q10. In some embodiments, the mutated VSV-G envelope protein comprises an insertion of TT between N9 and Q10. In some embodiments, the mutated VSV-G envelope protein comprises an insertion of GGS between P46 and K47. In other embodiments, the mutated VSV-G envelope protein is as described in Nikolic et al., "Structural basis for the recognition of LDL-receptor family members by VSV glycoprotein." *Nature Comm.*, 2018, 9:1029, the relevant disclosures of which are incorporated by reference herein.

In specific embodiments, the mutant VSV envelope protein comprises a K47Q mutation and R354A mutation. In specific embodiments, the mutant VSV-G envelope protein has an amino acid sequence according to SEQ ID NO: 74.

In specific embodiments, the mutant VSV envelope protein comprises a N180A mutation, an I182A mutation, a T352A mutation, and an E353A mutation. In specific embodiments, the mutant VSV-G envelope protein has an amino acid sequence according to SEQ ID NO: 93.

In specific embodiments, the mutant VSV envelope protein comprises a T352W mutation and an E353A mutation. In specific embodiments, the mutant VSV-G envelope protein has an amino acid sequence according to SEQ ID NO: 95.

In specific embodiments, the mutant VSV envelope protein comprises a N9A mutation, a Q10A mutation, and a N180A mutation. In specific embodiments, the mutant VSV-G envelope protein has an amino acid sequence according to SEQ ID NO: 97.

In specific embodiments, the mutant VSV envelope protein comprises an insertion of TT between N9 and Q10 mutation. In specific embodiments, the mutant VSV-G envelope protein has an amino acid sequence according to SEQ ID NO: 99.

In specific embodiments, the mutant VSV envelope protein comprises an insertion of GGS between P46 and K47 mutation. In specific embodiments, the mutant VSV-G envelope protein has an amino acid sequence according to SEQ ID NO: 101.

In specific embodiments, the mutant VSV envelope protein comprises an insertion of GGS between H8 and N9 and an insertion of GGS between N9 and Q10. In specific embodiments, the mutant VSV-G envelope protein has an amino acid sequence according to SEQ ID NO: 103.

Targeting Protein

The targeting protein is a membrane-bound protein displayed on the viral envelope and includes an extracellular domain that includes a lymphocyte targeting domain and a transmembrane domain. A lymphocyte targeting domain is any protein or peptide that has an amino acid sequence and is a binding partner for a target molecule or ligand (e.g., a cognate protein or ligand) on a target lymphocyte cell surface. In some embodiments, a lymphocyte targeting domain is a T cell targeting domain. In some embodiments, a lymphocyte targeting domain is a NK cell targeting domain. In some embodiments, a lymphocyte targeting domain is a B cell targeting domain. For example, in certain embodiments, the extracellular domain of the targeting protein includes a lymphocyte targeting domain that specifically binds a protein or ligand on the surface of a defined population of cells, such as a population of lymphocytes characterized by the presence of the targeted protein or ligand on the cell surface. In some embodiments, a lymphocyte targeting domain targets a specific type of lymphocyte, such as for example, T cells, B cells, or natural killer (NK) cells. In some embodiments, the targeting protein additionally includes an extracellular linker or hinge domain positioned between the transmembrane domain and the extracellular domain.

In some embodiments, the targeting protein is a full-length cell surface protein or receptor, wherein each component (e.g., each of the extracellular domain, transmembrane domain, and intracellular domain) derived from a single protein or receptor. In other embodiments, the targeting protein is a chimeric protein, having at least two components derived from a different protein or receptor. In some embodiments, the targeting protein is obtained from a mammalian species, including humans, primates, cows, horses, goats, sheep, dogs, cats, mice, rats, rabbits, guinea pigs, and pigs. In some embodiments, the targeting protein is a fully human sequence. In some embodiments, the targeting protein is a chimeric sequence comprising human sequence component(s) and component(s) from another species or synthetic component(s). In some embodiments, a chimeric targeting protein may be a fully synthetic protein. In still other embodiments, a chimeric targeting protein may include one or more of an extracellular domain, an extracellular binding domain, a transmembrane domain, an intracellular domain, a hinge domain, or a linker that is a fully synthetic protein.

In some embodiments, the lymphocyte targeting domain includes an antibody. In such embodiments, the extracellular targeting domain may be a full-length antibody, an antibody fragment, a nanobody, or a single chain Fv fragment (scFv).

In particular embodiments, the targeting molecule includes a T cell targeting domain that specifically binds to a T cell surface marker, including, for example, a T cell antigen, a T cell surface receptor, or any other protein present on the surface of a targeted T cell. In some embodiments, the targeting protein specifically binds to a T cell marker selected from CD3, CD28, CD80, 4-1BB, AhR, CD3, CD2, CD7, CD4, CD8, CD25, CD44, CD45RA, CD47, CD62L, CD69, CD94, CD95, CD127, CD161, CD183 (CXCR3), CD184 (CXCR4), CD185 (CXCR5), CD193 (CCR3), CD194 (CCR4), CD195 (CCR5), CD196 (CCR6), CD197 (CCR7), CCR10, PD-1, TCRa/b, CD5, CD27, CD45RO, CD45RB, CD57, CD103, CD122, P2RX7, TIGIT, LAG-3, TIM-3, IL6ST, and any combination thereof.

In further embodiments, the targeting protein specifically binds to a 76 T cell marker selected from γδ TCR, Vdelta1, Vdelta2, NKG2D (KLRK1, CD314), and any combination thereof.

In other embodiments, the targeting protein specifically binds to an NK T cell marker selected from Invariant TCR (Va24-Ja18), CD185 (CXCR5), CXCR6, IL-21R, and any combination thereof.

In other embodiments, the targeting protein specifically binds to a MAIT cell marker selected from Va7.2, Ja33, CXCR6, IL-18R, KLRB1 (CD161), VLA4 (alpha4beta1 integrin), and any combination thereof.

In other embodiments, the targeting protein specifically binds to an NK cell marker selected from CD56, NKp46, CD16, KIR(s), NKG2 proteins (e.g., NKG2D (KLRK1, CD314)), KLRB1 (CD161), KLRD1 (cd94), IL2Rb (CD122), IL-21R, SLAMF6 (CD352), SLAMF7 (CD319), IL-18R, and any combination thereof.

In other embodiments, the targeting protein specifically binds to a B cell marker selected from CD19, CD20, CD21, CD22, CD24, CD38, CD40, CD72, CD32b, CD268, CD269, CD267, CD86, CD80, CD52, CD138, CD27, CD28, CD23, CD84, CD257, CD270, CD37, CD74, and CD269, and any combination thereof.

In embodiments, the targeting protein specifically binds to a lymphocyte marker (e.g., B cell and T cells) selected from CD80, CD27, CD28, and any combination thereof.

In some embodiments of the targeting protein, a linker is positioned between the transmembrane domain and the lymphocyte targeting domain. A linker is an amino acid linker and may be a rigid linker, a flexible linker, or an oligomerized linker. A rigid linker is an amino acid sequence that lacks flexibility (e.g., may comprise at least one proline). In some embodiments, a rigid linker comprises a platelet-derived growth factor receptor (PDGFR) stalk or a CD8a stalk. In some embodiments, a PDGFR stalk comprises an amino acid sequence comprising AVGQDTQEVIVVPHSLPFK (SEQ ID NO: 104). In some embodiments, a PDGFR stalk comprises an amino acid sequence comprising (SEQ ID NO: 105)
ASAKPTTTPAPRPPTPAPTIASQPLSLRPEAARPAAGGAVHTRGLDFAK.

A flexible linker is an amino acid sequence that has many degrees of freedom (e.g., may comprise a plurality of amino acids with small side chains, e.g., glycine or alanine). In some embodiments, a flexible linker comprises an amino acid sequence comprising GAPGAS. In some embodiments, a flexible linker comprises an amino acid sequence consisting of GAPGSGGGGSGGGGSAS (SEQ ID NO: 106). In some embodiments, a flexible linker comprises an amino acid sequence comprising GGGGS.

In some embodiments, a flexible linker comprises an amino acid sequence comprising GGGS. In some embodiments, a flexible linker comprises an amino acid sequence comprising $(GAPGAS)_N$, $(G3S)_N$, or $(G4S)_N$, wherein N is 1, 2, 3, 4, 5, 6, 7, 8, 9, 10, or more.

An oligomerized linker is an amino acid that can oligomerize to another related amino acid. In some embodiments, an oligomerized linker is an amino acid sequence that can form a dimer, trimer, or tetramer. In some embodiments, an oligomerized linker comprises an IgG4 hinge domain (e.g., ESKYGPPCPPCPAVGQDTQEVIVVPHSLPFK (SEQ ID NO: 107)). In some embodiments, an oligomerized linker comprises an amino acid sequence that can form a tetrameric coiled coil (e.g., ASGGGGSGELAAIKQELAAI-KKELAAIKWELAAIKQGAG (SEQ ID NO: 108)). In some embodiments, an oligomerized linker comprises an amino acid sequence that can form a dimeric coiled coil (e.g., ASESKYGPPCPPCP (SEQ ID NO: 109)).

The targeting protein will typically include a signal sequence (also referred to as a signal peptide of localization sequence). The signal sequence can be located at the N- or C-terminal ends of the targeting protein. A signal sequence functions to translocate the targeting protein to the membrane that serves as the envelope of the lentiviral vector. Non-limiting examples of signal sequences that might be included in a targeting protein as described herein include an Ig Kappa leader sequence (e.g., a murine Ig Kappa leader sequence comprising: METDTLLLWVLLLWVPGSTG (SEQ ID NO: 110)), CD8a signal peptide sequence (e.g., a CD8a signal peptide comprising: MALPVTALLLPLALLL-HAARP (SEQ ID NO: 12)), and a B2M signal peptide sequence (e.g., a B2M signal peptide sequence comprising: MSRSVALAVLALLSLSGLEA (SEQ ID NO: 123)). In certain embodiments, a mature targeting protein has a partially cleaved signal sequence that retains one or more amino acids of the full-length signal sequence. In other embodiments, cleavage by a signal peptidase results in complete removal of the signal sequence, resulting in a mature targeting protein that lacks a signal sequence entirely.

In some embodiments, the targeting protein is a CD80 protein. Where the targeting protein is a CD80 protein, it may include an extracellular domain according to SEQ ID NO: 6. In such embodiments, a CD80 protein may include a signal peptide according to SEQ ID NO: 4 and a transmembrane and intracellular domain according to SEQ ID NO: 8. In a specific embodiment, a CD80 targeting protein included in a lentiviral vector as described herein includes an amino acid sequence according to SEQ ID NO: 2 or SEQ ID NO: 2 absent the signal peptide of SEQ ID NO: 4.

In some embodiments, where the targeting protein is a CD80 protein, it may include an extracellular domain that has at least about 75%, 80%, 85%, 90%, 91%, 92%, 93%, 94%, 95%, 96%, 97%, 98%, 99%, 99.5%, or 100% identity to SEQ ID NO: 6. In such embodiments, a CD80 protein may include a signal peptide that has at least about 75%, 80%, 85%, 90%, 91%, 92%, 93%, 94%, 95%, 96%, 97%, 98%, 99%, 99.5%, or 100% identity to SEQ ID NO: 4, and/or a transmembrane and intracellular domain that has at least about 75%, 80%, 85%, 90%, 91%, 92%, 93%, 94%, 95%, 96%, 97%, 98%, 99%, 99.5%, or 100% identity to SEQ ID NO: 8. In a specific embodiment, a CD80 targeting protein included in a lentiviral vector as described herein includes an amino acid sequence that has at least about 75%, 80%, 85%, 90%, 91%, 92%, 93%, 94%, 95%, 96%, 97%, 98%, 99%, 99.5%, or 100% identity to SEQ ID NO: 2 or SEQ ID NO: 2 absent the signal peptide of SEQ ID NO: 4.

TABLE 1

| CD80 T cell targeting molecule |  |
|---|---|
| Full molecule |  |
| Nucleotide | Amino acid (signal peptide underlined) |
| ATGGGTCATACACGCCGCCAAGGA ACCTCACCATCTAAGTGCCCATAT CTGAATTTCTTTCAACTTCTCGTGC TGGCGGGGCTCAGTCATTTCTGCA GTGGGGTCATTCACGTTACTAAAG AGGTCAAGGAGGTCGCAACATTGA GTTGTGGCCATAACGTATCAGTTG AAGAACTCGCGCAGACACGGATTT ACTGGCAAAAGGAAAAGAAGATG GTGTTGACAATGATGAGCGGTGAC ATGAACATTTGGCCAGAGTACAAA AATCGAACGATATTCGATATAACC AATAACTTGTCCATAGTAATACTT GCCTTGCGACCTTCTGACGAGGGA ACGTATGAATGTGTAGTGCTTAAG TATGAAAAAGATGCCTTTAAGCGG GAACACTTGGCTGAGGTTACACTC TCCGTTAAGGCGGACTTTCCTACG CCGTCTATATCCGACTTCGAGATA CCCACTTCTAACATTCGACGCATC ATTTGCTCAACCTCAGGTGGTTTCC CAGAGCCTCACTTGAGCTGGCTGG AGAATGGCGAAGAACTTAACGCA ATCAATACCACGGTGTCCCAAGAC CCGGAGACAGAGCTGTACGCCGTG TCATCCAAACTGGATTTTAACATG ACGACAAATCATAGTTTCATGTGT CTGATCAAATATGGGCATCTCAGG GTGAATCAGACTTTTAATTGGAAC ACTACCAAACAAGAGCACTTCCCA GATAATCTGTTGCCAAGCTGGGCG ATAACTCTTATCTCCGTCAACGGT ATCTTCGTAATTTGCTGCCTCACCT ATTGTTTCGCGCCTCGATGCCGAG AA (SEQ ID NO: 1) | MGHTRRQGTSPSKCPYLNFFQLLVL AGLSHFCSGVIHVTKEVKEVATLSC GHNVSVEELAQTRIYWQKEKKMVL TMMSGDMNIWPEYKNRTIFDITNNL SIVILALRPSDEGTYECVVLKYEKDA FKREHLAEVTLSVKADFPTPSISDFEI PTSNIRRIICSTSGGFPEPHLSWLENG EELNAINTTVSQDPETELYAVSSKLD FNMTTNHSFMCLIKYGHLRVNQTEN WNTTKQEHFPDNLLPSWAITLISVN GIFVICCLTYCFAPRCRE (SEQ ID NO: 2) |
| CD80 signal peptide |  |
| Nucleotide | Amino acid |
| ATGGGTCATACACGCCGCCAAGGA ACCTCACCATCTAAGTGCCCATAT CTGAATTTCTTTCAACTTCTCGTGC TGGCGGGGCTCAGTCATTTCTGCA GTGGGGTC (SEQ ID NO: 3) | MGHTRRQGTSPSKCPYLNFFQLLVL AGLSHFCSGV (SEQ ID NO: 4) |
| CD80 extracellular domain (ECD) |  |
| Nucleotide | Amino acid |
| ATTCACGTTACTAAAGAGGTCAAG GAGGTCGCAACATTGAGTTGTGGC CATAACGTATCAGTTGAAGAACTC GCGCAGACACGGATTTACTGGCAA AAGGAAAAGAAGATGGTGTTGAC AATGATGAGCGGTGACATGAACAT TTGGCCAGAGTACAAAAATCGAAC GATATTCGATATAACCAATAACTT GTCCATAGTAATACTTGCCTTGCG ACCTTCTGACGAGGGAACGTATGA ATGTGTAGTGCTTAAGTATGAAAA AGATGCCTTTAAGCGGGAACACTT GGCTGAGGTTACACTCTCCGTTAA GGCGGACTTTCCTACGCCGTCTAT ATCCGACTTCGAGATACCCACTTC TAACATTCGACGCATCATTTGCTC AACCTCAGGTGGTTTCCCAGAGCC TCACTTGAGCTGGCTGGAGAATGG CGAAGAACTTAACGCAATCAATAC CACGGTGTCCCAAGACCCGGAGAC AGAGCTGTACGCCGTGTCATCCAA | IHVTKEVKEVATLSCGHNVSVEELA QTRIYWQKEKKMVLTMMSGDMNI WPEYKNRTIFDITNNLSIVILALRPSD EGTYECVVLKYEKDAFKREHLAEV TLSVKADFPTPSISDFEIPTSNIRRIICS TSGGFPEPHLSWLENGEELNAINTTV SQDPETELYAVSSKLDFNMTTNHSF MCLIKYGHLRVNQTFNWNTTKQEH FPDNLLPS (SEQ ID NO: 6) |

TABLE 1-continued

CD80 T cell targeting molecule

ACTGGATTTTAACATGACGACAAA
TCATAGTTTCATGTGTCTGATCAAA
TATGGGCATCTCAGGGTGAATCAG
ACTTTTAATTGGAACACTACCAAA
CAAGAGCACTTCCCAGATAATCTG
TTGCCAAGC (SEQ ID NO: 5)

CD80 transmembrane and intracellular domain

| Nucleotide | Amino acid |
|---|---|
| TGGGCGATAACTCTTATCTCCGTC<br>AACGGTATCTTCGTAATTTGCTGCC<br>TCACCTATTGTTTCGCGCCTCGATG<br>CCGAGAA (SEQ ID NO: 7) | WAITLISVNGIFVICCLTYCFAPRCRE<br>(SEQ ID NO: 8) |

In some embodiments, lentiviral vectors comprising a CD80 targeting protein exhibit enhanced transduction CD4 T cells over CD8 T cells as a relative percentage of total CD4 and CD8 T cells compared to the transduction by standard LVV. As used herein, "standard lentiviral vector" or "standard LVV" refers to a lentiviral vector which does not contain a mutated VSV-G envelope protein and a lymphocyte targeting protein of the present disclosure. In some embodiments, a standard LVV is generated using a 3$^{rd}$ generation LVV packaging system. In some embodiments, lentiviral vectors comprising a CD80 targeting protein enhance transduction of CD4 T cells over CD8 T cells as a relative percentage of total CD4 and CD8 T cells at least 5%, 10%, 15%, 20%, 25%, 30%, 35%, 40%, 45%, 50%, 55%, 60%, 65%, 70%, 75%, 80%, 85%, 90%, 95%, 99% or more compared to standard LVV.

In some embodiments, the targeting protein is an anti-CD3 targeting protein. In some embodiments, an anti-CD3 targeting protein is an antibody or binding fragment thereof, including for example, a scFv. Where the targeting protein is an anti-CD3 targeting protein, it may include an anti-CD3 scFv having a light chain variable region according to SEQ ID NO: 14, a G3S linker according to SEQ ID NO: 16, and a heavy chain variable region according to SEQ ID NO: 18. In some embodiments, an anti-CD3 targeting protein may comprise an anti-CD3 scFv having a light chain variable region according to SEQ ID NO: 115, a G3S linker according to SEQ ID NO: 16, and a heavy chain variable region according to SEQ ID NO: 113. An anti-CD3 targeting protein as described may include a signal peptide according to SEQ ID NO: 12 and a hinge and transmembrane domain according to SEQ ID NO: 20. In a specific embodiment, an anti-CD3 targeting protein included in a lentiviral vector as described herein includes an amino acid sequence according to SEQ ID NO: 10 or SEQ ID NO: 10 absent the signal peptide of SEQ ID NO: 12. In another specific embodiment, an anti-CD3 targeting protein included in a lentiviral vector as described herein includes an amino acid sequence according to SEQ ID NO: 117 or SEQ ID NO: 117 absent the signal peptide of SEQ ID NO: 12.

In some embodiments, where the targeting protein is an anti-CD3 targeting protein, it may include an anti-CD3 scFv having a light chain variable region that has at least about 75%, 80%, 85%, 90%, 91%, 92%, 93%, 94%, 95%, 96%, 97%, 98%, 99%, 99.5%, or 100% identity to SEQ ID NO: 14, and a heavy chain variable region that has at least about 75%, 80%, 85%, 90%, 91%, 92%, 93%, 94%, 95%, 96%, 97%, 98%, 99%, 99.5%, or 100% identity to SEQ ID NO: 18. An anti-CD3 targeting protein as described may include a signal peptide that has at least about 75%, 80%, 85%, 90%, 91%, 92%, 93%, 94%, 95%, 96%, 97%, 98%, 99%, 99.5%, or 100% identity to SEQ ID NO: 12 and a hinge and transmembrane domain that has at least about 75%, 80%, 85%, 90%, 91%, 92%, 93%, 94%, 95%, 96%, 97%, 98%, 99%, 99.5%, or 100% identity to SEQ ID NO: 20. In a specific embodiment, an anti-CD3 targeting protein included in a lentiviral vector as described herein includes an amino acid sequence that has at least about 75%, 80%, 85%, 90%, 91%, 92%, 93%, 94%, 95%, 96%, 97%, 98%, 99%, 99.5%, or 100% identity to SEQ ID NO: 10 or SEQ ID NO: 10 absent the signal peptide of SEQ ID NO: 12.

In some embodiments, where the targeting protein is an anti-CD3 targeting protein, it may include an anti-CD3 scFv having a light chain variable region that has at least about 75%, 80%, 85%, 90%, 91%, 92%, 93%, 94%, 95%, 96%, 97%, 98%, 99%, 99.5%, or 100% identity to SEQ ID NO: 115, and a heavy chain variable region that has at least about 75%, 80%, 85%, 90%, 91%, 92%, 93%, 94%, 95%, 96%, 97%, 98%, 99%, 99.5%, or 100% identity to SEQ ID NO: 113. An anti-CD3 targeting protein as described may include a signal peptide that has at least about 75%, 80%, 85%, 90%, 91%, 92%, 93%, 94%, 95%, 96%, 97%, 98%, 99%, 99.5%, or 100% identity to SEQ ID NO: 12 and a hinge and transmembrane domain that has at least about 75%, 80%, 85%, 90%, 91%, 92%, 93%, 94%, 95%, 96%, 97%, 98%, 99%, 99.5%, or 100% identity to SEQ ID NO: 20. In a specific embodiment, an anti-CD3 targeting protein included in a lentiviral vector as described herein includes an amino acid sequence that has at least about 75%, 80%, 85%, 90%, 91%, 92%, 93%, 94%, 95%, 96%, 97%, 98%, 99%, 99.5%, or 100% identity to SEQ ID NO: 117 or SEQ ID NO: 117 absent the signal peptide of SEQ ID NO: 12.

TABLE 2

Anti-CD3 T cell targeting molecules

Anti-CD3 (UCTH1) Full molecule

| Nucleotide | Amino acid (signal peptide underlined) |
|---|---|
| ATGGCCTTACCAGTGACCGCCTTG CTCCTGCCGCTGGCCTTGCTGCTCC ACGCCGCCAGGCCGGACATCCAGA TGACCCAGACCACCTCCTCCCTGT CTGCCTCTCTGGGAGACAGAGTCA CCATCAGTTGCAGGGCAAGTCAGG ACATTAGAAATTATTTAAACTGGT ATCAACAGAAACCAGATGGAACTG TTAAACTCCTGATCTACTACACATC AAGATTACACTCAGGAGTCCCATC AAAGTTCAGTGGCAGTGGGTCTGG AACAGATTATTCTCTCACCATTAG CAACCTGGAGCAAGAGGATATTGC CACTTACTTTTGCCAACAGGGTAA TACGCTTCCGTGGACGTTCGCTGG AGGCACCAAGCTGGAAATCAAAC GGGCTGGAGGCGGTAGTGGCGGTG GATCAGGTGGAGGCAGCGGTGGC GGATCTGAGGTGCAGCTCCAGCAG TCTGGACCTGAGCTGGTGAAGCCT GGAGCTTCAATGAAGATATCCTGC AAGGCTTCTGGTTACTCATTCACTG GCTACACCATGAACTGGGTGAAGC AGAGTCATGGAAAGAACCTTGAGT GGATGGGACTTATTAATCCTTACA AAGGTGTTAGTACCTACAACCAGA AGTTCAAGGACAAGGCCACATTAA CTGTAGACAAGTCATCCAGCACAG CCTACATGGAACTCCTCAGTCTGA CATCTGAGGACTCTGCAGTCTATT ACTGTGCAAGATCGGGGTACTACG GTGATAGTGACTGGTACTTCGATG TCTGGGGCGCAGGGACCACGGTCA CCGTCTCCTCAACCACtAcaCCAGCa CCtaGACCACCAACACCIGCGCCaAC CATCGCaTCGCAGCCaCTGTCtCTGC GCCCAGAGGCaTGCCGGCCAGCaG CtGGGGGCGCAGTGCACACaAGGG GGCTGGACTTCGCaTGTGATATCTA CATCTGGGCaCCaTTGGCaGGGACT TGTGGGGTCCTTCTCCTGTCACTGG TTATCACCCTTTACTGC (SEQ ID NO: 9) | MALPVTALLLPLALLLHAARPDIQM TQTTSSLSASLGDRVTISCRASQDIR NYLNWYQQKPDGTVKLLIYYTSRL HSGVPSKFSGSGSGTDYSLTISNLEQ EDIATYFCQQGNTLPWTFAGGTKLE IKRAGGSGGGSGGGSGGGSEVQLQ QSGPELVKPGASMKISCKASGYSFT GYTMNWVKQSHGKNLEWMGLINP YKGVSTYNQKFKDKATLTVDKSSST AYMELLSLTSEDSAVYYCARSGYY GDSDWYFDVWGAGTTVTVSSTTTP APRPPTPAPTIASQPLSLRPEACRPAA GGAVHTRGLDFACDIYIWAPLAGTC GVLLLSLVITLYC (SEQ ID NO: 10) |

CD8a signal peptide

| Nucleotide | Amino acid |
|---|---|
| ATGGCCTTACCAGTGACCGCCTTG CTCCTGCCGCTGGCCTTGCTGCTCC ACGCCGCCAGGCCG (SEQ ID NO: 11) | MALPVTALLLPLALLLHAARP (SEQ ID NO: 12) |

Anti-CD3 (UCTH1) Light chain variable region

| Nucleotide | Amino acid |
|---|---|
| GACATCCAGATGACCCAGACCACC TCCTCCCTGTCTGCCTCTCTGGGAG ACAGAGTCACCATCAGTTGCAGGG CAAGTCAGGACATTAGAAATTATT TAAACTGGTATCAACAGAAACCAG ATGGAACTGTTAAACTCCTGATCT ACTACACATCAAGATTACACTCAG GAGTCCCATCAAAGTTCAGTGGCA GTGGGTCTGGAACAGATTATTCTC TCACCATTAGCAACCTGGAGCAAG AGGATATTGCCACTTACTTTTGCCA ACAGGGTAATACGCTTCCGTGGAC GTTCGCTGGAGGCACCAAGCTGGA AATCAAACGGGCT (SEQ ID NO: 13) | DIQMTQTTSSLSASLGDRVTISCRAS QDIRNYLNWYQQKPDGTVKLLIYYT SRLHSGVPSKFSGSGSGTDYSLTISN LEQEDIATYFCQQGNTLPWTFAGGT KLEIKRA (SEQ ID NO: 14) |

TABLE 2-continued

Anti-CD3 T cell targeting molecules

G₃S linker

| Nucleotide | Amino acid |
|---|---|
| GGAGGCGGTAGTGGCGGTGGATCA GGTGGAGGCAGCGGTGGCGGATCT (SEQ ID NO: 15) | GGGSGGGSGGGSGGGS (SEQ ID NO: 16) |

Anti-CD3 (UCTH1) heavy chain variable region

| Nucleotide | Amino acid |
|---|---|
| GAGGTGCAGCTCCAGCAGTCTGGA CCTGAGCTGGTGAAGCCTGGAGCT TCAATGAAGATATCCTGCAAGGCT TCTGGTTACTCATTCACTGGCTACA CCATGAACTGGGTGAAGCAGAGTC ATGGAAAGAACCTTGAGTGGATGG GACTTATTAATCCTTACAAAGGTG TTAGTACCTACAACCAGAAGTTCA AGGACAAGGCCACATTAACTGTAG ACAAGTCATCCAGCACAGCCTACA TGGAACTCCTCAGTCTGACATCTG AGGACTCTGCAGTCTATTACTGTG CAAGATCGGGGTACTACGGTGATA GTGACTGGTACTTCGATGTCTGGG GCGCAGGGACCACGGTCACCGTCT CCTCA (SEQ ID NO: 17) | EVQLQQSGPELVKPGASMKISCKAS GYSFTGYTMNWVKQSHGKNLEWM GLINPYKGVSTYNQKFKDKATLTVD KSSSTAYMELLSLTSEDSAVYYCAR SGYYGDSDWYFDVWGAGTTVTVSS (SEQ ID NO: 18) |

CD8a hinge and transmembrane

| Nucleotide | Amino acid |
|---|---|
| ACCACTACACCAGCACCTAGACCA CCAACACCTGCGCCAACCATCGCA TCGCAGCCACTGTCTCTGCGCCCA GAGGCATGCCGGCCAGCAGCTGGG GGCGCAGTGCACACAAGGGGGCT GGACTTCGCATGTGATATCTACAT CTGGGCACCATTGGCAGGGACTTG TGGGGTCCTTCTCCTGTCACTGGTT ATCACCCTTTACTGC (SEQ ID NO: 19) | TTTPAPRPPTPAPTIASQPLSLRPEAC RPAAGGAVHTRGLDFACDIYIWAPL AGTCGVLLLSLVITLYC (SEQ ID NO: 20) |

Anti-CD3 (12F6) heavy chain variable region

| Nucleotide | Amino Acid |
|---|---|
| CAAGTGCAGCTCCAGCAGAGCGGC GCTGAGCTGGCCCGGCCCGGCGCC AGCGTGAAGATGAGCTGTAAAGCC AGCGGCTATACATTTACCAGCTAC ACCATGCACTGGGTCAAGCAGCGG CCTGGCCAGGGCCTGGAATGGATT GGATATATCAACCCCAGCAGCGGC TACACCAAGTACAACCAGAAATTC AAGGACAAGGCCACCCTGACCGCC GACAAGAGCTCCTCAACAGCCTAC ATGCAACTGAGCAGCCTGACCAGC GAGGATAGCGCCGTGTACTACTGC GCCAGATGGCAGGACTACGACGTG TACTTCGACTACTGGGGCCAAGGC ACAACACTGACCGTGTCCAGC (SEQ ID NO: 112) | QVQLQQSGAELARPGASVKMSCKA SGYTFTSYTMHWVKQRPGQGLEWI GYINPSSGYTKYNQKFKDKATLTAD KSSSTAYMQLSSLTSEDSAVYYCAR WQDYDVYFDYWGQGTTLTVSS (SEQ ID NO: 113) |

Anti-CD3 (12F6) light chain variable region

| Nucleotide | Amino Acid |
|---|---|
| CAGATCGTGCTGAGCCAGTCCCCA GCCATCCTGTCTGCCAGCCCTGGC GAGAAGGTGACCATGACCTGCAGA GCCTCTTCTTCTGTTTCCTACATGC ACTGGTATCAGAAAGCCCCGGCA GCTCTCCTAAGCCTTGGATCTACG CCACAAGCAACCTGGCTAGCGGCG TGCCTGCTCGCTTCAGCGGCAGCG GCAGCGGCACCAGCTACAGCCTGA | QIVLSQSPAILSASPGEKVTMTCRAS SSVSYMHWYQQKPGSSPKPWIYATS NLASGVPARFSGSGSGTSYSLTISRV EAEDAATYYCQQWSSNPPTFGGGT KLETKR (SEQ ID NO: 115) |

TABLE 2-continued

Anti-CD3 T cell targeting molecules

CCATCAGCAGAGTGGAAGCCGAG
GACGCCGCCACCTACTACTGCCAG
CAGTGGTCCTCTAATCCTCCAACA
TTCGGCGGCGGCACCAAGCTGGAA
ACCAAAAGA (SEQ ID NO: 114)

Anti-CD3 (12F6) Full molecule

| Nucleotide | Amino Acid (signal peptide underlined) |
|---|---|
| ATGGCCTTACCAGTGACCGCCTTG | MALPVTALLLPLALLLHAARP |
| CTCCTGCCGCTGGCCTTGCTGCTCC | QVQLQQSGAELARPGASVKMSCKA |
| ACGCCGCCAGGCCGCAAGTGCAGC | SGYTFTSYTMHWVKQRPGQGLEWI |
| TCCAGCAGAGCGGCGCTGAGCTGG | GYINPSSGYTKYNQKFKDKATLTAD |
| CCCGGCCCGGCCGCCAGCGTGAAGA | KSSSTAYMQLSSLTSEDSAVYYCAR |
| TGAGCTGTAAAGCCAGCGGCTATA | WQDYDVYFDYWGQGTTLTVSSGG |
| CATTTACCAGCTACACCATGCACT | GSGGGSGGGSGGGS |
| GGGTCAAGCAGCGGCCTGGCCAGG | QIVLSQSPAILSASPGEKVTMTCRAS |
| GCCTGGAATGGATTGGATATATCA | SSVSYMHWYQQKPGSSPKPWIYATS |
| ACCCCAGCAGCGGCTACACCAAGT | NLASGVPARFSGSGSGTSYSLTISRV |
| ACAACCAGAAATTCAAGGACAAG | EAEDAATYYCQQWSSNPPTFGGGT |
| GCCACCCTGACCGCCGACAAGAGC | KLETKRTTTPAPRPPTPAPTIASQPLS |
| TCCTCAACAGCCTACATGCAACTG | LRPEACRPAAGGAVHTRGLDFACDI |
| AGCAGCCTGACCAGCGAGGATAGC | YIWAPLAGTCGVLLLSLVITLYC |
| GCCGTGTACTACTGCGCCAGATGG | (SEQ ID NO: 117) |
| CAGGACTACGACGTGTACTTCGAC | |
| TACTGGGGCCAAGGCACAACACTG | |
| ACCGTGTCCAGCGGAGGCGGTAGT | |
| GGCGGTGGATCAGGTGGAGGCAG | |
| CGGTGGCGGATCTCAGATCGTGCT | |
| GAGCCAGTCCCCAGCCATCCTGTC | |
| TGCCAGCCCTGGCGAGAAGGTGAC | |
| CATGACCTGCAGAGCCTCTTCTTCT | |
| GTTTCCTACATGCACTGGTATCAG | |
| CAAAAGCCCGGCAGCTCTCCTAAG | |
| CCTTGGATCTACGCCACAAGCAAC | |
| CTGGCTAGCGGCGTGCCTGCTCGC | |
| TTCAGCGGCAGCGGCAGCGGCACC | |
| AGCTACAGCCTGACCATCAGCAGA | |
| GTGGAAGCCGAGGACGCCGCCACC | |
| TACTACTGCCAGCAGTGGTCCTCT | |
| AATCCTCCAACATTCGGCGGCGGC | |
| ACCAAGCTGGAAACCAAAAGAAC | |
| CACTACACCAGCACCTAGACCACC | |
| AACACCTGCGCCAACCATCGCATC | |
| GCAGCCACTGTCTCTGCGCCCAGA | |
| GGCATGCCGGCCAGCAGCTGGGGG | |
| CGCAGTGCACACAAGGGGGCTGG | |
| ACTTCGCATGTGATATCTACATCTG | |
| GGCACCATTGGCAGGGACTTGTGG | |
| GGTCCTTCTCCTGTCACTGGTTATC | |
| ACCCTTTACTGC (SEQ ID NO: 116) | |

In still further embodiments, a lentiviral vector according to the present description may include multiple targeting proteins or a single targeting protein having multiple different lymphocyte targeting domains. For example, the lentiviral vectors described herein can include at least two targeting proteins, with each of the targeting proteins having a NK cell targeting domain that specifically binds a different target. In another example, the lentiviral vectors described herein can include at least two targeting proteins, with each of the targeting proteins having a T cell targeting domain that specifically binds a different target. In another example, the lentiviral vectors described herein can include at least two targeting proteins, with each of the targeting proteins having a B cell targeting domain that specifically binds a different target. In yet another example, the lentiviral vectors described herein can include at least two targeting proteins, with a first targeting protein having a T cell targeting domain and a second targeting protein having a NK cell targeting domain. In yet another example, the lentiviral vectors described herein can include at least two targeting proteins, with a first targeting protein having a T cell targeting domain and a second targeting protein having a B cell targeting domain. In yet another example, the lentiviral vectors described herein can include at least two targeting proteins, with a first targeting protein having a B cell targeting domain and a second targeting protein having a NK cell targeting domain. In alternative embodiments, the lentiviral vectors described herein include a single targeting protein having two or more different lymphocyte targeting domains, two or more different T cell targeting domains, two or more different NK cell targeting domains, or two or more different B cell targeting domains (e.g., a bi-specific or multi-specific targeting protein). In any such embodiments, the T lymphocyte targeting domains included in the targeting proteins can be selected from any of those described herein. In yet another example, the lentiviral vectors described herein can include at least two targeting proteins, with a first targeting protein having a lymphocyte targeting domain and a second targeting protein having a T cell targeting domain. In yet another example, the lentiviral vectors described herein can include at least two targeting proteins, with a first targeting protein having a lymphocyte targeting domain and a second targeting protein having a B cell targeting domain.

In an exemplary embodiment, a lentiviral vector having multiple targeting proteins includes a CD80 targeting protein and an anti-CD3 targeting protein as detailed in Table 1 and Table 2, respectively. In some embodiments, a CD80 targeting protein includes an amino acid sequence according to SEQ ID NO: 2 or SEQ ID NO: 2 absent the signal peptide of SEQ ID NO: 4. In some embodiments, an anti-CD3 targeting protein includes an amino acid sequence according to SEQ ID NO: 10 or SEQ ID NO: 10 absent the signal peptide of SEQ ID NO: 12. In some embodiments, an anti-CD3 targeting protein includes an amino acid sequence according to SEQ ID NO: 117 or SEQ ID NO: 117 absent the signal peptide of SEQ ID NO: 12. Where the lentiviral vector includes a CD80 targeting protein and an anti-CD3 targeting protein, the targeting proteins may be encoded on separate expression vectors used in producing the lentiviral vector. Alternatively, both a CD80 targeting protein and an anti-CD3 targeting protein may be encoded on a tandem expression cassette, providing a single expression cassette in a single expression vector that provides expression of both targeting proteins for production of the lentiviral vector. Exemplary embodiments of nucleic acid sequences and the corresponding amino acid sequences for a CD80 targeting protein and an anti-CD3 targeting protein expressed from the same expression cassette are provided in Table 3. In such an embodiment, the two targeting proteins may be linked by a P2A self-cleaving peptide. Table 3 provides an exemplary nucleic acid that may be used in a tandem expression cassette that includes a CD80 binding protein linked to an anti-CD3 binding protein via a P2A sequence. In a particular embodiment, the P2A sequence is encoded by a nucleic acid sequence that has at least about 75%, 80%, 85%, 90%, 91%, 92%, 93%, 94%, 95%, 96%, 97%, 98%, 99%, 99.5%, or 100% identity to SEQ ID NO: 29 and the amino acid sequence of the P2A sequence has an amino acid sequence that has at least about 75%, 80%, 85%, 90%, 91%, 92%, 93%, 94%, 95%, 96%, 97%, 98%, 99%, 99.5%, or 100% identity to SEQ ID NO: 30. In some embodiments, the tandem expression cassette that includes a CD80 binding protein linked to an anti-CD3 binding protein comprises the nucleic acid sequence of SEQ ID NO: 21 or has at least about 75%, 80%, 85%, 90%, 91%, 92%, 93%, 94%, 95%, 96%, 97%, 98%, 99%, 99.5%, or 100% identity to SEQ ID: 21. In some embodiments, the tandem expression cassette that includes a CD80 binding protein linked to an anti-CD3 binding protein encodes an amino acid sequence of SEQ ID NO: 22 or SEQ ID NO: 22 absent the signal peptide of SEQ ID NO: 24. In some embodiments, the tandem expression cassette that includes a CD80 binding protein linked to an anti-CD3 binding protein encodes an amino acid sequence having at least about 75%, 80%, 85%, 90%, 91%, 92%, 93%, 94%, 95%, 96%, 97%, 98%, 99%, 99.5%, or 100% identity to SEQ ID NO: 22 or SEQ ID NO: 22 absent the signal peptide of SEQ ID NO: 24.

TABLE 3

Co-expressed CD80 and anti-CD3 T cell targeting molecules

Full molecule

| Nucleotide | Amino acid (Signal peptide underlined) |
|---|---|
| ATGGGTCATACACGCCGCCAAGGA | MGHTRRQGTSPSKCPYLNFFQLLVL |
| ACCTCACCATCTAAGTGCCCATAT | AGLSHFCSGVIHVTKEVKEVATLSC |
| CTGAATTTCTTTCAACTTCTCGTGC | GHNVSVEELAQTRIYWQKEKKMVL |
| TGGCGGGGCTCAGTCATTTCTGCA | TMMSGDMNIWPEYKNRTIFDITNNL |
| GTGGGGTCATTCACGTTACTAAAG | SIVILALRPSDEGTYECVVLKYEKDA |
| AGGTCAAGGAGGTCGCAACATTGA | FKREHLAEVTLSVKADFPTPSISDFEI |
| GTTGTGGCCATAACGTATCAGTTG | PTSNIRRIICSTSGGFPEPHLSWLENG |
| AAGAACTCGCGCAGACACGGATTT | EELNAINTTVSQDPETELYAVSSKLD |
| ACTGGCAAAAGGAAAAGAAGATG | FNMTTNHSFMCLIKYGHLRVNQTFN |
| GTGTTGACAATGATGAGCGGTGAC | WNTTKQEHFPDNLLPSWAITLISVN |
| ATGAACATTTGGCCAGAGTACAAA | GIFVICCLTYCFAPRCREGSGATNFS |
| AATCGAACGATATTCGATATAACC | LLKQAGDVEENPGPMALPVTALLLP |
| AATAACTTGTCCATAGTAATACTT | LALLLHAARPDIQMTQTTSSLSASLG |
| GCCTTGCGACCTTCTGACGAGGGA | DRVTISCRASQDIRNYLNWYQQKPD |
| ACGTATGAATGTGTAGTGCTTAAG | GTVKLLIYYTSRLHSGVPSKFSGSGS |
| TATGAAAAAGATGCCTTTAAGCGG | GTDYSLTISNLEQEDIATYFCQQGNT |
| GAACACTTGGCTGAGGTTACACTC | LPWTFAGGTKLEIKRAGGGSGGGSG |
| TCCGTTAAGGCGGACTTTCCTACG | GGSGGGSEVQLQQSGPELVKPGAS |
| CCGTCTATATCCGACTTCGAGATA | MKISCKASGYSFTGYTMNWVKQSH |
| CCCACTTCTAACATTCGACGCATC | GKNLEWMGLINPYKGVSTYNQKFK |
| ATTTGCTCAACCTCAGGTGGTTTCC | DKATLTVDKSSSTAYMELLSLTSED |
| CAGAGCCTCACTTGAGCTGGCTGG | SAVYYCARSGYYGDSDWYFDVWG |
| AGAATGGCGAAGAACTTAACGCA | AGTTVTVSSTTTPAPRPPTPAPTIASQ |
| ATCAATACCACGGTGTCCCAAGAC | PLSLRPEACRPAAGGAVHTRGLDFA |
| CCGGAGACAGAGCTGTACGCCGTG | CDIYIWAPLAGTCGVLLLSLVITLYC |
| TCATCCAAACTGGATTTTAACATG | (SEQ ID NO: 22) |
| ACGACAAATCATAGTTTCATGTGT | |
| CTGATCAAATATGGGCATCTCAGG | |
| GTGAATCAGACTTTTAATTGGAAC | |
| ACTACCAAACAAGAGCACTTCCCA | |
| GATAATCTGTTGCCAAGCTGGGCG | |
| ATAACTCTTATCTCCGTCAACGGT | |
| ATCTTCGTAATTTGCTGCCTCACCT | |
| ATTGTTTCGCGCCTCGATGCCGAG | |
| AAGGCAGCGGCGCCACCAACTTCT | |
| CCCTGCTGAAGCAGGCCGGCGACG | |

TABLE 3-continued

Co-expressed CD80 and anti-CD3 T cell targeting molecules

TGGAAGAAAACCCTGGCCCCATGG
CCTTACCAGTGACCGCCTTGCTCCT
GCCGCTGGCCTTGCTGCTCCACGC
CGCCAGGCCGGACATCCAGATGAC
CCAGACCACCTCCTCCCTGTCTGCC
TCTCTGGGAGACAGAGTCACCATC
AGTTGCAGGGCAAGTCAGGACATT
AGAAATTATTTAAACTGGTATCAA
CAGAAACCAGATGGAACTGTTAAA
CTCCTGATCTACTACACATCAAGA
TTACACTCAGGAGTCCCATCAAAG
TTCAGTGGCAGTGGGTCTGGAACA
GATTATTCTCTCACCATTAGCAACC
TGGAGCAAGAGGATATTGCCACTT
ACTTTTGCCAACAGGGTAATACGC
TTCCGTGGACGTTCGCTGGAGGCA
CCAAGCTGGAAATCAAACGGGCTG
GAGGCGGTAGTGGCGGTGGATCAG
GTGGAGGCAGCGGTGGCGGATCTG
AGGTGCAGCTCCAGCAGTCTGGAC
CTGAGCTGGTGAAGCCTGGAGCTT
CAATGAAGATATCCTGCAAGGCTT
CTGGTTACTCATTCACTGGCTACAC
CATGAACTGGGTGAAGCAGAGTCA
TGGAAAGAACCTTGAGTGGATGGG
ACTTATTAATCCTTACAAAGGTGTT
AGTACCTACAACCAGAAGTTCAAG
GACAAGGCCACATTAACTGTAGAC
AAGTCATCCAGCACAGCCTACATG
GAACTCCTCAGTCTGACATCTGAG
GACTCTGCAGTCTATTACTGTGCA
AGATCGGGGTACTACGGTGATAGT
GACTGGTACTTCGATGTCTGGGGC
GCAGGGACCACGGTCACCGTCTCC
TCAACCACtACaCCAGCaCCtaGACC
ACCAACACCtGCGCCaACCATCGCa
TCGCAGCCaCTGTCtCTGCGCCCAG
AGGCaTGCCGGCCAGCaGCtGGGGG
CGCAGTGCACACaAGGGGGCTGGA
CTTCGCaTGTGATATCTACATCTGG
GCaCCaTTGGCaGGGACTTGTGGGG
TCCTTCTCCTGTCACTGGTTATCAC
CCTTTACTGC
(SEQ ID NO: 21)

CD80 signal peptide

| Nucleotide | Amino acid |
|---|---|
| ATGGGTCATACACGCCGCCAAGGA<br>ACCTCACCATCTAAGTGCCCATAT<br>CTGAATTTCTTTCAACTTCTCGTGC<br>TGGCGGGGCTCAGTCATTTCTGCA<br>GTGGGGTC (SEQ ID NO: 23) | MGHTRRQGTSPSKCPYLNFFQLLVL<br>AGLSHFCSGV (SEQ ID NO: 24) |

CD80 extracellular domain (ECD)

| Nucleotide | Amino acid |
|---|---|
| ATTCACGTTACTAAAGAGGTCAAG<br>GAGGTCGCAACATTGAGTTGTGGC<br>CATAACGTATCAGTTGAAGAACTC<br>GCGCAGACACGGATTTACTGGCAA<br>AAGGAAAGAAGATGGTGTTGAC<br>AATGATGAGCGGTGACATGAACAT<br>TTGGCCAGAGTACAAAAATCGAAC<br>GATATTCGATATAACCAATAACTT<br>GTCCATAGTAATACTTGCCTTGCG<br>ACCTTCTGACGAGGGAACGTATGA<br>ATGTGTAGTGCTTAAGTATGAAAA<br>AGATGCCTTTAAGCGGGAACACTT<br>GGCTGAGGTTACACTCTCCGTTAA<br>GGCGGACTTTCCTACGCCGTCTAT<br>ATCCGACTTCGAGATACCCACTTC<br>TAACATTCGACGCATCATTTGCTC<br>AACCTCAGGTGGTTTCCCAGAGCC<br>TCACTTGAGCTGGCTGGAGAATGG<br>CGAAGAACTTAACGCAATCAATAC | IHVTKEVKEVATLSCGHNVSVEELA<br>QTRIYWQKEKKMVLTMMSGDMNI<br>WPEYKNRTIFDITNNLSIVILALRPSD<br>EGTYECVVLKYEKDAFKREHLAEV<br>TLSVKADFPTPSISDFEIPTSNIRRIICS<br>TSGGFPEPHLSWLENGEELNAINTTV<br>SQDPETELYAVSSKLDFNMTTNHSF<br>MCLIKYGHLRVNQTFNWNTTKQEH<br>FPDNLLPS (SEQ ID NO: 26) |

TABLE 3-continued

Co-expressed CD80 and anti-CD3 T cell targeting molecules

CACGGTGTCCCAAGACCCGGAGAC
AGAGCTGTACGCCGTGTCATCCAA
ACTGGATTTTAACATGACGACAAA
TCATAGTTTCATGTGTCTGATCAAA
TATGGGCATCTCAGGGTGAATCAG
ACTTTTAATTGGAACACTACCAAA
CAAGAGCACTTCCCAGATAATCTG
TTGCCAAGC (SEQ ID NO: 25)

CD80 transmembrane and intracellular domain

| Nucleotide | Amino acid |
| --- | --- |
| TGGGCGATAACTCTTATCTCCGTC AACGGTATCTTCGTAATTTGCTGCC TCACCTATTGTTTCGCGCCTCGATG CCGAGAA (SEQ ID NO: 27) | WAITLISVNGIFVICCLTYCFAPRCRE (SEQ ID NO: 28) |

P2A self-cleaving peptide

| Nucleotide | Amino acid |
| --- | --- |
| GGCAGCGGCGCCACCAACTTCTCC CTGCTGAAGCAGGCCGGCGACGTG GAAGAAAACCCTGGCCCC (SEQ ID NO: 29) | GSGATNFSLLKQAGDVEENPGP (SEQ ID NO: 30) |

CD8a signal peptide

| Nucleotide | Amino acid |
| --- | --- |
| ATGGCCTTACCAGTGACCGCCTTG CTCCTGCCGCTGGCCTTGCTGCTCC ACGCCGCCAGGCCG (SEQ ID NO: 31) | MALPVTALLLPLALLLHAARP (SEQ ID NO: 32) |

Anti-CD3 Light chain variable region

| Nucleotide | Amino acid |
| --- | --- |
| GACATCCAGATGACCCAGACCACC TCCTCCCTGTCTGCCTCTCTGGGAG ACAGAGTCACCATCAGTTGCAGGG CAAGTCAGGACATTAGAAATTATT TAAACTGGTATCAACAGAAACCAG ATGGAACTGTTAAACTCCTGATCT ACTACACATCAAGATTACACTCAG GAGTCCCATCAAAGTTCAGTGGCA GTGGGTCTGGAACAGATTATTCTC TCACCATTAGCAACCTGGAGCAAG AGGATATTGCCACTTACTTTTGCCA ACAGGGTAATACGCTTCCGTGGAC GTTCGCTGGAGGCACCAAGCTGGA AATCAAACGGGCT (SEQ ID NO: 33) | DIQMTQTTSSLSASLGDRVTISCRAS QDIRNYLNWYQQKPDGTVKLLIYYT SRLHSGVPSKFSGSGSGTDYSLTISN LEQEDIATYFCQQGNTLPWTFAGGT KLEIKRA (SEQ ID NO: 34) |

G$_3$S linker

| Nucleotide | Amino acid |
| --- | --- |
| GGAGGCGGTAGTGGCGGTGGATCA GGTGGAGGCAGCGGTGGCGGATCT (SEQ ID NO: 35) | GGGSGGGSGGGSGGGS (SEQ ID NO: 36) |

Anti-CD3 heavy chain variable region

| Nucleotide | Amino acid |
| --- | --- |
| GAGGTGCAGCTCCAGCAGTCTGGA CCTGAGCTGGTGAAGCCTGGAGCT TCAATGAAGATATCCTGCAAGGCT TCTGGTTACTCATTCACTGGCTACA CCATGAACTGGGTGAAGCAGAGTC ATGGAAAGAACCTTGAGTGGATGG GACTTATTAATCCTTACAAAGGTG TTAGTACCTACAACCAGAAGTTCA AGGACAAGGCCACATTAACTGTAG ACAAGTCATCCAGCACAGCCTACA TGGAACTCCTCAGTCTGACATCTG | EVQLQQSGPELVKPGASMKISCKAS GYSFTGYTMNWVKQSHGKNLEWM GLINPYKGVSTYNQKFKDKATLTVD KSSSTAYMELLSLTSEDSAVYYCAR SGYYGDSDWYFDVWGAGTTVTVSS (SEQ ID NO: 38) |

TABLE 3-continued

Co-expressed CD80 and anti-CD3 T cell targeting molecules

AGGACTCTGCAGTCTATTACTGTG
CAAGATCGGGGTACTACGGTGATA
GTGACTGGTACTTCGATGTCTGGG
GCGCAGGGACCACGGTCACCGTCT
CCTCA (SEQ ID NO: 37)

CD8a hinge and transmembrane

| Nucleotide | Amino acid |
|---|---|
| ACCACTACACCAGCACCTAGACCA CCAACACCTGCGCCAACCATCGCA TCGCAGCCACTGTCTCTGCGCCCA GAGGCATGCCGGCCAGCAGCTGGG GGCGCAGTGCACACAAGGGGCT GGACTTCGCATGTGATATCTACAT CTGGGCACCATTGGCAGGGACTTG TGGGGTCCTTCTCCTGTCACTGGTT ATCACCCTTTACTGC (SEQ ID NO: 39) | TTTPAPRPPTPAPTIASQPLSLRPEAC RPAAGGAVHTRGLDFACDIYIWAPL AGTCGVLLLSLVITLYC (SEQ ID NO: 40) |

Transgene

The lentiviral vectors described herein include a transgene encoding one or more proteins that is delivered to and expressed by a lymphocyte (e.g., T cell, B cell, or NK cell) targeted by the vector. In particular embodiments, the transgene encodes a chimeric antigen receptor (CAR) that includes: an extracellular domain comprising a binding domain that specifically binds to a target molecule; an intracellular signaling domain, wherein the intracellular signaling domain comprises an immunoreceptor tyrosine-based activation motif (ITAM); and a transmembrane domain connecting the extracellular domain and intracellular signaling domain.

Binding domains suitable for use in CARs of the present disclosure include any antigen-binding polypeptide. A binding domain may comprise an antibody or antigen binding fragment thereof, including for example, a full length heavy chain, Fab fragment, Fab', F(ab')$_2$, sFv, VH domain, VL domain, dAb, VHH, CDR, and scFv, specific for a target disease antigen. In certain embodiments, a CAR binding domain is murine, chimeric, human, or humanized. In further embodiments, CAR binding domain is an scFv having V$_H$ and V$_L$ regions that are human or humanized. In further embodiments, the CAR binding domain is an scFv having a (GGGS)$_N$ linker or (GGGGS)$_N$ linker, wherein N=1-10, joining the V$_H$ and V$_L$ regions. In other embodiments, the CAR binding domain is an scFv having a linker comprising SEQ ID NO: 64 joining the V$_H$ and V$_L$ regions.

A target molecule that is bound by an extracellular domain of a CAR of the present disclosure may be found on or in association with a target cell. Exemplary target cells include a cancer cell, a cell associated with an autoimmune disease or disorder, a neurodegenerative disease, or with an inflammatory disease or disorder, an infectious microbe (e.g., bacteria, virus, or fungi), and an infected cell (e.g., virus-infected cell). A cell of an infectious organism, such as a mammalian parasite, is also contemplated as a target cell.

The extracellular domain included in a CAR as described herein can include a binding domain that targets one or more of a variety of target molecules. In certain embodiments, the CAR includes a binding domain that specifically binds a tumor antigen. In some such embodiments, the CAR binding domain specifically binds one or more of CD19, BCMA, alpha folate receptor, 5T4, Ab integrin, B7-H3, B7-H6, CAIX, CD20, CD22, CD23, CD30, CD33, CD38, CD44, CD44v6, CD44v7/8, CD52, CD70, CD79a, CD79b, CD80, CD123, CD138, CD171, CEA, CSPG4, EGFR, ErbB2 (HER2), EGFRvIII, EGP2, EGP40, EpCAM, FAP, fetal AchR, FLT3, Fra, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, HLADR, IL-11Ralpha, IL-13 Ralpha2, Lambda, Lewis-Y, Kappa, mesothelin, Muc1, Muc16, NCAM, NKG2d ligands, NY-ESO-1, PRAME, PSCA, PSMA, ROR1, SSX, Survivin, TAG72, TEMs, VEGFR2, BAFF-R, Claudin18.2, CD86, FcRL5, GPRC5, and TACI.

In certain embodiments, the extracellular domain of a CAR encoded by the transgene of the lentiviral vectors described the present disclosure optionally comprises an extracellular, non-signaling spacer or linker domain between the binding domain and the transmembrane domain. Where included, such a spacer or linker domain may position the binding domain away from the host cell surface to further enable proper cell-to-cell contact, binding, and activation. An extracellular spacer domain is generally located between the extracellular binding domain and the transmembrane domain of the CAR. The length of the extracellular spacer may be varied to optimize target molecule binding based on the selected target molecule, selected binding epitope, binding domain size and affinity (see, e.g., Guest et al., J. Immunother. 28:203-11, 2005; PCT Publication No. WO 2014/031687). In certain embodiments, an extracellular spacer domain is an immunoglobulin hinge region (e.g., IgG1, IgG2, IgG3, IgG4, IgA, IgD). An immunoglobulin hinge region may be a wild type immunoglobulin hinge region or an altered wild type immunoglobulin hinge region. An altered IgG4 hinge region is described in PCT Publication No. WO 2014/031687, which hinge region is incorporated herein by reference in its entirety. In some embodiments, an extracellular spacer domain comprises a modified IgG4 hinge region having an amino acid sequence of ESKYGPPCPPCP (SEQ ID NO: 118).

Other examples of hinge regions that may be used in the CARs described herein include the hinge region from the extracellular regions of type 1 membrane proteins, such as CD8a, CD4, CD28 and CD7, which may be wild-type or variants thereof. In some embodiments, an extracellular spacer domain comprises all or a portion of an immunoglobulin Fc domain selected from: a CH1 domain, a CH2 domain, a CH3 domain, or combinations thereof (see, e.g., PCT Publication WO2014/031687, which spacers are incorporated herein by reference in their entirety). In yet further embodiments, an extracellular spacer domain may comprise a stalk region of a type II C-lectin (the extracellular domain located between the C-type lectin domain and the transmembrane domain). Type II C-lectins include CD23, CD69, CD72, CD94, NKG2A, and NKG2D.

CARs of the present disclosure comprise a transmembrane domain that connects and is positioned between the extracellular domain and the intracellular signaling domain. The transmembrane domain typically ranges in length from about 15 amino acids to about 30 amino acids. The transmembrane domain is a hydrophobic alpha helix that transverses the host cell membrane and anchors the CAR in the host cell membrane. The transmembrane domain may be directly fused to the binding domain or to the extracellular spacer domain if present. In certain embodiments, the transmembrane domain is derived from an integral membrane protein (e.g., receptor, cluster of differentiation (CD) molecule, enzyme, transporter, cell adhesion molecule, or the like). The transmembrane domain can be selected from the same molecule as the extracellular domain or the intracellular signaling domain. In some embodiments, the transmembrane domain and the extracellular domain are each selected from different molecules. In some embodiments, the transmembrane domain and the intracellular signaling domain are each selected from different molecules. In yet other embodiments, the transmembrane domain, the extracellular domain, and the intracellular signaling domain are each selected from different molecules.

Exemplary transmembrane domains for use in CARs of the present disclosure include a CD28, CD2, CD4, CD8a, CD5, CD3E, CD36, CD3ζ, CD9, CD16, CD22, CD25, CD27, CD33, CD37, CD40, CD45, CD64, CD79A, CD79B, CD80, CD86, CD95 (Fas), CD134 (OX40), CD137 (4-1BB), CD150 (SLAMF1), CD152 (CTLA4), CD154 (CD40L), CD200R, CD223 (LAG3), CD270 (HVEM), CD272 (BTLA), CD273 (PD-L2), CD274 (PD-L1), CD278 (ICOS), CD279 (PD-1), CD300, CD357 (GITR), A2aR, DAP10, FcRα, FcRβ, FcRγ, Fyn, GAL9, KIR, Lck, LAT, LRP, NKG2D, NOTCH1, NOTCH2, NOTCH3, NOTCH4, PTCH2, ROR2, Ryk, Slp76, SIRPα, pTα, TCRα, TCRβ, TIM3, TRIM, LPA5, and Zap70 transmembrane domain. An exemplary CD8a transmembrane domain with CD8a hinge region comprises an amino acid sequence of SEQ ID NO: 52.

The intracellular signaling domain of a CAR is an intracellular effector domain and is capable of transmitting functional signals to a cell in response to binding of the extracellular domain of the CAR to a target molecule and activates at least one of the normal effector functions or responses of the immune cell, e.g., a T cell engineered to express the CAR. In some embodiments, the CAR induces a function of a T cell such as cytolytic activity or T helper activity, such as secretion of cytokines or other factors. The intracellular signaling domain may be any portion of an intracellular signaling molecule that retains sufficient signaling activity. In some embodiments, the intracellular signaling domain is obtained from an antigen receptor component (e.g., TCR) or costimulatory molecule. In some embodiments, a full-length intracellular signaling domain of an antigen receptor or costimulatory molecule is used. In some embodiments, a truncated portion of an intracellular signaling domain of an antigen receptor or costimulatory molecule is used, provided that the truncated portion retains sufficient signal transduction activity. In further embodiments, an intracellular signaling domain is a variant of a full length or truncated portion of an intracellular signaling domain of an antigen receptor co stimulatory molecule, provided that the variant retains sufficient signal transduction activity (i.e., is a functional variant).

In certain embodiments, the intracellular signaling domain of a CAR comprises an immunoreceptor tyrosine-based activation motif (ITAM) containing signaling domain. An ITAM containing signaling domain generally contains at least one (one, two, three, four, or more) ITAMs, which refer to a conserved motif of YXXLII-X&$_8$-YXXL/I. An ITAM containing signaling domain may initiate T cell activation signaling following antigen binding or ligand engagement. ITAM-signaling domains include, for example, intracellular signaling domains of CD3γ, CD3δ, CD3ε, CD3ζ, CD5, CD22, CD79a, CD278 (ICOS), DAP10, DAP12, FcRγ, and CD66d. Exemplary CD3ζ (signaling domains that may be used in CARs of the present disclosure comprise an amino acid sequence of SEQ ID NO: 56 or SEQ ID NO: 122.

CAR intracellular signaling domains optionally comprise a costimulatory signaling domain, which, when activated in conjunction with a primary or classic (e.g., ITAM-driven) activation signal, promotes or enhances T cell response, such as T cell activation, cytokine production, proliferation, differentiation, survival, effector function, or combinations thereof. Costimulatory signaling domains for use in CARs include, for example, CD27, CD28, CD40L, GITR, NKG2C, CARD1, CD2, CD7, CD27, CD30, CD40, CD54 (ICAM), CD83, CD134 (OX-40), CD137 (4-1BB), CD150 (SLAMF1), CD152 (CTLA4), CD223 (LAG3), CD226, CD270 (HVEM), CD273 (PD-L2), CD274 (PD-L1), CD278 (ICOS), DAP10, LAT, LFA-1, LIGHT, NKG2C, NKD2C, SLP76, TRIM, ZAP70, or any combination thereof. In a particular embodiment, the costimulatory signaling domain comprises a OX40, CD2, CD27, CD28, ICAM-1, LFA-1 (CD11a/CD18), ICOS (CD278), or 4-1BB (CD137) signaling domain. An exemplary 4-1BB costimulatory signaling domain comprises an amino acid sequence of SEQ ID NO: 54. In certain embodiments, a CAR comprises one, two, or more costimulatory signaling domains.

In some embodiments, a CAR of the present disclosure is a first generation CAR, a second generation CAR, or a third generation CAR. A first generation CAR generally has an intracellular signaling domain comprising an intracellular signaling domain of CD3ζ, FcγRI, or other ITAM-containing activating domain to provide a T cell activation signal. Second generation CARs further comprise a costimulatory signaling domain (e.g., a costimulatory signaling domain from an endogenous T cell costimulatory receptor, such as CD28, 4-1BB, or ICOS). Third generation CARs comprise an ITAM-containing activating domain, a first costimulatory signaling domain and a second costimulatory signaling domain.

In some embodiments, one or more of the extracellular domain, the binding domain, the linker, the transmembrane domain, the intracellular signaling domain, or the costimulatory domain comprises junction amino acids. "Junction amino acids" or "junction amino acid residues" refer to one or more (e.g., about 2-20) amino acid residues between two adjacent domains, motifs, regions, modules, or fragments of a protein, such as between a binding domain and an adjacent linker, between a transmembrane domain and an adjacent extracellular or intracellular domain, or on one or both ends of a linker that links two domains, motifs, regions, modules, or fragments (e.g., between a linker and an adjacent binding domain or between a linker and an adjacent hinge). Junction amino acids may result from the construct design of a fusion protein (e.g., amino acid residues resulting from the use of a restriction enzyme site or self-cleaving peptide sequences during the construction of a polynucleotide encoding a fusion protein). For example, a transmembrane domain of a fusion protein may have one or more junction amino acids at the amino-terminal end, carboxy-terminal end, or both. In specific embodiments, the transgene encodes an anti-CD19 CAR molecule. In such embodiments, the extracellular binding domain may include an scFv as detailed in Table 4, having an anti-CD19 light chain variable region of SEQ ID NO: 46, a G4S linker of SEQ ID NO: 48, and an anti-CD19 heavy chain variable region of SEQ ID NO: 50. An anti-CD19 CAR useful in the context of the present description may include a CD8a hinge and transmembrane domain of SEQ ID NO: 52. In certain embodiments, the anti-CD19 CAR includes a 4-1BB costimulatory domain according to SEQ ID NO: 54 and a CD3ζ effector domain according to SEQ ID NO: 56. In a specific embodiment, an anti-CD19 CAR encoded by the transgene has an amino acid sequence according to SEQ ID NO: 42 or SEQ ID NO: 42 absent the signal peptide of SEQ ID NO: 44.

In other embodiments, the transgene encodes an anti-CD19 CAR molecule and extracellular binding domain may include an scFv having an anti-CD19 light chain variable region that has at least about 75%, 80%, 85%, 90%, 91%, 92%, 93%, 94%, 95%, 96%, 97%, 98%, 99%, 99.5%, or 100% identity to SEQ ID NO: 46, and an anti-CD19 heavy chain variable region that has at least about 75%, 80%, 85%, 90%, 91%, 92%, 93%, 94%, 95%, 96%, 97%, 98%, 99%, 99.5%, or 100% identity to SEQ ID NO: 50. An anti-CD19 CAR useful in the context of the present description may include a CD8a hinge and transmembrane domain that has at least about 75%, 80%, 85%, 90%, 91%, 92%, 93%, 94%, 95%, 96%, 97%, 98%, 99%, 99.5%, or 100% identity to SEQ ID NO: 52. In certain embodiments, the anti-CD19 CAR includes a 4-1BB costimulatory domain that has at least about 75%, 80%, 85%, 90%, 91%, 92%, 93%, 94%, 95%, 96%, 97%, 98%, 99%, 99.5%, or 100% identity to SEQ ID NO: 54 and a CD3ζ effector domain that has at least about 75%, 80%, 85%, 90%, 91%, 92%, 93%, 94%, 95%, 96%, 97%, 98%, 99%, 99.5%, or 100% identity to SEQ ID NO: 56. In a specific embodiment, an anti-CD19 CAR encoded by the transgene has an amino acid sequence that has at least about 75%, 80%, 85%, 90%, 91%, 92%, 93%, 94%, 95%, 96%, 97%, 98%, 99%, 99.5%, or 100% identity to SEQ ID NO: 42 or SEQ ID NO: 42 absent the signal peptide of SEQ ID NO: 44.

TABLE 4

Anti-CD19 CAR molecule

Full molecule

| Nucleotide | Amino acid (signal peptide underlined) |
|---|---|
| ATGGCCTTACCAGTGACCGCCTTG | MALPVTALLLPLALLLHAARPDIQM |
| CTCCTGCCGCTGGCCTTGCTGCTCC | TQTTSSLSASLGDRVTISCRASQDISK |
| ACGCCGCCAGGCCGGACATCCAGA | YLNWYQQKPDGTVKLLIYHTSRLHS |
| TGACACAGACTACATCCTCCCTGT | GVPSRFSGSGSGTDYSLTISNLEQEDI |
| CTGCCTCTCTGGGAGACAGAGTCA | ATYFCQQGNTLPYTFGGGTKLEITG |
| CCATCAGTTGCAGGGCAAGTCAGG | GGGSGGGGSGGGGSEVKLQESGPG |
| ACATTAGTAAATATTTAAATTGGT | LVAPSQSLSVTCTVSGVSLPDYGVS |
| ATCAGCAGAAACCAGATGGAACTG | WIRQPPRKGLEWLGVIWGSETTYYN |
| TTAAACTCCTGATCTACCATACATC | SALKSRLTIIKDNSKSQVFLKMNSLQ |
| AAGATTACACTCAGGAGTCCCATC | TDDTAIYYCAKHYYYGGSYAMDY |
| AAGGTTCAGTGGCAGTGGGTCTGG | WGQGTSVTVSSTTTPAPRPPTPAPTI |
| AACAGATTATTCTCTCACCATTAG | ASQPLSLRPEACRPAAGGAVHTRGL |
| CAACCTGGAGCAAGAAGATATTGC | DFACDIYIWAPLAGTCGVLLLSLVIT |
| CACTTACTTTTGCCAACAGGGTAA | LYCKRGRKKLLYIFKQPFMRPVQTT |
| TACGCTTCCGTACACGTTCGGAGG | QEEDGCSCRFPEEEEGGCELRVKFSR |
| GGGGACCAAGCTGGAGATCACAG | SADAPAYKQGQNQLYNELNLGRRE |
| GTGGaGGTGGaTCGGCGGTGGTG | EYDVLDKRRGRDPEMGGKPRRKNP |
| GGTCGGGTGGCGGCGGATCTGAGG | QEGLYNELQKDKMAEAYSEIGMKG |
| TGAAACTGCAGGAGTCAGGACCTG | ERRRGKGHDGLYQGLSTATKDTYD |
| GCCTGGTGGCGCCCTCACAGAGCC | ALHMQALPPR (SEQ ID NO: 42) |
| TGTCCGTCACATGCACTGTCTCAG | |
| GGGTCTCATTACCCGACTATGGTG | |
| TAAGCTGGATTCGCCAGCCTCCAC | |
| GAAAGGGTCTGGAGTGGCTGGGA | |
| GTAATATGGGGTAGTGAAACCACA | |
| TACTATAATTCAGCTCTCAAATCC | |
| AGACTGACCATCATCAAGGACAAC | |
| TCCAAGAGCCAAGTTTTCTTAAAA | |
| ATGAACAGTCTGCAAACTGATGAC | |
| ACAGCCATTTACTACTGTGCCAAA | |
| CATTATTACTACGGTGGTAGCTAT | |
| GCTATGGACTACTGGGGCCAAGGA | |
| ACCTCAGTCACCGTCTCCTCAACC | |
| ACtACaCCAGCaCCtaGACCACCAAC | |
| ACCtGCGCCaACCATCGCaTCGCAG | |
| CCaCTGTCtCTGCGCCCAGAGGCaT | |
| GCCGGCCAGCaGCtGGGGGCGCAG | |
| TGCACACaAGGGGGCTGGACTTCG | |
| CaTGTGATATCTACATCTGGGCaCC | |
| aTTGGCaGGGACTTGTGGGGTCCTT | |
| CTCCTGTCACTGGTTATCACCCTTT | |
| ACTGCAAACGGGGCAGAAAGAAA | |
| CTCCTGTATATATTCAAACAACCA | |
| TTTATGAGACCAGTACAAACTACT | |

TABLE 4-continued

Anti-CD19 CAR molecule

CAAGAGGAAGATGGCTGTAGCTGC
CGATTTCCAGAAGAAGAAGAAGG
AGGATGTGAACTGAGAGTGAAGTT
CAGCAGGAGCGCAGACGCCCCCGC
GTACAAGCAGGGCCAGAACCAGCT
CTATAACGAGCTCAATCTAGGACG
AAGAGAGGAGTACGATGTTTTGGA
CAAGAGACGTGGCCGGGACCCTGA
GATGGGGGGAAAGCCGAGAAGGA
AGAACCCTCAGGAAGGCCTGTACA
ATGAACTGCAGAAAGATAAGATG
GCGGAGGCCTACAGTGAGATTGGG
ATGAAAGGCGAGCGCCGGAGGGG
CAAGGGGCACGATGGCCTTTACCA
GGGTCTCAGTACAGCCACCAAGGA
CACCTACGACGCCCTTCACATGCA
GGCCCTGCCCCTCGC (SEQ ID NO: 41)

CD8a signal peptide

| Nucleotide | Amino acid |
|---|---|
| ATGGCCTTACCAGTGACCGCCTTG CTCCTGCCGCTGGCCTTGCTGCTCC ACGCCGCCAGGCCG (SEQ ID NO: 43) | MALPVTALLLPLALLLHAARP (SEQ ID NO: 44) |

Anti-CD19 light chain variable region

| Nucleotide | Amino acid |
|---|---|
| GACATCCAGATGACACAGACTACA TCCTCCCTGTCTGCCTCTCTGGGAG ACAGAGTCACCATCAGTTGCAGGG CAAGTCAGGACATTAGTAAATATT TAAATTGGTATCAGCAGAAACCAG ATGGAACTGTTAAACTCCTGATCT ACCATACATCAAGATTACACTCAG GAGTCCCATCAAGGTTCAGTGGCA GTGGGTCTGGAACAGATTATTCTC TCACCATTAGCAACCTGGAGCAAG AAGATATTGCCACTTACTTTTGCCA ACAGGGTAATACGCTTCCGTACAC GTTCGGAGGGGGGACCAAGCTGG AGATCACA (SEQ ID NO: 45) | DIQMTQTTSSLSASLGDRVTISCRAS QDISKYLNWYQQKPDGTVKLLIYHT SRLHSGVPSRFSGSGSGTDYSLTISN LEQEDIATYFCQQGNTLPYTFGGGT KLEIT (SEQ ID NO: 46) |

G4S Linker

| Nucleotide | Amino acid |
|---|---|
| GGTGGaGGTGGaTCGGGCGGTGGT GGGTCGGGTGGCGGCGGATCT (SEQ ID NO: 47) | GGGGSGGGGSGGGGS (SEQ ID NO: 48) |

Anti-CD19 heavy chain variable region

| Nucleotide | Amino acid |
|---|---|
| GAGGTGAAACTGCAGGAGTCAGG ACCTGGCCTGGTGGCGCCCTCACA GAGCCTGTCCGTCACATGCACTGT CTCAGGGGTCTCATTACCCGACTA TGGTGTAAGCTGGATTCGCCAGCC TCCACGAAAGGGTCTGGAGTGGCT GGGAGTAATATGGGGTAGTGAAAC CACATACTATAATTCAGCTCTCAA ATCCAGACTGACCATCATCAAGGA CAACTCCAAGAGCCAAGTTTTCTT AAAAATGAACAGTCTGCAAACTGA TGACACAGCCATTTACTACTGTGC CAAACATTATTACTACGGTGGTAG CTATGCTATGGACTACTGGGGCCA AGGAACCTCAGTCACCGTCTCCTC A (SEQ ID NO: 49) | EVKLQESGPGLVAPSQSLSVTCTVS GVSLPDYGVSWIRQPPRKGLEWLGV IWGSETTYYNSALKSRLTIIKDNSKS QVFLKMNSLQTDDTAIYYCAKHYY YGGSYAMDYWGQGTSVTVSS (SEQ ID NO: 50) |

TABLE 4-continued

Anti-CD19 CAR molecule

CD8a Hinge and Transmembrane

| Nucleotide | Amino acid |
|---|---|
| ACCACTACACCAGCACCTAGACCA CCAACACCTGCGCCAACCATCGCA TCGCAGCCACTGTCTCTGCGCCCA GAGGCATGCCGGCCAGCAGCTGGG GGCGCAGTGCACACAAGGGGGCT GGACTTCGCATGTGATATCTACAT CTGGGCACCATTGGCAGGGACTTG TGGGGTCCTTCTCCTGTCACTGGTT ATCACCCTTTACTGC (SEQ ID NO: 51) | TTTPAPRPPTPAPTIASQPLSLRPEAC RPAAGGAVHTRGLDFACDIYIWAPL AGTCGVLLLSLVITLYC (SEQ ID NO: 52) |

4-1BB costimulatory domain

| Nucleotide | Amino acid |
|---|---|
| AAACGGGGCAGAAAGAAACTCCT GTATATATTCAAACAACCATTTAT GAGACCAGTACAAACTACTCAAGA GGAAGATGGCTGTAGCTGCCGATT TCCAGAAGAAGAAGAAGGAGGAT GTGAACTG (SEQ ID NO: 53) | KRGRKKLLYIFKQPFMRPVQTTQEE DGCSCRFPEEEEGGCEL (SEQ ID NO: 54) |

CD3 zeta effector domain #1

| Nucleotide | Amino acid |
|---|---|
| AGAGTGAAGTTCAGCAGGAGCGC AGACGCCCCGCGTACAAGCAGGG CCAGAACCAGCTCTATAACGAGCT CAATCTAGGACGAAGAGAGGAGT ACGATGTTTTGGACAAGAGACGTG GCCGGGACCCTGAGATGGGGGGA AAGCCGAGAAGGAAGAACCCTCA GGAAGGCCTGTACAATGAACTGCA GAAAGATAAGATGGCGGAGGCCT ACAGTGAGATTGGGATGAAAGGC GAGCGCCGGAGGGGCAAGGGGCA CGATGGCCTTTACCAGGGTCTCAG TACAGCCACCAAGGACACCTACGA CGCCCTTCACATGCAGGCCCTGCC CCCTCGC (SEQ ID NO: 55) | RVKFSRSADAPAYKQGQNQLYNEL NLGRREEYDVLDKRRGRDPEMGGK PRRKNPQEGLYNELQKDKMAEAYS EIGMKGERRRGKGHDGLYQGLSTA TKDTYDALHMQALPPR (SEQ ID NO: 56) |

In other embodiments, the transgene encodes an anti-BCMA CAR molecule. In such embodiments, the extracellular binding domain may include an scFv as detailed in Table 5, having an anti-BCMA light chain variable region of SEQ ID NO: 62, a linker of SEQ ID NO: 64, and an anti-BCMA heavy chain variable region of SEQ ID NO: 66. An anti-BCMA CAR useful in the context of the present description may include a CD8a hinge and transmembrane domain of SEQ ID NO: 52. In certain embodiments, the anti-BCMA CAR includes a 4-1BB costimulatory domain according to SEQ ID NO: 54 and a CD3ζ effector domain according to SEQ ID NO: 122. In a specific embodiment, an anti-BCMA CAR encoded by the transgene has an amino acid sequence according to SEQ ID NO: 58 or SEQ ID NO: 58 absent the signal peptide of SEQ ID NO: 60.

In some embodiments, the transgene encodes an anti-BCMA CAR molecule. In such embodiments, the extracellular binding domain may include an scFv having an anti-BCMA light chain variable region that has at least about 75%, 80%, 85%, 90%, 91%, 92%, 93%, 94%, 95%, 96%, 97%, 98%, 99%, 99.5%, or 100% identity to SEQ ID NO: 62, and an anti-BCMA heavy chain variable region that has at least about 75%, 80%, 85%, 90%, 91%, 92%, 93%, 94%, 95%, 96%, 97%, 98%, 99%, 99.5%, or 100% identity to SEQ ID NO: 66. An anti-BCMA CAR useful in the context of the present description may include a CD8a hinge and transmembrane domain that has at least about 75%, 80%, 85%, 90%, 91%, 92%, 93%, 94%, 95%, 96%, 97%, 98%, 99%, 99.5%, or 100% identity to SEQ ID NO: 52. In certain embodiments, the anti-BCMA CAR includes a 4-1BB costimulatory domain that has at least about 75%, 80%, 85%, 90%, 91%, 92%, 93%, 94%, 95%, 96%, 97%, 98%, 99%, 99.5%, or 100% identity to SEQ ID NO: 54 and a CD3ζ effector domain that has at least about 75%, 80%, 85%, 90%, 91%, 92%, 93%, 94%, 95%, 96%, 97%, 98%, 99%, 99.5%, or 100% identity to SEQ ID NO: 122. In a specific embodiment, an anti-BCMA CAR encoded by the transgene has an amino acid sequence that has at least about 75%, 80%, 85%, 90%, 91%, 92%, 93%, 94%, 95%, 96%, 97%, 98%, 99%, 99.5%, or 100% identity to SEQ ID NO: 58 or SEQ ID NO: 58 absent the signal peptide of SEQ ID NO: 60.

TABLE 5

Anti-BCMA CAR molecule

Full molecule

| Nucleotide | Amino acid (signal peptide underlined) |
|---|---|
| ATGGCACTCCCCGTCACCGCCCTT CTCTTGCCCCTCGCCCTGCTGCTGC ATGCTGCCAGGCCCGACATTGTGC TCACTCAGTCACCTCCCAGCCTGG CCATGAGCCTGGGAAAAAGGGCC ACCATCTCCTGTAGAGCCAGTGAG TCCGTCACAATCTTGGGGAGCCAT CTTATTCACTGGTATCAGCAGAAG CCCGGGCAGCCTCCAACCCTTCTT ATTCAGCTCGCGTCAAACGTCCAG ACGGGTGTACCTGCCAGATTTTCT GGTAGCGGGTCCCGCACTGATTTT ACACTGACCATAGATCCAGTGGAA GAAGACGATGTGGCCGTGTATTAT TGTCTGCAGAGCAGAACGATTCCT CGCACATTTGGTGGGGGTACTAAG CTGGAGATTAAGGGAAGCACGTCC GGCTCAGGGAAGCCGGGCTCCGGC GAGGGAAGCACGAAGGGGCAAAT TCAGCTGGTCCAGAGCGGACCTGA GCTGAAAAAACCCGGCGAGACTGT TAAGATCAGTTGTAAAGCATCTGG CTATACCTTCACCGACTACAGCAT AAATTGGGTGAAACGAGCCCCTGG AAAGGGCCTCAAATGGATGGGTTG GATCAATACCGAAACTAGGGAGCC TGCTTATGCATATGACTTCCGCGG GAGATTCGCCTTTTCACTCGAGAC ATCTGCCTCTACTGCTTACCTCCAA ATAAACAACCTCAAGTATGAAGAT ACAGCCACTTACTTTTGCGCCCTCG ACTATAGTTACGCCATGGACTACT GGGGACAGGGAACCTCCGTTACCG TCAGTTCCGCGGCCGCAACCACAA CACCTGCTCCAAGGCCCCCCACAC CCGCTCCAACTATAGCCAGCCAAC CATTGAGCCTCAGACCTGAAGCTT GCAGGCCCGCAGCAGGAGGCGCC GTCCATACGCGAGGCCTGGACTTC GCGTGTGATATTTATATTTGGGCA CCTTTGGCCGGAACATGTGGGGTG TTGCTTCTCTCCCTTGTGATCACTC TGTATTGTAAGCGCGGGAGAAAGA AGCTCCTGTACATCTTCAAGCAGC CTTTTATGCGACCTGTGCAAACCA CTCAGGAAGAAGATGGGTGTTCAT GCCGCTTCCCCGAGGAGGAAGAAG GAGGGTGTGAACTGAGGGTGAAAT TTTCTAGAAGCGCCGATGCTCCCG CATATCAGCAGGGTCAGAATCAGC TCTACAATGAATTGAATCTCGGCA GGCGAGAAGAGTACGATGTTCTGG ACAAGAGACGGGGCAGGGATCCC GAGATGGGGGGAAAGCCCCGGAG AAAAAATCCTCAGGAGGGGTTGTA CAATGAGCTGCAGAAGGACAAGA TGGCTGAAGCCTATAGCGAGATCG GAATGAAAGGCGAAAGACGCAGA GGCAAGGGGCATGACGGTCTGTAC CAGGGTCTCTCTACAGCCACCAAG GACACTTATGATGCGTTGCATATG CAAGCCTTGCCACCCCGC (SEQ ID NO: 57) | MALPVTALLLPLALLLHAARPDIVL TQSPPSLAMSLGKRATISCRASESVTI LGSHLIHWYQQKPGQPPTLLIQLASN VQTGVPARFSGSGSRTDFTLTIDPVE EDDVAVYYCLQSRTIPRTFGGGTKL EIKGSTSGSGKPGSGEGSTKGQIQLV QSGPELKKPGETVKISCKASGYTFTD YSINWVKRAPGKGLKWMGWINTET REPAYAYDFRGRFAFSLETSASTAY LQINNLKYEDTATYFCALDYSYAM DYWGQGTSVTVSSAAATTTPAPRPP TPAPTIASQPLSLRPEACRPAAGGAV HTRGLDFACDIYIWAPLAGTCGVLL LSLVITLYCKRGRKKLLYIFKQPFMR PVQTTQEEDGCSCRFPEEEEGGCELR VKFSRSADAPAYQQGQNQLYNELN LGRREEYDVLDKRRGRDPEMGGKP RRKNPQEGLYNELQKDKMAEAYSEI GMKGERRRGKGHDGLYQGLSTATK DTYDALHMQALPPR (SEQ ID NO: 58) |

CD8a signal peptide

| Nucleotide | Amino acid |
|---|---|
| ATGGCACTCCCCGTCACCGCCCTT CTCTTGCCCCTCGCCCTGCTGCTGC ATGCTGCCAGGCCC (SEQ ID NO: 59) | MALPVTALLLPLALLLHAARP (SEQ ID NO: 60) |

TABLE 5-continued

Anti-BCMA CAR molecule

Anti-BCMA light chain variable region

| Nucleotide | Amino acid |
|---|---|
| GACATTGTGCTCACTCAGTCACCT CCCAGCCTGGCCATGAGCCTGGGA AAAAGGGCCACCATCTCCTGTAGA GCCAGTGAGTCCGTCACAATCTTG GGGAGCCATCTTATTCACTGGTAT CAGCAGAAGCCCGGGCAGCCTCCA ACCCTTCTTATTCAGCTCGCGTCAA ACGTCCAGACGGGTGTACCTGCCA GATTTTCTGGTAGCGGGTCCCGCA CTGATTTTACACTGACCATAGATC CAGTGGAAGAAGACGATGTGGCC GTGTATTATTGTCTGCAGAGCAGA ACGATTCCTCGCACATTTGGTGGG GGTACTAAGCTGGAGATTAAG (SEQ ID NO: 61) | DIVLTQSPPSLAMSLGKRATISCRAS ESVTILGSHLIHWYQQKPGQPPTLLI QLASNVQTGVPARFSGSGSRTDFTL TIDPVEEDDVAVYYCLQSRTIPRTFG GGTKLEIK (SEQ ID NO: 62) |

218 Linker

| Nucleotide | Amino acid |
|---|---|
| GGAAGCACGTCCGGCTCAGGGAA GCCGGGCTCCGGCGAGGGAAGCA CGAAGGGG (SEQ ID NO: 63) | GSTSGSGKPGSGEGSTKG (SEQ ID NO: 64) |

Anti-BCMA heavy chain variable region

| Nucleotide | Amino acid |
|---|---|
| CAAATTCAGCTGGTCCAGAGCGGA CCTGAGCTGAAAAAACCCGGCGAG ACTGTTAAGATCAGTTGTAAAGCA TCTGGCTATACCTTCACCGACTAC AGCATAAATTGGGTGAAACGAGCC CCTGGAAAGGGCCTCAAATGGATG GGTTGGATCAATACCGAAACTAGG GAGCCTGCTTATGCATATGACTTC CGCGGGAGATTCGCCTTTTCACTC GAGACATCTGCCTCTACTGCTTAC CTCCAAATAAACAACCTCAAGTAT GAAGATACAGCCACTTACTTTTGC GCCCTCGACTATAGTTACGCCATG GACTACTGGGGACAGGGAACCTCC GTTACCGTCAGTTCC (SEQ ID NO: 65) | QIQLVQSGPELKKPGETVKISCKASG YTFTDYSINWVKRAPGKGLKWMG WINTETREPAYAYDFRGRFAFSLETS ASTAYLQINNLKYEDTATYFCALDY SYAMDYWGQGTSVTVSS (SEQ ID NO: 66) |

CD8a Hinge and Transmembrane

| Nucleotide | Amino acid |
|---|---|
| ACCACAACACCTGCTCCAAGGCCC CCCACACCCGCTCCAACTATAGCC AGCCAACCATTGAGCCTCAGACCT GAAGCTTGCAGGCCCGCAGCAGGA GGCGCCGTCCATACGCGAGGCCTG GACTTCGCGTGTGATATTTATATTT GGGCACCTTTGGCCGGAACATGTG GGGTGTTGCTTCTCTCCCTTGTGAT CACTCTGTATTGT (SEQ ID NO: 119) | TTTPAPRPPTPAPTIASQPLSLRPEAC RPAAGGAVHTRGLDFACDIYIWAPL AGTCGVLLLSLVITLYC (SEQ ID NO: 52) |

4-1BB costimulatory domain

| Nucleotide | Amino acid |
|---|---|
| AAGCGCGGGAGAAAGAAGCTCCT GTACATCTTCAAGCAGCCTTTTATG CGACCTGTGCAAACCACTCAGGAA GAAGATGGGTGTTCATGCCGCTTC CCCGAGGAGGAAGAAGGAGGGTG TGAACTG (SEQ ID NO: 120) | KRGRKKLLYIFKQPFMRPVQTTQEE DGCSCRFPEEEEGGCEL (SEQ ID NO: 54) |

CD3 zeta effector domain #2

| Nucleotide | Amino acid |
|---|---|

TABLE 5-continued

Anti-BCMA CAR molecule

| |  |
|---|---|
| AGGGTGAAATTTTCTAGAAGCGCC | RVKFSRSADAPAYQQGQNQLYNEL |
| GATGCTCCCGCATATCAGCAGGGT | NLGRREEYDVLDKRRGRDPEMGGK |
| CAGAATCAGCTCTACAATGAATTG | PRRKNPQEGLYNELQKDKMAEAYS |
| AATCTCGGCAGGCGAGAAGAGTAC | EIGMKGERRRGKGHDGLYQGLSTA |
| GATGTTCTGGACAAGAGACGGGGC | TKDTYDALHMQALPPR (SEQ ID NO: |
| AGGGATCCCGAGATGGGGGGAAA | 122) |
| GCCCCGGAGAAAAAATCCTCAGGA | |
| GGGGTTGTACAATGAGCTGCAGAA | |
| GGACAAGATGGCTGAAGCCTATAG | |
| CGAGATCGGAATGAAAGGCGAAA | |
| GACGCAGAGGCAAGGGGCATGAC | |
| GGTCTGTACCAGGGTCTCTCTACA | |
| GCCACCAAGGACACTTATGATGCG | |
| TTGCATATGCAAGCCTTGCCACCC | |
| CGC (SEQ ID NO: 121) | |

CARs of the present disclosure may comprise polynucleotide sequences derived from any mammalian species, including humans, primates, cows, horses, goats, sheep, dogs, cats, mice, rats, rabbits, guinea pigs, pigs, transgenic species thereof, or any combination thereof. In some embodiments, the chimeric antigen receptor is murine, chimeric, human, or humanized.

Methods for Producing Lentiviral Vectors

Methods for producing the LVV disclosed are provided herein. LVV have been developed and based on the retroviral genome by combining its components into recombinant plasmid DNA vectors. The plasmid DNA vectors can then be transfected into producer cell lines to transfer genes required for lentiviral particle production. LVV packaging systems generally comprise a transfer plasmid encoding the transgene of interest, an envelope plasmid (e.g., VSV-G), and packaging plasmid(s). Second generation LVV packaging systems contain a single packaging plasmid encoding Gag, Pol, Rev, and Tat genes and a separate Env plasmid. In some embodiments, the methods described herein utilize a third generation vector system for producing LVV. Third generation vector production systems improve upon the safety of $2^{nd}$ generation LVV packaging systems and are typically four plasmid systems that include a transgene plasmid combined with three packaging plasmids, VSV-G, GagPol, and Rev. Thus, Rev and GagPol are separated into two plasmids. Tat is also eliminated from $3^{rd}$ generation LVV packaging systems by the addition of a chimeric 5' LTR fused to a heterologous promoter (e.g., CMV or RSV promoter) on the transfer plasmid. The gag gene encodes a Gag polyprotein precursor comprising structural proteins of the lentivirus, including matrix, capsid, and nucleocapsid. The pol gene encodes a Pol polyprotein precursor supplying enzymatic functions of the lentivirus essential for replication, including protease, reverse transcriptase, and integrase. The rev gene encodes the Rev protein which binds to the Rev Response Element (RRE) to allow nuclear export of unspliced and singly spliced HIV RNA during viral replication. The Gag and Pol polyprotein precursors are cleaved during production of viral particles.

Producer cells that may be used for making LVV of the present disclosure include human embryonic kidney (HEK) 293 cells and derivatives thereof. Producer cells may be an adherent cell line, such as HEK293T producer cells, or a suspension cell line, such as HEK293T/17 SF producer cells.

The transgene plasmid is combined with the three packaging plasmids, GagPol plasmid, VSV-G env plasmid, and Rev plasmid, and used to transfect producer cells, such as HEK293 producer cells. In some embodiments, the producer cells are transfected with a defined ratio of the transgene plasmid, GagPol plasmid, VSV-G env plasmid, and Rev plasmid. In some embodiments, the ratios of the packaging plasmids are determined by mass. In some embodiments, the mass of each of the transgene plasmid and GagPol plasmid are higher than the the mass of each of the VSV-G env plasmid and Rev plasmid. In some embodiments, the defined ratio of transgene plasmid, GagPol plasmid, VSV-G env plasmid, and Rev plasmid is at about 1:1:1:1 to about 5:4:1:1. In some embodiments, the the producer cells are transfected with a defined ratio of the transgene plasmid, GagPol plasmid, VSV-G env plasmid, and Rev plasmid at about 2:1:1:1 to about 5:4:1:1. In some embodiments, the the producer cells are transfected with a defined ratio of the transgene plasmid, GagPol plasmid, VSV-G env plasmid, and Rev plasmid at about 2:1:1:1. In some embodiments, the the producer cells are transfected with a defined ratio of the transgene plasmid, GagPol plasmid, VSV-G env plasmid, and Rev plasmid at about 3:1:1:1. In some embodiments, the the producer cells are transfected with a defined ratio of the transgene plasmid, GagPol plasmid, VSV-G env plasmid, and Rev plasmid at about 3.125:3.125:2.5:1.25. In some embodiments, the the producer cells are transfected with a defined ratio of the transgene plasmid, GagPol plasmid, VSV-G env plasmid, and Rev plasmid at about 4:2:1:1. In some embodiments, the the producer cells are transfected with a defined ratio of the transgene plasmid, GagPol plasmid, VSV-G env plasmid, and Rev plasmid at about 5:4:1:1. Productive lentiviral particles are harvested from the producer cell culture media. Exemplary materials and methods for producing LVV particles are described in *Production of Lentiviral Vectors*, Merten et al., Molecular Therapy—Methods & Clinical Development (2016), 3, 16017, the contents of which are incorporated herein by reference. Third generation production systems are used for research and development and clinical purposes. Schematic representations of helper plasmids suitable for use in a third generation LVV production system are provided in FIG. 1.

The transgene plasmid encodes the only genetic materials that is transferred to the lymphocytes (e.g., T cells or NK cells) targeted by the resulting LVV and comprises a lentiviral backbone containing the transgene expression cassette flanked by cis-acting elements for encapsidation, reverse transcription and integration. In specific embodiments, the transgene plasmid includes a deletion in the U3 element of the 3' LTR that causes loss of transcriptional capacity of the viral LTR once transferred into the target cells. The expression cassette included in the transgene plasmid may encode a single heterologous protein (e.g., a single CAR as described herein) or multiple heterologous proteins (e.g., multiple CARs as described herein) for introduction into and expression by the target cell.

In some embodiments of a four plasmid LVV system, the VSV-G env plasmid includes a tandem expression cassette that encodes a mutated VSV-G envelope protein and a targeting protein as disclosed herein. In specific embodiments, the tandem expression cassette included in the VSV-G env plasmid includes a polynucleotide that encodes a first signal peptide, a polynucleotide that encodes a targeting protein, a polynucleotide that encodes one of an internal ribosomal entry site (IRES), a furin cleavage site, or a viral 2A peptide, a polynucleotide that encodes a second signal peptide, and a polynucleotide that encodes a mutated VSV-G envelope protein. In certain embodiments, the polynucleotide encoding the mutant VSV-G envelope protein is positioned 5' to the polynucleotide encoding the targeting protein. In other embodiments, the polynucleotide encoding the mutant VSV-G envelope protein is positioned 3' to the polynucleotide encoding the targeting protein. The polynucleotide that encodes the targeting protein and the polynucleotide that encodes the mutated VSV-G are separated in the tandem cassette by the polynucleotide that encodes the IRES, furin cleavage site, or viral 2A peptide, which allows for co-expression of the two proteins from a single mRNA. In certain embodiments, a viral 2A peptide is a porcine teschovirus-1 (P2A), Thosea asigna virus (T2A), equine rhinitis A virus (E2A), foot-and-mouth disease virus (F2A), or a variant thereof. Specific examples of amino acid and nucleotide sequences for the viral 2A peptides are provided in Table 7.

comprises an expression cassette comprising a polynucleotide encoding a CAR; and the VSV-G env plasmid comprises a tandem expression cassette, wherein the tandem expression cassette comprises a polynucleotide encoding a mutated VSV-G envelope protein as disclosed herein and a polynucleotide encoding a lymphocyte targeting protein as disclosed herein and the VSV-G env plasmid is capable of expressing the mutated VSV-G envelope protein and the lymphocyte targeting protein within the producer cell; culturing the producer cell in a culture medium; and harvesting lentiviral vector from the culture medium.

In some embodiments, the producer cells are transfected with a defined ratio of the transgene plasmid, GagPol plasmid, VSV-G env plasmid, and Rev plasmid. In some embodiments, the defined ratio of transgene plasmid, GagPol plasmid, VSV-G env plasmid, and Rev plasmid at about 1:1:1:1 to about 5:4:1:1. In some embodiments, the the producer cells are transfected with a defined ratio of the transgene plasmid, GagPol plasmid, VSV-G env plasmid, and Rev plasmid at about 2:1:1:1 to about 5:4:1:1. In some embodiments, the the producer cells are transfected with a defined ratio of the transgene plasmid, GagPol plasmid, VSV-G env plasmid, and Rev plasmid at about 2:1:1:1. In some embodiments, the the producer cells are transfected with a defined ratio of the transgene plasmid, GagPol plasmid, VSV-G env plasmid, and Rev plasmid at about 3:1:1:1. In some embodiments, the the producer cells are transfected with a defined ratio of the transgene plasmid, GagPol plasmid, VSV-G env plasmid, and Rev plasmid at about 3.125:3.125:2.5:1.25. In some embodiments, the the producer cells are transfected with a defined ratio of the transgene plasmid, GagPol plasmid, VSV-G env plasmid,

TABLE 7

| 2A sequences | | |
|---|---|---|
| T2A peptide from Thosea asigna virus capsid protein | EGRGSLLTCGD VEENPGP (SEQ ID NO: 79) | GAGGGCAGGGGAAGTCTTC TAACATGCGGGGACGTGGA GGAAAATCCCGGCCCC (SEQ ID NO: 80) |
| P2A peptide from porcine teschovirus-1 polyprotein | ATNFSLLKQAG DVEENPGP (SEQ ID NO: 81) | GCCACGAACTTCTCTCTGTT AAAGCAAGCAGGAGACGT GGAAGAAAACCCCGGTCCT (SEQ ID NO: 82) |
| F2A peptide from foot-and-mouth disease virus polyprotein | VKQTLNFDLLK LAGDVESNPGP (SEQ ID NO: 83) | GTGAAACAGACTTTGAATT TTGACCTTCTCAAGTTGGC GGGAGACGTCGAGTCCAAC CCTGGGCCC (SEQ ID NO: 84) |
| E2A peptide from equine rhinitis A virus polyprotein | QCTNYALLKLA GDVESNPGP (SEQ ID NO: 85) | CAGTGTACTAATTATGCTC TCTTGAAATTGGCTGGAGA TGTTGAGAGCAACCCAGGT CCC (SEQ ID NO: 86) |

In certain embodiments, the present disclosure provides a method for producing a lymphocyte targeted lentiviral vector according to any one of the preceding claims, the method comprising: transfecting a producer cell with a GagPol plasmid, a Rev plasmid, a transgene plasmid, and a VSV-G env plasmid, wherein; the GagPol plasmid comprises a one or more polynucleotides encoding a lentiviral gag gene and a lentiviral pol gene and is capable of expressing a lentiviral gag polyprotein and a lentiviral pol polyprotein within the producer cell;
the Rev plasmid comprises a polynucleotide encoding a lentiviral rev gene and is capable expressing a lentiviral rev protein within the producer cell; the transgene plasmid and Rev plasmid at about 4:2:1:1. In some embodiments, the the producer cells are transfected with a defined ratio of the transgene plasmid, GagPol plasmid, VSV-G env plasmid, and Rev plasmid at about 5:4:1:1.

In one embodiment, the tandem expression cassette of the VSV-G env plasmid encodes an anti-CD3 targeting protein and a mutated VSV-G envelope protein. For example, in a specific embodiment, the tandem expression cassette may comprise a polynucleotide that has at least about 75%, 80%, 85%, 90%, 91%, 92%, 93%, 94%, 95%, 96%, 97%, 98%, 99%, 99.5%, or 100% identity to SEQ ID NO: 67, which encodes an amino acid sequence that has at least about 75%, 80%, 85%, 90%, 91%, 92%, 93%, 94%, 95%, 96%, 97%, 98%, 99%, 99.5%, or 100% identity to SEQ ID NO: 68. Such an embodiment is described in more detail in Table 8. In another embodiment, the tandem expression cassette may comprise a polynucleotide that has about 75%, 80%, 85%, 90%, 91%, 92%, 93%, 94%, 95%, 96%, 97%, 98%, 99%, 99.5%, or 100% identity to SEQ ID NO: 67 absent the signal peptide of SEQ ID NO: 31, which encodes an amino acid sequence that has at least about 75%, 80%, 85%, 90%, 91%, 92%, 93%, 94%, 95%, 96%, 97%, 98%, 99%, 99.5%, or 100% identity to SEQ ID NO: 68 absent the signal peptide of SEQ ID NO: 32. As illustrated in Table 8, the anti-CD3 targeting protein is separated from the mutated VSV-G envelope protein via a P2A self-cleaving peptide. In certain embodiments, that P2A peptide may be encoded by a nucleic acid sequence that has at least about 75%, 80%, 85%, 90%, 91%, 92%, 93%, 94%, 95%, 96%, 97%, 98%, 99%, 99.5%, or 100% identity to SEQ ID NO: 69, and the P2A peptide may have an amino acid sequence that has at least about 75%, 80%, 85%, 90%, 91%, 92%, 93%, 94%, 95%, 96%, 97%, 98%, 99%, 99.5%, or 100% identity to SEQ ID NO: 70.

TABLE 8

Anti-CD3 targeting molecule co-expressed with mutant VSV-G

Full molecule

| Nucleotide | Amino acid (signal peptide underlined) |
|---|---|
| ATGGCCTTACCAGTGACCGCCTTG CTCCTGCCGCTGGCCTTGCTGCTCC ACGCCGCCAGGCCGGACATCCAGA TGACCCAGACCACCTCCTCCCTGT CTGCCTCTCTGGGAGACAGAGTCA CCATCAGTTGCAGGGCAAGTCAGG ACATTAGAAATTATTTAAACTGGT ATCAACAGAAACCAGATGGAACTG TTAAACTCCTGATCTACTACACATC AAGATTACACTCAGGAGTCCCATC AAAGTTCAGTGGCAGTGGGTCTGG AACAGATTATTCTCTCACCATTAG CAACCTGGAGCAAGAGGATATTGC CACTTACTTTTGCCAACAGGGTAA TACGCTTCCGTGGACGTTCGCTGG AGGCACCAAGCTGGAAATCAAAC GGGCTGGAGGCGGTAGTGGCGGTG GATCAGGTGGAGGCAGCGGTGGC GGATCTGAGGTGCAGCTCCAGCAG TCTGGACCTGAGCTGGTGAAGCCT GGAGCTTCAATGAAGATATCCTGC AAGGCTTCTGGTTACTCATTCACTG GCTACACCATGAACTGGGTGAAGC AGAGTCATGGAAAGAACCTTGAGT GGATGGGACTTATTAATCCTTACA AAGGTGTTAGTACCTACAACCAGA AGTTCAAGGACAAGGCCACATTAA CTGTAGACAAGTCATCCAGCACAG CCTACATGGAACTCCTCAGTCTGA CATCTGAGGACTCTGCAGTCTATT ACTGTGCAAGATCGGGGTACTACG GTGATAGTGACTGGTACTTCGATG TCTGGGGCGCAGGGACCACGGTCA CCGTCTCCTCAACCACTACACCAG CACCTAGACCACCAACACCTGCGC CAACCATCGCATCGCAGCCACTGT CTCTGCGCCCAGAGGCATGCCGGC CAGCAGCTGGGGGCGCAGTGCACA CAAGGGGGCTGGACTTCGCATGTG ATATCTACATCTGGGCACCATTGG CAGGGACTTGTGGGGTCCTTCTCC TGTCACTGGTTATCACCCTTTACTG CGGCAGCGGCGCCACCAACTTCTC CCTGCTGAAGCAGGCCGGCGACGT GGAAGAAAACCCTGGCCCCATGAA GTGTCTGCTGTACCTGGCGTTCCTG TTTATCGGGGTGAACTGCAAGTTC ACTATCGTGTTTCCGCACAACCAA AAGGGCAACTGGAAAAACGTGCCT TCAAATTACCATTATTGCCCCAGC AGCTCGGACCTGAACTGGCACAAT GACCTCATTGGAACCGCGCTGCAG GTGAAGATGCCACAGAGCCACAA GGCTATCCAGGCTGACGGATGGAT GTGCCACGCGTCAAAATGGGTGAC TACCTGCGATTTCCGCTGGTACGG ACCAAAATACATCACGCACAGCAT CAGATCATTCACCCCGTCAGTGGA ACAATGCAAAGAATCCATCGAACA GACTAAGCAGGGAACCTGGCTGAA | MALPVTALLLPLALLLHAARPDIQM TQTTSSLSASLGDRVTISCRASQDIR NYLNWYQQKPDGTVKLLIYYTSRL HSGVPSKFSGSGSGTDYSLTISNLEQ EDIATYFCQQGNTLPWTFAGGTKLE IKRAGGGSGGSGGGSGGGSEVQLQ QSGPELVKPGASMKISCKASGYSFT GYTMNWVKQSHGKNLEWMGLINP YKGVSTYNQKFKDKATLTVDKSSST AYMELLSLTSEDSAVYYCARSGYY GDSDWYFDVWGAGTTVTVSSTTTP APRPPTPAPTIASQPLSLRPEACRPAA GGAVHTRGLDFACDIYIWAPLAGTC GVLLLSLVITLYCGSGATNFSLLKQA GDVEENPGPMKCLLYLAFLFIGVNC KFTIVFPHNQKGNWKNVPSNYHYCP SSSDLNWHNDLIGTALQVKMPQSH KAIQADGWMCHASKWVTTCDFRW YGPKYITHSIRSFTPSVEQCKESIEQT KQGTWLNPGFPPQSCGYATVTDAE AVIVQVTPHHVLVDEYTGEWVDSQ FINGKCSNYICPTVHNSTTWHSDYK VKGLCDSNLISMDITFFSEDGELSSL GKEGTGFRSNYFAYETGGKACKMQ YCKHWGVRLPSGVWFEMADKDLF AAARFPECPEGSSISAPSQTSVDVSLI QDVERILDYSLCQETWSKIRAGLPIS PVDLSYLAPKNPGTGPAFTIINGTLK YFETRYIRVDIAAPILSRMVGMISGT TTEAELWDDWAPYEDVEIGPNGVL RTSSGYKFPLYMIGHGMLDSDLHLS SKAQVFEHPHIQDAASQLPDDESLFF GDTGLSKNPIELVEGWFSSWKSSIAS FFFIIGLIIGLFLVLRVGIHLCIKLKHT KKRQIYTDIEMNRLGK (SEQ ID NO: 68) |

TABLE 8-continued

| Anti-CD3 targeting molecule co-expressed with mutant VSV-G |
|---|
| CCCTGGATTTCCGCCGCAGTCGTG<br>TGGGTACGCAACCGTGACCGATGC<br>AGAGGCCGTGATCGTGCAAGTCAC<br>GCCGCATCACGTGCTTGTGGACGA<br>GTACACCGGAGAATGGGTCGATTC<br>CCAGTTCATCAACGGCAAGTGCTC<br>CAACTACATTTGCCCAACCGTGCA<br>CAACAGCACTACTTGGCATAGCGA<br>CTACAAAGTGAAGGGTCTGTGTGA<br>TTCCAACCTGATCTCCATGGATATC<br>ACTTTCTTCTCGGAAGACGGCGAA<br>CTGTCCTCACTGGGCAAAGAAGGA<br>ACTGGGTTTCGCTCAAATTACTTCG<br>CCTACGAAACTGGAGGAAAAGCCT<br>GCAAGATGCAGTACTGCAAGCACT<br>GGGGCGTGAGACTACCCAGCGGTG<br>TCTGGTTCGAGATGGCCGATAAGG<br>ACCTGTTTGCAGCAGCGAGATTCC<br>CGGAATGCCCTGAGGGATCGAGCA<br>TCTCCGCTCCAAGCCAAACTTCAG<br>TGGACGTGAGCCTGATCCAGGACG<br>TGGAACGGATTCTCGACTACTCGC<br>TGTGCCAGGAGACCTGGTCGAAGA<br>TCAGAGCGGGACTGCCCATCTCAC<br>CGGTGGACCTGTCCTACCTGGCGC<br>CAAAGAATCCGGGCACTGGACCGG<br>CGTTCACCATCATCAACGGCACCC<br>TCAAATACTTCGAGACGCGGTACA<br>TCCGGGTGGACATCGCAGCTCCGA<br>TCCTCTCCCGGATGGTGGGAATGA<br>TCTCGGGGACTACTACCGAAGCCG<br>AGCTCTGGGACGACTGGGCACCTT<br>ACGAGGATGTCGAGATCGGACCTA<br>ACGGAGTGCTCCGGACCTCCTCCG<br>GGTACAAGTTCCCTCTGTACATGA<br>TCGGCCATGGCATGCTGGACTCGG<br>ATCTGCATCTGTCGTCCAAAGCAC<br>AGGTGTTTGAACACCCACACATTC<br>AAGACGCCGCCAGCCAGCTGCCGG<br>ACGATGAGTCGCTGTTCTTCGGAG<br>ACACGGGCTTGTCAAAGAATCCCA<br>TCGAGCTGGTGGAAGGATGGTTTT<br>CATCCTGGAAAAGCAGCATCGCTT<br>CATTCTTCTTCATCATTGGCCTGAT<br>CATCGGCCTATTTCTAGTCCTGCGG<br>GTGGGAATTCATCTGTGCATCAAG<br>CTCAAGCACACTAAGAAGCGGCAA<br>ATCTACACTGATATCGAGATGAAT<br>CGCCTGGGCAAG (SEQ ID NO: 67) |

| CD8a signal peptide | |
|---|---|
| Nucleotide | Amino acid |
| ATGGCCTTACCAGTGACCGCCTTG<br>CTCCTGCCGCTGGCCTTGCTGCTCC<br>ACGCCGCCAGGCCG (SEQ ID NO: 31) | MALPVTALLLPLALLLHAARP (SEQ ID NO: 32) |

| Anti-CD3 Light chain variable region | |
|---|---|
| Nucleotide | Amino acid |
| GACATCCAGATGACCCAGACCACC<br>TCCTCCCTGTCTGCCTCTCTGGGAG<br>ACAGAGTCACCATCAGTTGCAGGG<br>CAAGTCAGGACATTAGAAATTATT<br>TAAACTGGTATCAACAGAAACCAG<br>ATGGAACTGTTAAACTCCTGATCT<br>ACTACACATCAAGATTACACTCAG<br>GAGTCCCATCAAAGTTCAGTGGCA<br>GTGGGTCTGGAACAGATTATTCTC<br>TCACCATTAGCAACCTGGAGCAAG<br>AGGATATTGCCACTTACTTTTGCCA<br>ACAGGGTAATACGCTTCCGTGGAC<br>GTTCGCTGGAGGCACCAAGCTGGA<br>AATCAAACGGGCT (SEQ ID NO: 33) | DIQMTQTTSSLSASLGDRVTISCRAS<br>QDIRNYLNWYQQKPDGTVKLLIYYT<br>SRLHSGVPSKFSGSGSGTDYSLTISN<br>LEQEDIATYFCQQGNTLPWTFAGGT<br>KLEIKRA (SEQ ID NO: 34) |

TABLE 8-continued

| Anti-CD3 targeting molecule co-expressed with mutant VSV-G | |
|---|---|
| $G_3S$ linker | |
| Nucleotide | Amino acid |
| GGAGGCGGTAGTGGCGGTGGATCA GGTGGAGGCAGCGGTGGCGGATCT (SEQ ID NO: 35) | GGGSGGGSGGGSGGGS (SEQ ID NO: 36) |
| Anti-CD3 heavy chain variable region | |
| Nucleotide | Amino acid |
| GAGGTGCAGCTCCAGCAGTCTGGA CCTGAGCTGGTGAAGCCTGGAGCT TCAATGAAGATATCCTGCAAGGCT TCTGGTTACTCATTCACTGGCTACA CCATGAACTGGGTGAAGCAGAGTC ATGGAAAGAACCTTGAGTGGATGG GACTTATTAATCCTTACAAAGGTG TTAGTACCTACAACCAGAAGTTCA AGGACAAGGCCACATTAACTGTAG ACAAGTCATCCAGCACAGCCTACA TGGAACTCCTCAGTCTGACATCTG AGGACTCTGCAGTCTATTACTGTG CAAGATCGGGGTACTACGGTGATA GTGACTGGTACTTCGATGTCTGGG GCGCAGGGACCACGGTCACCGTCT CCTCA (SEQ ID NO: 37) | EVQLQQSGPELVKPGASMKISCKAS GYSFTGYTMNWVKQSHGKNLEWM GLINPYKGVSTYNQKFKDKATLTVD KSSSTAYMELLSLTSEDSAVYYCAR SGYYGDSDWYFDVWGAGTTVTVSS (SEQ ID NO: 38) |
| CD8a hinge and transmembrane | |
| Nucleotide | Amino acid |
| ACCACTACACCAGCACCTAGACCA CCAACACCTGCGCCAACCATCGCA TCGCAGCCACTGTCTCTGCGCCCA GAGGCATGCCGGCCAGCAGCTGGG GGCGCAGTGCACACAAGGGGGCT GGACTTCGCATGTGATATCTACAT CTGGGCACCATTGGCAGGGACTTG TGGGGTCCTTCTCCTGTCACTGGTT ATCACCCTTTACTGC (SEQ ID NO: 39) | TTTPAPRPPTPAPTIASQPLSLRPEAC RPAAGGAVHTRGLDFACDIYIWAPL AGTCGVLLLSLVITLYC (SEQ ID NO: 40) |
| P2A self-cleaving peptide | |
| Nucleotide | Amino acid |
| GGCAGCGGCGCCACCAACTTCTCC CTGCTGAAGCAGGCCGGCGACGTG GAAGAAAACCCTGGCCCC (SEQ ID NO: 69) | GSGATNFSLLKQAGDVEENPGP (SEQ ID NO: 70) |
| VSV-G signal sequence | |
| Nucleotide | Amino acid |
| ATGAAGTGTCTGCTGTACCTGGCG TTCCTGTTTATCGGGGTGAACTGC (SEQ ID NO: 71) | MKCLLYLAFLFIGVNC (SEQ ID NO: 72) |
| Mutant VSV-G (Trop-002) | |
| Nucleotide | Amino acid |
| AAGTTCACTATCGTGTTTCCGCAC AACCAAAAGGGCAACTGGAAAAA CGTGCCTTCAAATTACCATTATTGC CCCAGCAGCTCGGACCTGAACTGG CACAATGACCTCATTGGAACCGCG CTGCAGGTGAAGATGCCACAGAGC CACAAGGCTATCCAGGCTGACGGA TGGATGTGCCACGCGTCAAAATGG GTGACTACCTGCGATTTCCGCTGG TACGGACCAAAATACATCACGCAC AGCATCAGATCATTCACCCCGTCA GTGGAACAATGCAAAGAATCCATC GAACAGACTAAGCAGGGAACCTG | KFTIVFPHNQKGNWKNVPSNYHYCP SSSDLNWHNDLIGTALQVKMPQSH KAIQADGWMCHASKWVTTCDFRW YGPKYITHSIRSFTPSVEQCKESIEQT KQGTWLNPGFPPQSCGYATVTDAE AVIVQVTPHHVLVDEYTGEWVDSQ FINGKCSNYICPTVHNSTTWHSDYK VKGLCDSNLISMDITFFSEDGELSSL GKEGTGFRSNYFAYETGGKACKMQ YCKHWGVRLPSGVWFEMADKDLF AAARFPECPEGSSISAPSQTSVDVSLI QDVERILDYSLCQETWSKIRAGLPIS PVDLSYLAPKNPGTGPAFTIINGTLK |

TABLE 8-continued

Anti-CD3 targeting molecule co-expressed with mutant VSV-G

| | |
|---|---|
| GCTGAACCCTGGATTTCCGCCGCA<br>GTCGTGTGGGTACGCAACCGTGAC<br>CGATGCAGAGGCCGTGATCGTGCA<br>AGTCACGCCGCATCACGTGCTTGT<br>GGACGAGTACACCGGAGAATGGG<br>TCGATTCCCAGTTCATCAACGGCA<br>AGTGCTCCAACTACATTTGCCCAA<br>CCGTGCACAACAGCACTACTTGGC<br>ACAGCGACTACAAAGTGAAGGGTC<br>TGTGTGATTCCAACCTGATCTCCAT<br>GGATATCACTTTCTTCTCGGAAGA<br>CGGCGAACTGTCCTCACTGGGCAA<br>AGAAGGAACTGGGTTTCGCTCAAA<br>TTACTTCGCCTACGAAACTGGAGG<br>AAAAGCCTGCAAGATGCAGTACTG<br>CAAGCACTGGGGCGTGAGACTACC<br>CAGCGGTGTCTGGTTCGAGATGGC<br>CGATAAGGACCTGTTTGCAGCAGC<br>GAGATTCCCGGAATGCCCTGAGGG<br>ATCGAGCATCTCCGCTCCAAGCCA<br>AACTTCAGTGGACGTGAGCCTGAT<br>CCAGGACGTGGAACGGATTCTCGA<br>CTACTCGCTGTGCCAGGAGACCTG<br>GTCGAAGATCAGAGCGGGACTGCC<br>CATCTCACCGGTGGACCTGTCCTA<br>CCTGGCGCCAAAGAATCCGGGCAC<br>TGGACCGGCGTTCACCATCATCAA<br>CGGCACCCTCAAATACTTCGAGAC<br>GCGGTACATCCGGGTGGACATCGC<br>AGCTCCGATCCTCTCCCGGATGGT<br>GGGAATGATCTCGGGGACTACTAC<br>CGAAGCCGAGCTCTGGGACGACTG<br>GGCACCTTACGAGGATGTCGAGAT<br>CGGACCTAACGGAGTGCTCCGGAC<br>CTCCTCCGGGTACAAGTTCCCTCTG<br>TACATGATCGGCCATGGCATGCTG<br>GACTCGGATCTGCATCTGTCGTCC<br>AAAGCACAGGTGTTTGAACACCCA<br>CACATTCAAGACGCCGCCAGCCAG<br>CTGCCGGACGATGAGTCGCTGTTC<br>TTCGGAGACACGGGCTTGTCAAAG<br>AATCCCATCGAGCTGGTGGAAGGA<br>TGGTTTTCATCCTGGAAAAGCAGC<br>ATCGCTTCATTCTTCTTCATCATTG<br>GCCTGATCATCGGCCTATTTCTAGT<br>CCTGCGGGTGGGAATTCATCTGTG<br>CATCAAGCTCAAGCACACTAAGAA<br>GCGGCAAATCTACACTGATATCGA<br>GATGAATCGCCTGGGCAAG (SEQ ID NO: 73) | YFETRYIRVDIAAPILSRMVGMISGT<br>TTEAELWDDWAPYEDVEIGPNGVL<br>RTSSGYKFPLYMIGHGMLDSDLHLS<br>SKAQVFEHPHIQDAASQLPDDESLFF<br>GDTGLSKNPIELVEGWFSSWKSSIAS<br>FFFIIGLIIGLFLVLRVGIHLCIKLKHT<br>KKRQIYTDIEMNRLGK (SEQ ID NO: 74) |

In another embodiment, the tandem expression cassette of the VSV-G env plasmid encodes a CD80 targeting protein and a mutated VSV-G envelope protein. For example, in a specific embodiment, the tandem expression cassette may comprise a polynucleotide according to SEQ ID NO: 75, which encodes an amino acid sequence of SEQ ID NO: 76. Such an embodiment is described in more detail in Table 9. As illustrated in Table 9, the CD80 targeting protein is separated from the mutated VSV-G envelope protein via a P2A self-cleaving peptide encoded by SEQ ID NO: 69 and having an amino acid sequence according to SEQ ID NO: 70.

In some embodiments, where the tandem expression cassette of the VSV-G env plasmid encodes a CD80 targeting protein and a mutated VSV-G envelope protein, the tandem expression cassette may include a polynucleotide that has at least about 75%, 80%, 85%, 90%, 91%, 92%, 93%, 94%, 95%, 96%, 97%, 98%, 99%, 99.5%, or 100% identity to SEQ ID NO: 75, which encodes an amino acid sequence that has at least about 75%, 80%, 85%, 90%, 91%, 92%, 93%, 94%, 95%, 96%, 97%, 98%, 99%, 99.5%, or 100% identity to SEQ ID NO: 76. In certain embodiments, the CD80 targeting protein is separated from the mutated VSV-G envelope protein via a P2A self-cleaving peptide encoded a nucleic acid sequence that has at least about 75%, 80%, 85%, 90%, 91%, 92%, 93%, 94%, 95%, 96%, 97%, 98%, 99%, 99.5%, or 100% identity to SEQ ID NO: 69, and the P2A self-cleaving peptide includes an amino acid that has at least about 75%, 80%, 85%, 90%, 91%, 92%, 93%, 94%, 95%, 96%, 97%, 98%, 99%, 99.5%, or 100% identity to SEQ ID NO: 70.

TABLE 9

CD80 T cell targeting molecule co-expressed with mutant VSV-G

Full molecule

| Nucleotide | Amino acid (signal sequence underlined) |
|---|---|
| ATGGGTCATACACGCCGCCAAGGA | MGHTRRQGTSPSKCPYLNFFQLLVL |
| ACCTCACCATCTAAGTGCCCATAT | AGLSHFCSGVIHVTKEVKEVATLSC |
| CTGAATTTCTTTCAACTTCTCGTGC | GHNVSVEELAQTRIYWQKEKKMVL |
| TGGCGGGGCTCAGTCATTTCTGCA | TMMSGDMNIWPEYKNRTIFDITNNL |
| GTGGGGTCATTCACGTTACTAAAG | SIVILALRPSDEGTYECVVLKYEKDA |
| AGGTCAAGGAGGTCGCAACATTGA | FKREHLAEVTLSVKADFPTPSISDFEI |
| GTTGTGGCCATAACGTATCAGTTG | PTSNIRRIICSTSGGFPEPHLSWLENG |
| AAGAACTCGCGCAGACACGGATTT | EELNAINTTVSQDPETELYAVSSKLD |
| ACTGGCAAAAGGAAAGAAGATG | FNMTTNHSFMCLIKYGHLRVNQTFN |
| GTGTTGACAATGATGAGCGGTGAC | WNTTKQEHPPDNLLPSWAITLISVN |
| ATGAACATTTGGCCAGAGTACAAA | GIFVICCLTYCFAPRCREGSGATNFS |
| AATCGAACGATATTCGATATAACC | LLKQAGDVEENPGPMKCLLYLAFLF |
| AATAACTTGTCCATAGTAATACTT | IGVNCKFTIVFPHNQKGNWKNVPSN |
| GCCTTGCGACCTTCTGACGAGGGA | YHYCPSSSDLNWHNDLIGTALQVK |
| ACGTATGAATGTGTAGTGCTTAAG | MPQSHKAIQADGWMCHASKWVTT |
| TATGAAAAAGATGCCTTTAAGCGG | CDFRWYGPKYITHSIRSFTPSVEQCK |
| GAACACTTGGCTGAGGTTACACTC | ESIEQTKQGTWLNPGFPPQSCGYAT |
| TCCGTTAAGGCGGACTTTCCTACG | VTDAEAVIVQVTPHHVLVDEYTGE |
| CCGTCTATATCCGACTTCGAGATA | WVDSQFINGKCSNYICPTVHNSTTW |
| CCCACTTCTAACATTGACGCATC | HSDYKVKGLCDSNLISMDITFFSEDG |
| ATTTGCTCAACCTCAGGTGGTTTCC | ELSSLGKEGTGFRSNYFAYETGGKA |
| CAGAGCCTCACTTGAGCTGGCTGG | CKMQYCKHWGVRLPSGVWFEMAD |
| AGAATGGCGAAGAACTTAACGCA | KDLFAAARFPECPEGSSISAPSQTSV |
| ATCAATACCACGGTGTCCCAAGAC | DVSLIQDVERILDYSLCQETWSKIRA |
| CCGGAGACAGAGCTGTACGCCGTG | GLPISPVDLSYLAPKNPGTGPAFTIIN |
| TCATCCAAACTGGATTTTAACATG | GTLKYFETRYIRVDIAAPILSRMVGM |
| ACGACAAATCATAGTTTCATGTGT | ISGTTTEAELWDDWAPYEDVEIGPN |
| CTGATCAAATATGGGCATCTCAGG | GVLRTSSGYKFPLYMIGHGMLDSDL |
| GTGAATCAGACTTTTAATTGGAAC | HLSSKAQVFEHPHIQDAASQLPDDE |
| ACTACCAAACAAGAGCACTTCCCA | SLFFGDTGLSKNPIELVEGWFSSWKS |
| GATAAATCTGTTGCCAAGCTGGGCG | SIASFFFIIGLIIGLFLVLRVGIHLCIKL |
| ATAACTCTTATCTCCGTCAACGGT | KHTKKRQIYTDIEMNRLGK |
| ATCTTCGTAATTTGCTGCCTCACCT | (SEQ ID NO: 76) |
| ATTGTTTCGCGCCTCGATGCCGAG | |
| AAGGCAGCGGCGCCACCAACTTCT | |
| CCCTGCTGAAGCAGGCCGGCGACG | |
| TGGAAGAAAACCCTGGCCCCATGA | |
| AGTGTCTGCTGTACCTGGCGTTCCT | |
| GTTTATCGGGGTGAACTGCAAGTT | |
| CACTATCGTGTTTCCGCACAACCA | |
| AAAGGGCAACTGGAAAAACGTGC | |
| CTTCAAATTACCATTATTGCCCCAG | |
| CAGCTCGGACCTGAACTGGCACAA | |
| TGACCTCATTGGAACGCGCTGCA | |
| GGTGAAGATGCCACAGAGCCACA | |
| AGGCTATCCAGGCTGACGGATGGA | |
| TGTGCCACGCGTCAAATGGGTGA | |
| CTACCTGCGATTTCCGCTGGTACG | |
| GACCAAAATACATCACGCACAGCA | |
| TCAGATCATTCACCCCGTCAGTGG | |
| AACAATGCAAAGAATCCATCGAAC | |
| AGACTAAGCAGGGAACCTGGCTGA | |
| ACCCTGGATTTCCGCCGCAGTCGT | |
| GTGGGTACGCAACCGTGACCGATG | |
| CAGAGGCCGTGATCGTGCAAGTCA | |
| CGCCGCATCACGTGCTTGTGGACG | |
| AGTACACCGGAGAATGGGTCGATT | |
| CCCAGTTCATCAACGGCAAGTGCT | |
| CCAACTACATTTGCCCAACCGTGC | |
| ACAACAGCACTACTTGGCACAGCG | |
| ACTACAAAGTGAAGGGTCTGTGTG | |
| ATTCCAACCTGATCTCCATGGATA | |
| TCACTTTCTTCTCGGAAGACGGCG | |
| AACTGTCCTCACTGGGCAAAGAAG | |
| GAACTGGGTTTCGCTCAAATTACT | |
| TCGCCTACGAAACTGGAGGAAAAG | |
| CCTGCAAGATGCAGTACTGCAAGC | |
| ACTGGGGCGTGAGACTACCCAGCG | |
| GTGTCTGGTTCGAGATGGCCGATA | |
| AGGACCTGTTTGCAGCAGCGAGAT | |
| TCCCGGAATGCCCTGAGGGATCGA | |
| GCATCTCCGCTCCAAGCCAAACTT | |
| CAGTGGACGTGAGCCTGATCCAGG | |
| ACGTGGAACGGATTCTCGACTACT | |

TABLE 9-continued

| CD80 T cell targeting molecule co-expressed with mutant VSV-G |
|---|
| CGCTGTGCCAGGAGACCTGGTCGA<br>AGATCAGAGCGGGACTGCCCATCT<br>CACCGGTGGACCTGTCCTACCTGG<br>CGCCAAAGAATCCGGGCACTGGAC<br>CGGCGTTCACCATCATCAACGGCA<br>CCCTCAAATACTTCGAGACGCGGT<br>ACATCCGGGTGGACATCGCAGCTC<br>CGATCCTCTCCCGGATGGTGGGAA<br>TGATCTCGGGGACTACTACCGAAG<br>CCGAGCTCTGGGACGACTGGGCAC<br>CTTACGAGGATGTCGAGATCGGAC<br>CTAACGGAGTGCTCCGGACCTCCT<br>CCGGGTACAAGTTCCCTCTGTACA<br>TGATCGGCCATGGCATGCTGGACT<br>CGGATCTGCATCTGTCGTCCAAAG<br>CACAGGTGTTTGAACACCCACACA<br>TTCAAGACGCCGCCAGCCAGCTGC<br>CGGACGATGAGTCGCTGTTCTTCG<br>GAGACACGGGCTTGTCAAAGAATC<br>CCATCGAGCTGGTGGAAGGATGGT<br>TTTCATCCTGGAAAAGCAGCATCG<br>CTTCATTCTTCTTCATCATTGGCCT<br>GATCATCGGCCTATTTCTAGTCCTG<br>CGGGTGGGAATTCATCTGTGCATC<br>AAGCTCAAGCACACTAAGAAGCG<br>GCAAATCTACACTGATATCGAGAT<br>GAATCGCCTGGGCAAG<br>(SEQ ID NO: 75) |

| CD80 signal peptide | |
|---|---|
| Nucleotide | Amino acid |
| ATGGGTCATACACGCCGCCAAGGA<br>ACCTCACCATCTAAGTGCCCATAT<br>CTGAATTTCTTTCAACTTCTCGTGC<br>TGGCGGGGCTCAGTCATTTCTGCA<br>GTGGGGTC (SEQ ID NO: 3) | MGHTRRQGTSPSKCPYLNFFQLLVL<br>AGLSHFCSGV (SEQ ID NO: 4) |

| CD80 extracellular domain (ECD) | |
|---|---|
| Nucleotide | Amino acid |
| ATTCACGTTACTAAAGAGGTCAAG<br>GAGGTCGCAACATTGAGTTGTGGC<br>CATAACGTATCAGTTGAAGAACTC<br>GCGCAGACACGGATTTACTGGCAA<br>AAGGAAAAGAAGATGGTGTTGAC<br>AATGATGAGCGGTGACATGAACAT<br>TTGGCCAGAGTACAAAAATCGAAC<br>GATATTCGATATAACCAATAACTT<br>GTCCATAGTAATACTTGCCTTGCG<br>ACCTTCTGACGAGGGAACGTATGA<br>ATGTGTAGTGCTTAAGTATGAAAA<br>AGATGCCTTTAAGCGGGAACACTT<br>GGCTGAGGTTACACTCTCCGTTAA<br>GGCGGACTTTCCTACGCCGTCTAT<br>ATCCGACTTCGAGATACCCACTTC<br>TAACATTCGACGCATCATTTGCTC<br>AACCTCAGGTGGTTTCCCAGAGCC<br>TCACTTGAGCTGGCTGGAGAATGG<br>CGAAGAACTTAACGCAATCAATAC<br>CACGGTGTCCCAAGACCCGGAGAC<br>AGAGCTGTACGCCGTGTCATCCAA<br>ACTGGATTTTAACATGACGACAAA<br>TCATAGTTTCATGTGTCTGATCAAA<br>TATGGGCATCTCAGGGTGAATCAG<br>ACTTTTAATTGGAACACTACCAAA<br>CAAGAGCACTTCCCAGATAATCTG<br>TTGCCAAGC (SEQ ID NO: 5) | IHVTKEVKEVATLSCGHNVSVEELA<br>QTRIYWQKEKKMVLTMMSGDMNI<br>WPEYKNRTIFDITNNLSIVILALRPSD<br>EGTYECVVLKYEKDAFKREHLAEV<br>TLSVKADFPTPSISDFEIPTSNIRRIICS<br>TSGGFPEPHLSWLENGEELNAINTTV<br>SQDPETELYAVSSKLDFNMTTNHSF<br>MCLIKYGHLRVNQTFNWNTTKQEH<br>FPDNLLPS (SEQ ID NO: 6) |

TABLE 9-continued

CD80 T cell targeting molecule co-expressed with mutant VSV-G

CD80 transmembrane and intracellular domain

| Nucleotide | Amino acid |
|---|---|
| TGGGCGATAACTCTTATCTCCGTC AACGGTATCTTCGTAATTTGCTGCC TCACCTATTGTTTCGCGCCTCGATG CCGAGAA (SEQ ID NO: 7) | WAITLISVNGIFVICCLTYCFAPRCRE (SEQ ID NO: 8) |

P2A self-cleaving

| Nucleotide | Amino acid |
|---|---|
| GGCAGCGGCGCCACCAACTTCTCC CTGCTGAAGCAGGCCGGCGACGTG GAAGAAAACCCTGGCCCC (SEQ ID NO: 69) | GSGATNFSLLKQAGDVEENPGP (SEQ ID NO: 70) |

VSV-G signal sequence

| Nucleotide | Amino acid |
|---|---|
| ATGAAGTGTCTGCTGTACCTGGCG TTCCTGTTTATCGGGGTGAACTGC (SEQ ID NO: 71) | MKCLLYLAFLFIGVNC (SEQ ID NO: 72) |

Mutant VSV-G

| Nucleotide | Amino acid |
|---|---|
| AAGTTCACTATCGTGTTTCCGCAC AACCAAAAGGGCAACTGGAAAAA CGTGCCTTCAAATTACCATTATTGC CCCAGCAGCTCGGACCTGAACTGG CACAATGACCTCATTGGAACCGCG CTGCAGGTGAAGATGCCACAGAGC CACAAGGCTATCCAGGCTGACGGA TGGATGTGCCACGCGTCAAAATGG GTGACTACCTGCGATTTCCGCTGG TACGGACCAAAATACATCACGCAC AGCATCAGATCATTCACCCCGTCA GTGGAACAATGCAAAGAATCCATC GAACAGACTAAGCAGGGAACCTG GCTGAACCCTGGATTTCCGCCGCA GTCGTGTGGGTACGAACCGTGAC CGATGCAGAGGCCGTGATCGTGCA AGTCACGCCGCATCACGTGCTTGT GGACGAGTACACCGGAGAATGGG TCGATTCCCAGTTCATCAACGGCA AGTGCTCCAACTACATTTGCCCAA CCGTGCACAACAGCACTACTTGGC ACAGCGACTACAAAGTGAAGGGTC TGTGTGATTCCAACCTGATCTCCAT GGATATCACTTTCTTCTCGGAAGA CGGCGAACTGTCCTCACTGGGCAA AGAAGGAACTGGGTTTCGCTCAAA TTACTTCGCCTACGAAACTGGAGG AAAAGCCTGCAAGATGCAGTACTG CAAGCACTGGGCGTGAGACTACC CAGCGGTGTCTGGTTCGAGATGGC CGATAAGGACCTGTTTGCAGCAGC GAGATTCCCGGAATGCCCTGAGGG ATCGAGCATCTCCGCTCCAAGCCA AACTTCAGTGGACGTGAGCCTGAT CCAGGACGTGGAACGGATTCTCGA CTACTCGCTGTGCCAGGAGACCTG GTCGAAGATCAGAGCGGGACTGCC CATCTCACCGGTGGACCTGTCCTA CCTGGCGCCAAAGAATCCGGGCAC TGGACCGGCGTTCACCATCATCAA CGGCACCCTCAAATACTTCGAGAC GCGGTACATCCGGGTGGACATCGC AGCTCCGATCCTCTCCCGGATGGT GGGAATGATCTCGGGGACTACTAC CGAAGCCGAGCTCTGGGACGACTG GGCACCTTACGAGGATGTCGAGAT CGGACCTAACGGAGTGCTCCGGAC CTCCTCCGGGTACAAGTTCCCTCTG | KFTIVFPHNQKGNWKNVPSNYHYCP SSSDLNWHNDLIGTALQVKMPQSH KAIQADGWMCHASKWVTTCDFRW YGPKYITHSIRSFTPSVEQCKESIEQT KQGTWLNPGFPPQSCGYATVIDAE AVIVQVTPHHVLVDEYTGEWVDSQ FINGKCSNYICPTVHNSTTWHSDYK VKGLCDSNLISMDITFFSEDGELSSL GKEGTGFRSNYFAYETGGKACKMQ YCKHWGVRLPSGVWFEMADKDLF AAARFPECPEGSSISAPSQTSVDVSLI QDVERILDYSLCQETWSKIRAGLPIS PVDLSYLAPKNPGTGPAFTIINGTLK YFETRYIRVDIAAPILSRMVGMISGT TTEAELWDDWAPYEDVEIGPNGVL RTSSGYKFPLYMIGHGMLDSDLHLS SKAQVFEHPHIQDAASQLPDDESLFF GDTGLSKNPIELVEGWFSSWKSSIAS FFFIIGLIIGLFLVLRVGIHLCIKLKHT KKRQIYTDIEMNRLGK (SEQ ID NO: 74) |

TABLE 9-continued

CD80 T cell targeting molecule co-expressed with mutant VSV-G

TACATGATCGGCCATGGCATGCTG
GACTCGGATCTGCATCTGTCGTCC
AAAGCACAGGTGTTTGAACACCCA
CACATTCAAGACGCCGCCAGCCAG
CTGCCGGACGATGAGTCGCTGTTC
TTCGGAGACACGGGCTTGTCAAAG
AATCCCATCGAGCTGGTGGAAGGA
TGGTTTTCATCCTGGAAAAGCAGC
ATCGCTTCATTCTTCTTCATCATTG
GCCTGATCATCGGCCTATTTCTAGT
CCTGCGGGTGGGAATTCATCTGTG
CATCAAGCTCAAGCACACTAAGAA
GCGGCAAATCTACACTGATATCGA
GATGAATCGCCTGGGCAAG (SEQ
ID NO: 73)

In another embodiment, the tandem expression cassette of the VSV-G env plasmid encodes a CD80 targeting protein, an anti-CD3 targeting protein, and a mutated VSV-G envelope protein. For example, in a specific embodiment, the tandem expression cassette may comprise a CD80 targeting polynucleotide according to SEQ ID NO: 1, which encodes an amino acid sequence of SEQ ID NO: 2. In a specific embodiment, the tandem expression cassette may comprise an anti-CD3 targeting polynucleotide according to SEQ ID NO: 9, which encodes an amino acid sequence of SEQ ID NO: 10. Such an embodiment is described in more detail in Table 3. As illustrated in Table 3, the CD80 targeting protein is separated from the anti-CD3 targeting protein via a P2A self-cleaving peptide encoded by SEQ ID NO: 29 and having an amino acid sequence according to SEQ ID NO: 30.

In some embodiments, where the tandem expression cassette of the VSV-G env plasmid encodes a CD80 targeting protein, anti-CD3 targeting protein, and a mutated VSV-G envelope protein, the tandem expression cassette may include a polynucleotide encoding the CD80 targeting protein and anti-CD3 targeting protein that has at least about 75%, 80%, 85%, 90%, 91%, 92%, 93%, 94%, 95%, 96%, 97%, 98%, 99%, 99.5%, or 100% identity to SEQ ID NO: 21, which encodes an amino acid sequence that has at least about 75%, 80%, 85%, 90%, 91%, 92%, 93%, 94%, 95%, 96%, 97%, 98%, 99%, 99.5%, or 100% identity to SEQ ID NO: 22. In certain embodiments, the CD80 targeting protein is separated from the anti-CD3 targeting protein via a P2A self-cleaving peptide encoded a nucleic acid sequence that has at least about 75%, 80%, 85%, 90%, 91%, 92%, 93%, 94%, 95%, 96%, 97%, 98%, 99%, 99.5%, or 100% identity to SEQ ID NO: 29, and the P2A self-cleaving peptide includes an amino acid that has at least about 75%, 80%, 85%, 90%, 91%, 92%, 93%, 94%, 95%, 96%, 97%, 98%, 99%, 99.5%, or 100% identity to SEQ ID NO: 30.

In some embodiments, wherein the tandem expression cassette of the VSV-G env plasmid encodes a CD80 targeting protein, anti-CD3 targeting protein, and a mutated VSV-G envelope protein, the CD80 targeting protein and anti-CD3 targeting protein are separated from the mutated VSV-G envelope protein via a 2A self-cleaving peptide.

In some embodiments of a four plasmid LVV system, the GagPol plasmid includes a tandem expression cassette that encodes the Gag polyprotein precursor and Pol polyprotein precursor and a targeting protein as disclosed herein. In specific embodiments, the tandem expression cassette included in the GagPol plasmid includes a polynucleotide that encodes a first signal peptide, a polynucleotide that encodes a targeting protein, a polynucleotide that encodes one of an internal ribosomal entry site (IRES), a furin cleavage site, or a viral 2A peptide, a polynucleotide that encodes a second signal peptide, and a polynucleotide that encodes Gag polyprotein precursor and Pol polyprotein precursor. In certain embodiments, the polynucleotide encoding the Gag polyprotein precursor and Pol polyprotein precursor is positioned 5' to the polynucleotide encoding the targeting protein. In other embodiments, the polynucleotide encoding the Gag polyprotein precursor and Pol polyprotein precursor is positioned 3' to the polynucleotide encoding the targeting protein. The polynucleotide that encodes the targeting protein and the polynucleotide that encodes the Gag polyprotein precursor and Pol polyprotein precursor are separated in the tandem cassette by the polynucleotide that encodes the IRES, furin cleavage site, or viral 2A peptide, which allows for co-expression of Gag polyprotein precursor and Pol polyprotein precursor and the targeting protein from a single mRNA. In certain embodiments, a viral 2A peptide is a porcine teschovirus-1 (P2A), Thosea asigna virus (T2A), equine rhinitis A virus (E2A), foot-and-mouth disease virus (F2A), or a variant thereof. Specific examples of amino acid and nucleotide sequences for the viral 2A peptides are provided in Table 7.

In some embodiments, the GagPol plasmid containing the tandem expression cassette encoding Gag polyprotein precursor and Pol polyprotein precursor and the targeting protein is transfected into producer cells at a higher molar concentration than the VSV-G env plasmid. In some embodiments, the GagPol plasmid containing the tandem expression cassette encoding Gag polyprotein precursor and Pol polyprotein precursor and the targeting protein is transfected into producer cells at a lower molar concentration than the VSV-G env plasmid.

In one embodiment, the tandem expression cassette of the GagPol plasmid encodes an anti-CD3 targeting protein and Gag polyprotein precursor and Pol polyprotein precursor. In some embodiments, the anti-CD3 targeting protein is separated from the Gag polyprotein precursor and Pol polyprotein precursor via a P2A self-cleaving peptide.

In another embodiment, the tandem expression cassette of the GagPol plasmid encodes a CD80 targeting protein and Gag polyprotein precursor and Pol polyprotein precursor. In some embodiments, the CD80 targeting protein is separated from Gag polyprotein precursor and Pol polyprotein precursor via a P2A self-cleaving peptide.

In some embodiments of a four plasmid LVV system, the Rev plasmid includes a tandem expression cassette that encodes the Rev protein and a targeting protein as disclosed herein. In specific embodiments, the tandem expression cassette included in the Rev plasmid includes a polynucleotide that encodes a first signal peptide, a polynucleotide that encodes a targeting protein, a polynucleotide that encodes one of an internal ribosomal entry site (IRES), a furin cleavage site, or a viral 2A peptide, a polynucleotide that encodes a second signal peptide, and a polynucleotide that encodes a Rev protein. In certain embodiments, the polynucleotide encoding the Rev protein is positioned 5' to the polynucleotide encoding the targeting protein. In other embodiments, the polynucleotide encoding the Rev protein is positioned 3' to the polynucleotide encoding the targeting protein. The polynucleotide that encodes the targeting protein and the polynucleotide that encodes the Rev protein are separated in the tandem cassette by the polynucleotide that encodes the IRES, furin cleavage site, or viral 2A peptide, which allows for co-expression of the Rev protein and the targeting protein from a single mRNA. In certain embodiments, a viral 2A peptide is a porcine teschovirus-1 (P2A), Thosea asigna virus (T2A), equine rhinitis A virus (E2A), foot-and-mouth disease virus (F2A), or a variant thereof. Specific examples of amino acid and nucleotide sequences for the viral 2A peptides are provided in Table 7.

In some embodiments, the Rev plasmid containing the tandem expression cassette encoding the Rev protein and the targeting protein is transfected into producer cells at a higher molar concentration than the VSV-G env plasmid. In some embodiments, the Rev plasmid containing the tandem expression cassette encoding the Rev protein and the targeting protein is transfected into producer cells at a lower molar concentration than the VSV-G env plasmid.

In one embodiment, the tandem expression cassette of the Rev plasmid encodes an anti-CD3 targeting protein and a Rev protein. In some embodiments, the anti-CD3 targeting protein is separated from the Rev protein via a P2A self-cleaving peptide.

In another embodiment, the tandem expression cassette of the GagPol plasmid encodes a CD80 targeting protein and a Rev protein. In some embodiments, the CD80 targeting protein is separated from the Rev protein via a P2A self-cleaving peptide.

Examples of mutated VSV-G sequences that may be used in the four plasmid, $3^{rd}$ generation lentiviral vector system of the present disclosure are provided in Table 10.

TABLE 10

| WT VSV-G reference and mutant sequences |  |
|---|---|
| WT VSV-G | |
| Nucleotide | Amino acid (signal sequence underlined) |
| ATGAAGTGTCTGCTGTACCTGGCGT | MKCLLYLAFLFIGVNCKFTIVFPHN |
| TCCTGTTTATCGGGGTGAACTGCAA | QKGNWKNVPSNYHYCPSSSDLNW |
| GTTCACTATCGTGTTTCCGCACAAC | HNDLIGTALQVKMPKSHKAIQADG |
| CAAAAGGGCAACTGGAAAAACGTG | WMCHASKWVTTCDFRWYGPKYIT |
| CCTTCAAATTACCATTATTGCCCCA | HSIRSFTPSVEQCKESIEQTKQGTWL |
| GCAGCTCGGACCTGAACTGGCACA | NPGFPPQSCGYATVTDAEAVIVQVT |
| ATGACCTCATTGGAACCGCGCTGCA | PHHVLVDEYTGEWVDSQFINGKCS |
| GGTGAAGATGCCAAAGAGCCACAA | NYICPTVHNSTTWHSDYKVKGLCD |
| GGCTATCCAGGCTGACGGATGGAT | SNLISMDITFFSEDGELSSLGKEGTG |
| GTGCCACGCGTCAAAATGGGTGAC | FRSNYFAYETGGKACKMQYCKHW |
| TACCTGCGATTTCCGCTGGTACGGA | GVRLPSGVWFEMADKDLFAAARFP |
| CCAAAATACATCACGCACAGCATC | ECPEGSSISAPSQTSVDVSLIQDVERI |
| AGATCATTCACCCCGTCAGTGGAAC | LDYSLCQETWSKIRAGLPISPVDLS |
| AATGCAAAGAATCCATCGAACAGA | YLAPKNPGTGPAFTIINGTLKYFETR |
| CTAAGCAGGGAACCTGGCTGAACC | YIRVDIAAPILSRMVGMISGTTTERE |
| CTGGATTTCCGCCGCAGTCGTGTGG | LWDDWAPYEDVEIGPNGVLRTSSG |
| GTACGCAACCGTGACCGATGCAGA | YKFPLYMIGHGMLDSDLHLSSKAQ |
| GGCCGTGATCGTGCAAGTCACGCC | VFEHPHIQDAASQLPDDESLFFGDT |
| GCATCACGTGCTTGTGGACGAGTAC | GLSKNPIELVEGWFSSWKSSIASFFF |
| ACCGGAGAATGGGTCGATTCCCAG | IIGLIIGLFLVLRVGIHLCIKLKHTKK |
| TTCATCAACGGCAAGTGCTCCAACT | RQIYTDIEMNRLGK (SEQ ID NO: 78) |
| ACATTTGCCCAACCGTGCACAACAG | |
| CACTACTTGGCACAGCGACTACAA | |
| AGTGAAGGGTCTGTGTGATTCCAAC | |
| CTGATCTCCATGGATATCACTTTCT | |
| TCTCGGAAGACGGCGAACTGTCCTC | |
| ACTGGGCAAAGAAGGAACTGGGTT | |
| TCGCTCAAATTACTTCGCCTACGAA | |
| ACTGGAGGAAAAGCCTGCAAGATG | |
| CAGTACTGCAAGCACTGGGGCGTG | |
| AGACTACCCAGCGGTGTCTGGTTCG | |
| AGATGGCCGATAAGGACCTGTTTGC | |
| AGCAGCGAGATTCCCGGAATGCCC | |
| TGAGGGATCGAGCATCTCCGCTCCA | |
| AGCCAAACTTCAGTGGACGTGAGC | |
| CTGATCCAGGACGTGGAACGGATT | |
| CTCGACTACTCGCTGTGCCAGGAGA | |
| CCTGGTCGAAGATCAGAGCGGGAC | |
| TGCCCATCTCACCGGTGGACCTGTC | |
| CTACCTGGCGCCAAAGAATCCGGG | |
| CACTGGACCGGCGTTCACCATCATC | |
| AACGGCACCCTCAAATACTTCGAG | |
| ACGCGGTACATCCGGGTGGACATC | |
| GCAGCTCCGATCCTCTCCCGGATGG | |
| TGGGAATGATCTCGGGGACTACTAC | |

TABLE 10-continued

WT VSV-G reference and mutant sequences

CGAACGCGAGCTCTGGGACGACTG
GGCACCTTACGAGGATGTCGAGAT
CGGACCTAACGGAGTGCTCCGGAC
CTCCTCCGGGTACAAGTTCCCTCTG
TACATGATCGGCCATGGCATGCTGG
ACTCGGATCTGCATCTGTCGTCCAA
AGCACAGGTGTTTGAACACCCACA
CATTCAAGACGCCGCCAGCCAGCT
GCCGGACGATGAGTCGCTGTTCTTC
GGAGACACGGGCTTGTCAAAGAAT
CCCATCGAGCTGGTGGAAGGATGG
TTTTCATCCTGGAAAAGCAGCATCG
CTTCATTCTTCTTCATCATTGGCCTG
ATCATCGGCCTATTTCTAGTCCTGC
GGGTGGGAATTCATCTGTGCATCAA
GCTCAAGCACACTAAGAAGCGGCA
AATCTACACTGATATCGAGATGAAT
CGCCTGGGCAAG (SEQ ID NO: 77)

WT VSV-G Signal Sequence

| Nucleotide | Amino acid |
| --- | --- |
| ATGAAGTGTCTGCTGTACCTGGCGT<br>TCCTGTTTATCGGGGTGAACTGC<br>(SEQ ID NO: 87) | MKCLLYLAFLFIGVNC<br>(SEQ ID NO: 88) |

WT VSV-G without signal sequence

| Nucleotide | Amino acid |
| --- | --- |
| AAGTTCACTATCGTGTTTCCGCACA<br>ACCAAAAGGGCAACTGGAAAAACG<br>TGCCTTCAAATTACCATTATTGCCC<br>CAGCAGCTCGGACCTGAACTGGCA<br>CAATGACCTCATTGGAACCGCGCTG<br>CAGGTGAAGATGCCAAAGAGCCAC<br>AAGGCTATCCAGGCTGACGGATGG<br>ATGTGCCACGCGTCAAAATGGGTG<br>ACTACCTGCGATTTCCGCTGGTACG<br>GACCAAAATACATCACGCACAGCA<br>TCAGATCATTCACCCCGTCAGTGGA<br>ACAATGCAAAGAATCCATCGAACA<br>GACTAAGCAGGGAACCTGGCTGAA<br>CCCTGGATTTCCGCCGCAGTCGTGT<br>GGGTACGCAACCGTGACCGATGCA<br>GAGGCCGTGATCGTGCAAGTCACG<br>CCGCATCACGTGCTTGTGGACGAGT<br>ACACCGGAGAATGGGTCGATTCCC<br>AGTTCATCAACGGCAAGTGCTCCAA<br>CTACATTTGCCCAACCGTGCACAAC<br>AGCACTACTTGGCACAGCGACTAC<br>AAAGTGAAGGGTCTGTGTGATTCCA<br>ACCTGATCTCCATGGATATCACTTT<br>CTTCTCGGAAGACGGCGAACTGTCC<br>TCACTGGGCAAAGAAGGAACTGGG<br>TTTCGCTCAAATTACTTCGCCTACG<br>AAACTGGAGGAAAAGCCTGCAAGA<br>TGCAGTACTGCAAGCACTGGGGCG<br>TGAGACTACCCAGCGGTGTCTGGTT<br>CGAGATGGCCGATAAGGACCTGTTT<br>GCAGCAGCGAGATTCCCGGAATGC<br>CCTGAGGGATCGAGCATCTCCGCTC<br>CAAGCCAAACTTCAGTGGACGTGA<br>GCCTGATCCAGGACGTGGAACGGA<br>TTCTCGACTACTCGCTGTGCCAGGA<br>GACCTGGTCGAAGATCAGAGCGGG<br>ACTGCCCATCTCACCGGTGACCTG<br>TCCTACCTGGCGCCAAAGAATCCGG<br>GCACTGGACCGGCGTTCACCATCAT<br>CAACGGCACCCTCAAATACTTCGAG<br>ACGCGGTACATCCGGGTGGACATC<br>GCAGCTCCGATCCTCTCCCGGATGG<br>TGGGAATGATCTCGGGGACTACTAC<br>CGAACGCGAGCTCTGGGACGACTG<br>GGCACCTTACGAGGATGTCGAGAT<br>CGGACCTAACGGAGTGCTCCGGAC<br>CTCCTCCGGGTACAAGTTCCCTCTG | KFTIVFPHNQKGNWKNVPSNYHYC<br>PSSSDLNWHNDLIGTALQVKMPKS<br>HKAIQADGWMCHASKWVTTCDFR<br>WYGPKYITHSIRSFTPSVEQCKESIE<br>QTKQGTWLNPGFPPQSCGYATVTD<br>AEAVIVQVTPHHVLVDEYTGEWVD<br>SQFINGKCSNYICPTVHNSTTWHSD<br>YKVKGLCDSNLISMDITFFSEDGEL<br>SSLGKEGTGFRSNYFAYETGGKAC<br>KMQYCKHWGVRLPSGVWFEMAD<br>KDLFAAARFPECPEGSSISAPSQTSV<br>DVSLIQDVERILDYSLCQETWSKIR<br>AGLPISPVDLSYLAPKNPGTGPAFTI<br>INGTLKYFETRYIRVDIAAPILSRMV<br>GMISGTTTERELWDDWAPYEDVEI<br>GPNGVLRTSSGYKFPLYMIGHGML<br>DSDLHLSSKAQVFEHPHIQDAASQL<br>PDDESLFFGDTGLSKNPIELVEGWF<br>SSWKSSIASFFFIIGLIIGLFLVLRVGI<br>HLCIKLKHTKKRQIYTDIEMNRLGK<br>(SEQ ID NO: 90) |

TABLE 10-continued

WT VSV-G reference and mutant sequences

TACATGATCGGCCATGGCATGCTGG
ACTCGGATCTGCATCTGTCGTCCAA
AGCACAGGTGTTTGAACACCCACA
CATTCAAGACGCCGCCAGCCAGCT
GCCGGACGATGAGTCGCTGTTCTTC
GGAGACACGGGCTTGTCAAAGAAT
CCCATCGAGCTGGTGGAAGGATGG
TTTTCATCCTGGAAAAGCAGCATCG
CTTCATTCTTCTTCATCATTGGCCTG
ATCATCGGCCTATTTCTAGTCCTGC
GGGTGGGAATTCATCTGTGCATCAA
GCTCAAGCACACTAAGAAGCGGCA
AATCTACACTGATATCGAGATGAAT
CGCCTGGGCAAG
(SEQ ID NO: 89)

Trop-002 Mutated VSV-G

| Nucleotide | Amino Acid |
| --- | --- |
| AAGTTCACTATCGTGTTTCCGCACA | KFTIVFPHNQKGNWKNVPSNYHYC |
| ACCAAAAGGGCAACTGGAAAAACG | PSSSDLNWHNDLIGTALQVKMPQS |
| TGCCTTCAAATTACCATTATTGCCC | HKAIQADGWMCHASKWVTTCDFR |
| CAGCAGCTCGGACCTGAACTGGCA | WYGPKYITHSIRSFTPSVEQCKESIE |
| CAATGACCTCATTGGAACCGCGCTG | QTKQGTWLNPGFPPQSCGYATVTD |
| CAGGTGAAGATGCCACAGAGCCAC | AEAVIVQVTPHHVLVDEYTGEWVD |
| AAGGCTATCCAGGCTGACGGATGG | SQFINGKCSNYICPTVHNSTTWHSD |
| ATGTGCCACGCGTCAAAATGGGTG | YKVKGLCDSNLISMDITFFSEDGEL |
| ACTACCTGCGATTTCCGCTGGTACG | SSLGKEGTGFRSNYFAYETGGKAC |
| GACCAAAATACATCACGCACAGCA | KMQYCKHWGVRLPSGVWFEMAD |
| TCAGATCATTCACCCCGTCAGTGGA | KDLFAAARFPECPEGSSISAPSQTSV |
| ACAATGCAAAGAATCCATCGAACA | DVSLIQDVERILDYSLCQETWSKIR |
| GACTAAGCAGGGAACCTGGCTGAA | AGLPISPVDLSYLAPKNPGTGPAFTI |
| CCCTGGATTTCCGCCGCAGTCGTGT | INGTLKYFETRYIRVDIAAPILSRMV |
| GGGTACGCAACCGTGACCGATGCA | GMISGTTTEAELWDDWAPYEDVEI |
| GAGGCCGTGATCGTGCAAGTCACG | GPNGVLRTSSGYKFPLYMIGHGML |
| CCGCATCACGTGCTTGTGGACGAGT | DSDLHLSSKAQVFEHPHIQDAASQL |
| ACACCGGAGAATGGGTCGATTCCC | PDDESLFFGDTGLSKNPIELVEGWF |
| AGTTCATCAACGGCAAGTGCTCCAA | SSWKSSIASFFFIIGLIIGLFLVLRVGI |
| CTACATTTGCCCAACCGTGCACAAC | HLCIKLKHTKKRQIYTDIEMNRLGK |
| AGCACTACTTGGCACAGCGACTAC | (SEQ ID NO: 74) |
| AAAGTGAAGGGTCTGTGTGATTCCA | |
| ACCTGATCTCCATGGATATCACTTT | |
| CTTCTCGGAAGACGGCGAACTGTCC | |
| TCACTGGGCAAAGAAGGAACTGGG | |
| TTTCGCTCAAATTACTTCGCCTACG | |
| AAACTGGAGGAAAAGCCTGCAAGA | |
| TGCAGTACTGCAAGCACTGGGGCG | |
| TGAGACTACCCAGCGGTGTCTGGTT | |
| CGAGATGGCCGATAAGGACCTGTTT | |
| GCAGCAGCGAGATTCCCGGAATGC | |
| CCTGAGGGATCGAGCATCTCCGCTC | |
| CAAGCCAAACTTCAGTGGACGTGA | |
| GCCTGATCCAGGACGTGGAACGGA | |
| TTCTCGACTACTCGCTGTGCCAGGA | |
| GACCTGGTCGAAGATCAGAGCGGG | |
| ACTGCCCATCTCACCGGTGGACCTG | |
| TCCTACCTGGCGCCAAAGAATCCGG | |
| GCACTGGACCGGCGTTCACCATCAT | |
| CAACGGCACCCTCAAATACTTCGAG | |
| ACGCGGTACATCCGGGTGGACATC | |
| GCAGCTCCGATCCTCTCCCGGATGG | |
| TGGGAATGATCTCGGGGACTACTAC | |
| CGAAGCCGAGCTCTGGGACGACTG | |
| GGCACCTTACGAGGATGTCGAGAT | |
| CGGACCTAACGGAGTGCTCCGGAC | |
| CTCCTCCGGGTACAAGTTCCCTCTG | |
| TACATGATCGGCCATGGCATGCTGG | |
| ACTCGGATCTGCATCTGTCGTCCAA | |
| AGCACAGGTGTTTGAACACCCACA | |
| CATTCAAGACGCCGCCAGCCAGCT | |
| GCCGGACGATGAGTCGCTGTTCTTC | |
| GGAGACACGGGCTTGTCAAAGAAT | |
| CCCATCGAGCTGGTGGAAGGATGG | |
| TTTTCATCCTGGAAAAGCAGCATCG | |
| CTTCATTCTTCTTCATCATTGGCCTG | |
| ATCATCGGCCTATTTCTAGTCCTGC | |
| GGGTGGGAATTCATCTGTGCATCAA | |

TABLE 10-continued

WT VSV-G reference and mutant sequences

GCTCAAGCACACTAAGAAGCGGCA
AATCTACACTGATATCGAGATGAAT
CGCCTGGGCAAG (SEQ ID NO: 73)

Trop-002 Mutated VSV-G

| Nucleotide | Amino acid |
|---|---|
| AAGTTCACTATCGTGTTTCCGCACA | KFTIVFPHNQKGNWKNVPSNYHYC |
| ACCAAAAGGGCAACTGGAAAAACG | PSSSDLNWHNDLIGTALQVKMPQS |
| TGCCTTCAAATTACCATTATTGCCC | HKAIQADGWMCHASKWVTTCDFR |
| CAGCAGCTCGGACCTGAACTGGCA | WYGPKYITHSIRSFTPSVEQCKESIE |
| CAATGACCTCATTGGAACCGCCTG | QTKQGTWLNPGFPPQSCGYATVTD |
| CAGGTGAAGATGCCACAGAGCCAC | AEAVIVQVTPHHVLVDEYTGEWVD |
| AAGGCTATCCAGGCTGACGGATGG | SQFINGKCSNYICPTVHNSTTWHSD |
| ATGTGCCACGCGTCAAAATGGGTG | YKVKGLCDSNLISMDITFFSEDGEL |
| ACTACCTGCGATTTCCGCTGGTACG | SSLGKEGTGFRSNYFAYETGGKAC |
| GACCAAAATACATCACGCACAGCA | KMQYCKHWGVRLPSGVWFEMAD |
| TCAGATCATTCACCCCGTCAGTGGA | KDLFAAARFPECPEGSSISAPSQTSV |
| ACAATGCAAAGAATCCATCGAACA | DVSLIQDVERILDYSLCQETWSKIR |
| GACTAAGCAGGGAACCTGGCTGAA | AGLPISPVDLSYLAPKNPGTGPAFTI |
| CCCTGGATTTCCGCCGCAGTCGTGT | INGTLKYFETRYIRVDIAAPILSRMV |
| GGGTACGCAACCGTGACCGATGCA | GMISGTTTEAELWDDWAPYEDVEI |
| GAGGCCGTGATCGTGCAAGTCACG | GPNGVLRTSSGYKFPLYMIGHGML |
| CCGCATCACGTGCTTGTGGACGAGT | DSDLHLSSKAQVFEHPHIQDAASQL |
| ACACCGGAGAATGGGTCGATTCCC | PDDESLFFGDTGLSKNPIELVEGWF |
| AGTTCATCAACGGCAAGTGCTCCAA | SSWKSSIASFFFIIGLIIGLFLVLRVGI |
| CTACATTTGCCCAACCGTGCACAAC | HLCIKLKHTKKRQIYTDIEMNRLGK |
| AGCACTACTTGGCATAGCGACTACA | (SEQ ID NO: 74) |
| AAGTGAAGGGTCTGTGTGATTCCAA | |
| CCTGATCTCCATGGATATCACTTTC | |
| TTCTCGGAAGACGGCGAACTGTCCT | |
| CACTGGGCAAAGAAGGAACTGGGT | |
| TTCGCTCAAATTACTTCGCCTACGA | |
| AACTGGAGGAAAAGCCTGCAAGAT | |
| GCAGTACTGCAAGCACTGGGCGT | |
| GAGACTACCCAGCGGTGTCTGGTTC | |
| GAGATGGCCGATAAGGACCTGTTT | |
| GCAGCAGCGAGATTCCCGGAATGC | |
| CCTGAGGGATCGAGCATCTCCGCTC | |
| CAAGCCAAACTTCAGTGGACGTGA | |
| GCCTGATCCAGGACGTGGAACGGA | |
| TTCTCGACTACTCGCTGTGCCAGGA | |
| GACCTGGTCGAAGATCAGAGCGGG | |
| ACTGCCCATCTCACCGGTGGACCTG | |
| TCCTACCTGGCGCCAAAGAATCCGG | |
| GCACTGGACCGGCGTTCACCATCAT | |
| CAACGGCACCCTCAAATACTTCGAG | |
| ACGCGGTACATCCGGGTGGACATC | |
| GCAGCTCCGATCCTCTCCCGGATGG | |
| TGGGAATGATCTCGGGGACTACTAC | |
| CGAAGCCGAGCTCTGGGACGACTG | |
| GGCACCTTACGAGGATGTCGAGAT | |
| CGGACCTAACGGAGTGCTCCGGAC | |
| CTCCTCCGGGTACAAGTTCCCTCTG | |
| TACATGATCGGCCATGGCATGCTGG | |
| ACTCGGATCTGCATCTGTCGTCCAA | |
| AGCACAGGTGTTTGAACACCCACA | |
| CATTCAAGACGCCGCCAGCCAGCT | |
| GCCGGACGATGAGTCGCTGTTCTTC | |
| GGAGACACGGGCTTGTCAAAGAAT | |
| CCCATCGAGCTGGTGGAAGGATGG | |
| TTTTCATCCTGGAAAAGCAGCATCG | |
| CTTCATTCTTCTTCATCATTGGCCTG | |
| ATCATCGGCCTATTTCTAGTCCTGC | |
| GGGTGGGAATTCATCTGTGCATCAA | |
| GCTCAAGCACACTAAGAAGCGGCA | |
| AATCTACACTGATATCGAGATGAAT | |
| CGCCTGGGCAAGTAG (SEQ ID NO: 91) | |

Trop-051 Mutated VSV-G

| Nucleotide | Amino acid |
|---|---|
| AAGTTCACTATCGTGTTTCCGCACA | KFTIVFPHNQKGNWKNVPSNYHYC |
| ACCAAAAGGGCAACTGGAAAAACG | PSSSDLNWHNDLIGTALQVKMPKS |
| TGCCTTCAAATTACCATTATTGCCC | HKAIQADGWMCHASKWVTTCDFR |

TABLE 10-continued

| WT VSV-G reference and mutant sequences | |
|---|---|
| CAGCAGCTCGGACCTGAACTGGCA | WYGPKYITHSIRSFTPSVEQCKESIE |
| CAATGACCTCATTGGAACCGCGCTG | QTKQGTWLNPGFPPQSCGYATVTD |
| CAGGTGAAGATGCCAAAGAGCCAC | AEAVIVQVTPHHVLVDEYTGEWVD |
| AAGGCTATCCAGGCTGACGGATGG | SQFINGKCSNYICPTVHNSTTWHSD |
| ATGTGCCACGCGTCAAAATGGGTG | YKVKGLCDSALASMDITFFSEDGEL |
| ACTACCTGCGATTTCCGCTGGTACG | SSLGKEGTGFRSNYFAYETGGKAC |
| GACCAAAATACATCACGCACAGCA | KMQYCKHWGVRLPSGVWFEMAD |
| TCAGATCATTCACCCCGTCAGTGGA | KDLFAAARFPECPEGSSISAPSQTSV |
| ACAATGCAAAGAATCCATCGAACA | DVSLIQDVERILDYSLCQETWSKIR |
| GACTAAGCAGGGAACCTGGCTGAA | AGLPISPVDLSYLAPKNPGTGPAFTI |
| CCCTGGATTTCCGCCGCAGTCGTGT | INGTLKYFETRYIRVDIAAPILSRMV |
| GGGTACGCAACCGTGACCGATGCA | GMISGTTAARELWDDWAPYEDVEI |
| GAGGCCGTGATCGTGCAAGTCACG | GPNGVLRTSSGYKFPLYMIGHGML |
| CCGCATCACGTGCTTGTGGACGAGT | DSDLHLSSKAQVFEHPHIQDAASQL |
| ACACCGGAGAATGGGTCGATTCCC | PDDESLFFGDTGLSKNPIELVEGWF |
| AGTTCATCAACGGCAAGTGCTCCAA | SSWKSSIASFFFIIGLIIGLFLVLRVGI |
| CTACATTTGCCCAACCGTGCACAAC | HLCIKLKHTKKRQIYTDIEMNRLGK |
| AGCACTACTTGGCACAGCGACTAC | (SEQ ID NO: 93) |
| AAAGTGAAGGGTCTGTGTGATTCCG | |
| CCCTGGCCTCCATGGATATCACTTT | |
| CTTCTCGGAAGACGGCGAACTGTCC | |
| TCACTGGGCAAAGAAGGAACTGGG | |
| TTTCGCTCAAATTACTTCGCCTACG | |
| AAACTGGAGGAAAAGCCTGCAAGA | |
| TGCAGTACTGCAAGCACTGGGGCG | |
| TGAGACTACCCAGCGGTGTCTGGTT | |
| CGAGATGGCCGATAAGGACCTGTTT | |
| GCAGCAGCGAGATTCCCGGAATGC | |
| CCTGAGGGATCGAGCATCTCCGCTC | |
| CAAGCCAAACTTCAGTGGACGTGA | |
| GCCTGATCCAGGACGTGGAACGGA | |
| TTCTCGACTACTCGCTGTGCCAGGA | |
| GACCTGGTCGAAGATCAGAGCGGG | |
| ACTGCCCATCTCACCGGTGGACCTG | |
| TCCTACCTGGCGCCAAAGAATCCGG | |
| GCACTGGACCGGCGTTCACCATCAT | |
| CAACGGCACCCTCAAATACTTCGAG | |
| ACGCGGTACATCCGGGTGGACATC | |
| GCAGCTCCGATCCTCTCCCGGATGG | |
| TGGGAATGATCTCGGGGACTACTGC | |
| CGCCCGCGAGCTCTGGGACGACTG | |
| GGCACCTTACGAGGATGTCGAGAT | |
| CGGACCTAACGGAGTGCTCCGGAC | |
| CTCCTCCGGGTACAAGTTCCCTCTG | |
| TACATGATCGGCCATGGCATGCTGG | |
| ACTCGGATCTGCATCTGTCGTCCAA | |
| AGCACAGGTGTTTGAACACCCACA | |
| CATTCAAGACGCCGCCAGCCAGCT | |
| GCCGGACGATGAGTCGCTGTTCTTC | |
| GGAGACACGGGCTTGTCAAAGAAT | |
| CCCATCGAGCTGGTGGAAGGATGG | |
| TTTTCATCCTGGAAAAGCAGCATCG | |
| CTTCATTCTTCTTCATCATTGGCCTG | |
| ATCATCGGCCTATTTCTAGTCCTGC | |
| GGGTGGGAATTCATCTGTGCATCAA | |
| GCTCAAGCACACTAAGAAGCGGCA | |
| AATCTACACTGATATCGAGATGAAT | |
| CGCCTGGGCAAGTAG (SEQ ID NO: 92) | |

| Trop-052 Mutated VSV-G | |
|---|---|
| Nucleotide | Amino acid |
| AAGTTCACTATCGTGTTTCCGCACA | KFTIVFPHNQKGNWKNVPSNYHYC |
| ACCAAAAGGGCAACTGGAAAAACG | PSSSDLNWHNDLIGTALQVKMPKS |
| TGCCTTCAAATTACCATTATTGCCC | HKAIQADGWMCHASKWVTTCDFR |
| CAGCAGCTCGGACCTGAACTGGCA | WYGPKYITHSIRSFTPSVEQCKESIE |
| CAATGACCTCATTGGAACCGCGCTG | QTKQGTWLNPGFPPQSCGYATVTD |
| CAGGTGAAGATGCCAAAGAGCCAC | AEAVIVQVTPHHVLVDEYTGEWVD |
| AAGGCTATCCAGGCTGACGGATGG | SQFINGKCSNYICPTVHNSTTWHSD |
| ATGTGCCACGCGTCAAAATGGGTG | YKVKGLCDSNLISMDITFFSEDGEL |
| ACTACCTGCGATTTCCGCTGGTACG | SSLGKEGTGFRSNYFAYETGGKAC |
| GACCAAAATACATCACGCACAGCA | KMQYCKHWGVRLPSGVWFEMAD |
| TCAGATCATTCACCCCGTCAGTGGA | KDLFAAARFPECPEGSSISAPSQTSV |
| ACAATGCAAAGAATCCATCGAACA | DVSLIQDVERILDYSLCQETWSKIR |
| GACTAAGCAGGGAACCTGGCTGAA | AGLPISPVDLSYLAPKNPGTGPAFTI |
| CCCTGGATTTCCGCCGCAGTCGTGT | INGTLKYFETRYIRVDIAAPILSRMV |

TABLE 10-continued

WT VSV-G reference and mutant sequences

| | |
|---|---|
| GGGTACGCAACCGTGACCGATGCA GAGGCCGTGATCGTGCAAGTCACG CCGCATCACGTGCTTGTGGACGAGT ACACCGGAGAATGGGTCGATTCCC AGTTCATCAACGGCAAGTGCTCCAA CTACATTTGCCCAACCGTGCACAAC AGCACTACTTGGCACAGCGACTAC AAAGTGAAGGGTCTGTGTGATTCCA ACCTGATCTCCATGGATATCACTTT CTTCTCGGAAGACGGCGAACTGTCC TCACTGGGCAAAGAAGGAACTGGG TTTCGCTCAAATTACTTCGCCTACG AAAACTGGAGGAAAAGCCTGCAAGA TGCAGTACTGCAAGCACTGGGGCG TGAGACTACCCAGCGGTGTCTGTT CGAGATGGCCGATAAGGACCTGTTT GCAGCAGCGAGATTCCCGGAATGC CCTGAGGGATCG

TABLE 10-continued

WT VSV-G reference and mutant sequences

TTTCGCTCAAATTACTTCGCCTACG
AAACTGGAGGAAAAGCCTGCAAGA
TGCAGTACTGCAAGCACTGGGGCG
TGAGACTACCCAGCGGTGTCTGGTT
CGAGATGGCCGATAAGGACCTGTTT
GCAGCAGCGAGATTCCCGGAATGC
CCTGAGGGATCGAGCATCTCCGCTC
CAAGCCAAACTTCAGTGGACGTGA
GCCTGATCCAGGACGTGGAACGGA
TTCTCGACTACTCGCTGTGCCAGGA
GACCTGGTCGAAGATCAGAGCGGG
ACTGCCCATCTCACCGGTGGACCTG
TCCTACCTGGCGCCAAAGAATCCGG
GCACTGGACCGGCGTTCACCATCAT
CAACGGCACCCTCAAATACTTCGAG
ACGCGGTACATCCGGGTGGACATC
GCAGCTCCGATCCTCTCCCGGATGG
TGGGAATGATCTCGGGGACTACTAC
CGAACGCGAGCTCTGGGACGACTG
GGCACCTTACGAGGATGTCGAGAT
CGGACCTAACGGAGTGCTCCGGAC
CTCCTCCGGGTACAAGTTCCCTCTG
TACATGATCGGCCATGGCATGCTGG
ACTCGGATCTGCATCTGTCGTCCAA
AGCACAGGTGTTTGAACACCCACA
CATTCAAGACGCCGCCAGCCAGCT
GCCGGACGATGAGTCGCTGTTCTTC
GGAGACACGGGCTTGTCAAAGAAT
CCCATCGAGCTGGTGGAAGGATGG
TTTTCATCCTGGAAAAGCAGCATCG
CTTCATTCTTCTTCATCATTGGCCTG
ATCATCGGCCTATTTCTAGTCCTGC
GGGTGGGAATTCATCTGTGCATCAA
GCTCAAGCACACTAAGAAGCGGCA
AATCTACACTGATATCGAGATGAAT
CGCCTGGGCAAGTAG (SEQ ID NO:
96)

Trop-056 Mutated VSV-G

| Nucleotide | Amino acid |
|---|---|
| AAGTTCACTATCGTGTTTCCGCACA | KFTIVFPHNTTQKGNWKNVPSNYH |
| ACACCACACAAAAGGGCAACTGGA | YCPSSSDLNWHNDLIGTALQVKMP |
| AAAACGTGCCTTCAAATTACCATTA | KSHKAIQADGWMCHASKWVTTCD |
| TTGCCCCAGCAGCTCGGACCTGAAC | FRWYGPKYITHSIRSFTPSVEQCKES |
| TGGCACAATGACCTCATTGGAACCG | IEQTKQGTWLNPGFPPQSCGYATVT |
| CGCTGCAGGTGAAGATGCCAAAGA | DAEAVIVQVTPHHVLVDEYTGEWV |
| GCCACAAGGCTATCCAGGCTGACG | DSQFINGKCSNYICPTVHNSTTWHS |
| GATGGATGTGCCACGCGTCAAAAT | DYKVKGLCDSNLISMDITFFSEDGE |
| GGGTGACTACCTGCGATTTCCGCTG | LSSLGKEGTGFRSNYFAYETGGKA |
| GTACGGACCAAAATACATCACGCA | CKMQYCKHWGVRLPSGVWFEMA |
| CAGCATCAGATCATTCACCCCGTCA | DKDLFAAARFPECPEGSSISAPSQTS |
| GTGGAACAATGCAAAGAATCCATC | VDVSLIQDVERILDYSLCQETWSKI |
| GAACAGACTAAGCAGGGAACCTGG | RAGLPISPVDLSYLAPKNPGTGPAF |
| CTGAACCCTGGATTTCCGCCGCAGT | TIINGTLKYFETRYIRVDIAAPILSR |
| CGTGTGGGTACGCAACCGTGACCG | MVGMISGTTTERELWDDWAPYED |
| ATGCAGAGGCCGTGATCGTGCAAG | VEIGPNGVLRTSSGYKFPLYMIGHG |
| TCACGCCGCATCACGTGCTTGTGGA | MLDSDLHLSSKAQVFEHPHIQDAA |
| CGAGTACACCGGAGAATGGGTCGA | SQLPDDESLFFGDTGLSKNPIELVEG |
| TTCCCAGTTCATCAACGGCAAGTGC | WFSSWKSSIASFFFIIGLIIGLFLVLR |
| TCCAACTACATTTGCCCAACCGTGC | VGIHLCIKLKHTKKRQIYTDIEMNR |
| ACAACAGCACTACTTGGCACAGCG | LGK (SEQ ID NO: 99) |
| ACTACAAAGTGAAGGGTCTGTGTG | |
| ATTCCAACCTGATCTCCATGGATAT | |
| CACTTTCTTCTCGGAAGACGGCGAA | |
| CTGTCCTCACTGGGCAAAGAAGGA | |
| ACTGGGTTTCGCTCAAATTACTTCG | |
| CCTACGAAACTGGAGGAAAAGCCT | |
| GCAAGATGCAGTACTGCAAGCACT | |
| GGGGCGTGAGACTACCCAGCGGTG | |
| TCTGGTTCGAGATGGCCGATAAGG | |
| ACCTGTTTGCAGCAGCGAGATTCCC | |
| GGAATGCCCTGAGGGATCGAGCAT | |
| CTCCGCTCCAAGCCAAACTTCAGTG | |
| GACGTGAGCCTGATCCAGGACGTG | |
| GAACGGATTCTCGACTACTCGCTGT | |
| GCCAGGAGACCTGGTCGAAGATCA | |

TABLE 10-continued

WT VSV-G reference and mutant sequences

```
GAGCGGGACTGCCCATCTCACCGGT
GGACCTGTCCTACCTGGCGCCAAAG
AATCCGGGCACTGGACCGGCGTTC
ACCATCATCAACGGCACCCTCAAAT
ACTTCGAGACGCGGTACATCCGGGT
GGACATCGCAGCTCCGATCCTCTCC
CGGATGGTGGGAATGATCTCGGGG
ACTACTACCGAACGCGAGCTCTGG
GACGACTGGGCACCTTACGAGGAT
GTCGAGATCGGACCTAACGGAGTG
CTCCGGACCTCCTCCGGGTACAAGT
TCCCTCTGTACATGATCGGCCATGG
CATGCTGGACTCGGATCTGCATCTG
TCGTCCAAAGCACAGGTGTTTGAAC
ACCCACACATTCAAGACGCCGCCA
GCCAGCTGCCGGACGATGAGTCGC
TGTTCTTCGGAGACACGGGCTTGTC
AAAGAATCCCATCGAGCTGGTGGA
AGGATGGTTTTCATCCTGGAAAAGC
AGCATCGCTTCATTCTTCTTCATCAT
TGGCCTGATCATCGGCCTATTTCTA
GTCCTGCGGGTGGGAATTCATCTGT
GCATCAAGCTCAAGCACACTAAGA
AGCGGCAAATCTACACTGATATCG
AGATGAATCGCCTGGGCAAGTAG
(SEQ ID NO: 98)
```

Trop-058 Mutated VSV-G

| Nucleotide | Amino acid |
|---|---|
| AAGTTCACTATCGTGTTTCCGCACA | KFTIVFPHNQKGNWKNVPSNYHYC |
| ACCAAAAGGGCAACTGGAAAAACG | PSSSDLNWHNDLIGTALQVKMPGG |
| TGCCTTCAAATTACCATTATTGCCC | SKSHKAIQADGWMCHASKWVTTC |
| CAGCAGCTCGGACCTGAACTGGCA | DFRWYGPKYITHSIRSFTPSVEQCK |
| CAATGACCTCATTGGAACCGCGCTG | ESIEQTKQGTWLNPGFPPQSCGYAT |
| CAGGTGAAGATGCCAGGCGGCAGC | VTDAEAVIVQVTPHHVLVDEYTGE |
| AAGAGCCACAAGGCTATCCAGGCT | WVDSQFINGKCSNYICPTVHNSTT |
| GACGGATGGATGTGCCACGCGTCA | WHSDYKVKGLCDSNLISMDITFFSE |
| AAATGGGTGACTACCTGCGATTTCG | DGELSSLGKEGTGFRSNYFAYETG |
| GCTGGTACGGACCAAAATACATCA | GKACKMQYCKHWGVRLPSGVWFE |
| CGCACAGCATCAGATCATTCACCCC | MADKDLFAAARFPECPEGSSISAPS |
| GTCAGTGGAACAATGCAAAGAATC | QTSVDVSLIQDVERILDYSLCQETW |
| CATCGAACAGATCTAAGCAGGGAAC | SKIRAGLPISPVDLSYLAPKNPGTGP |
| CTGGCTGAACCCTGGATTTCCGCCG | AFTIINGTLKYFETRYIRVDIAAPILS |
| CAGTCGTGTGGGTACGCAACCGTG | RMVGMISGTTTERELWDDWAPYE |
| ACCGATGCAGAGGCCGTGATCGTG | DVEIGPNGVLRTSSGYKFPLYMIGH |
| CAAGTCACGCCGCATCACGTGCTTG | GMLDSDLHLSSKAQVFEHPHIQDA |
| TGGACGAGTACACCGGAGAATGGG | ASQLPDDESLFFGDTGLSKNPIELVE |
| TCGATTCCCAGTTCATCAACGGCAA | GWFSSWKSSIASFFFIIGLIIGLFLVL |
| GTGCTCCAACTACATTTGCCCAACC | RVGIHLCIKLKHTKKRQIYTDIEMN |
| GTGCACAACAGCACTACTTGGCAC | RVGIHLCIKLKHTKKRQIYTDIEMN |
| AGCGACTACAAAGTGAAGGGTCTG | RLGK (SEQ ID NO: 101) |
| TGTGATTCCAACCTGATCTCCATGG | |
| ATATCACTTTCTTCTCGGAAGACGG | |
| CGAACTGTCCTCACTGGGCAAAGA | |
| AGGAACTGGGTTTCGCTCAAATTAC | |
| TTCGCCTACGAAACTGGAGGAAAA | |
| GCCTGCAAGATGCAGTACTGCAAG | |
| CACTGGGGCGTGAGACTACCCAGC | |
| GGTGTCTGGTTCGAGATGGCCGATA | |
| AGGACCTGTTTGCAGCAGCGAGATT | |
| CCCGGAATGCCCTGAGGGATCGAG | |
| CATCTCCGCTCCAAGCCAAACTTCA | |
| GTGGACGTGAGCCTGATCCAGGAC | |
| GTGGAACGGATTCTCGACTACTCGC | |
| TGTGCCAGGAGACCTGGTCGAAGA | |
| TCAGAGCGGGACTGCCCATCTCACC | |
| GGTGGACCTGTCCTACCTGGCGCCA | |
| AAGAATCCGGGCACTGGACCGGCG | |
| TTCACCATCATCAACGGCACCCTCA | |
| AATACTTCGAGACGCGGTACATCCG | |
| GGTGGACATCGCAGCTCCGATCCTC | |
| TCCCGGATGGTGGGAATGATCTCGG | |
| GGACTACTACCGAACGCGAGCTCT | |
| GGGACGACTGGGCACCTTACGAGG | |
| ATGTCGAGATCGGACCTAACGGAG | |
| TGCTCCGGACCTCCTCCGGGTACAA | |

TABLE 10-continued

| WT VSV-G reference and mutant sequences |
|---|
| GTTCCCTCTGTACATGATCGGCCAT<br>GGCATGCTGGACTCGGATCTGCATC<br>TGTCGTCCAAAGCACAGGTGTTTGA<br>ACACCCACACATTCAAGACGCCGC<br>CAGCCAGCTGCCGGACGATGAGTC<br>GCTGTTCTTCGGAGACACGGGCTTG<br>TCAAAGAATCCCATCGAGCTGGTG<br>GAAGGATGGTTTTCATCCTGGAAAA<br>GCAGCATCGCTTCATTCTTCTTCAT<br>CATTGGCCTGATCATCGGCCTATTT<br>CTAGTCCTGCGGGTGGGAATTCATC<br>TGTGCATCAAGCTCAAGCACACTAA<br>GAAGCGGCAAATCTACACTGATAT<br>CGAGATGAATCGCCTGGGCAAGTA<br>G (SEQ ID NO: 100) |

| Trop-061 Mutated VSV-G | |
|---|---|
| Nucleotide | Amino acid |
| AAGTTCACTATCGTGTTTCCGCAC<br>GGCGGAAGCAACGGCGGGAGCCA<br>AAAGGGCAACTGGAAAAACGTGC<br>GCAGCTCGGACCTGAACTGGCAC<br>AATGACCTCATTGGAACCGCGCT<br>GCAGGTGAAGATGCCAAAGAGCC<br>ACAAGGCTATCCAGGCTGACGGA<br>TGGATGTGCCACGCGTCAAAATG<br>GGTGACTACCTGCGATTTCCGCTG<br>GTACGGACCAAAATACATCACGC<br>ACAGCATCAGATCATTCACCCCGT<br>CAGTGGAACAATGCAAAGAATCC<br>ATCGAACAGACTAAGCAGGGAAC<br>CTGGCTGAACCCTGGATTTCCGCC<br>GCAGTCGTGTGGGTACGCAACCG<br>TGACCGATGCAGAGGCCGTGATC<br>GTGCAAGTCACGCCGCATCACGT<br>GCTTGTGGACGAGTACACCGGAG<br>AATGGGTCGATTCCCAGTTCATCA<br>ACGGCAAGTGCTCCAACTACATTT<br>GCCCAACCGTGCACAACAGCACT<br>ACTTGGCACAGCGACTACAAAGT<br>GAAGGGTCTGTGTGATTCCAACCT<br>GATCTCCATGGATATCACTTTCTT<br>CTCGGAAGACGGCGAACTGTCCT<br>CACTGGGCAAAGAAGGAACTGGG<br>TTTCGCTCAAATTACTTCGCCTAC<br>GAAACTGGAGGAAAAGCCTGCAA<br>GATGCAGTACTGCAAGCACTGGG<br>GCGTGAGACTACCCAGCGGTGTC<br>TGGTTCGAGATGGCCGATAAGGA<br>CCTGTTTGCAGCAGCGAGATTCCC<br>GGAATGCCCTGAGGGATCGAGCA<br>TCTCCGCTCCAAGCCAAACTTCAG<br>TGGACGTGAGCCTGATCCAGGAC<br>GTGGAACGGATTCTCGACTACTCG<br>CTGTGCCAGGAGACCTGGTCGAA<br>GATCAGAGCGGGACTGCCCATCT<br>CACCGGTGGACCTGTCCTACCTGG<br>CGCCAAAGAATCCGGGCACTGGA<br>CCGGCGTTCACCATCATCAACGGC<br>ACCCTCAAATACTTCGAGACGCG<br>GTACATCCGGGTGGACATCGCAG<br>CTCCGATCCTCTCCCGGATGGTGG<br>GAATGATCTCGGGGACTACTACC<br>GAACGCGAGCTCTGGGACGACTG<br>GGCACCTTACGAGGATGTCGAGA<br>TCGGACCTAACGGAGTGCTCCGG<br>ACCTCCTCCGGGTACAAGTTCCCT<br>CTGTACATGATCGGCCATGGCATG<br>CTGGACTCGGATCTGCATCTGTCG<br>TCCAAAGCACAGGTGTTTGAACA<br>CCCACACATTCAAGACGCCGCCA<br>GCCAGCTGCCGGACGATGAGTCG<br>CTGTTCTTCGGAGACACGGGCTTG<br>TCAAAGAATCCCATCGAGCTGGT<br>GGAAGGATGGTTTTCATCCTGGA<br>AAAGCAGCATCGCTTCATTCTTCT | KFTIVFPHGGSNGGSQKGNWKNVPS<br>NYHYCPSSSDLNWHNDLIGTALQVK<br>MPKSHKAIQADGWMCHASKWVTTC<br>DFRWYGPKYITHSIRSFTPSVEQCKES<br>IEQTKQGTWLNPGFPPQSCGYATVTD<br>AEAVIVQVTPHHVLVDEYTGEWVDS<br>QFINGKCSNYICPTVHNSTTWHSDYK<br>VKGLCDSNLISMDITFFSEDGELSSLG<br>KEGTGFRSNYFAYETGGKACKMQYC<br>KHWGVRLPSGVWFEMADKDLFAAA<br>RFPECPEGSSISAPSQTSVDVSLIQDVE<br>RILDYSLCQETWSKIRAGLPISPVDLS<br>YLAPKNPGTGPAFTIINGTLKYFETRY<br>IRVDIAAPILSRMVGMISGTTTERELW<br>DDWAPYEDVEIGPNGVLRTSSGYKFP<br>LYMIGHGMLDSDLHLSSKAQVFEHP<br>HIQDAASQLPDDESLFFGDTGLSKNPI<br>ELVEGWFSSWKSSIASFFFIIGLIIGLFL<br>VLRVGIHLCIKLKHTKKRQIYTDIEM<br>NRLGK (SEQ ID NO: 103) |

TABLE 10-continued

WT VSV-G reference and mutant sequences

```
TCATCATTGGCCTGATCATCGGCC
TATTTCTAGTCCTGCGGGTGGGAA
TTCATCTGTGCATCAAGCTCAAGC
ACACTAAGAAGCGGCAAATCTAC
ACTGATATCGAGATGAATCGCCT
GGGCAAGTAG (SEQ ID NO: 102)
```

In other embodiments, the methods for producing LVV according to the present disclosure may utilize a five plasmid system. Where a five plasmid system is used, the LVV production system utilizes four plasmids from a third generation vector system (i.e., a transgene plasmid, a GagPol plasmid, an Env plasmid, and a VSV-G env plasmid). In addition, a five plasmid system as described herein includes a fifth plasmid that encodes a targeting protein (the "targeting protein plasmid"). The GagPol and Env packaging plasmids included in a five plasmid system may be standard packaging plasmids as described in *Production of Lentiviral Vectors*, Merten et al., *Molecular Therapy—Methods & Clinical Development* (2016), 3, 16017. The transgene plasmid includes an expression cassette that encodes one or more CAR transgenes according to the present disclosure, and the VSV-G env plasmid includes an expression cassette that encodes a mutant VSV-G as described herein.

In some embodiment, the fifth plasmid comprises an expression cassette encoding a CD80 targeting protein In some embodiments, the fifth plasmid comprises an expression cassette encoding an anti-CD3 targeting protein. In some embodiments, the fifth plasmid comprises an expression cassette encoding a CD80 targeting protein and an anti-CD3 targeting protein. Examples of CD80 targeting protein and anti-CD3 targeting proteins that may be used in the fifth plasmid are provided in Tables 1-3.

In certain embodiments, the present disclosure provides a method for producing a lymphocyte targeted lentiviral vector according to any one of the preceding claims, the method comprising: transfecting a producer cell with a GagPol plasmid, a Rev plasmid, a transgene plasmid, a VSV-G env plasmid, and a lymphocyte targeting protein plasmid; the GagPol plasmid comprises a one or more polynucleotides encoding a lentiviral gag gene and a lentiviral pol gene and is capable of expressing a lentiviral gag protein and a lentiviral pol protein within the producer cell; the Rev plasmid comprises a polynucleotide encoding a lentiviral rev gene and is capable expressing a lentiviral rev protein within the producer cell; the transgene plasmid comprises an expression cassette comprising a polynucleotide encoding a CAR; and the VSV-G env plasmid comprises a polynucleotide encoding a mutated VSV-G envelope protein as described herein and is capable of expressing the mutated VSV-G envelope protein within the producer cell; and the lymphocyte targeting protein plasmid comprises a polynucleotide encoding a lymphocyte targeting protein as described herein and is capable of expressing the lymphocyte targeting protein within the producer cell; culturing the producer cell in a culture medium; and harvesting lentiviral vector from the culture medium.

In some embodiments, the producer cells are transfected with a defined ratio of the transgene plasmid, GagPol plasmid, VSV-G env plasmid, Rev plasmid, and lymphocyte targeting plasmid. The lymphocyte targeting plasmid may be at a ratio of about 0.25 to about 5 relative to the VSV-G env plasmid (by mass). For example, using the defined ratios for the four packaging plasmid system (transgene plasmid, GagPol plasmid, VSV-G env plasmid, Rev plasmid) described herein, the ratio of the lymphocyte targeting protein plasmid can be adjusted relative to the VSV-G env plasmid. For example, the lymphocyte targeting plasmid may be at a ratio of about 0.25:1, 0.5:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1 or 5:1 relative to the VSV-G env plasmid.

In embodiments of LVV production methods that utilize a combination of five plasmids, the fifth plasmid is a targeting protein plasmid and includes an expression cassette that encodes one or more targeting proteins. For example the targeting protein plasmid may include an expression cassette that includes a polynucleotide that encodes a CD80 targeting protein, an anti-CD3 targeting protein, or both a CD80 targeting protein and an anti-CD3 targeting protein. In certain embodiments, a targeting protein vector plasmid an expression cassette comprising a polynucleotide according to SEQ ID NO: 1, which encodes a CD80 targeting protein according to SEQ ID NO: 2. In other embodiments, a targeting protein plasmid includes an expression cassette comprising a polynucleotide according to SEQ ID NO: 9, which encodes an anti-CD3 targeting protein according to SEQ ID NO: 10. In other embodiments, a targeting protein plasmid includes an expression cassette comprising a polynucleotide according to SEQ ID NO: 116, which encodes an anti-CD3 targeting protein according to SEQ ID NO: 117. In other embodiments, a targeting protein plasmid includes a tandem expression cassette that comprises a polynucleotide according to SEQ ID NO: 21, which encodes a polypeptide according to SEQ ID NO: 22. Examples of mutated VSV-G sequences that may be used in the five plasmid, 3rd generation lentiviral vector system of the present disclosure are provided in Table 10.

In the four plasmid packaging system, the concentration of the lymphocyte targeting protein on the surface of the transduced cells may be associated with the concentration of the plasmid containing the targeting protein. For example if the lymphocyte targeting protein plasmid plasmid is contained in the VSV-G env plasmid, the concentration of the lymphocyte targeting protein on the surface of the transduced cells may be associated with the concentration of the VSV-G env plasmid. In another example, if the lymphocyte targeting protein plasmid plasmid is contained in the GagPol plasmid, the concentration of the lymphocyte targeting protein on the surface of the transduced cells may be associated with the concentration of the GagPol plasmid. In another example, if the lymphocyte targeting protein plasmid plasmid is contained in the Rev plasmid, the concentration of the lymphocyte targeting protein on the surface of the transduced cells may be associated with the concentration of the Rev plasmid. In the five plasmid packaging system, the concentration of the lymphocyte targeting protein on the surface of the transduced cells may be associated with the concentration of the plasmid containing the targeting protein.

In the four plasmid packaging system, the transduction efficiency may be associated with the concentration of the plasmid containing the targeting protein. For example if the lymphocyte targeting protein plasmid plasmid is contained in the VSV-G env plasmid, the transduction efficiency may be associated with the concentration of the VSV-G env plasmid. In another example, if the lymphocyte targeting protein plasmid plasmid is contained in the GagPol plasmid, the transduction efficiency may be associated with the concentration of the GagPol plasmid. In another example, if the lymphocyte targeting protein plasmid plasmid is contained in the Rev plasmid, the transduction efficiency may be associated with the concentration of the Rev plasmid. In the five plasmid packaging system, the transduction efficiency of may be associated with the concentration of the lymphocyte targeting protein plasmid.

Following transfection of producer cells, the lentiviral particles product may be harvested from the cell supernatant or culture media. Downstream processes of LVV to maximize LVV recovery while minimizing components which may negatively impact efficacy or safety are known in the art. A typical process, involves sequential purification steps comprising removing cells and their debris followed by enrichment of LVV and the removal of host cell or serum proteins, nucleic acids and lipids. The LVV product may be further concentrated prior to exchanging into a suitable formulation buffer for stability and then finally undergoing sterile filtration prior to storage or application. A clarification step may be initially performed on the harvested LVV supernatants to remove large impurities such as aggregates and cell debris. In some embodiments, the clarification step comprises centrifugation and/or conventional flow filtration. In some embodiments, the clarification step includes a nuclease digestion step. In some embodiments, the LVV product undergoes further purification steps, including for example, ion exchange chromatography (e.g., anion exchange chromatography). The LVV may also be concentrated, e.g., by tangential flow filtration or ultrafiltration/diafiltration. In some embodiments, harvesting LVV from culture medium comprises centrifugation. In some embodiments, harvesting LVV from culture medium comprises anion exchange chromatography, In some embodiments, harvesting LVV from culture medium comprises anion exchange chromatography and tangential flow filtration.

In some embodiments, the lentiviral vectors described herein, which incorporate a mutated VSV-G env and one or more lymphocyte targeting proteins, are capable of producing a high titer LVV product, as compared to standard LVV incorporating another fusogenic env protein (e.g., cocal env, paramyxovirus env, truncated VSV-G env). As used herein viral titer refers to infectious virus particle titer as measured by transducing units (TU) per mL. In some embodiments, the titer of LVV described herein is at least 1e7 TU/mL, at least 1e8 TU/mL, at least 1e9 TU/mL, at least 1e10 TU/mL, at least 1e11 TU/mL, or at least 1e12 TU/mL as measured in concentrated LVV product. In some embodiments, the titer of LVV described herein is about 1e7 TU/mL to about 1e12 TU/mL in concentrated LVV product.

Engineered Lymhocytes

The LVV described herein can be used to modify targeted lymphocytes (e.g., T cells, B cells, or NK cells) to express a CAR encoded by a transgene carried by the LVV. In certain embodiments, the engineered lymphocytes have been transduced by an LVV according to the present disclosure by contacting the lymphocytes with the LVV of the present disclosure. In such embodiments, the engineered lymphocytes (e.g., T cells, B cells, or NK cells) express a CAR encoded by the transgene carried by the LVV. These lymphocytes are also referred to herein as "CAR modified lymphocytes." In specific embodiments, the engineered T cells are referred to herein as "CAR modified T cells." In other specific embodiments, the engineered NK cells are referred to herein as "CAR modified NK cells." In specific embodiments, the engineered T cells are referred to herein as "CAR modified B cells." In specific embodiments the CAR modified T cell expresses a CAR encoded by a transgene carried by an LVV described herein and is selected from naïve T cells (CD45RA+, CCR7+, CD62L+, CD27+, CD45RO−), central memory T cells (CD45RA−, CD45RO$^+$, CD62L$^+$, CCR7+, CD27+), effector memory T cells (CD45RA−, CD45RO+, CCR7−, CD62L−, CD27−), 76 T cells, mucosal-associated invariant T (MAIT) cells, Tregs, natural killer T cells, and tissue resident T cells.

Transduction of targeted lymphocytes (e.g., T cells, B cells, or NK cells) by LVV described herein may be performed ex vivo or in vivo.

In certain embodiments, the lymphocytes (e.g., T cells, B cells, or NK cells) can be primary cells or cell lines derived from human, mouse, rat, or other mammals. If obtained from a mammal, a lymphocyte can be obtained from numerous sources, including blood, bone marrow, lymph node, thymus, or other tissues or fluids. A lymphocyte composition (e.g., T cell composition, B cell composition, or NK cell composition) may be enriched or purified. T cell lines are well known in the art, some of which are described in Sandberg et al., *Leukemia* 21:230, 2000. In certain embodiments, the T cells lack endogenous expression of a TCRα gene, TCRβ gene, or both. Such T cells may naturally lack endogenous expression of TCRα and β chains, or may have been modified to block expression (e.g., T cells from a transgenic mouse that does not express TCR α and β chains or cells that have been manipulated to inhibit expression of TCR α and β chains) or to knockout a TCRα chain, a TCRρ chain, or both genes.

In some embodiments, prior to genetic modification of the lymphocytes (e.g., T cells, B cells, or NK cells) with a polynucleotide encoding a CAR molecule, a source of lymphocytes (e.g., T cells or NK cells) may be obtained from a subject (e.g., whole blood, peripheral blood mononuclear cells (PBMCs), bone marrow, lymph node tissue, cord blood, thymus tissue, tissue from a site of infection, ascites, pleural effusion, spleen tissue). The lymphocytes, T cells, B cells, or NK cells can be enriched or isolated from a sample taken from the subject using methods known in the art. For example, T cells can be enriched in a whole blood sample taken from a subject using known methods for hypotonic lysis of red blood cells or T cells can be isolated from a sample taken from a subject using known gradient sedimentation, e.g., Ficoll® reduction) techniques. Alternatively, T cells can be isolated from whole blood using magnetic antibody-labeled beads followed by column separation. Specific host cell subsets can be collected in accordance with known techniques and enriched or depleted by known techniques, such as affinity binding to antibodies, flow cytometry and/or immunomagnetic selection. In some embodiments, after enrichment and/or depletion steps, the T cells are placed in contact with LVV as disclosed such that T cells obtained from the subject are transduced by the LVV and express the CAR encoded by the transgene carried by the LVV. In some embodiments, after enrichment and/or depletion steps, the NK cells are placed in contact with LVV as disclosed such that NK cells obtained from the subject are transduced by the LVV and express the CAR encoded by the transgene carried by the LVV. In some embodiments, after enrichment and/or depletion steps, the B cells are placed in contact with LVV as disclosed such that B cells obtained from the subject are transduced by the LVV and express the CAR encoded by the transgene carried by the LVV.

Generally, resting T cells, such as resting CD4 and CD8 lymphocytes, resting B cells, and resting NK cells are refractory to genetic transduction by lentiviral vectors. Resting T cells, also known as quiescent T cells or naïve T cells, refer to T cells that are not mitotically active or have not been exposed to a cognate antigen presented on an antigen presenting cell, such as a macrophage or dendritic cell. An example of a marker for resting T cells is CD28. Alternatively, markers that are expressed on activated T cells but not resting T cells include, for example, 4-1BB, PD-1, and HLA-DR. Similarly, resting B cells and resting NK cells, refer to B cells and NK cells that are not mitotically active or have not been exposed to a cognate antigen, respectively. Examples of markers for resting B cells include CD21 and CD23, and the absence of CD80, CD86, CD95, or CD25. CD137 and GITR, which are expressed on activated NK cells, are absent on resting NK cells. As a result, in order to facilitate transduction of T cells, B cells, or NK cells using a lentiviral vector, the T cells, B cells, or NK cells are typically activated in vitro using stimulation reagents before genetic modification via a lentiviral vector can occur. Following stimulation and transduction, the genetically modified cells are then typically expanded in vitro and subsequently reintroduced into a patient. However, LVV described herein are capable of transducing resting T cells, B cells, and/or resting NK cells. In certain embodiments, methods of transducing T cells with an LVV according to the present description include, placing the LVV in contact with a population of T cells, wherein in the T cells are not activated and the T cells are not exposed to an exogenous stimulating agent during the transduction process. In some such embodiments, the methods of transducing T cells wherein the T cells are not activated and the T cells are not exposed to an exogenous stimulating agent during the transduction process comprises transducing T cells with a LVV comprising a CD80 targeting protein, an anti-CD3 targeting protein, or both a CD80 targeting protein and an anti-CD3 targeting protein. Examples of exogenous T cell stimulating agents include an anti-CD3 antibody or antigen binding fragment thereof (i.e., anti-CD3 antibody or antigen binding fragment thereof that is not part of the LVV), an anti-CD28 antibody or antigen binding fragment thereof (i.e., anti-CD28 antibody or antigen binding fragment thereof that is not part of the LVV), anti-CD2 antibody or antigen binding fragment thereof, IL-2, IL-7, IL-15, PHA, or any combination thereof. Exogenous stimulating agents may be contacted to the T cell in soluble form or immobilized on a solid substrate, such as a bead or cell culture plate. In some embodiments, an anti-CD3 antibody or antigen binding fragment thereof, an anti-CD28 antibody or antigen binding fragment thereof, or both the anti-CD3 antibody and anti-CD28 antibody or antigen binding fragments thereof are contacted to the T cells in soluble form or immobilized on a solid substrate. Examples of anti-CD3 antibodies include OKT3, UCTH1, and BW264/56. An example of an anti-CD2 antibody is LT2. An example of an anti-CD28 antibody is 15E8. In certain embodiments, methods of transducing NK cells with an LVV according to the present description include, placing the LVV in contact with a population of NK cells, wherein in the NK cells are not activated and the NK cells are not exposed to an exogenous stimulating agent during the transduction process. Examples of exogenous NK cell stimulating agents include anti-CD2 antibody or antigen binding fragment thereof, anti-CD335 antibody or antigen binding fragment thereof, IL-2, IL-15, IL-12, IL-18, IL-21, or any combination thereof. In certain embodiments, methods of transducing B cells with an LVV according to the present description include, placing the LVV in contact with a population of B cells, wherein in the B cells are not activated and the B cells are not exposed to an exogenous stimulating agent during the transduction process. Examples of exogenous B cell stimulating agents include CD154 and mixed Ig F(ab)$_2$.

In some embodiments, a lentiviral vector having a CD80 targeting protein and an anti-CD3 targeting protein is capable of efficiently transducing both CD4 and CD8 T cells as compared to standard LVV.

In some embodiments, a lentiviral vector having a CD80 targeting protein and an anti-CD3 targeting protein is capable of activating T cells without exogenous stimulation (e.g., T cell stimulating agent) to a comparable level as T cells transduced with standard LVV that are treated with exogenous stimulation. Examples of exogenous T cell stimulating agents include an anti-CD3 antibody or antigen binding fragment thereof (i.e., anti-CD3 antibody or antigen binding fragment thereof that is not part of the LVV), an anti-CD28 antibody or antigen binding fragment thereof (i.e., anti-CD28 antibody or antigen binding fragment thereof that is not part of the LVV), anti-CD2 antibody or antigen binding fragment thereof, IL-2, IL-7, IL-15, PHA, or any combination thereof.

In certain embodiments, methods of transducing T cells with an LVV according to the present description exhibit enhanced transduction of CD4 T cells compared to standard LVV. In some such embodiments, the methods of enhancing transduction of CD4 T cells in a mixed population of T cells (e.g., composed of CD4 and CD8 T cells) comprises transducing the mixed population of T cells with a LVV according to the present description comprising a CD80 targeting protein.

In certain embodiments, methods of transducing T cells with an LVV according to the present description efficiently transduce both CD4 and CD8 T cells. In some such embodiments, the methods of transducing T cells wherein both CD4 and CD8 T cells are efficiently transduced comprises transducing T cells with a LVV comprising a CD80 targeting protein and an anti-CD3 targeting protein.

In certain embodiments, an LVV according to the present description is capable of transducing T cells under "stressed" conditions, e.g., at low multiplicity of infection (MOI) or without treatment with exogenous IL-2 during transduction. In some embodiments, the LVV comprises a CD80 targeting protein and an anti-CD3 targeting protein. In some embodiments, the LVV according to the present description is capable of transducing T cells at a LVV concentration about 5 to about 25× lower than a non-lymphocyte targeting LVV.

The expression of a CAR molecule on host cells may be assessed by methods known in the art, such as quantitative PCR or flow cytometry following staining with a fluorescently labeled antigen for the CAR binding domain.

The expression of a CAR molecule on host cells may be functionally characterized according to any of a large number of art-accepted methodologies for assaying host T cell activity, including determination of T cell binding, activation or induction and also including determination of T cell responses that are antigen-specific. Examples include determination of T cell proliferation, T cell cytokine release, antigen-specific T cell stimulation, CTL activity (e.g., by detecting $^{51}$Cr or Europium release from pre-loaded target cells, induction of caspase activity in target cells, extracellular release of lactate dehydrogenase by target cells), changes in T cell phenotypic marker expression, and other measures of T cell functions. Assaying host NK cell activity may also be assayed using similar methodologies. Procedures for performing these and similar assays are may be found, for example, in Lefkovits (*Immunology Methods Manual: The Comprehensive Sourcebook of Techniques*, 1998). See, also, *Current Protocols in Immunology*; Weir, *Handbook of Experimental Immunology*, Blackwell Scientific, Boston, M A (1986); Mishell and Shigii (eds.) *Selected Methods in Cellular Immunology*, Freeman Publishing, San Francisco, C A (1979); Green and Reed, Science 281:1309 (1998) and references cited therein. Cytokine levels may be determined according to methods known in the art, including for example, ELISA, ELISPOT, intracellular cytokine staining, flow cytometry, and any combination thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like.

Methods of & Compositions for Treatment

In one aspect, the present disclosure provides methods of treating a disease in a subject comprising administering to the subject an effective amount of an LVV as described herein, a CAR modified lymphocyte (e.g., T cell, B cell, or NK cell) as described herein, or pharmaceutical compositions thereof. In another aspect, the methods of treating a disease in a subject according to the present description include administering to the subject an effective amount of an LVV as described herein, a CAR modified lymphocyte (e.g., T cell, B cell, or NK cell) as described herein, or pharmaceutical compositions thereof, in combination with one or more additional therapeutic agents.

Diseases that may be treated with the LVV or CAR modified lymphocytes (e.g., T cells, B cells, or NK cells) according to the present description include cancers. Adoptive immune and gene therapies are promising treatments for various types of cancer (Morgan et al., Science 314:126, 2006; Schmitt et al., Hum. Gene Ther. 20:1240, 2009; June, J. Clin. Invest. 117:1466, 2007) and infectious disease (Kitchen et al., PLoS One 4:38208, 2009; Rossi et al., Nat. Biotechnol. 25:1444, 2007; Zhang et al., PLoS Pathog. 6:e1001018, 2010; Luo et al., J. Mol. Med. 89:903, 2011).

A wide variety of cancers, including solid tumors and leukemias are amenable to the compositions and methods disclosed herein. Exemplary cancers that may be treated using the receptors, modified host cells, and composition described herein include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated using the receptors, modified host cells, and composition described herein include histiocytic disorders; malignant histiocytosis; leukemia; Hodgkin's disease; immunoproliferative small; non-Hodgkin's lymphoma; plasmacytoma; multiple myeloma; chronic myeloid leukemia (CML); acute myeloid leukemia (AML); plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment using the receptors, modified host cells, and composition described herein: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; cervical dysplasia, and peritoneal cancer.

Examples of hyperproliferative disorders amenable to therapy using the receptors, modified host cells, and composition described herein include B-cell cancers (B-cell malignancies), including B-cell lymphomas (such as various forms of Hodgkin's disease, non-Hodgkin's lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia, acute myeloid leukemia (AML), chronic myeloid leukemia, and myelomas (such as multiple myeloma). Additional B cell cancers that may be treated using the receptors, modified host cells, and composition described herein include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

The CAR modified lymphocytes included in the compositions disclosed herein and administered to a subject may include, CAR modified T cells, e.g., CD4+ T cells, CD8+ T cells, Natural Killer T cells, gamma delta T cells, or MAIT cells; CAR modified B cells, or CAR modified NK cells. In certain embodiments, methods of treating a subject comprise administering an effective amount of an LVV as described herein or CAR modified lymphocytes (i.e., recombinant cells that express one or more CARs) according to the present disclosure. In some embodiments, CAR modified T cells are administered to a subject. In some embodiments, CAR modified NK cells are administered to a subject. In some embodiments, CAR modified B cells are administered to a subject. The CAR modified lymphocytes (e.g., T cells, B cells, or NK cells) may be xenogeneic, syngeneic, allogeneic, or autologous to the subject.

Pharmaceutical compositions including the LVV or CAR engineered lymphocytes may be administered in a manner appropriate to the disease or condition to be treated (or prevented) as determined by persons skilled in the medical art. An appropriate dose, suitable duration, and frequency of administration of the compositions will be determined by such factors as the condition of the patient, size, weight, body surface area, age, sex, type and severity of the disease, particular therapy to be administered, particular form of the active ingredient, time and the method of administration, and other drugs being administered concurrently. The present disclosure provides pharmaceutical compositions comprising LVV or CAR modified lymphocytes and a pharmaceutically acceptable carrier, diluent, or excipient. Suitable excipients include water, saline, dextrose, glycerol, or the like and combinations thereof. Other suitable infusion medium can be any isotonic medium formulation, including saline, Normosol R (Abbott), Plasma-Lyte A (Baxter), 5% dextrose in water, or Ringer's lactate.

A treatment effective amount of engineered lymphocytes (e.g., T cells, B cells, or NK cells) in a pharmaceutical composition is at least one cell (for example, one CAR modified T cell) and is more typically greater than $10^2$ cells, for example, up to $10^6$, up to $10^7$, up to $10^8$ cells, up to $10^9$ cells, up to $10^{10}$ cells, or up to $10^{11}$ cells or more. In certain embodiments, the cells are administered in a range from about $10^6$ to about $10^{10}$ cells/m$^2$, preferably in a range of about $10^7$ to about $10^9$ cells/m$^2$. The number of cells will depend upon the ultimate use for which the composition is intended as well the type of cells included therein. For example, a composition comprising T cells modified to contain a CAR will comprise a T cell population containing from about 5% to about 95% or more of such cells. In certain embodiments, a composition comprising CAR modified T cells comprises a cell population comprising at least 5%, 10%, 15%, 20%, 25%, 30%, 35%, 40%, 45%, 50%, 55%, 60%, 65%, 70%, 75%, 80%, 85%, 90%, 95% or more of such cells. In certain embodiments, a composition comprising CAR modified NK cells comprises a cell population comprising at least 5%, 10%, 15%, 20%, 25%, 30%, 35%, 40%, 45%, 50%, 55%, 60%, 65%, 70%, 75%, 80%, 85%, 90%, 95% or more of such cells. In certain embodiments, a composition comprising CAR modified B cells comprises a cell population comprising at least 5%, 10%, 15%, 20%, 25%, 30%, 35%, 40%, 45%, 50%, 55%, 60%, 65%, 70%, 75%, 80%, 85%, 90%, 95% or more of such cells. For uses provided herein, the lymphocytes (e.g., T cells, B cells, or NK cells) are generally in a volume of a liter or less, 500 mls or less, 250 mls or less, or 100 mls or less. Hence the density of the desired cells is typically greater than 104 cells/ml and generally is greater than $10^7$ cells/ml, generally $10^8$ cells/ml or greater. The lymphocytes (e.g., T cells, B cells, or NK cells) may be administered as a single infusion or in multiple infusions over a range of time. Repeated infusions of CAR modified lymphocytes (e.g., T cells, B cells, or NK cells) may be separated by days, weeks, months, or even years if relapses of disease or disease activity are present. A clinically relevant number of immune cells can be apportioned into multiple infusions that cumulatively equal or exceed $10^6$, $10^7$, $10^8$, $10^9$, $10^{10}$, or $10^{11}$ cells. A preferred dose for administration of a host cell comprising a recombinant expression vector as described herein is about $10^7$ cells/m$^2$, about 5×$10^7$ cells/m$^2$, about $10^8$ cells/m$^2$, about 5×$10^8$ cells/m$^2$, about $10^9$ cells/m$^2$, about 5×$10^9$ cells/m$^2$, about $10^{10}$ cells/m$^2$, about 5×$10^{10}$ cells/m$^2$, or about $10^{11}$ cells/m$^2$.

The LVV and/or CAR modified lymphocyte (e.g., T cell, B cell, or NK cell) compositions as described herein may be administered to a subject intravenously, intraperitoneally, intratumorly, into the bone marrow (e.g., intraosseous administration), into the lymph node (intranodally), and/or into cerebrospinal fluid.

The LVV vectors and/or CAR modified lymphocyte (e.g., T cell, B cell, or NK cell) compositions may be administered to a subject in combination with one or more additional therapeutic agents. Examples of therapeutic agents that may be administered in combination with the LVV vectors or CAR modified lymphocyte (e.g., T cell, B cell, or NK cell) according to the present description include radiation therapy, adoptive cellular immunotherapy agent (e.g., recombinant TCR, enhanced affinity TCR, CAR, TCR-CAR, scTCR fusion protein, dendritic cell vaccine), antibody therapy, immune checkpoint molecule inhibitor therapy, UV light therapy, electric pulse therapy, high intensity focused ultrasound therapy, oncolytic virus therapy, or a pharmaceutical therapy, such as a chemotherapeutic agent, a therapeutic peptide, a hormone, an aptamer, antibiotic, anti-viral agent, anti-fungal agent, anti-inflammatory agent, a small molecule therapy, or any combination thereof.

Radiation therapy includes external beam radiation therapy (e.g., conventional external beam radiation therapy, stereotactic radiation, 3-dimensional conformal radiation therapy, intensity-modulated radiation therapy, volumetric modulated arc therapy, particle therapy, proton therapy, and auger therapy), brachytherapy, systemic radioisotope therapy, intraoperative radiotherapy, or any combination thereof.

Exemplary antibodies that may be used in conjunction with the LVV or CAR modified lymphocyte (e.g., T cell, B cell, or NK cell) compositions described herein include rituxmab, pertuzumab, trastuzumab, alemtuzumab, Ibritumomab tiuxetan, Brentuximab vedotin, cetuximab, bevacizumab, abciximab, adalimumab, alefacept, basilizimab, belimumab, bezlotoxumab, canakinumab, certolizumab pegol, daclizumab, denosumab, efalizumab, golimumab, olaratumab, palivizumab, panitumumab, and tocilizumab.

Exemplary inhibitors of immune checkpoint molecules that that may be used in conjunction with the LVV or CAR modified lymphocyte (e.g., T cell, B cell, or NK cell) compositions described herein include checkpoint inhibitors targeting PD-L1, PD-L2, CD80, CD86, B7-H3, B7-H4, HVEM, adenosine, GAL9, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof. In certain embodiments, an immune checkpoint inhibitor may be an antibody, a peptide, an RNAi agent, or a small molecule. An antibody specific for CTLA-4 may be ipilimumab or tremelimumab. An antibody specific for PD-1 may be pidilizumab, nivolumab, or pembrolizumab. An antibody specific for PD-L1 may be durvalumab, atezolizumab, or avelumab.

Exemplary chemotherapeutics that may be used in conjunction with the LVV or CAR modified lymphocyte (e.g., T cell, B cell, or NK cell) compositions described herein may include an alkylating agent, a platinum based agent, a cytotoxic agent, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

As referred to herein, a chemotherapeutic includes non-specific cytotoxic agents that inhibit mitosis or cell division, as well as molecularly targeted therapy that blocks the growth and spread of cancer cells by targeting specific molecules that are involved in tumor growth, progression, and metastasis (e.g., oncogenes). Exemplary non-specific chemotherapeutics for use in conjunction with the expression cassette compositions described herein may include an alkylating agent, a platinum based agent, a cytotoxic agent, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), hypomethylating agent, and a DNA repair inhibitor.

Examples of chemotherapeutic agents considered for use in combination therapies contemplated herein include vemurafenib, dabrafenib, trametinib, cobimetinib, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), fdabra tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), ibrutinib, venetoclax, crizotinib, alectinib, brigatinib, ceritinib, and vinorelbine (Navelbine®).

Exemplary alkylating agents for use in combination therapies contemplated herein include nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents for use in combination therapies contemplated herein include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary platinum based agents for use in combination therapies contemplated herein include carboplatin, cisplatin, oxaliplatin, nedaplatin, picoplatin, satraplatin, phenanthriplatin, and triplatin tetranitrate.

Exemplary hypomethylating agents for use in combination therapies include azacitidine and decitabine.

Exemplary molecularly targeted inhibitors for use in combination therapies contemplated herein include small molecules that target molecules involved in cancer cell growth and survival, including for example, receptor tyrosine kinase inhibitors, RAF inhibitors, BCL-2 inhibitors, ABL inhibitors, TRK inhibitors, c-KIT inhibitors, c-MET inhibitors, CDK4/6 inhibitors, FAK inhibitors, FGFR inhibitors, FLT3 inhibitors, IDH1 inhibitors, IDH2 inhibitors, PDGFRA inhibitors, and RET inhibitors Exemplary molecularly targeted therapy includes hormone antagonists, signal transduction inhibitors, gene expression inhibitors (e.g., translation inhibitors), apoptosis inducers, angiogenesis inhibitors (e.g., a VEGF pathway inhibitor), tyrosine kinase inhibitors (e.g., an EGF/EGFR pathway inhibitor), growth factor inhibitors, GTPase inhibitors, serine/threonine kinase inhibitors, transcription factor inhibitors, inhibitors of driver mutations associated with cancer, B-Raf inhibitors, RAF inhibitors, a MEK inhibitors, mTOR inhibitors, adenosine pathway inhibitors, EGFR inhibitors, PI3K inhibitors, BCL2 inhibitors, VEGFR inhibitors, MET inhibitors, MYC inhibitors, BCR-ABL inhibitors, ABL inhibitors, HER2 inhibitors, H-RAS inhibitors, K-RAS inhibitors, PDGFR inhibitors, ALK inhibitors, ROS1 inhibitors, BTK inhibitors, TRK inhibitors, c-KIT inhibitors, c-MET inhibitors, CDK4/6 inhibitors, FAK inhibitors, FGFR inhibitors, FLT3 inhibitors, IDH1 inhibitors, IDH2 inhibitors, PARP inhibitors, PARP inhibitors, PDGFRA inhibitors, and RET inhibitors.

Exemplary angiogenesis inhibitors include, without limitation A6 (Angstrom Pharmaceuticals), ABT-510 (Abbott Laboratories), ABT-627 (Atrasentan) (Abbott Laboratories/Xinlay), ABT-869 (Abbott Laboratories), Actimid (CC4047, Pomalidomide) (Celgene Corporation), AdGVPEDF.IID (GenVec), ADH-1 (Exherin) (Adherex Technologies), AEE788 (Novartis), AG-013736 (Axitinib) (Pfizer), AG3340 (Prinomastat) (Agouron Pharmaceuticals), AGX1053 (AngioGenex), AGX51 (AngioGenex), ALN-VSP (ALN-VSP 02) (Alnylam Pharmaceuticals), AMG 386 (Amgen), AMG706 (Amgen), Apatinib (YN968D1) (Jiangsu Hengrui Medicine), AP23573 (Ridaforolimus/MK8669) (Ariad Pharmaceuticals), AQ4N (Novavea), ARQ 197 (ArQule), ASA404 (Novartis/Antisoma), Atiprimod (Callisto Pharmaceuticals), ATN-161 (Attenuon), AV-412 (Aveo Pharmaceuticals), AV-951 (Aveo Pharmaceuticals), Avastin (Bevacizumab) (Genentech), AZD2171 (Cediranib/Recentin) (AstraZeneca), BAY 57-9352 (Telatinib) (Bayer), BEZ235 (Novartis), BIBF1120 (Boehringer Ingelheim Pharmaceuticals), BIBW 2992 (Boehringer Ingelheim Pharmaceuticals), BMS-275291 (Bristol-Myers Squibb), BMS-582664 (Brivanib) (Bristol-Myers Squibb), BMS-690514 (Bristol-Myers Squibb), Calcitriol, CCI-779 (Torisel) (Wyeth), CDP-791 (ImClone Systems), Ceflatonin (Homoharringtonine/HHT) (ChemGenex Therapeutics), Celebrex (Celecoxib) (Pfizer), CEP-7055 (Cephalon/Sanofi), CHIR-265 (Chiron Corporation), NGR-TNF, COL-3 (Metastat) (Collagenex Pharmaceuticals), Combretastatin (Oxigene), CP-751,871 (Figitumumab) (Pfizer), CP-547,632 (Pfizer), CS-7017 (Daiichi Sankyo Pharma), CT-322 (Angiocept) (Adnexus), Curcumin, Dalteparin (Fragmin) (Pfizer), Disulfiram (Antabuse), E7820 (Eisai Limited), E7080 (Eisai Limited), EMD 121974 (Cilengitide) (EMD Pharmaceuticals), ENMD-1198 (EntreMed), ENMD-2076 (EntreMed), Endostar (Simcere), Erbitux (ImClone/Bristol-Myers Squibb), EZN-2208 (Enzon Pharmaceuticals), EZN-2968 (Enzon Pharmaceuticals), GC1008 (Genzyme), Genistein, GSK1363089 (Foretinib) (GlaxoSmithKline), GW786034 (Pazopanib) (GlaxoSmithKline), GT-111 (Vascular Biogenics Ltd.), IMC-1121B (Ramucirumab) (ImClone Systems), IMC-18F1 (ImClone Systems), IMC-3G3 (ImClone LLC), INCB007839 (Incyte Corporation), INGN 241 (Introgen Therapeutics), Iressa (ZD1839/Gefitinib), LBH589 (Faridak/Panobinostst) (Novartis), Lucentis (Ranibizumab) (Genentech/Novartis), LY317615 (Enzastaurin) (Eli Lilly and Company), Macugen (Pegaptanib) (Pfizer), MEDI522 (Abegrin) (MedImmune), MLN518 (Tandutinib) (Millennium), Neovastat (AE941/Benefin) (Aetema Zentaris), Nexavar (Bayer/Onyx), NM-3 (Genzyme Corporation), Noscapine (Cougar Biotechnology), NPI-2358 (Nereus Pharmaceuticals), OSI-930 (OSI), Palomid 529 (Paloma Pharmaceuticals, Inc.), Panzem Capsules (2ME2) (EntreMed), Panzem NCD (2ME2) (EntreMed), PF-02341066 (Pfizer), PF-04554878 (Pfizer), PI-88 (Progen Industries/Medigen Biotechnology), PKC412 (Novartis), Polyphenon E (Green Tea Extract) (Polypheno E International, Inc.), PPI-2458 (Praecis Pharmaceuticals), PTC299 (PTC Therapeutics), PTK787 (Vatalanib) (Novartis), PXD101 (Belinostat) (CuraGen Corporation), RAD001 (Everolimus) (Novartis), RAF265 (Novartis), Regorafenib (BAY73-4506) (Bayer), Revlimid (Celgene), Retaane (Alcon Research), SN38 (Liposomal) (Neopharm), SNS-032 (BMS-387032) (Sunesis), SOM230 (Pasireotide) (Novartis), Squalamine (Genaera), Suramin, Sutent (Pfizer), Tarceva (Genentech), TB-403 (Thrombogenics), Tempostatin (Collard Biopharmaceuticals), Tetrathiomolybdate (Sigma-Aldrich), TG100801 (TargeGen), Thalidomide (Celgene Corporation), Tinzaparin Sodium, TKI258 (Novartis), TRC093 (Tracon Pharmaceuticals Inc.), VEGF Trap (Aflibercept) (Regeneron Pharmaceuticals), VEGF Trap-Eye (Regeneron Pharmaceuticals), Veglin (VasGene Therapeutics), Bortezomib (Millennium), XL184 (Exelixis), XL647 (Exelixis), XL784 (Exelixis), XL820 (Exelixis), XL999 (Exelixis), ZD6474 (AstraZeneca), Vorinostat (Merck), and ZSTK474.

Exemplary B-Raf inhibitors include vemurafenib, dabrafenib, and encorafenib.

Exemplary MEK inhibitors include binimetinib, cobimetinib, refametinib, selumetinib, and trametinib.

Exemplary BTK inhibitors include ibrutinib, Loxo-305, tirabrutinib, GDC-0853, acalabrutinib, ONO-4059, spebrutinib, BGB-3111, HM71224, and M7583.

Exemplary TRK inhibitors include entrectinib, larotrectinib, CH7057288, ONO-7579, LOXO-101, lestaurtinib, and LOXO-195.

Exemplary c-KIT inhibitors include imatinb, sunitinb, and ponatinib.

Exemplary c-MET inhibitors include capmatinib, crizotinib, tivantinib, onartuzumab, INCB28060, AMG-458, savolitinib, and tepotinib.

Exemplary CDK4/6 inhibitors include palbociclib, ribociclib, abemaciclib, and trilaciclib.

Exemplary FAK inhibitors include defactinib, GSK2256098, BI853520, and PF-00562271.

Exemplary FGFR inhibitors include erdafitinib, pemigatinib, infigratinib, rogaratinib, AZD4547, BGJ398, FP-1039, and ARQ 087.

Exemplary FLT-3 inhibitors include quizartinib, crenolanib, gilteritinib, midostaurin, and lestaurtinib.

Exemplary IDH1 inhibitors include ivosidenib, BAY-1436032, and AGI-5198.

An exemplary IDH2 inhibitor includes enasidenib.

Exemplary PARP inhibitors include talazoparib, niraparib, rucaparib, olaparib, veliparib, CEP 9722, E7016, AG014699, MK4827, BMN-673, and Pamiparib (BGB-290).

Exemplary PDGFRA inhibitors include imatinib, regorafenib, crenolanib, and olaratumab.

Exemplary pan-RAF inhibitors include belvarafenib, LXH254, LY3009120, INU-152, and HM95573.

Exemplary RET inhibitors include lenvatinib, alectinib, vandetanib, cabozantinib, BLU-667, and LOXO-292.

Exemplary ROS1 inhibitors include ceritinib, lorlatinib, entrectinib, crizotinib, TPX-0005, and DS-6051b.

Exemplary Vascular Endothelial Growth Factor (VEGF) receptor inhibitors include, but are not limited to, Bevacizumab (Avastin®), axitinib (Inlyta®); Brivanib alaninate (BMS-582664, (S)-((R)-1-(4-(4-Fluoro-2-methyl-1H-indol-5-yloxy)-5-methylpyrrolo[2,1-f][1,2,4]triazin-6-yloxy) propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl] methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)

methyl)piperidin-3-ol (BMS690514); N-(3,4-Dichloro-2-fluorophenyl)-6-methoxy-7-[[(3aa,5p,6aa)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary EGF pathway inhibitors include, without limitation tyrphostin 46, EKB-569, erlotinib (Tarceva®), gefitinib (Iressa®), erbitux, nimotuzumab, lapatinib (Tykerb®), cetuximab (anti-EGFR mAb), [188]Re-labeled nimotuzumab (anti-EGFR mAb), and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980. Exemplary EGFR antibodies include, but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1). Exemplary Epidermal growth factor receptor (EGFR) inhibitors include, but not limited to, Erlotinib hydrochloride (Tarceva®); ceritinib; brigatinib; osimeritinib; icotinib; Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aa,5p,6aa)-octahydro-2-methylcyclopenta[c]pyrrol-5-yl]methoxy]-4-quinazolinamine (XL647, CAS 781613-23-8); 4-[[(1R)-1-Phenylethyl]amino]-7H-pyrrolo[2,3-d]pyrimidin-6-yl]-phenol (PKI166, CAS 187724-61-4); rocelitinib.

Exemplary mTOR inhibitors include, without limitation, rapamycin (Rapamune®), and analogs and derivatives thereof; SDZ-RAD; Temsirolimus (Torisel®; also known as CCI-779); Ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.04]hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and $N^2$-[1,4-dioxo-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1).

Exemplary Phosphoinositide 3-kinase (PI3K) inhibitors include, but are not limited to, duvelisib, idelalisib, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6).

Exemplary Protein Kinase B (PKB) or AKT inhibitors include, but are not limited to. 8-[4-(1-Aminocyclobutyl)phenyl]-9-phenyl-1,2,4-triazolo[3,4-f][1,6]naphthyridin-3(2H)-one (MK-2206, CAS 1032349-93-1); Perifosine (KRX0401); 4-Dodecyl-N-1,3,4-thiadiazol-2-yl-benzenesulfonamide (PHT-427, CAS 1191951-57-1); 4-[2-(4-Amino-1,2,5-oxadiazol-3-yl)-1-ethyl-7-[(3S)-3-piperidinylmethoxy]-1H-imidazo[4,5-c]pyridin-4-yl]-2-methyl-3-butyn-2-ol (GSK690693, CAS 937174-76-0); 8-(1-Hydroxyethyl)-2-methoxy-3-[(4-methoxyphenyl)methoxy]-6H-dibenzo[b,d]pyran-6-one (palomid 529, P529, or SG-00529); Tricirbine (6-Amino-4-methyl-8-(O-D-ribofuranosyl)-4H,8H-pyrrolo[4,3,2-de]pyrimido[4,5-c]pyridazine); (αS)-α-[[[5-(3-Methyl-1H-indazol-5-yl)-3-pyridinyl]oxy]methyl]-benzeneethanamine (A674563, CAS 552325-73-2); 4-[(4-Chlorophenyl)methyl]-1-(7H-pyrrolo[2,3-d]pyrimidin-4-yl)-4-piperidinamine (CCT128930, CAS 885499-61-6); 4-(4-Chlorophenyl)-4-[4-(1H pyrazol-4-yl)phenyl]-piperidine (AT7867, CAS 857531-00-1); and Archexin (RX-0201, CAS 663232-27-7).

In certain embodiments, a tyrosine kinase inhibitor used in combination with the LVV or CAR modified T cells is an anaplastic lymphoma kinase (ALK) inhibitor. Exemplary ALK inhibitors include crizotinib, ceritinib, alectinib, brigatinib, dalantercept, entrectinib, and lorlatinib.

In certain embodiments where the LVV or CAR modified lymphocytes (e.g., T cells or NK cells) are administered in combination with one or more additional therapies, the LVV, CAR modified lymphocytes (e.g., T cells or NK cells), or one or more additional therapies may be administered at a dose that might otherwise be considered sub-therapeutic if administered as a monotherapy. Combination therapy includes administration of an LVV or CAR modified lymphocyte (e.g., T cell or NK cell) composition as described herein before an additional therapy (e.g., 1 day to 30 days or more before the additional therapy), concurrently with an additional therapy (on the same day), or after an additional therapy (e.g., 1 day-30 days or more after the additional therapy). In certain embodiments, the LVV or CAR modified lymphocytes (e.g., T cells or NK cells) are administered concurrently with the one or more additional therapies. In further embodiments, the LVV or CAR modified lymphocytes (e.g., T cells or NK cells) are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days before or after administration of the one or more additional therapies. In still further embodiments, the LVV or CAR modified lymphocytes (e.g., T cells or NK cells) are administered within 4 weeks, within 3 weeks, within 2 weeks, or within 1 week before or after administration of the one or more additional therapies. Where the one or more additional therapies involves multiple doses, the LVV or CAR modified lymphocytes (e.g., T cells or NK cells) may be administered before or after the initial dose of the one or more additional therapies, after the final dose of the one or more additional therapies, or in between multiple doses of the one or more additional therapies.

Subjects that can be treated by the compositions and methods of the present disclosure include animals, such as humans, primates, cows, horses, sheep, dogs, cats, mice, rats, rabbits, guinea pigs, or pigs. The subject may be male or female, and can be any suitable age, including infant, juvenile, adolescent, adult, and geriatric subjects.

EXAMPLES

Example 1: Methods for Generating Lentiviral Vectors with Defined Tropism

Self-inactivating lentiviral vectors (LVV) as described herein were produced using a third generation production system. An expression plasmid that contains the gene sequences desired for delivery by the LVV was combined at defined ratios with three packaging plasmids, VSV-G, GagPol, and Rev, and used to transfect HEK293 producer cells. Productive viral particles were harvested from the HEK293 culture media 2-3 days later.

The tropism of the resulting LVV was tested to determine whether it can be redirected using a non-viral targeting protein as described herein expressed from one of the three packaging plasmids or by addition of a fifth plasmid to the transfection mix. The LVV vector includes a mutated VSV-G envelope protein, where the mutated VSV-G includes mutations that abolish binding of the mutated VSV-G to its native receptor such that viral entry occurs via the non-viral, tropism defining targeting protein. Mutations in the LDL-receptor binding site of VSV-G were found to abolish binding to its natural receptor. VSV-G bearing a variety of mutations (Trop-002 (SEQ ID NO: 74), Trop-051 (SEQ ID NO: 93), Trop-052 (SEQ ID NO: 95), Trop-055 (SEQ ID NO: 97), or Trop-061 (SEQ ID NO: 103)) was expressed together with CD80 (SEQ ID NO: 2) on the LVV. CD80 is the natural ligand to T cell surface receptors, CD28 and CTLA4, and provides tropism to T cells and not B cells. Binding to the natural receptor for VSV-G is assessed by transduction of Raji B cells. Several mutations in VSV-G prohibit transduction of Raji B cells yet transduction of Jurkat T cells is maintained (FIGS. 2A-2B).

In a first method, a tropism-defining targeting protein derived from CD80 (SEQ ID NO: 76) was expressed from the VSV-G packaging plasmid. CD80 is the natural ligand to T cell surface receptors, CD28 and CTLA4, and provides tropism to T cells. A codon optimized CD80 molecule (encoding SEQ ID NO: 2) was cloned downstream of the mutated VSV-G (Trop-002, encoding SEQ ID NO: 74), which contains mutations to abolish LDL receptor binding and was used to package a green fluorescent protein (GFP)-expressing LVV. CD80 and VSV-G were expressed at relatively equivalent levels on the surface of HEK293 producer cells, suggesting comparable decoration of the LVV particles (FIG. 3A). LVV generated with this approach were capable of transducing T cells as assessed by GFP expression (FIG. 3B).

In a second method, the tropism-defining CD80 targeting protein (encoding SEQ ID NO: 2) was cloned into the Rev packaging plasmid and transfected at a lower molar concentration to the VSV-G env (encoding Trop-002 (SEQ ID NO: 74)) plasmid. The modified plasmids was used to package a GFP-expressing LVV. Assessment of VSV-G and CD80 expression on the HEK-293 producer cells showed relative expression levels trended with the molar concentrations of the packaging plasmids. LVV generated with these packaging approaches were capable of transducing T cells as assessed by GFP expression (FIG. 4). Reduced expression of CD80 was observed in LVVs packaged with CD80 targeting protein contained in the Rev packaging plasmid due to the lower ratio of the Rev plasmid.

In a third method, the tropism defining CD80 targeting protein (encoding SEQ ID NO: 2) was added as an additional plasmid during transfection of HEK293 cells intended to produce LVV (Trop-002 VSV-G env). The amount of the CD80 plasmid used during LVV production was associated with the expression on HEK293 producer cells and is likely representative of decoration of the LVV particles. LVV generated with this packaging approach were capable of transducing T cells as assessed by GFP expression and transduction efficiency was associated with CD80 levels on the LVV particles (FIG. 5).

Regardless of the method selected, high titer, tropism-redirected LVV can be generated with adherent or suspension HEK293 producer cells and concentrated by centrifugation or anion exchange chromatography (AEX) followed by tangential flow filtration (TFF) (FIGS. 6A-6C). Concentration by AEX/TFF resulted in LVV preparations with a high level of purity and recovery (FIG. 6D).

Example 2: CD4 T Cells Enriched by CD80 LVV

The tropism-defining targeting molecule precisely defines the specific cell type transduced with this LVV. The ligand for CD80, CD28, is naturally expressed on T cells. However, a higher frequency of CD4 T cells express CD28 in human peripheral blood compared to CD8 T cells (80% vs 50%). When a LVV was packaged to decorate the Trop-002 VSV-G envelope with a CD80 targeting protein (SEQ ID NO: 76) was used to transduce human PBMC, a higher composition of transduced CD4 T cells was observed compared to transduced CD8 T cells and was maintained for up to a week in culture (FIG. 13).

Example 3: Methods for Ex Vitro Generation of Tumor-Reactive T Cells Engineered to Express a Chimeric Antigen Receptor (CAR) Using a Lentiviral Vector Containing T Cell-Specific Tropism Compared to standard lentiviral vectors (LVV) that use common third generation packaging systems, LVV packaged to redirect tropism as provided herein may have improved transduction efficiencies and specificity. The levels of available viral particles are likely increased when transducing a specific cell type as part of a heterogeneous mixture, as the LVV particles are not taken up by other, non-desired cell types. Whether improved transduction of T cells with a CAR molecule is possible in a heterogenous peripheral blood mononuclear cell (PBMC) mixture was evaluated. A representative anti-BCMA CAR (SEQ ID NO: 58) used to treat Multiple Myeloma or a representative anti-CD19 CAR (SEQ ID NO: 42) used to treat non-Hodgkin Lymphoma was used. GFP reporter was used as control. The LVV was packaged to decorate the envelope with anti-CD3 targeting protein and CD80 targeting protein and redirect tropism toward the T cell surface molecules, CD3, CD28 and CTLA4. The CD80 targeting protein was cloned into the Trop-002 VSV-G env packaging plasmid (SEQ ID NO: 76) and the anti-CD3 targeting protein (encoding SEQ ID NO: 10) was expressed from a fifth packaging plasmid.

Figure 7:
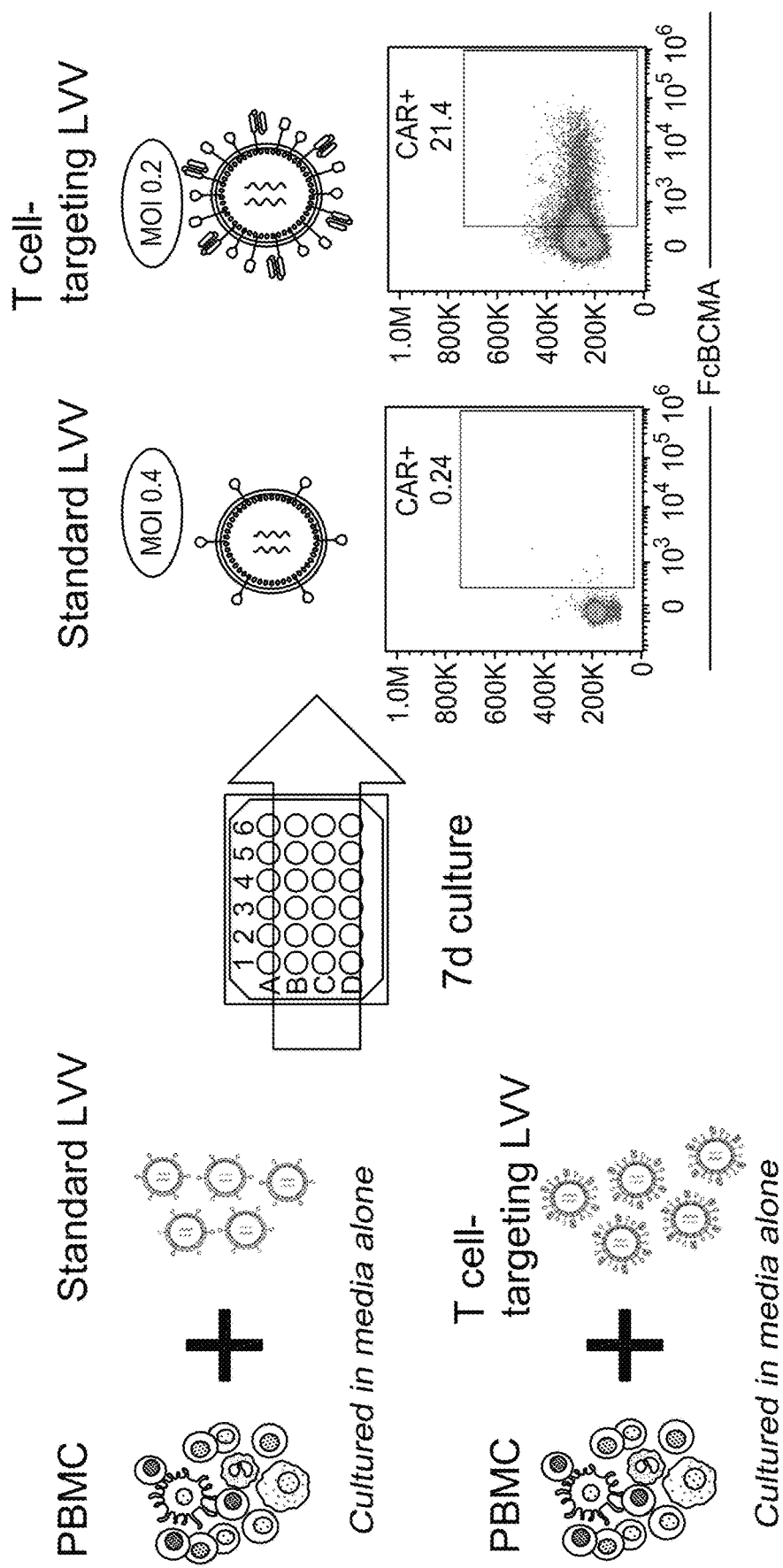
FIG. 7 depicts a schematic for testing T cell transduction in PBMCs from healthy human donors with LVV comprising a BCMA CAR transgene or T cell targeting LVV (anti-CD3 and CD80) comprising a BCMA CAR trasngene. Graphs shown on lower right indicate that even at low MOI, the T cell targeting LVV transduced T cells at a higher level than standard LVV and that T cell targeting LVV is capable of transducing T cells without the presence of IL-2 and exogenous activating antibodies (anti-CD3 and anti-CD28) in contrast to standard LVV.

The efficiency of T cell transduction within PBMC obtained from healthy donors leukapheresis after informed consent was tested. The PBMC were enriched using red cell lysis and matched donors were transduced with standard LVV or LVV with T cell redirected tropism (anti-CD3 and CD80) at LVV concentrations 5 to 25 times lower than typically used for CAR T cell transduction. Expression of an anti-BCMA CAR was assessed by flow cytometry after staining with a fluorescently labeled BCMA molecule to specifically detect anti-BCMA CAR T cells. Even with extremely low viral levels, T cells transduced using the T cell tropic LVV showed higher levels of transduction compared to standard LVV (FIG. 7).

Figure 8:
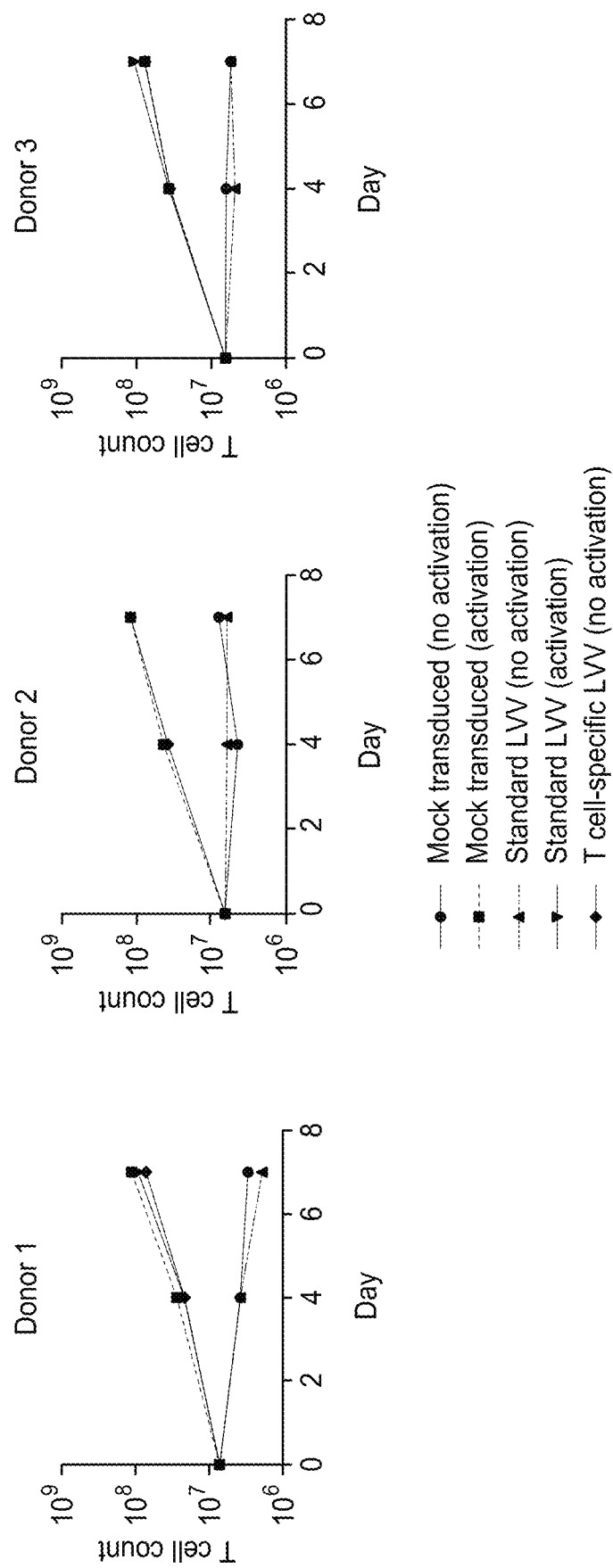
FIG. 8 depicts graphs showing T cell expansion from PBMCs obtained from three different donors and transduced using standard LVV or T cell redirected LVV (anti-CD3 and CD80) in the presence or absence of exogenous activating anti-CD3 and anti-CD28 antibodies
Figure 9:
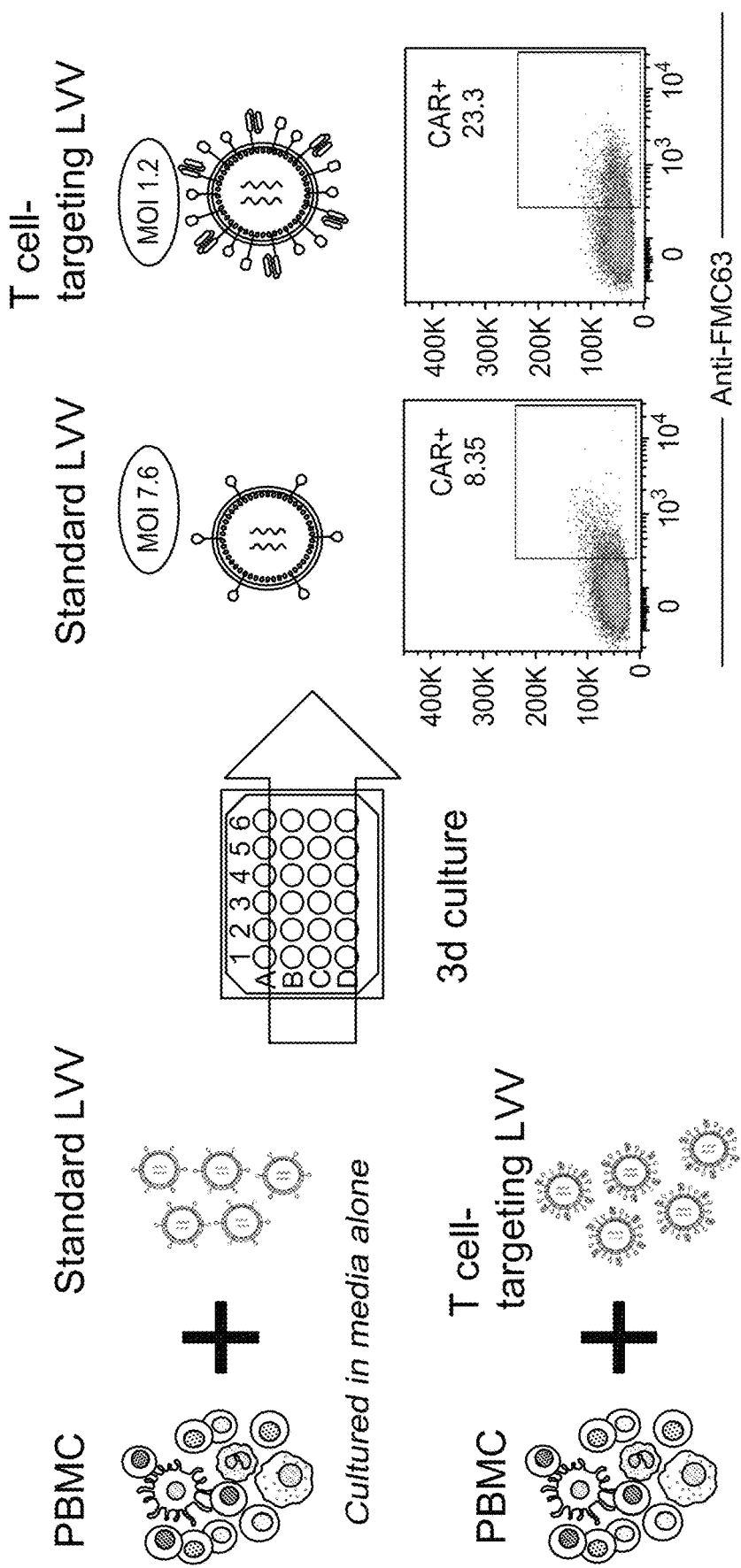
FIG. 9 depicts a schematic for testing T cell transduction in PBMCs from healthy human donors with LVV comprising a CD19 CAR transgene or T cell targeting LVV (anti-CD3 and CD80) comprising a CD19 CAR trasngene. Graphs shown on lower right show that the T cell targeting LVV transduced T cells at a higher level than standard LVV and that T cell targeting LVV is capable of transducing T cells without the presence of exogenous activating antibodies (anti-CD3 and anti-CD28) in contrast to standard LVV.

In the same study whether anti-BCMA CAR T cells can be generated without antibodies to activate T cells was evaluated. T cell activating antibodies (e.g., anti-CD28 and anti-CD3) are typically required for transduction using standard LVV during CAR T cell generation. It was confirmed that standard LVV indeed requires activation using antibodies to transduce normal human primary T cells (FIG. 7). By contrast, a T cell redirected LVV (anti-CD3 and CD80) can cause transduction even in the absence of prior T cell activation (without the presence of IL-2 and exogenous activating antibodies anti-CD3 and anti-CD28) (FIG. 7). A consequence of T cell activation is the subsequent cellular expansion when cultured in media containing IL-2. PBMCs transduced in the presence or absence of exogenous activating anti-CD3 and anti-CD28 antibodies after standard LVV or T cell redirected LVV (anti-CD3 and CD80) showed that T cell redirected LVV was uniquely able to expand T cells even in the absence of antibody activation (FIG. 8). In another example, transduction of an anti-CD19 CAR also was achieved without prior T cell activation when using the T cell redirected LVV (anti-CD3 and CD80) (FIG. 9).

Figure 10:
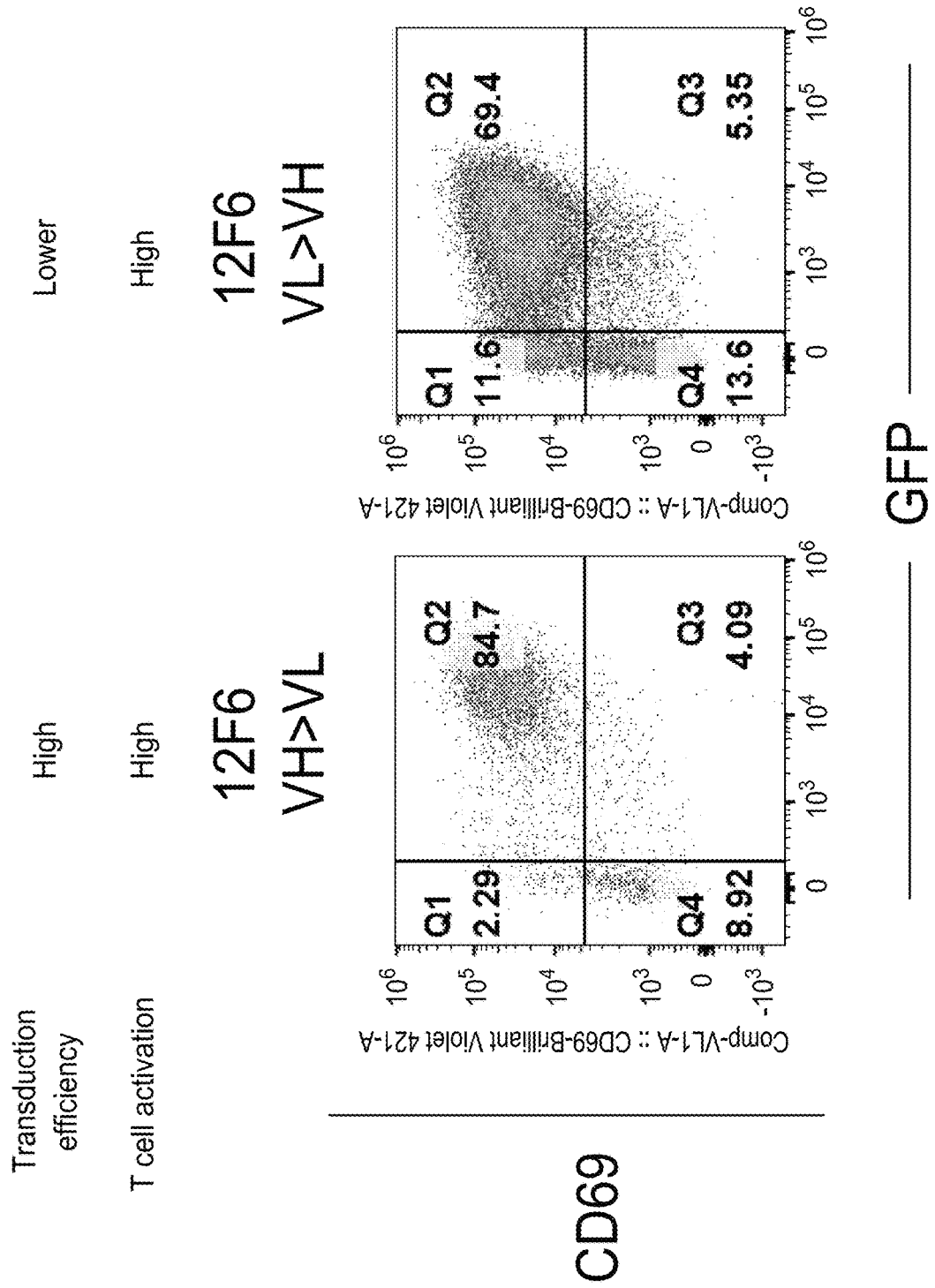
FIG. 10 depicts graphs showing levels of T cell transduction efficiency and T cell activation with anti-CD3 targeting proteins (12F6 in VH-VL orientation and VL-VH orientation) used to generate T cell targeting LVV.

T cell activation and transduction efficiency can be dictated by the selection of anti-CD3 antibodies used to generate the T cell redirected LVV. Examples of envelope-bound anti-CD3 binding proteins having 12F6 binding domains in VH (SEQ ID NO:113)-VL (SEQ ID NO: 115) orientation and VL (SEQ ID NO:115)-VH (SEQ ID NO:113) orientation are shown to cause a variable amount of T cell transduction as well as T cell activation (FIG. 10).

Example 4: T Cell Specificity of T Cel Targeted Lentiviral Vector

Figure 14:
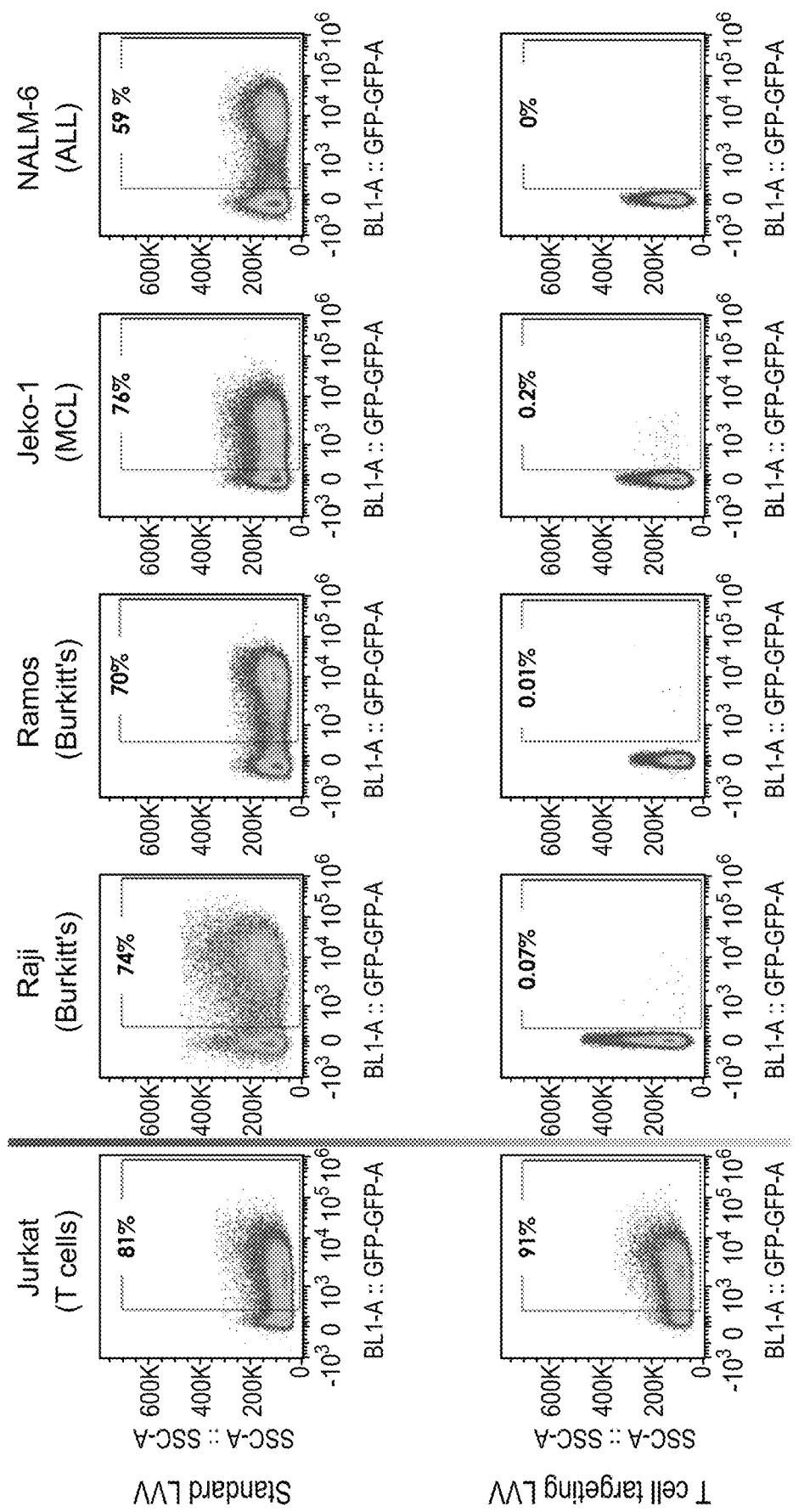
FIG. 14 depicts graphs showing that T cell targeting (anti-CD3 and CD80) LVVs transduce target Jurkat T cells but do not transduce off-target tumor cells (Raji, Ramos, Jeko-1, and NALM-6) compared to standard LVV.

The T cell specificity of an LVV packaged to decorate the envelope (Trop-002 VSV-G env) with an anti-CD3 targeting protein (SEQ ID NO: 10) and CD80 targeting protein (SEQ ID NO: 2) was confirmed by transduction of a T cell line and a panel of B cell lines (Raji, Ramos, Jeko-1, NALM-6). Transduction of these cell lines assessed by flow cytometry for a GFP transgene was compared to standard LVV. Both standard LVV and a T cell-targeted LVV effectively transduced the T cell line (Jurkat). The standard LVV effectively transduced all the B cell lines, confirming these lines are sensitive to LVV transduction, but no substantial transduction by the T cell-targeting LVV was detected in any of the B cell lines (FIG. 14).

Example 5: Tumor-Specific T Cells Generated Using a T Cell Targeted Lentiviral Vector Using methods described herein, T cells expressing an anti-BCMA CAR (SEQ ID NO: 58) were generated by transducing PBMC from healthy donors with LVVs having Trop-002 VSV-G env and CD80 targeting protein and anti-CD3 targeting protein. The CD80 targeting protein was cloned into the Trop-002 VSV-G env packaging plasmid (SEQ ID NO: 76) and the anti-CD3 targeting protein (encoding SEQ ID NO: 10) was expressed from a fifth packaging plasmid to produce the T cell targeting LVVs. The T cell transductions were performed in the absence of any T cell stimulation typically required for efficient LVV-mediated gene transfer (exogenous anti-CD3 and anti-CD28).

Figure 11:
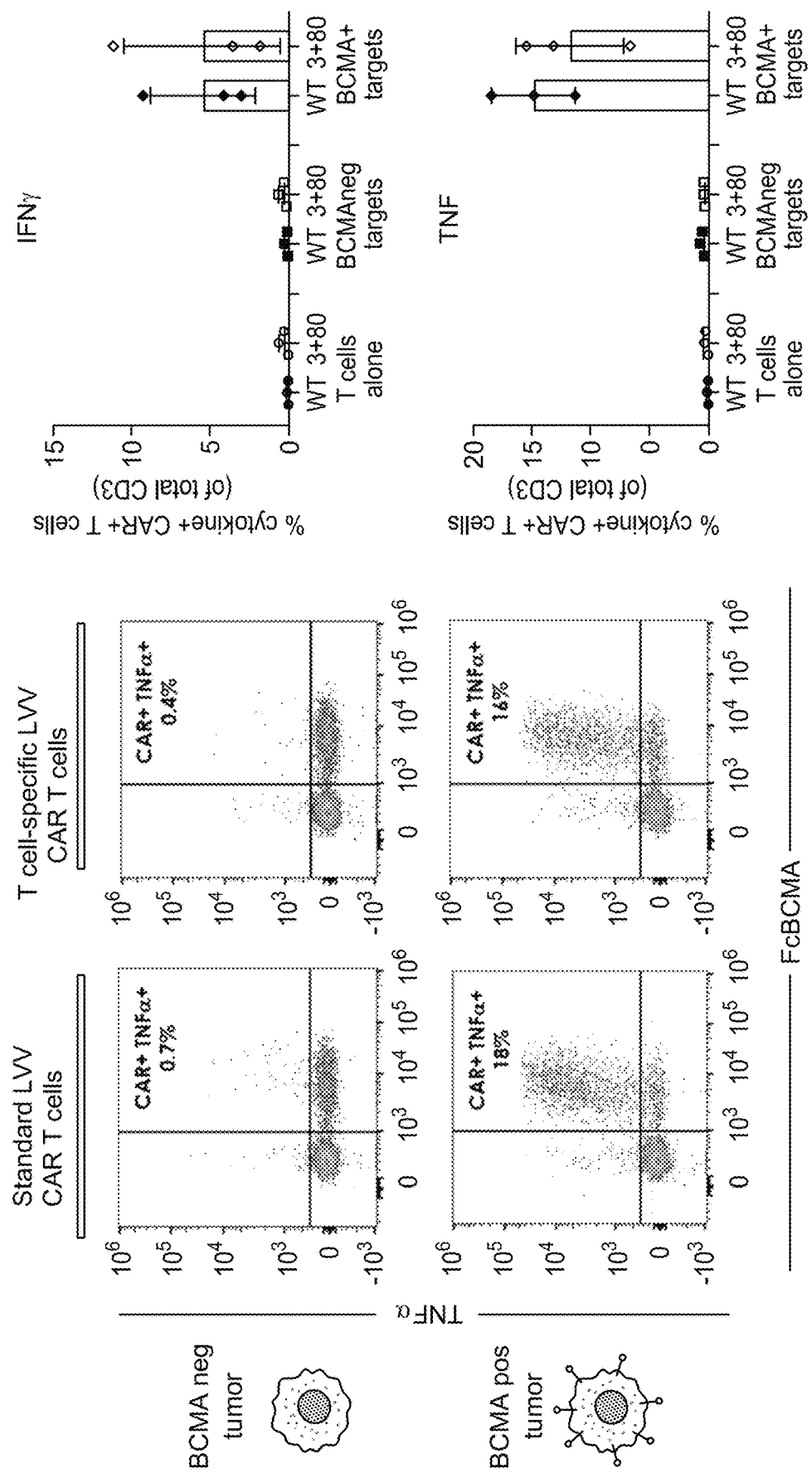
FIG. 11 depicts graphs showing that BCMA CAR T cells exhibited increased expression of T cell effector cytokines (TNFα—left; TNFα and IFNγ—right) after culture with BCMA-positive cell lines that is not observed with BCMA-negative cell lines whether generated by standard LVV or T cell-redirected LVV (anti-CD3 and CD80).

First, the activity of anti-BCMA CAR T cells generated by T cell-redirected LVV was examined compared to standard LVV. Anti-tumor activity was assessed by intracellular cytokine staining for interferon-gamma and tumor necrosis factor-alpha after co-culture with a BCMA-negative cell line (Nalm-6) or BCMA-positive cell line (RPMI-8826). Anti-BCMA CAR T cells exhibited increased expression of T cell effector cytokines after culture with BCMA-positive cell lines that is not observed with BCMA-negative cell lines whether generated by standard LVV or T cell-redirected LVV (FIG. 11).

Figure 12A:
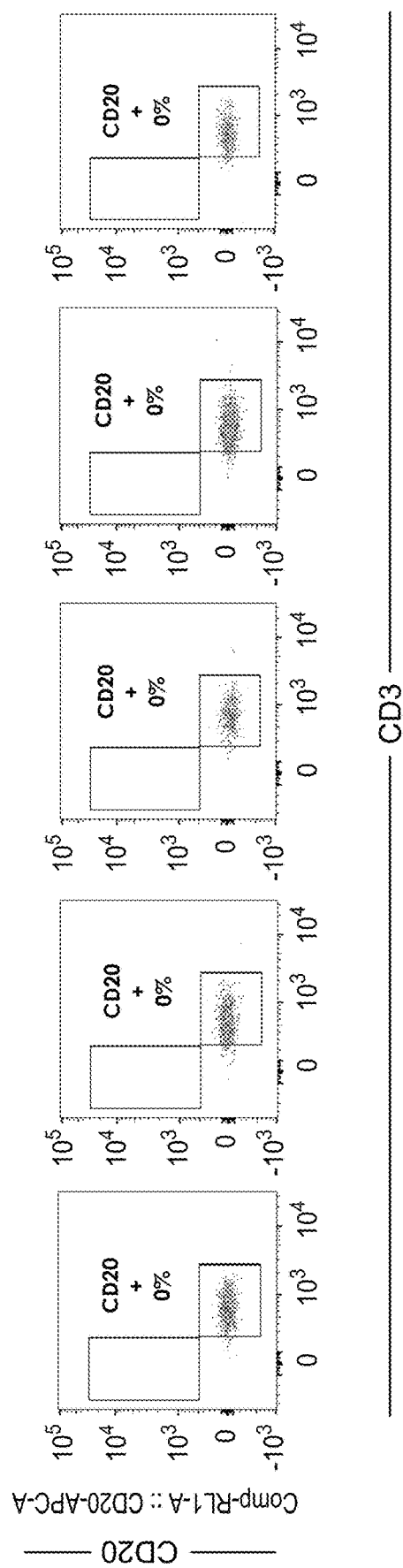
FIGS. 12A-12B depict graphs showing in vivo delivery of transgene using T cell targeting LVV.
Figure 12B:
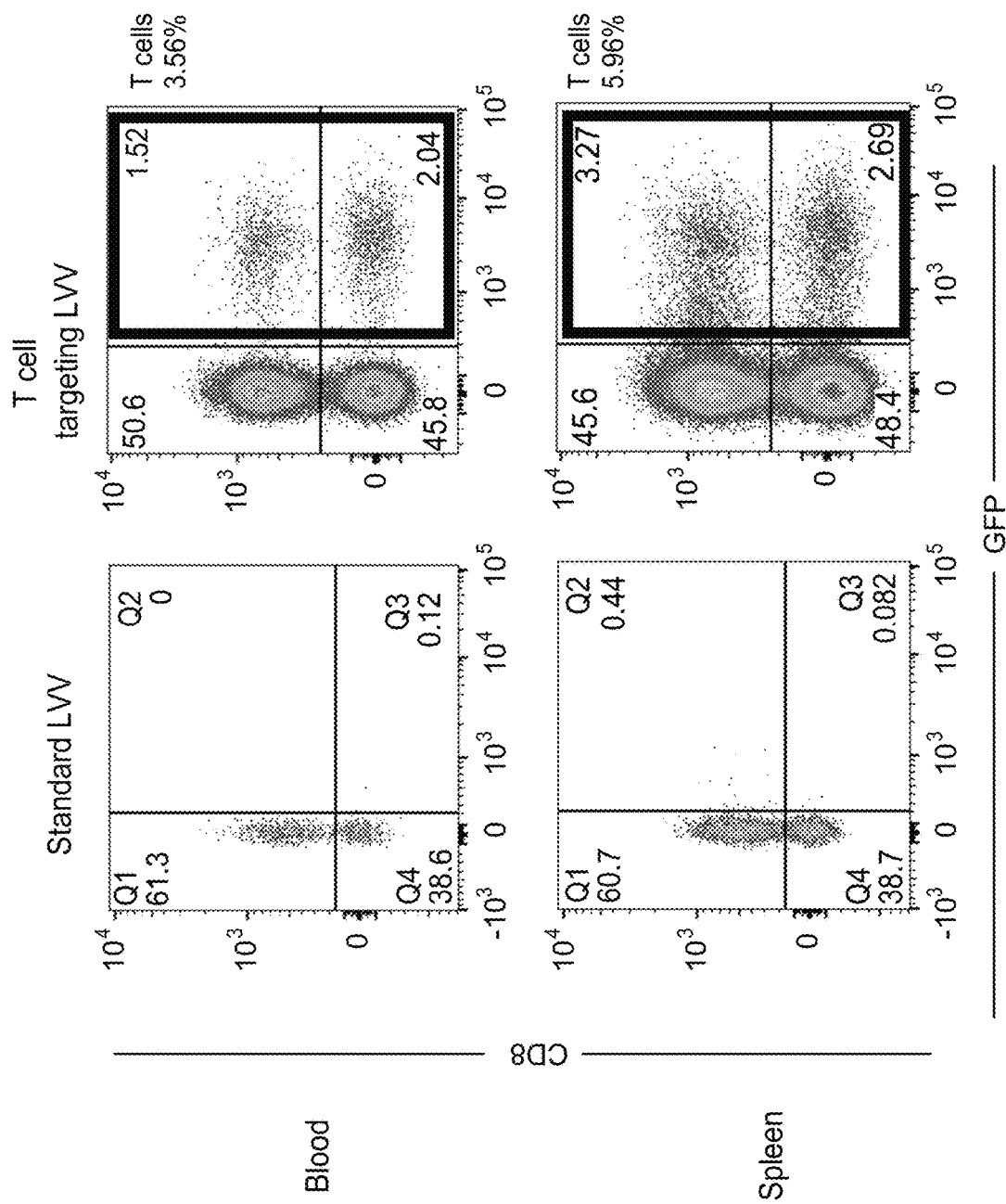
Figure 13:
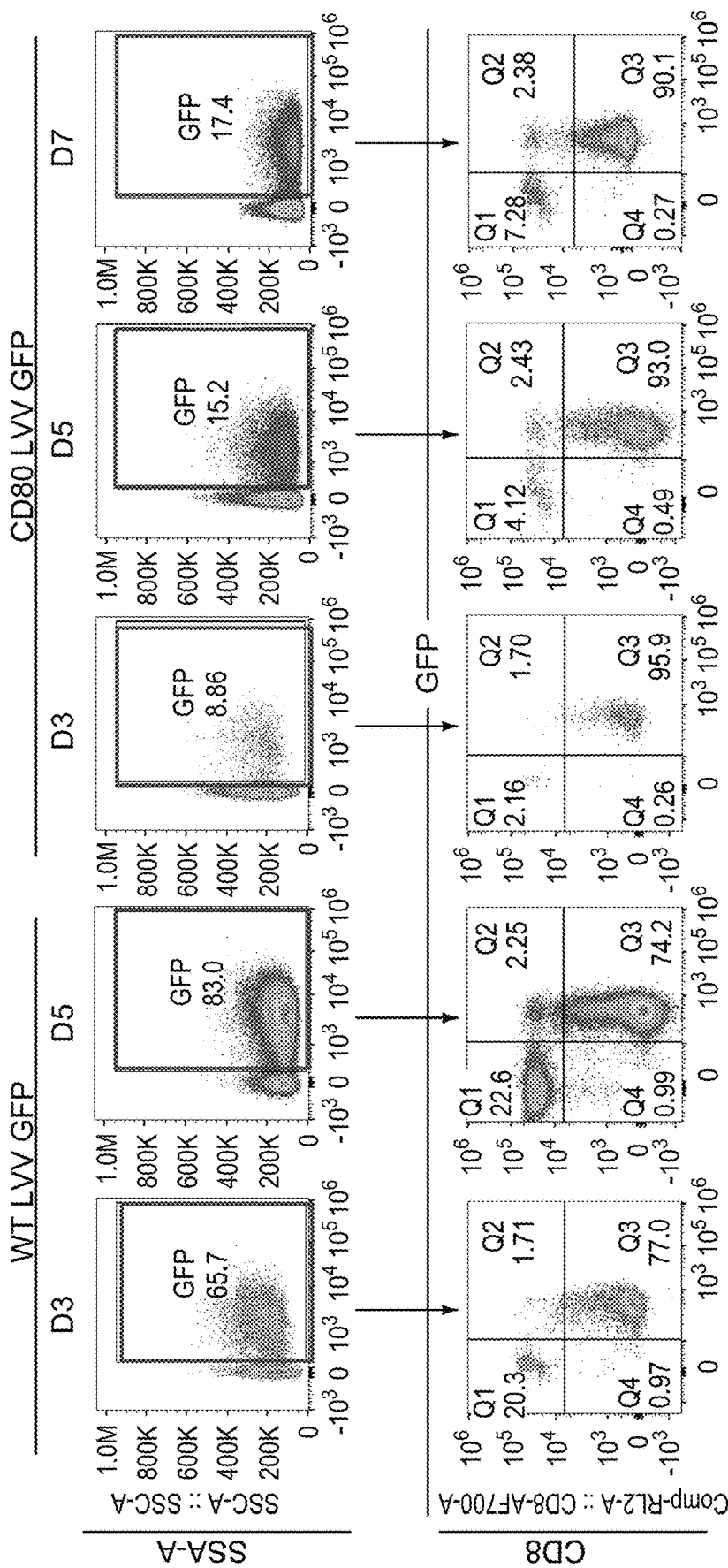
FIG. 13 depicts graphs showing that CD80 targeting LVVs enhance transduction of CD4 T cells compared to standard LVVs.

Example 6: Methods of T Cell-Specific In Vivo Delivery of Genetic Material Using a T Cell Tropic Lentiviral Vector The efficient and specific transduction of T cells with a T cell targeted LVV could permit safe and effective delivery of genetic material to T cells in vivo. A humanized mouse model infused intravenously with a GFP-expressing, T cell targeted LVV was used to test this hypothesis. LVVs having Trop-002 mutated VSV-G and coated with anti-CD3 targeting protein and CD80 targeting protein were produced. The CD80 targeting protein was cloned into the Trop-002 VSV-G env packaging plasmid (SEQ ID NO: 76) and the anti-CD3 targeting protein (encoding SEQ ID NO: 10) was expressed from a fifth packaging plasmid to produce the T cell targeting LVVs. Immunocompromised NCG mice were humanized via intravenous injection of human PBMC and supported by daily intraperitoneal administratin of recombinant IL-2 for 4 days. One day after PBMC administration, the T cell targeted lentiviral vector is administered intravenously to the mice Peripheral blood and splenic cells were harvested on day 7, and T cell specificity was assessed by flow cytometry. GFP positive cells were only detected in human T cells (CD3+) and not human B cells (CD20+), confirming T cell specificity of LVV transduction (FIG. 12A). GFP was detected in both CD8+ and CD8− (CD4) T cells, indicating that the T cell specific LVV transduces both CD4 and CD8 T cells in vivo (FIG. 12B).

Specific T cell transduction has a key safety advantages to other in vivo CAR delivery approaches by minimizing risk of transducing tumor cells. Transduction of T cells without transduction of tumor cells is evaluated using PBMCs from chronic lymphocytic leukemia patients with detectable CD19 tumor cells. The PBMC are transduced with T cell targeted LVV and transduced cells are assessed using flow cytometry.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 63/154,639, filed on Feb. 26, 2021, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A polypeptide comprising an amino acid sequence set forth in SEQ ID NO: 90, wherein the polypeptide comprises an amino acid substitution at position 182.

2. The polypeptide of claim 1, further comprising an amino acid substitution at position 352.

3. The polypeptide of claim 2, wherein the amino acid substitution at position 352 is from threonine to an amino acid selected from the group consisting of: alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

4. The polypeptide of claim 1, wherein the amino acid substitution at position 182 is from isoleucine to an amino acid selected from the group consisting of: alanine, arginine, asparagine, aspartic acid, cysteine, glutamine, glutamic acid, glycine, histidine, leucine, lysine, methionine, phenylalanine, proline, serine, threonine, tryptophan, tyrosine, and valine.

5. The polypeptide of claim 4, further comprising an amino acid substitution at position 352.

6. The polypeptide of claim 5, wherein the amino acid substitution at position 352 is from threonine to an amino acid selected from the group consisting of: alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine.

7. A nucleic acid encoding the polypeptide of claim 1.

8. A lentiviral vector comprising an envelope comprising the polypeptide of claim 1.

9. The lentiviral vector of claim 8, wherein the envelope further comprises a heterologous lymphocyte targeting protein comprising an extracellular domain comprising a lymphocyte targeting domain and a transmembrane domain.

10. The lentiviral vector of claim 9, further comprising an expression cassette that comprises a heterologous transgene encoding a chimeric antigen receptor.

* * * * *

```
                              SEQUENCE LISTING

Sequence total quantity: 123
SEQ ID NO: 1            moltype = DNA   length = 819
FEATURE                 Location/Qualifiers
misc_feature            1..819
                        note = CD80 Targeting Full molecule
source                  1..819
                        mol_type = other DNA
                        organism = synthetic construct
SEQUENCE: 1
atgggtcata cacgccgcca aggaacctca ccatctaagt gcccatatct gaatttcttt   60
caacttctcg tgctggcggg gctcagtcat ttctgcagtg gggtcattca cgttactaaa  120
gaggtcaagg aggtcgcaac attgagttgt ggccataacg tatcagttga agaactcgcg  180
cagacacgga tttactggca aaaggaaaag aagatggtgt tgacaatgat gagcggtgac  240
atgaacattt ggccagagta caaaaatcga acgatattcg atataaccaa taacttgtcc  300
atagtaatac ttgccttgcg accttctgac gagggaacgt atgaatgtgt agtgcttaag  360
tatgaaaaag atgcctttaa gcgggaacac ttggctgagg ttacactctc cgttaaggcg  420
gactttccta cgccgtctat atccgacttc gagataccca cttctaacat tcgacgcatc  480
atttgctcaa cctcaggtgg tttcccagag cctcacttga gctggctgga aatggcgaa   540
gaacttaacg caatcaatac cacggtgtcc caagacccgg agacagagct gtacgccgtg  600
tcatccaaac tggattttaa catgacgaca aatcatatgt tcatgtgtct gatcaaatat  660
gggcatctca gggtgaatca gactttaat tggaacacta ccaaacaaga gcacttccca   720
gataatctgt tgccaagctg ggcgataact cttatctccg tcaacggtat cttcgtaatt  780
tgctgcctca cctattgttt cgcgcctcga tgccgagaa                         819

SEQ ID NO: 2            moltype = AA    length = 273
FEATURE                 Location/Qualifiers
REGION                  1..273
                        note = CD80 Targeting Full molecule
REGION                  1..35
                        note = MISC_FEATURE - signal peptide
source                  1..273
                        mol_type = protein
                        organism = synthetic construct
SEQUENCE: 2
MGHTRRQGTS PSKCPYLNFF QLLVLAGLSH FCSGVIHVTK EVKEVATLSC GHNVSVEELA   60
QTRIYWQKEK KMVLTMMSGD MNIWPEYKNR TIFDITNNLS IVILALRPSD EGTYECVVLK  120
YEKDAFKREH LAEVTLSVKA DFPTPSISDF EIPTSNIRRI ICSTSGGFPE PHLSWLENGE  180
ELNAINTTVS QDPETELYAV SSKLDFNMTT NHSFMCLIKY GHLRVNQTFN WNTTKQEHFP  240
DNLLPSWAIT LISVNGIFVI CCLTYCFAPR CRE                               273

SEQ ID NO: 3            moltype = DNA   length = 105
FEATURE                 Location/Qualifiers
misc_feature            1..105
                        note = CD80 signal peptide
source                  1..105
                        mol_type = other DNA
                        organism = synthetic construct
SEQUENCE: 3
atgggtcata cacgccgcca aggaacctca ccatctaagt gcccatatct gaatttcttt   60
caacttctcg tgctggcggg gctcagtcat ttctgcagtg gggtc                  105

SEQ ID NO: 4            moltype = AA    length = 35
FEATURE                 Location/Qualifiers
REGION                  1..35
                        note = CD80 signal peptide
source                  1..35
                        mol_type = protein
                        organism = synthetic construct
SEQUENCE: 4
MGHTRRQGTS PSKCPYLNFF QLLVLAGLSH FCSGV                              35

SEQ ID NO: 5            moltype = DNA   length = 633
FEATURE                 Location/Qualifiers
misc_feature            1..633
                        note = CD80 extracellular domain (ECD)
source                  1..633
                        mol_type = other DNA
                        organism = synthetic construct
SEQUENCE: 5
attcacgtta ctaaagaggt caaggaggtc gcaacattga gttgtggcca taacgtatca   60
gttgaagaac tcgcgcagac acggatttac tggcaaaagg aaaagaagat ggtgttgaca  120
```

```
atgatgagcg gtgacatgaa catttggcca gagtacaaaa atcgaacgat attcgatata    180
accaataact tgtccatagt aatacttgcc ttgcgacctt ctgacgaggg aacgtatgaa    240
tgtgtagtgc ttaagtatga aaaagatgcc tttaagcggg aacacttggc tgaggttaca    300
ctctccgtta aggcggactt tcctacgccg tctatatccg acttcgagat acccacttct    360
aacattcgac gcatcatttg ctcaacctca ggtggtttcc cagagcctca cttgagctgg    420
ctggagaatg gcgaagaact taacgcaatc aataccacgg tgtcccaaga cccggagaca    480
gagctgtacg ccgtgtcatc caaactggat tttaacatga cgacaaatca tagtttcatg    540
tgtctgatca aatatgggca tctcagggtg aatcagactt taattggaa cactaccaaa     600
caagagcact tcccagataa tctgttgcca agc                                 633

SEQ ID NO: 6               moltype = AA  length = 211
FEATURE                    Location/Qualifiers
REGION                     1..211
                           note = CD80 extracellular domain (ECD)
source                     1..211
                           mol_type = protein
                           organism = synthetic construct
SEQUENCE: 6
IHVTKEVKEV ATLSCGHNVS VEELAQTRIY WQKEKKMVLT MMSGDMNIWP EYKNRTIFDI    60
TNNLSIVILA LRPSDEGTYE CVVLKYEKDA FKREHLAEVT LSVKADFPTP SISDFEIPTS    120
NIRRIICSTS GGFPEPHLSW LENGEELNAI NTTVSQDPET ELYAVSSKLD FNMTTNHSFM    180
CLIKYGHLRV NQTFNWNTTK QEHFPDNLLP S                                   211

SEQ ID NO: 7               moltype = DNA  length = 81
FEATURE                    Location/Qualifiers
misc_feature               1..81
                           note = CD80 transmembrane and intracellular domain
source                     1..81
                           mol_type = other DNA
                           organism = synthetic construct
SEQUENCE: 7
tgggcgataa ctcttatctc cgtcaacggt atcttcgtaa tttgctgcct cacctattgt    60
ttcgcgcctc gatgccgaga a                                              81

SEQ ID NO: 8               moltype = AA  length = 27
FEATURE                    Location/Qualifiers
REGION                     1..27
                           note = CD80 transmembrane and intracellular domain
source                     1..27
                           mol_type = protein
                           organism = synthetic construct
SEQUENCE: 8
WAITLISVNG IFVICCLTYC FAPRCRE                                         27

SEQ ID NO: 9               moltype = DNA  length = 1011
FEATURE                    Location/Qualifiers
misc_feature               1..1011
                           note = Anti-CD3 (UCTH1) Full molecule
source                     1..1011
                           mol_type = other DNA
                           organism = synthetic construct
SEQUENCE: 9
atggccttac cagtgaccgc cttgctcctg ccgctggcct tgctgctcca cgccgccagg    60
ccggacatcc agatgaccca gaccacctcc tccctgtctg cctctctggg agacagagtc    120
accatcagtt gcagggcaag tcaggacatt agaaattatt taaactggta tcaacagaaa    180
ccagatggaa ctgttaaact cctgatctac tacacatcaa gattacactc aggagtccca    240
tcaaagttca gtggcagtgg gtctgggaca gattattctc tcaccattag caacctggag    300
caagaggata ttgccactta cttttgccaa cagggtaata cgcttccgtg gacgttcgct    360
ggaggcacca agctggaaat caaacgggct ggaggcggta gtggcggtgg atcaggtgga    420
ggcagcgcctg gcggatctga ggtgcagctc cagcagtctg gacctgagct ggtgaagcct    480
ggagcttcaa tgaagatatc ctgcaaggct tctggttact cattcactgg ctacaccatg    540
aactgggtga agcagagtca tggaaagaac cttgagtgga tgggacttat taatcctac    600
aaaggtgtta gtacctacaa ccagaagttc aaggacaagg ccacattaac tgtagacaag    660
tcatccagca cagcctacat ggaactcctc agtctgacat ctgaggactc tgcagtctat    720
tactgtgcaa gatcggggta ctacggtgat agtgactgga cttcgatgt ctggggcgca    780
gggaccacgg tcaccgtctc ctcaaccact acaccagcac ctagaccacc aacacctgcg    840
ccaaccatcg catcgcagcc actgtctctg cgcccagagg catgccggcc agcagctggg    900
ggcgcagtgc acacaagggg gctggacttc gcatgtgata tctacatctg gcaccattg    960
gcagggactt gtgggtcct tctcctgtca ctggttatca cccttactg c              1011

SEQ ID NO: 10              moltype = AA  length = 337
FEATURE                    Location/Qualifiers
REGION                     1..337
                           note = Anti-CD3 (UCTH1) Full molecule
REGION                     1..21
                           note = MISC_FEATURE - signal peptide
source                     1..337
                           mol_type = protein
                           organism = synthetic construct
```

```
SEQUENCE: 10
MALPVTALLL PLALLLHAAR PDIQMTQTTS SLSASLGDRV TISCRASQDI RNYLNWYQQK    60
PDGTVKLLIY YTSRLHSGVP SKFSGSGSGT DYSLTISNLE QEDIATYFCQ QGNTLPWTFA   120
GGTKLEIKRA GGGSGGGSGG GSGGGSEVQL QQSGPELVKP GASMKISCKA SGYSFTGYTM   180
NWVKQSHGKN LEWMGLINPY KGVSTYNQKF KDKATLTVDK SSSTAYMELL SLTSEDSAVY   240
YCARSGYYGD SDWYFDVWGA GTTVTVSSTT TPAPRPPTPA PTIASQPLSL RPEACRPAAG   300
GAVHTRGLDF ACDIYIWAPL AGTCGVLLLS LVITLYC                            337

SEQ ID NO: 11            moltype = DNA  length = 63
FEATURE                  Location/Qualifiers
misc_feature             1..63
                         note = CD8a signal peptide
source                   1..63
                         mol_type = other DNA
                         organism = synthetic construct
SEQUENCE: 11
atggccttac cagtgaccgc cttgctcctg ccgctggcct tgctgctcca cgccgccagg    60
ccg                                                                 63

SEQ ID NO: 12            moltype = AA   length = 21
FEATURE                  Location/Qualifiers
REGION                   1..21
                         note = CD8a signal peptide
source                   1..21
                         mol_type = protein
                         organism = synthetic construct
SEQUENCE: 12
MALPVTALLL PLALLLHAAR P                                              21

SEQ ID NO: 13            moltype = DNA  length = 327
FEATURE                  Location/Qualifiers
misc_feature             1..327
                         note = Anti-CD3 (UCTH1) Light chain variable region
source                   1..327
                         mol_type = other DNA
                         organism = synthetic construct
SEQUENCE: 13
gacatccaga tgacccagac cacctcctcc ctgtctgcct ctctgggaga cagagtcacc    60
atcagttgca gggcaagtca ggacattaga aattatttaa actgtgggaga acagaaacca   120
gatggaactg ttaaactcct gatctactac acatcaagat tacactcagg agtcccatca   180
aagttcagtg gcagtgggtc tggaacagat tattctctca ccattagcaa cctggagcaa   240
gaggatattg ccacttactt ttgccaacag ggtaatacgc ttccgtggac gttcgctgga   300
ggcaccaagc tggaaatcaa acgggct                                       327

SEQ ID NO: 14            moltype = AA  length = 109
FEATURE                  Location/Qualifiers
REGION                   1..109
                         note = Anti-CD3 (UCTH1) Light chain variable region
source                   1..109
                         mol_type = protein
                         organism = synthetic construct
SEQUENCE: 14
DIQMTQTTSS LSASLGDRVT ISCRASQDIR NYLNWYQQKP DGTVKLLIYY TSRLHSGVPS    60
KFSGSGSGTD YSLTISNLEQ EDIATYFCQQ GNTLPWTFAG GTKLEIKRA              109

SEQ ID NO: 15            moltype = DNA  length = 48
FEATURE                  Location/Qualifiers
misc_feature             1..48
                         note = G3S linker
source                   1..48
                         mol_type = other DNA
                         organism = synthetic construct
SEQUENCE: 15
ggaggcggta gtggcggtgg atcaggtgga ggcagcggtg gcggatct                 48

SEQ ID NO: 16            moltype = AA  length = 16
FEATURE                  Location/Qualifiers
REGION                   1..16
                         note = G3S linker
source                   1..16
                         mol_type = protein
                         organism = synthetic construct
SEQUENCE: 16
GGGSGGGSGG GSGGGS                                                    16

SEQ ID NO: 17            moltype = DNA  length = 366
FEATURE                  Location/Qualifiers
misc_feature             1..366
                         note = Anti-CD3 (UCTH1) heavy chain variable region
```

```
source                  1..366
                        mol_type = other DNA
                        organism = synthetic construct
SEQUENCE: 17
gaggtgcagc tccagcagtc tggacctgag ctggtgaagc ctggagcttc aatgaagata    60
tcctgcaagg cttctggtta ctcattcact ggctacacca tgaactgggt gaagcagagt   120
catggaaaga accttgagtg gatgggactt attaatcctt acaaaggtgt tagtacctac   180
aaccagaagt tcaaggacaa ggccacatta actgtagaca agtcatccag cacagcctac   240
atggaactcc tcagtctgac atctgaggac tctgcagtct attactgtgc aagatcgggg   300
tactacggtg atagtgactg gtacttcgat gtctggggcg cagggaccac ggtcaccgtc   360
tcctca                                                              366

SEQ ID NO: 18           moltype = AA  length = 122
FEATURE                 Location/Qualifiers
REGION                  1..122
                        note = Anti-CD3 (UCTH1) heavy chain variable region
source                  1..122
                        mol_type = protein
                        organism = synthetic construct
SEQUENCE: 18
EVQLQQSGPE LVKPGASMKI SCKASGYSFT GYTMNWVKQS HGKNLEWMGL INPYKGVSTY    60
NQKFKDKATL TVDKSSSTAY MELLSLTSED SAVYYCARSG YYGDSDWYFD VWGAGTTVTV   120
SS                                                                  122

SEQ ID NO: 19           moltype = DNA  length = 207
FEATURE                 Location/Qualifiers
misc_feature            1..207
                        note = CD8a hinge and transmembrane
source                  1..207
                        mol_type = other DNA
                        organism = synthetic construct
SEQUENCE: 19
accactacac cagcacctag accaccaaca cctgcgccaa ccatcgcatc gcagccactg    60
tctctgcgcc cagaggcatg ccggccagca gctgggggcg cagtgcacac aagggggctg   120
gacttcgcat gtgatatcta catctgggca ccattgcag ggacttgtgg ggtccttctc    180
ctgtcactgg ttatcaccct ttactgc                                       207

SEQ ID NO: 20           moltype = AA  length = 69
FEATURE                 Location/Qualifiers
REGION                  1..69
                        note = CD8a hinge and transmembrane
source                  1..69
                        mol_type = protein
                        organism = synthetic construct
SEQUENCE: 20
TTTPAPRPPT PAPTIASQPL SLRPEACRPA AGGAVHTRGL DFACDIYIWA PLAGTCGVLL    60
LSLVITLYC                                                            69

SEQ ID NO: 21           moltype = DNA  length = 1896
FEATURE                 Location/Qualifiers
misc_feature            1..1896
                        note = Co-expressed CD80 and anti-CD3 T cell targeting
                        molecules
source                  1..1896
                        mol_type = other DNA
                        organism = synthetic construct
SEQUENCE: 21
atgggtcata cacgccgcca aggaacctca ccatctaagt gcccatatct gaatttcttt    60
caacttctcg tgctggcggg gctcagtcat ttctgcagtg gggtcattca cgttactaaa   120
gaggtcaagg aggtcgcaac attgagttgt ggccataacg tatcagttga agaactcgcg   180
cagacacgga tttactggca aaaggaaaag aagatggtgt tgacaatgat gagcggtgac   240
atgaacattt ggcagagta caaaaatcga acgatattcg atataaccaa taacttgtcc   300
atagtaatac ttgccttgcg accttctgac gagggaacga tgaatgtgt agtgcttaag   360
tatgaaaaag atgcctttaa gcgggaacac ttggctgaag ttacactctc cgttaaggcg   420
gactttccta cgccgtctat atccgacttc gagataccca cttctaacat tcgacgcatc   480
atttgctcaa cctcaggtgg tttcccagag cctcacttga gctggctgga aatggcgaa    540
gaacttaacg caatcaatac cacggtgtcc caagacccgg agacagagct gtacgccgtg   600
tcatccaaac tggatttaa catgacgaca aatcatagtt tcatgtgtct gatcaaatat   660
gggcatctca gggtgaatca gactttaat tggaacacta ccaaacaaga gcacttcctc   720
gataatctgt tgccaagctg ggcgataact cttatctccg tcaacggtat cttcgtaatt   780
tgctgcctca cctattgttt cgcgcctcga tgccgagaag gcagcggcgc caccaacttc   840
tccctgctga gcaggccgg cgacgtgaa gaaaaccctg gccccatggc cttaccagtg    900
accgccttgc tcctgccgct ggccttgctg ctccacgccg ccaggccgga catccagatg   960
acccagacca cctcctccct gtctgcctct ctgggaagaca gagtcaccat cagttgcagg  1020
gcaagtcagg acattagaaa ttatttaaac tggtatcaac agaaaccaga tggaactgtt  1080
aaactcctga tctactacac atcaagatta cactcaggag tcccatcaaa gttcagtggc  1140
agtgggtctg gaacagatta ttctctcacc attagcaacc tggagcaaga ggatattgcc  1200
acttactttt gccaacaggg taatacgctt ccgtggacgt tcgctggagg caccaagctg  1260
gaaatcaaac gggctggagg cggtagtggc ggtggatcag gtgaggcag cggtggcgga  1320
```

```
tctgaggtgc agctccagca gtctggacct gagctggtga agcctggagc ttcaatgaag   1380
atatcctgca aggcttctgg ttactcattc actggctaca ccatgaactg ggtgaagcag   1440
agtcatggaa agaaccttga gtggatggga cttattaatc cttacaaagg tgttagtacc   1500
tacaaccaga agttcaagga caaggccaca ttaactgtag acaagtcatc cagcacagcc   1560
tacatggaac tcctcagtct gacatctgag gactctgcaa tctattactg tgcaagatcg   1620
gggtactacg gtgatagtga ctggtacttc gatgtctggg gcgcagggac cacggtcacc   1680
gtctcctcaa ccactacacc agcacctaga ccaccaacac ctgcgccaac catcgcatcg   1740
cagccactgt ctctgcgccc agaggcatgc cggccagcag ctgggggcgc agtgcacaca   1800
agggggctgg acttcgcatg tgatatctac atctgggcac cattggcagg gacttgtggg   1860
gtccttctcc tgtcactggt tatcaccctt tactgc                             1896

SEQ ID NO: 22           moltype = AA   length = 632
FEATURE                 Location/Qualifiers
REGION                  1..632
                        note = Co-expressed CD80 and anti-CD3 T cell targeting
                         molecules
REGION                  1..35
                        note = MISC_FEATURE - signal peptide
source                  1..632
                        mol_type = protein
                        organism = synthetic construct
SEQUENCE: 22
MGHTRRQGTS PSKCPYLNFF QLLVLAGLSH FCSGVIHVTK EVKEVATLSC GHNVSVEELA    60
QTRIYWQKEK KMVLTMMSGD MNIWPEYKNR TIFDITNNLS IVILALRPSD EGTYECVVLK   120
YEKDAFKREH LAEVTLSVKA DFPTPSISDF EIPTSNIRRI ICSTSGGFPE PHLSWLENGE   180
ELNAINTTVS QDPETELYAV SSKLDFNMTT NHSFMCLIKY GHLRVNQTFN WNTTKQEHFP   240
DNLLPSWAIT LISVNGIFVI CCLTYCFAPR CREGSGATNF SLLKQAGDVE ENPGPMALPV   300
TALLLPLALL LHAARPDIQM TQTTSSLSAS LGDRVTISCR ASQDIRNYLN WYQQKPDGTV   360
KLLIYYTSRL HSGVPSKFSG SGSGTDYSLT ISNLEQEDIA TYFCQQGNTL PWTFAGGTKL   420
EIKRAGGGSG GGSGGGSGGG SEVQLQQSGP ELVKPGASMK ISCKASGYSF TGYTMNWVKQ   480
SHGKNLEWMG LINPYKGVST YNQKFKDKAT LTVDKSSSTA YMELLSLTSE DSAVYYCARS   540
GYYGDSDWYF DVWGAGTTVT VSSTTTPAPR PPTPAPTIAS QPLSLRPEAC RPAAGGAVHT   600
RGLDFACDIY IWAPLAGTCG VLLLSLVITL YC                                 632

SEQ ID NO: 23           moltype = DNA   length = 105
FEATURE                 Location/Qualifiers
misc_feature            1..105
                        note = CD80 signal peptide
source                  1..105
                        mol_type = other DNA
                        organism = synthetic construct
SEQUENCE: 23
atgggtcata cacgccgcca aggaacctca ccatctaagt gcccatatct gaatttcttt    60
caacttctcg tgctggcggg gctcagtcat ttctgcagtg gggtc                   105

SEQ ID NO: 24           moltype = AA   length = 35
FEATURE                 Location/Qualifiers
REGION                  1..35
                        note = CD80 signal peptide
source                  1..35
                        mol_type = protein
                        organism = synthetic construct
SEQUENCE: 24
MGHTRRQGTS PSKCPYLNFF QLLVLAGLSH FCSGV                               35

SEQ ID NO: 25           moltype = DNA   length = 633
FEATURE                 Location/Qualifiers
misc_feature            1..633
                        note = CD80 extracellular domain (ECD)
source                  1..633
                        mol_type = other DNA
                        organism = synthetic construct
SEQUENCE: 25
attcacgtta ctaaagaggt caaggaggtc gcaacattga gttgtggcca taacgtatca    60
gttgaagaac tcgcgcagac acggatttac tggcaaaagg aaaagaagat ggtgttgaca   120
atgatgagcg gtgacatgaa catttggcca gagtacaaaa atcgaacgat attcgatata   180
accaataact tgtccatagt aatacttgcc ttgcgacctt ctgacgaggg aacgtatgaa   240
tgtgtagtgc ttaagtatga aaaagatgcc tttaagcggg aacacttggc tgaggttaca   300
ctctccgtta aggcggactt tcctacgccg tctatatccg acttcgagat acccacttct   360
aacattcgac gcatcatttg ctcaacctca ggtggtttcc cagagcctca cttgagctgg   420
ctggagaatg gcgaagaact taacgcaatc aataccacgg tgtcccaaga cccggagaca   480
gagctgtacg ccgtgtcatc caaactggat tttaacatga cgacaaatca tagttttatg   540
tgtctgatca aatatgggca tctcagggtg aatcagactt taattggaa cactaccaaa   600
caagagcact tcccagataa tctgttgcca agc                                633

SEQ ID NO: 26           moltype = AA   length = 211
FEATURE                 Location/Qualifiers
REGION                  1..211
                        note = CD80 extracellular domain (ECD)
```

-continued

```
source                  1..211
                        mol_type = protein
                        organism = synthetic construct
SEQUENCE: 26
IHVTKEVKEV ATLSCGHNVS VEELAQTRIY WQKEKKMVLT MMSGDMNIWP EYKNRTIFDI    60
TNNLSIVILA LRPSDEGTYE CVVLKYEKDA FKREHLAEVT LSVKADFPTP SISDFEIPTS   120
NIRRIICSTS GGFPEPHLSW LENGEELNAI NTTVSQDPET ELYAVSSKLD FNMTTNHSFM   180
CLIKYGHLRV NQTFNWNTTK QEHFPDNLLP S                                  211

SEQ ID NO: 27           moltype = DNA   length = 81
FEATURE                 Location/Qualifiers
misc_feature            1..81
                        note = CD80 transmembrane and intracellular domain
source                  1..81
                        mol_type = other DNA
                        organism = synthetic construct
SEQUENCE: 27
tgggcgataa ctcttatctc cgtcaacggt atcttcgtaa tttgctgcct cacctattgt    60
ttcgcgcctc gatgccgaga a                                             81

SEQ ID NO: 28           moltype = AA    length = 27
FEATURE                 Location/Qualifiers
REGION                  1..27
                        note = CD80 transmembrane and intracellular domain
source                  1..27
                        mol_type = protein
                        organism = synthetic construct
SEQUENCE: 28
WAITLISVNG IFVICCLTYC FAPRCRE                                       27

SEQ ID NO: 29           moltype = DNA   length = 66
FEATURE                 Location/Qualifiers
misc_feature            1..66
                        note = P2A self-cleaving peptide
source                  1..66
                        mol_type = other DNA
                        organism = synthetic construct
SEQUENCE: 29
ggcagcggcg ccaccaactt ctccctgctg aagcaggccg gcgacgtgga agaaaaccct    60
ggcccc                                                              66

SEQ ID NO: 30           moltype = AA    length = 22
FEATURE                 Location/Qualifiers
REGION                  1..22
                        note = P2A self-cleaving peptide
source                  1..22
                        mol_type = protein
                        organism = synthetic construct
SEQUENCE: 30
GSGATNFSLL KQAGDVEENP GP                                            22

SEQ ID NO: 31           moltype = DNA   length = 63
FEATURE                 Location/Qualifiers
misc_feature            1..63
                        note = CD8a signal peptide
source                  1..63
                        mol_type = other DNA
                        organism = synthetic construct
SEQUENCE: 31
atggccttac cagtgaccgc cttgctcctg ccgctggcct tgctgctcca cgccgccagg    60
ccg                                                                 63

SEQ ID NO: 32           moltype = AA    length = 21
FEATURE                 Location/Qualifiers
REGION                  1..21
                        note = CD8a signal peptide
source                  1..21
                        mol_type = protein
                        organism = synthetic construct
SEQUENCE: 32
MALPVTALLL PLALLLHAAR P                                             21

SEQ ID NO: 33           moltype = DNA   length = 327
FEATURE                 Location/Qualifiers
misc_feature            1..327
                        note = Anti-CD3 Light chain variable region
source                  1..327
                        mol_type = other DNA
                        organism = synthetic construct
```

```
SEQUENCE: 33
gacatccaga tgacccagac cacctcctcc ctgtctgcct ctctgggaga cagagtcacc    60
atcagttgca gggcaagtca ggacattaga aattatttaa actggtatca acagaaacca   120
gatggaactg ttaaactcct gatctactac acatcaagat tacactcagg agtcccatca   180
aagttcagtg gcagtgggtc tgggacagat tattctctca ccattagcaa cctggagcaa   240
gaggatattg ccacttactt ttgccaacag ggtaatacgc ttccgtggac gttcgctgga   300
ggcaccaagc tggaaatcaa acgggct                                       327

SEQ ID NO: 34               moltype = AA   length = 109
FEATURE                     Location/Qualifiers
REGION                      1..109
                            note = Anti-CD3 Light chain variable region
source                      1..109
                            mol_type = protein
                            organism = synthetic construct
SEQUENCE: 34
DIQMTQTTSS LSASLGDRVT ISCRASQDIR NYLNWYQQKP DGTVKLLIYY TSRLHSGVPS     60
KFSGSGSGTD YSLTISNLEQ EDIATYFCQQ GNTLPWTFAG GTKLEIKRA               109

SEQ ID NO: 35               moltype = DNA   length = 48
FEATURE                     Location/Qualifiers
misc_feature                1..48
                            note = G3S linker
source                      1..48
                            mol_type = other DNA
                            organism = synthetic construct
SEQUENCE: 35
ggaggcggta gtggcggtgg atcaggtgga ggcagcggtg gcggatct                 48

SEQ ID NO: 36               moltype = AA   length = 16
FEATURE                     Location/Qualifiers
REGION                      1..16
                            note = G3S linker
source                      1..16
                            mol_type = protein
                            organism = synthetic construct
SEQUENCE: 36
GGGSGGGSGG GSGGGS                                                    16

SEQ ID NO: 37               moltype = DNA   length = 366
FEATURE                     Location/Qualifiers
misc_feature                1..366
                            note = Anti-CD3 heavy chain variable region
source                      1..366
                            mol_type = other DNA
                            organism = synthetic construct
SEQUENCE: 37
gaggtgcagc tccagcagtc tggacctgag ctggtgaagc ctggagcttc aatgaagata    60
tcctgcaagg cttctggtta ctcattcact ggctacacca tgaactgggt gaagcagagt   120
catggaaaga accttgagtg gatgggactt attaatcctt acaaaggtgt tagtacctac   180
aaccagaagt tcaaggacaa ggccacatta actgtagaca agtcatccag cacagcctac   240
atggaactcc tcagtctgac atctgaggac tctgcagtct attactgtgc aagatcgggg   300
tactacggtg atagtgactg gtacttcgat gtctggggcg cagggaccac ggtcaccgtc   360
tcctca                                                              366

SEQ ID NO: 38               moltype = AA   length = 122
FEATURE                     Location/Qualifiers
REGION                      1..122
                            note = Anti-CD3 heavy chain variable region
source                      1..122
                            mol_type = protein
                            organism = synthetic construct
SEQUENCE: 38
EVQLQQSGPE LVKPGASMKI SCKASGYSFT GYTMNWVKQS HGKNLEWMGL INPYKGVSTY     60
NQKFKDKATL TVDKSSSTAY MELLSLTSED SAVYYCARSG YYGDSDWYFD VWGAGTTVTV   120
SS                                                                  122

SEQ ID NO: 39               moltype = DNA   length = 207
FEATURE                     Location/Qualifiers
misc_feature                1..207
                            note = CD8a hinge and transmembrane
source                      1..207
                            mol_type = other DNA
                            organism = synthetic construct
SEQUENCE: 39
accactacac cagcacctag accaccaaca cctcgcgcca accatcgcatc gcagccactg    60
tctctgcgcc cagaggcatg ccggccagca gctgggggcg cagtgcacac aaggggggctg   120
gacttcgcat gtgatatcta catctgggca ccattggcag ggacttgtgg ggtccttctc   180
ctgtcactgg ttatcaccct ttactgc                                       207
```

```
SEQ ID NO: 40           moltype = AA  length = 69
FEATURE                 Location/Qualifiers
REGION                  1..69
                        note = CD8a hinge and transmembrane
source                  1..69
                        mol_type = protein
                        organism = synthetic construct
SEQUENCE: 40
TTTPAPRPPT PAPTIASQPL SLRPEACRPA AGGAVHTRGL DFACDIYIWA PLAGTCGVLL   60
LSLVITLYC                                                           69

SEQ ID NO: 41           moltype = DNA  length = 1458
FEATURE                 Location/Qualifiers
misc_feature            1..1458
                        note = Anti-CD19 CAR molecule
source                  1..1458
                        mol_type = other DNA
                        organism = synthetic construct
SEQUENCE: 41
atggccttac cagtgaccgc cttgctcctg ccgctggcct tgctgctcca cgccgccagg   60
ccggacatcc agatgacaca gactacatcc tccctgtctg cctctctggg agacagagtc  120
accatcagtt gcagggcaag tcaggacatt agtaaatatt taaattggta tcagcagaaa  180
ccagatggaa ctgttaaact cctgatctac catacatcaa gattacactc aggagtccca  240
tcaaggttca gtggcagtgg gtctggaaca gattattctc tcaccattag caacctggag  300
caagaagata ttgccactta cttttgccaa cagggtaata cgcttccgta cacgttcgga  360
ggggggacca agctggagat cacaggtgga ggtggatcgg gcggtggtgg gtcgggtggc  420
ggcggatctg aggtgaaact gcaggagtca ggacctggcc tggtggcgcc ctcacagagc  480
ctgtccgtca catgcactgt ctcaggggtc tcattacccg actatggtgt aagctggatt  540
cgccagcctc cacgaaaggg tctggagtgg ctgggagtaa tatggggtag tgaaaccaca  600
tactataatt cagctctcaa atccagactg accatcatca aggacaactc caagagccaa  660
gttttcttaa aaatgaacag tctgcaaact gatgacacag ccatttacta ctgtgccaaa  720
cattattact acggtggtag ctatgctatg gactactggg gccaaggaac ctcagtcacc  780
gtctcctcaa ccactacacc agcacctaga ccaccaactc cggccagcag ccactgt    840
cagccactgt ctctgcgccc agaggcatgc cggccagcag ctgggggcgc agtgcacaca  900
aggggggctgg acttcgcatg tgatatctac atctgggcac cattggcagg acttgtgggg  960
gtcctttctcc tgtcactggt tatcacccttt actgcaaac ggggcagaaa gaaactcctg 1020
tatatattca aacaaccatt tatgagacca gtacaaacta ctcaagagga gatggctgt 1080
agctgccgat ttcagaagaa agaagaagga ggatgtgaac tgagagtgaa gttcagcagg 1140
agcgcagacg ccccccgcgta caagcaggg cagaaccagc tctataacga gctcaatcta 1200
ggacgaagag aggagtacga tgttttggac aagagacgtg gccgggaccc tgagatgggg 1260
ggaaagccga aaggaagaa ccctcaggaa ggcctgtaca tgaactgca gaaagataag 1320
atggccgagg cctacagtga gattgggatg aaaggcgagc gccggaggg caagggcac 1380
gatggccttt accagggtct cagtacagcc accaaggaca cctacgacgc ccttcacatg 1440
caggccctgc cccctcgc                                                1458

SEQ ID NO: 42           moltype = AA  length = 486
FEATURE                 Location/Qualifiers
REGION                  1..486
                        note = Anti-CD19 CAR molecule
REGION                  1..21
                        note = MISC_FEATURE - signal peptide
source                  1..486
                        mol_type = protein
                        organism = synthetic construct
SEQUENCE: 42
MALPVTALLL PLALLLHAAR PDIQMTQTTS SLSASLGDRV TISCRASQDI SKYLNWYQQK   60
PDGTVKLLIY HTSRLHSGVP SRFSGSGSGT DYSLTISNLE QEDIATYFCQ QGNTLPYTFG  120
GGTKLEITGG GGSGGGGSGG GGSEVKLQES GPGLVAPSQS LSVTCTVSGV SLPDYGVSWI  180
RQPPRKGLEW LGVIWGSETT YYNSALKSRL TIIKDNSKSQ VFLKMNSLQT DDTAIYYCAK  240
HYYYGGSYAM DYWGQGTSVT VSSTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                              486

SEQ ID NO: 43           moltype = DNA  length = 63
FEATURE                 Location/Qualifiers
misc_feature            1..63
                        note = CD8a signal peptide
source                  1..63
                        mol_type = other DNA
                        organism = synthetic construct
SEQUENCE: 43
atggccttac cagtgaccgc cttgctcctg ccgctggcct tgctgctcca cgccgccagg   60
ccg                                                                 63

SEQ ID NO: 44           moltype = AA  length = 21
FEATURE                 Location/Qualifiers
```

```
REGION                  1..21
                        note = CD8a signal peptide
source                  1..21
                        mol_type = protein
                        organism = synthetic construct
SEQUENCE: 44
MALPVTALLL PLALLLHAAR P                                              21

SEQ ID NO: 45           moltype = DNA  length = 321
FEATURE                 Location/Qualifiers
misc_feature            1..321
                        note = Anti-CD19 light chain variable region
source                  1..321
                        mol_type = other DNA
                        organism = synthetic construct
SEQUENCE: 45
gacatccaga tgacacagac tacatcctcc ctgtctgcct ctctgggaga cagagtcacc      60
atcagttgca gggcaagtca ggacattagt aaatatttaa attggtatca gcagaaacca    120
gatggaactg ttaaactcct gatctaccat acatcaagat tacactcagg agtcccatca    180
aggttcagtg gcagtgggtc tggaacagat tattctctca ccattagcaa cctggagcaa    240
gaagatattg ccacttactt ttgccaacag ggtaatacgc ttccgtacac gttcggaggg    300
gggaccaagc tggagatcac a                                              321

SEQ ID NO: 46           moltype = AA  length = 107
FEATURE                 Location/Qualifiers
REGION                  1..107
                        note = Anti-CD19 light chain variable region
source                  1..107
                        mol_type = protein
                        organism = synthetic construct
SEQUENCE: 46
DIQMTQTTSS LSASLGDRVT ISCRASQDIS KYLNWYQQKP DGTVKLLIYH TSRLHSGVPS     60
RFSGSGSGTD YSLTISNLEQ EDIATYFCQQ GNTLPYTFGG GTKLEIT                 107

SEQ ID NO: 47           moltype = DNA  length = 45
FEATURE                 Location/Qualifiers
misc_feature            1..45
                        note = G4S Linker
source                  1..45
                        mol_type = other DNA
                        organism = synthetic construct
SEQUENCE: 47
ggtggaggtg gatcgggcgg tggtgggtcg ggtggcggcg gatct                     45

SEQ ID NO: 48           moltype = AA  length = 15
FEATURE                 Location/Qualifiers
REGION                  1..15
                        note = G4S Linker
source                  1..15
                        mol_type = protein
                        organism = synthetic construct
SEQUENCE: 48
GGGGSGGGGS GGGGS                                                      15

SEQ ID NO: 49           moltype = DNA  length = 360
FEATURE                 Location/Qualifiers
misc_feature            1..360
                        note = Anti-CD19 heavy chain variable region
source                  1..360
                        mol_type = other DNA
                        organism = synthetic construct
SEQUENCE: 49
gaggtgaaac tgcaggagtc aggacctggc ctggtggcgc cctcacagag cctgtccgtc     60
acatgcactg tctcagggg ctcattaccc gactatgtg taagctggat tcgccagcct    120
ccacgaaagg gtctggagtg gctgggagta atatgggta gtgaaaccac atactataat    180
tcagctctca aatccagact gaccatcatc aaggacaact ccaagagcca gttttctta    240
aaaatgaaca gtctgcaaac tgatgacaca gccatttact actgtgccaa acattattac    300
tacggtggta gctatgctat ggactactgg ggccaaggaa cctcagtcac cgtctcctca    360

SEQ ID NO: 50           moltype = AA  length = 120
FEATURE                 Location/Qualifiers
REGION                  1..120
                        note = Anti-CD19 heavy chain variable region
source                  1..120
                        mol_type = protein
                        organism = synthetic construct
SEQUENCE: 50
EVKLQESGPG LVAPSQSLSV TCTVSGVSLP DYGVSWIRQP PRKGLEWLGV IWGSETTYYN     60
SALKSRLTII KDNSKSQVFL KMNSLQTDDT AIYYCAKHYY YGGSYAMDYW GQGTSVTVSS    120
```

```
SEQ ID NO: 51              moltype = DNA  length = 207
FEATURE                    Location/Qualifiers
misc_feature               1..207
                           note = CD8a Hinge and Transmembrane
source                     1..207
                           mol_type = other DNA
                           organism = synthetic construct
SEQUENCE: 51
accactacac cagcacctag accaccaaca cctgcgccaa ccatcgcatc gcagccactg    60
tctctgcgcc cagaggcatg ccggccagca gctgggggcg cagtgcacac aaggggggctg  120
gacttcgcat gtgatatcta catctgggca ccattggcag ggacttgtgg ggtccttctc  180
ctgtcactgg ttatcaccct ttactgc                                      207

SEQ ID NO: 52              moltype = AA  length = 69
FEATURE                    Location/Qualifiers
REGION                     1..69
                           note = CD8a Hinge and Transmembrane
source                     1..69
                           mol_type = protein
                           organism = synthetic construct
SEQUENCE: 52
TTTPAPRPPT PAPTIASQPL SLRPEACRPA AGGAVHTRGL DFACDIYIWA PLAGTCGVLL    60
LSLVITLYC                                                           69

SEQ ID NO: 53              moltype = DNA  length = 126
FEATURE                    Location/Qualifiers
misc_feature               1..126
                           note = 4-1BB costimulatory domain
source                     1..126
                           mol_type = other DNA
                           organism = synthetic construct
SEQUENCE: 53
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

SEQ ID NO: 54              moltype = AA  length = 42
FEATURE                    Location/Qualifiers
REGION                     1..42
                           note = 4-1BB costimulatory domain
source                     1..42
                           mol_type = protein
                           organism = synthetic construct
SEQUENCE: 54
KRGRKKLLYI FKQPFMRPVQ TTQEEDGCSC RFPEEEEGGC EL                      42

SEQ ID NO: 55              moltype = DNA  length = 336
FEATURE                    Location/Qualifiers
misc_feature               1..336
                           note = CD3 zeta effector domain no. 1
source                     1..336
                           mol_type = other DNA
                           organism = synthetic construct
SEQUENCE: 55
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc    240
cggaagggca aggggcacga tggcctttac caggtctcag tacgccac caaggacacc     300
tacgacgccc ttcacatgca ggccctgccc cctcgc                             336

SEQ ID NO: 56              moltype = AA  length = 112
FEATURE                    Location/Qualifiers
REGION                     1..112
                           note = CD3 zeta effector domain no. 1
source                     1..112
                           mol_type = protein
                           organism = synthetic construct
SEQUENCE: 56
RVKFSRSADA PAYKQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 57              moltype = DNA  length = 1479
FEATURE                    Location/Qualifiers
misc_feature               1..1479
                           note = Anti-BCMA CAR full molecule
source                     1..1479
                           mol_type = other DNA
```

```
                          organism = synthetic construct
SEQUENCE: 57
atggcactcc ccgtcaccgc ccttctcttg cccctcgccc tgctgctgca tgctgccagg    60
cccgacattg tgctcactca gtcacctccc agcctggcca tgagcctggg aaaaagggcc   120
accatctcct gtagagccag tgagtccgtc acaatcttgg ggagccatct tattcactgg   180
tatcagcaga agcccgggca gcctccaacc cttcttattc agctcgcgtc aaacgtccag   240
acgggtgtac ctgccagatt ttctggtagc gggtcccgca ctgattttac actgaccata   300
gatccagtgg aagaagacga tgtggccgtg tattattgtc tgcagagcag aacgattcct   360
cgcacatttg gtggggtac taagctggag attaagggaa gcacgtccgg ctcagggaag   420
ccgggctccg gcgagggaag cacgagggg caaattcagc tggtccagag cggacctgag   480
ctgaaaaaac ccggcgagac tgttaagatc agttgtaaag catctggcta ccttcacc    540
gactacagca taaattgggt gaaacgagcc cctggaaagg cctcaaatg gatgggttgg   600
atcaataccg aaactaggga gcctgcttat gcatatgact tccgcgggag attcgccttt   660
tcactcgaga catctgcctc tactgcttac ctccaaataa caacctcaa gtatgaagat   720
acagccactt acttttgcgc cctcgactat agttacgcca tggactactg gggacaggga   780
acctccgtta ccgtcagttc cgcggccgca accacaacac tgctccaag gccccccaca    840
cccgctccaa ctatagccag ccaaccattg agcctcagac tgaagcttg caggcccgca   900
gcaggaggcg ccgtccatac gcgaggcctg gacttcgcgt gtgatattta tatttgggca   960
cctttggccg gaacatgtgg ggtgttgctt ctctcccttg tgatcactct gtattgtaag   1020
cgcgggagaa agaagctcct gtacatcttc aagcagcctt ttatgcgacc tgtgcaaacc   1080
actcaggaag aagatgggtg ttcatgccgc ttccccgagg aggaagaagg agggtgtgaa   1140
ctgagggtga aattttctag aagcgccgat gctcccgcat atcagcaggg tcagaatcag   1200
ctctacaatg aattgaatct cggcaggcga aagagtacg atgttctgga caagagacgg   1260
gcagggatc ccgagatggg gggaaagccc cggagaaaaa atcctcagga ggggttgtac   1320
aatgagctgc agaaggacaa gatggctgaa gcctatagcg agatcggaat gaaaggcgaa   1380
agacgcagag gcaaggggca tgacggtctg taccagggtc tctctacagc caccaaggac   1440
acttatgatg cgttgcatat gcaagccttg ccaccccgc                          1479

SEQ ID NO: 58                moltype = AA   length = 493
FEATURE                      Location/Qualifiers
REGION                       1..493
                             note = Anti-BCMA CAR full molecule
REGION                       1..21
                             note = MISC_FEATURE - signal peptide
source                       1..493
                             mol_type = protein
                             organism = synthetic construct
SEQUENCE: 58
MALPVTALLL PLALLLHAAR PDIVLTQSPP SLAMSLGKRA TISCRASESV TILGSHLIHW    60
YQQKPGQPPT LLIQLASNVQ TGVPARFSGS GSRTDFTLTI DPVEEDDVAV YYCLQSRTIP   120
RTFGGGTKLE IKGSTSGSGK PGSGEGSTKG QIQLVQSGPE LKKPGETVKI SCKASGYTFT   180
DYSINWVKRA PGKGLKWMGW INTETREPAY AYDFRGRFAF SLETSASTAY LQINNLKYED   240
TATYFCALDY SYAMDYWGQG TSVTVSSAAA TTTPAPRPPT PAPTIASQPL SLRPEACRPA   300
AGGAVHTRGL DFACDIYIWA PLAGTCGVLL LSLVITLYCK RGRKKLLYIF KQPFMRPVQT   360
TQEEDGCSCR FPEEEEGGCE LRVKFSRSAD APAYQQGQNQ LYNELNLGRR EEYDVLDKRR   420
GRDPEMGGKP RRKNPQEGLY NELQKDKMAE AYSEIGMKGE RRRGKGHDGL YQGLSTATKD   480
TYDALHMQAL PPR                                                      493

SEQ ID NO: 59                moltype = DNA   length = 63
FEATURE                      Location/Qualifiers
misc_feature                 1..63
                             note = CD8a signal peptide
source                       1..63
                             mol_type = other DNA
                             organism = synthetic construct
SEQUENCE: 59
atggcactcc ccgtcaccgc ccttctcttg cccctcgccc tgctgctgca tgctgccagg    60
ccc                                                                  63

SEQ ID NO: 60                moltype = AA   length = 21
FEATURE                      Location/Qualifiers
REGION                       1..21
                             note = CD8a signal peptide
source                       1..21
                             mol_type = protein
                             organism = synthetic construct
SEQUENCE: 60
MALPVTALLL PLALLLHAAR P                                              21

SEQ ID NO: 61                moltype = DNA   length = 333
FEATURE                      Location/Qualifiers
misc_feature                 1..333
                             note = Anti-BCMA light chain variable region
source                       1..333
                             mol_type = other DNA
                             organism = synthetic construct
SEQUENCE: 61
gacattgtgc tcactcagtc acctcccagc ctggccatga gcctgggaaa aagggccacc    60
atctcctgta gagccagtga gtccgtcaca atcttgggga gccatcttat tcactggtat   120
```

```
cagcagaagc ccgggcagcc tccaaccctt cttattcagc tcgcgtcaaa cgtccagacg    180
ggtgtacctg ccagattttc tggtagcggg tcccgcactg attttacact gaccatagat    240
ccagtggaag aagacgatgt ggccgtgtat tattgtctgc agagcagaac gattcctcgc    300
acatttggtg ggggtactaa gctggagatt aag                                 333

SEQ ID NO: 62          moltype = AA   length = 111
FEATURE                Location/Qualifiers
REGION                 1..111
                       note = Anti-BCMA light chain variable region
source                 1..111
                       mol_type = protein
                       organism = synthetic construct
SEQUENCE: 62
DIVLTQSPPS LAMSLGKRAT ISCRASESVT ILGSHLIHWY QQKPGQPPTL LIQLASNVQT     60
GVPARFSGSG SRTDFTLTID PVEEDDVAVY YCLQSRTIPR TFGGGTKLEI K             111

SEQ ID NO: 63          moltype = DNA   length = 54
FEATURE                Location/Qualifiers
misc_feature           1..54
                       note = 218 Linker
source                 1..54
                       mol_type = other DNA
                       organism = synthetic construct
SEQUENCE: 63
ggaagcacgt ccggctcagg gaagccgggc tccggcgagg gaagcacgaa gggg           54

SEQ ID NO: 64          moltype = AA   length = 18
FEATURE                Location/Qualifiers
REGION                 1..18
                       note = 218 Linker
source                 1..18
                       mol_type = protein
                       organism = synthetic construct
SEQUENCE: 64
GSTSGSGKPG SGEGSTKG                                                   18

SEQ ID NO: 65          moltype = DNA   length = 351
FEATURE                Location/Qualifiers
misc_feature           1..351
                       note = Anti-BCMA heavy chain variable region
source                 1..351
                       mol_type = other DNA
                       organism = synthetic construct
SEQUENCE: 65
caaattcagc tggtccagag cggacctgag ctgaaaaaac ccggcgagac tgttaagatc     60
agttgtaaag catctggcta taccttcacc gactacagca taaattgggt gaaacgagcc    120
cctggaaagg gcctcaaatg gatgggttgg atcaatacag aaactaggga gcctgcttat    180
gcatatgact tccgcgggag attcgccttt tcactcgaga catctgcctc tactgcttac    240
ctccaaataa acaacctcaa gtatgaagat acagccactt acttttgcgc cctcgactat    300
agttacgcca tggactactg gggacaggga acctccgtta ccgtcagttc c             351

SEQ ID NO: 66          moltype = AA   length = 117
FEATURE                Location/Qualifiers
REGION                 1..117
                       note = Anti-BCMA heavy chain variable region
source                 1..117
                       mol_type = protein
                       organism = synthetic construct
SEQUENCE: 66
QIQLVQSGPE LKKPGETVKI SCKASGYTFT DYSINWVKRA PGKGLKWMGW INTETREPAY     60
AYDFRGRFAF SLETSASTAY LQINNLKYED TATYFCALDY SYAMDYWGQG TSVTVSS       117

SEQ ID NO: 67          moltype = DNA   length = 2610
FEATURE                Location/Qualifiers
misc_feature           1..2610
                       note = Anti-CD3 targeting molecule co-expressed with mutant
                       VSV-G Full molecule
source                 1..2610
                       mol_type = other DNA
                       organism = synthetic construct
SEQUENCE: 67
atggccttac cagtgaccgc cttgctcctg ccgctggcct tgctgctcca cgccgccagg     60
ccggacatcc agatgaccca gaccacctcc tccctgtctg cctctctggg agacagagtc    120
accatcagtt gcagggcaag tcaggacatt agaaattatt taaactggta tcaacagaaa    180
ccagatggaa ctgttaaact cctgatctac tacacatcaa gattactctc aggagtccca    240
tcaaagttca gtggcagtgg gtctggaaca gattattctc tcaccattag caacctggag    300
caagaggata ttgccactta cttttgccaa cagggtaata cgcttccgtg acgttcgct     360
ggaggcacca agctggaaat caaacggggct ggaggcggta gtggcggtgg atcaggtgga    420
ggcagcggtg gcggatctga ggtgcagctc cagcagtctg acctgagct ggtgaagcct     480
```

```
ggagcttcaa tgaagatatc ctgcaaggct tctggttact cattcactgg ctacaccatg   540
aactgggtga agcagagtca tggaaagaac cttgagtgga tgggacttat taatccttac   600
aaaggtgtta gtacctacaa ccagaagttc aaggacaagg ccacattaac tgtagacaag   660
tcatccagca cagcctacat ggaactcctc agtctgacat ctgaggactc tgcagtctat   720
tactgtgcaa gatcggggta ctacggtgat agtgactggt acttcgatgt ctggggcgca   780
gggaccacgg tcaccgtctc ctcaaccact acaccagcac ctagaccacc aacacctgcg   840
ccaaccatcg catcgcagcc actgtctctg cgcccagagg catgccggcc agcagctggg   900
ggcgcagtgc acacaagggg gctggacttc gcatgtgata tctacatctg ggcaccattg   960
gcagggactt gtggggtcct tctcctgtca ctggttatca ccctttactg cggcagcggc  1020
gccaccaact tctccctgct gaagcaggcc ggcgacgtgg aagaaaaccc tggcccatg   1080
aagtgtctgc tgtacctggc gttcctgttt atcggggtga actgcaagtt cactatcgtg  1140
tttccgcaca accaaagggg caactggaaa acgtgccttc aaattaccat tattgcccc   1200
agcagctcgg acctgaactg gcacaatgac ctcattggaa ccgcgctgca ggtgaagatg  1260
ccacagagcc acaaggctat ccaggctgac ggatgatgt gccacgcgtc aaaatgggtg  1320
actacctgcg atttccgctg gtacggacca aaatacatca cgcacagcat cagatcattc  1380
acccccgtca gtggaacaatg caagaatcc atcgaacaga ctaagcaggg aacctggctg  1440
aaccctggat ttccgccgca gtcgtgtggg tacgcaaccg tgaccgatgc agaggccgtg  1500
atcgtgcaag tcacgccgca tcacgtgctt gtggacgagt acacggagga tgggtcgtg  1560
tcccagttca tcaacggcaa gtgctccaac tacatttgcc caaccgtgca caacagcact  1620
acttggcata cgactacaa agtgaagggt ctgtgtgatt ccaacctgat ctccatggat  1680
atcactttct tctcggaaga cggcgaactg tcctcactgg gcaagaagg aactgggttt  1740
cgctcaaatt acttcgccta cgaaactgga ggaaaagcct agaaaatgac gtactgcaag  1800
cactggggcg tgagactacc cagcggtgtc tggttcgaga tggccgataa ggacctgttt  1860
gcagcagcga gattcccgga atgccctgag ggatcgagca tctccgctcc aagccaaact  1920
tcagtggacg tgagcctgat ccaggacgtg gaacggattc tcgactactc gctgtgccag  1980
gagacctggt cgaagatcag agcgggactg cccatctcac gtcctacctg  2040
gcgccaaaga atccgggcac tggaccggcg ttcaccatca tcaacggcac cctcaaatac  2100
tcgagacgc ggtacatccg ggtggacatc gcagctccga tcctctcccg gatggtggga  2160
atgatctcgg ggactactac cgaagccgag ctctgggacg actgggcacc ttacgaggat  2220
gtcgagatcg gacctaacgg aagtgctccgg accttcctccg ggtacaagtt ccctctgtac  2280
atgatcggcc atggcatgct ggactcggat ctgcatctgt cgtccaaagc acaggtgttt  2340
gaacacccac acattcaaga cgccgccagc cagctgccgg acgatgagtc gctgttcttc  2400
ggagacacgg gcttgtcaaa gaatcccatc gagctggtgg aaggatggtt ttcatcctgg  2460
aaaagcagca tcgcttcatt cttcttcatc attggcctga tcatcggcct atttctagtc  2520
ctgcgggtgg gaattcatct gtgcatcaag ctcaagcaca ctaagaagcg gcaaatctac  2580
actgatatcg agatgaatcg cctgggcaag                                   2610

SEQ ID NO: 68         moltype = AA  length = 870
FEATURE               Location/Qualifiers
REGION                1..870
                      note = Anti-CD3 targeting molecule co-expressed with mutant
                      VSV-G Full molecule
REGION                1..21
                      note = MISC_FEATURE - signal peptide
source                1..870
                      mol_type = protein
                      organism = synthetic construct
SEQUENCE: 68
MALPVTALLL PLALLLHAAR PDIQMTQTTS SLSASLGDRV TISCRASQDI RNYLNWYQQK    60
PDGTVKLLIY YTSRLHSGVP SKFSGSGSGT DYSLTISNLE QEDIATYFCQ QGNTLPWTFA   120
GGTKLEIKRA GGGSGGGSGG GSGGGSEVQL QQSGPELVKP GASMKISCKA SGYSFTGYTM   180
NWVKQSHGKN LEWMGLINPY KGVSTYNQKF KDKATLTVDK SSSTAYMELL SLTSEDSAVY   240
YCARSGYYGD SDWYFDVWGA GTTVTVSSTT TPAPRPPTPA PTIASQPLSL RPEACRPAAG   300
GAVHTRGLDF ACDIYIWAPL AGTCGVLLLS LVITLYCGSG ATNFSLLKQA GDVEENPGPM   360
KCLLYLAFLF IGVNCKFTIV FPHNQKGNWK NVPSNYHYCP SSSDLNWHND LIGTALQVKM   420
PQSHKAIQAD GWMCHASKWV TTCDFRWYGP KYITHSIRSF TPSVEQCKES IEQTKQGTWL   480
NPGFPPQSCG YATVTDAEAV IVQVTPHHVL VDEYTGEWVD SQFINGKCSN YICPTVHNST   540
TWHSDYKVKG LCDSNLISMD ITFFSEDGEL SSLGKEGTGF RSNYFAYETG GKACKMQYCK   600
HWGVRLPSGV WFEMADKDLF AAARFPECPE GSSISAPSQT SVDVSLIQDV ERILDYSLCQ   660
ETWSKIRAGL PISPVDLSYL APKNPGTGPA FTIINGTLKY FETRYIRVDI AAPILSRMVG   720
MISGTTTEAE LWDDWAPYED VEIGPNGVLR TSSGYKFPLY MIGHGMLDSD LHLSSKAQVF   780
EHPHIQDAAS QLPDDESLFF GDTGLSKNPI ELVEGWFSSW KSSIASFFFI IGLIIGLFLV   840
LRVGIHLCIK LKHTKKRQIY TDIEMNRLGK                                   870

SEQ ID NO: 69         moltype = DNA  length = 66
FEATURE               Location/Qualifiers
misc_feature          1..66
                      note = P2A self-cleaving peptide
source                1..66
                      mol_type = other DNA
                      organism = synthetic construct
SEQUENCE: 69
ggcagcggcg ccaccaactt ctccctgctg aagcaggccg gcgacgtgga agaaaaccct    60
ggcccc                                                              66

SEQ ID NO: 70         moltype = AA  length = 22
FEATURE               Location/Qualifiers
REGION                1..22
                      note = P2A self-cleaving peptide
```

-continued

```
source                  1..22
                        mol_type = protein
                        organism = synthetic construct
SEQUENCE: 70
GSGATNFSLL KQAGDVEENP GP                                      22

SEQ ID NO: 71           moltype = DNA  length = 48
FEATURE                 Location/Qualifiers
misc_feature            1..48
                        note = VSV-G signal sequence
source                  1..48
                        mol_type = other DNA
                        organism = synthetic construct
SEQUENCE: 71
atgaagtgtc tgctgtacct ggcgttcctg tttatcgggg tgaactgc          48

SEQ ID NO: 72           moltype = AA  length = 16
FEATURE                 Location/Qualifiers
REGION                  1..16
                        note = VSV-G signal sequence
source                  1..16
                        mol_type = protein
                        organism = synthetic construct
SEQUENCE: 72
MKCLLYLAFL FIGVNC                                             16

SEQ ID NO: 73           moltype = DNA  length = 1485
FEATURE                 Location/Qualifiers
misc_feature            1..1485
                        note = Mutant VSV-G (Trop-002)
source                  1..1485
                        mol_type = other DNA
                        organism = synthetic construct
SEQUENCE: 73
aagttcacta tcgtgtttcc gcacaaccaa aagggcaact ggaaaaacgt gccttcaaat  60
taccattatt gccccagcag ctcggacctg aactggcaca atgacctcat tggaaccgcg  120
ctgcaggtga agatgccaca gagccacaag gctatccagg ctgacggatg gatgtgccac  180
gcgtcaaaat gggtgactac ctgcgatttc cgctggtacg gaccaaaata catcacgcac  240
agcatcagat cattcacccc gtcagtggaa caatgcaaag aatccatcga acagactaag  300
cagggaacct ggctgaaccc tggatttccg ccgcagtcgt gtgggtacgc aaccgtgacc  360
gatgcagagg ccgtgatcgt gcaagtcacg ccgcatcacg tgcttgtgga cgagtacacc  420
ggagaatggg tcgattccca gttcatcaac ggcaagtgct ccaactacat ttgcccaacc  480
gtgcacaaca gcactacttg gcacagcgac tacaaagtga agggtctgtg tgattccaac  540
ctgatctcca tggatatcac tttcttctcg gaagacggcg aactgtcctc actgggcaaa  600
gaaggaactg ggtttcgctc aaattacttc gcctacgaaa ctggaggaaa agcctgcaag  660
atgcagtact gcaagcactg gggcgtgaga ctacccagcg gtgtctggtt cgagatggcc  720
gataaggacc tgtttgcagc agcgagattc ccggaatgcc ctgagggatc gagcatctcc  780
gctccaagcc aaacttcagt ggacgtgagc ctgatccagg acgtggaacg gattctcgac  840
tactcgctgt gccaggagac ctggtcgaag atcagagcgg gactgcccat ctcaccggtg  900
gacctgtcct acctggcgcc aaagaatccg ggcactggac cggcgttcac catcatcaac  960
ggcaccctca aatacttcga gacgcggtac atccgggtgg acatcgcagc tccgatcctc  1020
tcccggatgg tgggaatgat ctcggggact actaccgaag ccgagctctg ggacgactgg  1080
gcaccttacg aggatgtcga gatcggacct aacggagtgc tccggacctc ctccgggtac  1140
aagttccctc tgtacatgat cggccatggc atgctggact cggatctgca tctgtcgtcc  1200
aaagcacagg tgtttgaaca cccacacatt caagacgccg ccagccagct gccggacgat  1260
gagtcgctgt tcttcggaga cacgggcttg tcaaagaatc ccatcgagct ggtggaagga  1320
tggttttcat cctggaaaag cagcatcgct tcattcttct tcatcattgg cctgatcatc  1380
ggcctatttc tagtcctgcg ggtgggaatt catctgtgca tcaagctcaa gcacactaag  1440
aagcggcaaa tctacactga tatcgagatg aatcgcctgg gcaag             1485

SEQ ID NO: 74           moltype = AA  length = 495
FEATURE                 Location/Qualifiers
REGION                  1..495
                        note = Mutant VSV-G (Trop-002)
source                  1..495
                        mol_type = protein
                        organism = synthetic construct
SEQUENCE: 74
KFTIVFPHNQ KGNWKNVPSN YHYCPSSSDL NWHNDLIGTA LQVKMPQSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTEAELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                              495

SEQ ID NO: 75           moltype = DNA  length = 2418
```

```
FEATURE                 Location/Qualifiers
misc_feature            1..2418
                        note = CD80 T cell targeting molecule co-expressed with
                         mutant VSV-G Full molecule
source                  1..2418
                        mol_type = other DNA
                        organism = synthetic construct
SEQUENCE: 75
atgggtcata cacgccgcca aggaacctca ccatctaagt gcccatatct gaatttcttt    60
caacttctcg tgctggcggg gctcagtcat ttctgcagtg gggtcattca cgttactaaa   120
gaggtcaagg aggtcgcaac attgagttgt ggccataacg tatcagttga agaactcgcg   180
cagacacgga tttactggca aaaggaaaag aagatggtgt tgacaatgat gagcggtgac   240
atgaacattt ggccagagta caaaaatcga acgatattcg atataaccaa taacttgtcc   300
atagtaatac ttgccttgcg accttctgac gagggaacgt atgaatgtgt agtgcttaag   360
tatgaaaaag atgcctttaa gcgggaacac ttggctgagg ttacactctc cgttaaggcg   420
gactttccta cgccgtctat atccgacttc gagatacccc cttctaacat tcgacgcatc   480
atttgctcaa cctcaggtgg tttcccagag cctcacttga gctggctgga aatggcgaa    540
gaacttaacg caatcaatac cacggtgtcc caagacccgg agacagagct gtacgccgtg   600
tcatccaaac tggatttaa catgacgaca aatcatagtt tcatgtgtct gatcaaatat    660
gggcatctca gggtgaatca gacttttaat tggaacacta ccaaacaaga gcacttccca   720
gataatctgt tgccaagctg gcgataact cttatctccg tcaacggtat cttcgtaatt    780
tgctgcctca cctattgttt cgccgcctcg tgccgagaag gcagcggcgc caccaacttc   840
tccctgctga gcaggccgg cgacgtggaa gaaaaccctg gccccatgaa gtgtctgctg    900
tacctggcgt tcctgtttat cggggtgaac tgcaagttca ctatcgtgtt ccgcacaac    960
caaaagggca actggaaaaa cgtgccttca aattaccatt attgccccag cagctcggac  1020
ctgaactggc acaatgacct cattggaacc gcgctgcagg tgaagatgcc acagagccat  1080
aaggctatcc aggctgacgg atggatgtgc cacgcgtgca aatgggtgac tacctgcgat  1140
ttccgctggt acggaccaaa atacatcacg cacagcatca gatcattcac cccgtcagtg  1200
gaacaatgca agaatccat cgaacagact aagcagggaa cctggctgaa ccctggattt   1260
ccgccgcagt cgtgtgggta cgcaaccgtg accgatgaag cggccgtagt cgtgcaagtc  1320
acgccgcatc acgtgcttgt ggacgagtac accggagaat gggtcgattc ccagttcatc  1380
aacggcaagt gctccaacta catttgccca accgtgcaca acagcactac ttggcacagc  1440
gactacaaag tgaagggtct gtgtgattcc aacctgatct ccatggatat cactttcttc  1500
tcggaagacg gcgaactgtc tcactgggc aaagaaggaa ctgggtttcg ctcaaattac   1560
ttcgcctacg aaactggagg aaaagcctgc aagatgcagt actgcaagca ctggggcgtg  1620
agactaccca cgcgtgtctg gttcgagatg gccgataagg acctgtttgc agcagcgaga  1680
ttcccggaat gccctgaggg atcgagcatc tccgctccaa gccaaacttc agtggacgtg  1740
agcctgatcc aggacgtgga acggattctc gactactcgc tgtgccagga gacctggtcg  1800
aagatcagag cgggactgcc catctcaccg gtggacctgt cctacctggc gccaaagaat  1860
ccgggcactg gaccgcgtt caccatcatc aacggcaccc tcaaatactt cgagacgcgg  1920
tacatccggg tggacatcgc agctccgatc ctctcccgga tggtgggaat gatctcgggg  1980
actactaccg aagccgagct ctgggacgac tgggcacctt acgaggatgt cgagatcgga  2040
cctaacggag tgctccggac ctcctccggg tacaagttcc tctgtacat gatcggccat   2100
ggcatgctgg actcggatct gcatctgtcg tccaaagcac aggtgtttga acacccacac  2160
attcaagacg ccgccagcca gctgccggac gatgagtcgc tgttcttcgg agacacgggc  2220
ttgtcaaaga atcccatcga gctggtgaa ggatggtttt catcctggaa aagcagcatc   2280
gcttcattct tcttcatcat tggcctgatc atcggcctac ttcagtcct gcgggtggga    2340
attcatctgt gcatcaagct caagcacact aagaagcggc aaatctacac tgatatcgag  2400
atgaatcgcc tgggcaag                                                 2418

SEQ ID NO: 76           moltype = AA  length = 806
FEATURE                 Location/Qualifiers
REGION                  1..806
                        note = CD80 T cell targeting molecule co-expressed with
                         mutant VSV-G Full molecule
REGION                  1..35
                        note = MISC_FEATURE - signal sequence
source                  1..806
                        mol_type = protein
                        organism = synthetic construct
SEQUENCE: 76
MGHTRRQGTS PSKCPYLNFF QLLVLAGLSH FCSGVIHVTK EVKEVATLSC GHNVSVEELA    60
QTRIYWQKEK KMVLTMMSGD MNIWPEYKNR TIFDITNNLS IVILALRPSD EGTYECVVLK   120
YEKDAFKREH LAEVTLSVKA DFPTPSISDF EIPTSNIRRI ICSTSGGFPE PHLSWLENGE   180
ELNAINTTVS QDPETELYAV SSKLDFNMTT NHSFMCLIKY GHLRVNQTFN WNTTKQEHFP   240
DNLLPSWAIT LISVNGIFVI CCLTYCFAPR CREGSGATNF SLLKQAGDVE ENPGPMKCLL   300
YLAFLFIGVN CKFTIVFPHN QKGNWKNVPS NYHYCPSSSD LNWHNDLIGT ALQVKMPQSH   360
KAIQADGWMC HASKWVTTCD FRWYGPKYIT HSIRSFTPSV EQCKESIEQT KQGTWLNPGF   420
PPQSCGYATV TDAEAVIVQV TPHHVLDEY TGEWVDSQFI NGKCSNYICP TVHNSTTWHS    480
DYKVKGLCDS NLISMDITFF SEDGELSSLG KEGTGFRSNY FAYETGGKAC KMQYCKHWGV   540
RLPSGVWFEM ADKDLFAAAR FPECPEGSSI SAPSQTSVDV SLIQDVERIL DYSLCQETWS   600
KIRAGLPISP VDLSYLAPKN PGTGPAFTII NGTLKYFETR YIRVDIAAPI LSRMVGMISG   660
TTTEAELWDD WAPYEDVEIG PNGVLRTSSG YKFPLYMIGH GMLDSDLHLS SKAQVFEHPH   720
IQDAASQLPD DESLFFGDTG LSKNPIELVE GWFSSWKSSI ASFFFIIGLI IGLFLVLRVG   780
IHLCIKLKHT KKRQIYTDIE MNRLGK                                        806

SEQ ID NO: 77           moltype = DNA  length = 1533
FEATURE                 Location/Qualifiers
misc_feature            1..1533
```

```
                        note = WT VSV-G
source                  1..1533
                        mol_type = other DNA
                        organism = synthetic construct
SEQUENCE: 77
atgaagtgtc tgctgtacct ggcgttcctg tttatcgggg tgaactgcaa gttcactatc    60
gtgtttccgc acaaccaaaa gggcaactgg aaaaacgtgc cttcaaatta ccattattgc   120
cccagcagct cggacctgaa ctggcacaat gacctcattg gaaccgcgct gcaggtgaag   180
atgccaaaga gccacaaggc tatccaggct gacggatgga tgtgccacag gtcaaaatgg   240
gtgactacct gcgatttccg ctggtacgga ccaaaataca tcacgcacag catcagatca   300
ttcaccccgt cagtggaaca atgcaaagaa tccatcgaac agactaagca gggaacctgg   360
ctgaaccctg gatttccgcc gcagtcgtgt gggtacgcaa ccgtgaccga tgcagaggcc   420
gtgatcgtgc aagtcacgcc gcatcacgtg cttgtggacg agtacaccgg agaatgggtc   480
gattcccagt tcatcaacgg caagtgctcc aactacataa gcccaaccgt gcacaacagt   540
actacttggc acagcgacta caaagtgaag ggtctgtgtg attccaacct gatctccatg   600
gatatcactt tcttctcgga agacggcgaa ctgtcctcac tgggcaaaga aggaactggg   660
tttcgctcaa attcttcgc ctacgaaact ggaggaaaag cctgcaagat gcagtactgc   720
aagcactggg gcgtgagact acccagcggt gtctggttcg agatggcgaa taaggacctg   780
tttgcagcag cgagattccc ggaatgcccc gagggatcga gcatctccgc tccaagccaa   840
acttcagtgg acgtgagcct gatccaggac gtggaacgga ttctcgacta ctcgctgtgc   900
caggagacct ggtcgaagat cagagcggga ctgcccatct caccggtgga cctgtcctac   960
ctggcgccaa agaatccggg cactggaccg gcgttcacca tcatcaacgg cacccctcaaa  1020
tacttcgaga cgcggtacat ccgggtggac atcgcagctc cgatcctctc ccggatggtg  1080
ggaatgatct cggggactac taccgaacgc gagctctggg acgactgggc accttacgag  1140
gatgtcgaga tcggacctaa cggagtgctc cggacctcct ccgggtacaa gttccctctg  1200
tacatgatcg gccatggcat gctggactcg gatctgcatc tgtcgtccaa agcacaggtg  1260
tttgaacacc cacacattca agacgccgcc agccagctgc cggacgatga gtcgctgttc  1320
ttcggagaca cgggcttgtc aaagaatccc atcgagctgg tggaaggatg gttttcatcc  1380
tggaaaagca gcatcgcttc attcttcttc atcattggcc tgatcatcgg cctatttcta  1440
gtcctgcggg tgggaattca tctgtgcatc aagctcaagc acactaagaa gcggcaaatc  1500
tacactgata tcgagatgaa tcgcctgggc aag                                1533

SEQ ID NO: 78          moltype = AA  length = 511
FEATURE                Location/Qualifiers
REGION                 1..511
                       note = WT VSV-G
REGION                 1..16
                       note = MISC_FEATURE - signal sequence
source                 1..511
                       mol_type = protein
                       organism = synthetic construct
SEQUENCE: 78
MKCLLYLAFL FIGVNCKFTI VFPHNQKGNW KNVPSNYHYC PSSSDLNWHN DLIGTALQVK    60
MPKSHKAIQA DGWMCHASKW VTTCDFRWYG PKYITHSIRS FTSVEQCKE SIEQTKQGTW    120
LNPGFPPQSC GYATVTDAEA VIVQVTPHHV LVDEYTGEWV DSQFINGKCS NYICPTVHNS   180
TTWHSDYKVK GLCDSNLISM DITFFSEDGE LSSLGKEGTG FRSNYFAYET GGKACKMQYC   240
KHWGVRLPSG VWFEMADKDL FAAARFPECP EGSSISAPSQ TSVDVSLIQD VERILDYSLC   300
QETWSKIRAG LPISPVDLSY LAPKNPGTGP AFTIINGTLK YFETRYIRVD IAAPILSRMV   360
GMISGTTTER ELWDDWAPYE DVEIGPNGVL RTSSGYKFPL YMIGHGMLDS DLHLSSKAQV   420
FEHPHIQDAA SQLPDDESLF FGDTGLSKNP IELVEGWFSS WKSSIASFFF IIGLIIGLFL   480
VLRVGIHLCI KLKHTKKRQI YTDIEMNRLG K                                  511

SEQ ID NO: 79          moltype = AA  length = 18
FEATURE                Location/Qualifiers
REGION                 1..18
                       note = T2A peptide from Thosea asigna virus capsid protein
source                 1..18
                       mol_type = protein
                       organism = synthetic construct
SEQUENCE: 79
EGRGSLLTCG DVEENPGP                                                  18

SEQ ID NO: 80          moltype = DNA  length = 54
FEATURE                Location/Qualifiers
misc_feature           1..54
                       note = T2A peptide from Thosea asigna virus capsid protein
source                 1..54
                       mol_type = other DNA
                       organism = synthetic construct
SEQUENCE: 80
gagggcaggg gaagtcttct aacatgcggg gacgtgagg aaaatcccgg cccc            54

SEQ ID NO: 81          moltype = AA  length = 19
FEATURE                Location/Qualifiers
REGION                 1..19
                       note = P2A peptide from porcine teschovirus-1 polyprotein
source                 1..19
                       mol_type = protein
                       organism = synthetic construct
```

```
SEQUENCE: 81
ATNFSLLKQA GDVEENPGP                                                    19

SEQ ID NO: 82           moltype = DNA  length = 57
FEATURE                 Location/Qualifiers
misc_feature            1..57
                        note = P2A peptide from porcine teschovirus-1 polyprotein
source                  1..57
                        mol_type = other DNA
                        organism = synthetic construct
SEQUENCE: 82
gccacgaact tctctctgtt aaagcaagca ggagacgtgg aagaaaaccc cggtcct       57

SEQ ID NO: 83           moltype = AA   length = 22
FEATURE                 Location/Qualifiers
REGION                  1..22
                        note = F2A peptide from foot-and-mouth disease virus
                         polyprotein
source                  1..22
                        mol_type = protein
                        organism = synthetic construct
SEQUENCE: 83
VKQTLNFDLL KLAGDVESNP GP                                                22

SEQ ID NO: 84           moltype = DNA  length = 66
FEATURE                 Location/Qualifiers
misc_feature            1..66
                        note = F2A peptide from foot-and-mouth disease virus
                         polyprotein
source                  1..66
                        mol_type = other DNA
                        organism = synthetic construct
SEQUENCE: 84
gtgaaacaga ctttgaattt tgaccttctc aagttggcgg gagacgtcga gtccaaccct    60
gggccc                                                                66

SEQ ID NO: 85           moltype = AA   length = 20
FEATURE                 Location/Qualifiers
REGION                  1..20
                        note = E2A peptide from equine rhinitis A virus polyprotein
source                  1..20
                        mol_type = protein
                        organism = synthetic construct
SEQUENCE: 85
QCTNYALLKL AGDVESNPGP                                                   20

SEQ ID NO: 86           moltype = DNA  length = 60
FEATURE                 Location/Qualifiers
misc_feature            1..60
                        note = E2A peptide from equine rhinitis A virus polyprotein
source                  1..60
                        mol_type = other DNA
                        organism = synthetic construct
SEQUENCE: 86
cagtgtacta attatgctct cttgaaattg gctggagatg ttgagagcaa cccaggtccc    60

SEQ ID NO: 87           moltype = DNA  length = 48
FEATURE                 Location/Qualifiers
misc_feature            1..48
                        note = WT VSV-G Signal Sequence
source                  1..48
                        mol_type = other DNA
                        organism = synthetic construct
SEQUENCE: 87
atgaagtgtc tgctgtacct ggcgttcctg tttatcgggg tgaactgc                 48

SEQ ID NO: 88           moltype = AA   length = 16
FEATURE                 Location/Qualifiers
REGION                  1..16
                        note = WT VSV-G Signal Sequence
source                  1..16
                        mol_type = protein
                        organism = synthetic construct
SEQUENCE: 88
MKCLLYLAFL FIGVNC                                                       16

SEQ ID NO: 89           moltype = DNA  length = 1485
FEATURE                 Location/Qualifiers
misc_feature            1..1485
```

-continued

```
                        note = WT VSV-G without signal sequence
source                  1..1485
                        mol_type = other DNA
                        organism = synthetic construct
SEQUENCE: 89
aagttcacta tcgtgtttcc gcacaaccaa aagggcaact ggaaaaacgt gccttcaaat  60
taccattatt gccccagcag ctcggacctg aactggcaca atgacctcat tggaaccgcg  120
ctgcaggtga agatgccaaa gagccacaag gctatccagg ctgacggatg gatgtgccac  180
gcgtcaaaat gggtgactac ctgcgatttc cgctggtacg gaccaaaata catcacgcac  240
agcatcagat cattcacccc gtcagtggaa caatgcaaag aatccatcga acagactaag  300
cagggaacct ggctgaaccc tggatttccg ccgcagtcgt gtgggtacgc aaccgtgacc  360
gatgcagagg ccgtgatcgt gcaagtcacg ccgcatcacg tgcttgtgga cgagtacacc  420
ggagaatggg tcgattccca gttcatcaac ggcaagtgct ccaactacat ttgcccaacc  480
gtgcacaaca gcactacttg gcacagcgac tacaaagtga agggtctgtg tgattccaac  540
ctgatctcca tggatatcac tttcttctcg gaagacggcg aactgtcctc actgggcaaa  600
gaaggaactg ggtttcgctc aaattacttc gcctacgaaa ctggaggaaa agcctgcaag  660
atgcagtact gcaagcactg gggcgtgaga ctacccagcg gtgtctggtt cgagatggcc  720
gataaggacc tgtttgcagc agcgagattc ccggaatgcc ctgagggatc gagcatctcc  780
gctccaagcc aaacttcagt ggacgtgagc ctgatccagg acgtggaacg gattctcgac  840
tactcgctgt gccaggagac ctggtcgaag atcagagcgg gactgcccat ctcaccggtg  900
gacctgtcct acctggcgcc aaagaatccg ggcactggac cggcgttcac catcatcaac  960
ggcaccctca aatacttcga gacgcggtac atccgggtgg acatcgcagc tccgatcctc  1020
tcccggatgg tgggaatgat ctcggggact actaccgaac gcgagctctg ggacgactgg  1080
gcaccttacg aggatgtcga gatcggacct aacggagtgc tccggacctc ctccgggtac  1140
aagttccctc tgtacatgat cggccatggc atgctggact cggatctgca tctgtcgtcc  1200
aaagcacagg tgtttgaaca cccacacatt caagacgccg ccagccagct gccggacgat  1260
gagtcgctgt tcttcggaga cacgggcttg tcaaagaatc ccatcgagct ggtggaagga  1320
tggttttcat cctggaaaag cagcatcgct tcattcttct tcatcattgg cctgatcatc  1380
ggcctatttc tagtcctgcg ggtgggaatt catctgtgca tcaagctcaa gcacactaag  1440
aagcggcaaa tctacactga tatcgagatg aatcgcctgg gcaag             1485

SEQ ID NO: 90           moltype = AA  length = 495
FEATURE                 Location/Qualifiers
REGION                  1..495
                        note = WT VSV-G without signal sequence
source                  1..495
                        mol_type = protein
                        organism = synthetic construct
SEQUENCE: 90
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 91           moltype = DNA  length = 1488
FEATURE                 Location/Qualifiers
misc_feature            1..1488
                        note = Trop-002 Mutated VSV-G
source                  1..1488
                        mol_type = other DNA
                        organism = synthetic construct
SEQUENCE: 91
aagttcacta tcgtgtttcc gcacaaccaa aagggcaact ggaaaaacgt gccttcaaat  60
taccattatt gccccagcag ctcggacctg aactggcaca atgacctcat tggaaccgcg  120
ctgcaggtga agatgccaca gagccacaag gctatccagg ctgacggatg gatgtgccac  180
gcgtcaaaat gggtgactac ctgcgatttc cgctggtacg gaccaaaata catcacgcac  240
agcatcagat cattcacccc gtcagtggaa caatgcaaag aatccatcga acagactaag  300
cagggaacct ggctgaaccc tggatttccg ccgcagtcgt gtgggtacgc aaccgtgacc  360
gatgcagagg ccgtgatcgt gcaagtcacg ccgcatcacg tgcttgtgga cgagtacacc  420
ggagaatggg tcgattccca gttcatcaac ggcaagtgct ccaactacat ttgcccaacc  480
gtgcacaaca gcactacttg gcatagcgac tacaaagtga agggtctgtg tgattccaac  540
ctgatctcca tggatatcac tttcttctcg gaagacggcg aactgtcctc actgggcaaa  600
gaaggaactg ggtttcgctc aaattacttc gcctacgaaa ctggaggaaa agcctgcaag  660
atgcagtact gcaagcactg gggcgtgaga ctacccagcg gtgtctggtt cgagatggcc  720
gataaggacc tgtttgcagc agcgagattc ccggaatgcc ctgagggatc gagcatctcc  780
gctccaagcc aaacttcagt ggacgtgagc ctgatccagg acgtggaacg gattctcgac  840
tactcgctgt gccaggagac ctggtcgaag atcagagcgg gactgcccat ctcaccggtg  900
gacctgtcct acctggcgcc aaagaatccg ggcactggac cggcgttcac catcatcaac  960
ggcaccctca aatacttcga gacgcggtac atccgggtgg acatcgcagc tccgatcctc  1020
tcccggatgg tgggaatgat ctcggggact actaccgaag ccgagctctg ggacgactgg  1080
gcaccttacg aggatgtcga gatcggacct aacggagtgc tccggacctc ctccgggtac  1140
aagttccctc tgtacatgat cggccatggc atgctggact cggatctgca tctgtcgtcc  1200
aaagcacagg tgtttgaaca cccacacatt caagacgccg ccagccagct gccggacgat  1260
gagtcgctgt tcttcggaga cacgggcttg tcaaagaatc ccatcgagct ggtggaagga  1320
```

```
tggttttcat cctggaaaag cagcatcgct tcattcttct tcatcattgg cctgatcatc    1380
ggcctatttc tagtcctgcg ggtgggaatt catctgtgca tcaagctcaa gcacactaag    1440
aagcggcaaa tctacactga tatcgagatg aatcgcctgg gcaagtag                1488

SEQ ID NO: 92           moltype = DNA  length = 1488
FEATURE                 Location/Qualifiers
misc_feature            1..1488
                        note = Trop-051 Mutated VSV-G
source                  1..1488
                        m

```
gacctgtcct acctggcgcc aaagaatccg ggcactggac cggcgttcac catcatcaac  960
ggcaccctca aatacttcga gacgcggtac atccgggtgg acatcgcagc tccgatcctc  1020
tcccggatgg tgggaatgat ctcggggact acttgggccc gcgagctctg ggacgactgg  1080
gcaccttacg aggatgtcga gatcggacct aacgagtgc tccggacctc ctccgggtac  1140
aagttccctc tgtacatgat cggccatggc atgctggact cggatctgca tctgtcgtcc  1200
aaagcacagg tgtttgaaca cccacacatt caagacgccg ccagccagct gccggacgat  1260
gagtcgctgt tcttcggaga cacgggcttg tcaaagaatc ccatcgagct ggtggaagga  1320
tggttttcat cctggaaaag cagcatcgct tcattcttct tcatcattgg cctgatcatc  1380
ggcctatttc tagtcctgcg ggtgggaatt catctgtgca tcaagctcaa gcacactaag  1440
aagcggcaaa tctacactga tatcgagatg aatcgcctgg gcaagtag            1488

SEQ ID NO: 95            moltype = AA   length = 495
FEATURE                  Location/Qualifiers
REGION                   1..495
                         note = Trop-052 Mutated VSV-G
source                   1..495
                         mol_type = protein -continued

```
KRQIYTDIEM NRLGK                                                    495

SEQ ID NO: 98           moltype = DNA  length = 1494
FEATURE                 Location/Qualifiers
misc_feature            1..1494
                        note = Trop-056 Mutated VSV-G
source                  1..1494
                        mol_type = other DNA
                        organism = synthetic construct
SEQUENCE: 98
aagttcacta tcgtgtttcc gcacaacacc acacaaaagg gcaactggaa aaacgtgcct  60
tcaaattacc attattgccc cagcagctcg gacctgaact ggcacaatga cctcattgga  120
accgcgctgc aggtgaagat gccaaagagc cacaaggcta tccaggctga cggatggatg  180
tgccacgcgt caaaatgggt gactacctgc gatttccgct ggtacggacc aaaatacatc  240
acgcacagca tcagatcatt caccccgtca gtggaacaat gcaaagaatc catcgaacag  300
actaagcagg gaacctggct gaaccctgga tttccgccgc agtcgtgtgg gtacgcaacc  360
gtgaccgatg cagaggccgt gatcgtgcaa gtcacgccgc atcacgtgct tgtggacgag  420
tacaccggag aatgggtcga ttcccagttc atcaacggca agtgctccaa ctacatttgc  480
ccaaccgtgc acaacagcac tacttggcac agcgactaca aagtgaaggg tctgtgtgat  540
tccaacctga tctccatgga tatcactttc ttctcggaag acggcgaact gtcctcactg  600
ggcaaagaag gaactgggtt tcgctcaaat tacttcgcct acgaaactgg aggaaaagcc  660
tgcaagatgc agtactgcaa gcactggggc gtgagactac ccagcggtgt ctggttcgag  720
atggccgata aggacctgtt tgcagcagcg agattcccgg aatgccctga gggatcgagc  780
atctccgctc caagccaaac ttcagtggac gtgagcctga tccaggacgt ggaacggatt  840
ctcgactact cgctgtgcca ggagacctgg tcgaagatca gagcgggact gcccatctca  900
ccggtggacc tgtcctacct ggcgccaaag aatccgggca ctggaccggc gttcaccatc  960
atcaacggca ccctcaaata cttcgagacg cggtacatcc gggtggacat cgcagctccg  1020
atcctctccc ggatggtggg aatgatctcg ggactacta ccgaacgcga gctctgggac  1080
gactgggcac cttacgagga tgtcgagatc ggacctaacg gagtgctccg gacctcctcc  1140
gggtacaagt tccctctgta catgatcggc catggcatgc tggactcgga tctgcatctg  1200
tcgtccaaag cacaggtgtt tgaacaccca cacattcaag acgccgccag ccagctgccg  1260
gacgatgagt cgctgttctt cggagacacg ggcttgtcaa agaatcccat cgagctggtg  1320
gaaggatggt tttcatcctg gaaaagcagc atcgcttcat tcttcttcat cattggcctg  1380
atcatcggcc tatttctagt cctgcgggtg ggaattcatc tgtgcatcaa gctcaagcac  1440
actaagaagc ggcaaatcta cactgatatc gagatgaatc gcctgggcaa gtag        1494

SEQ ID NO: 99           moltype = AA  length = 497
FEATURE                 Location/Qualifiers
REGION                  1..497
                        note = Trop-056 Mutated VSV-G
source                  1..497
                        mol_type = protein
                        organism = synthetic construct
SEQUENCE: 99
KFTIVFPHNT TQKGNWKNVP SNYHYCPSSS DLNWHNDLIG TALQVKMPKS HKAIQADGWM  60
CHASKWVTTC DFRWYGPKYI THSIRSFTPS VEQCKESIEQ TKQGTWLNPG FPPQSCGYAT  120
VTDAEAVIVQ VTPHHVLVDE YTGEWVDSQF INGKCSNYIC PTVHNSTTWH SDYKVKGLCD  180
SNLISMDITF FSEDGELSSL GKEGTGFRSN YFAYETGGKA CKMQYCKHWG VRLPSGVWFE  240
MADKDLFAAA RFPECPEGSS ISAPSQTSVD VSLIQDVERI LDYSLCQETW SKIRAGLPIS  300
PVDLSYLAPK NPGTGPAFTI INGTLKYFET RYIRVDIAAP ILSRMVGMIS GTTTERELWD  360
DWAPYEDVEI GPNGVLRTSS GYKFPLYMIG HGMLDSDLHL SSKAQVFEHP HIQDAASQLP  420
DDESLFFGDT GLSKNPIELV EGWFSSWKSS IASFFFIIGL IIGLFLVLRV GIHLCIKLKH  480
TKKRQIYTDI EMNRLGK                                                  497

SEQ ID NO: 100          moltype = DNA  length = 1497
FEATURE                 Location/Qualifiers
misc_feature            1..1497
                        note = Trop-058 Mutated VSV-G
source                  1..1497
                        mol_type = other DNA
                        organism = synthetic construct
SEQUENCE: 100
aagttcacta tcgtgtttcc gcacaaccaa aagggcaact ggaaaaacgt gccttcaaat  60
taccattatt gccccagcag ctcggacctg aactggcaca atgacctcat tggaaccgcg  120
ctgcaggtga agatgccagg cggcagcaag agccacaagg ctatccaggc tgacggatgg  180
atgtgccacg cgtcaaaatg ggtgactacc tgcgatttcc gctggtacgg accaaaatac  240
atcacgcaca gcatcagatc attcaccccg tcagtggaac aatgcaaaga atccatcgaa  300
cagactaagc agggaacctg gctgaaccct ggatttccgc cgcagtcgtg tgggtacgca  360
accgtgaccg atgcagaggc cgtgatcgtg caagtcacgc cgcatcacgt gcttgtggac  420
gagtacaccg gagaatgggt cgattcccag ttcatcaacg gcaagtgctc caactacatt  480
tgcccaaccg tgcacaacag cactacttgg cacagcgact acaaagtgaa gggtctgtgt  540
gattccaacc tgatctccat ggatatcact ttcttctcgg aagacggcga actgtcctca  600
ctgggcaaag aaggaactgg gtttcgctca aattacttcg cctacgaaac tggaggaaaa  660
gcctgcaaga tgcagtactg caagcactgg ggcgtgagac tacccagcgg tgtctggttc  720
gagatggccg ataaggacct gtttgcagca gcgagattcc cggaatgccc tgagggatcg  780
agcatctccg ctccaagcca aacttcagtg gacgtgagcc tgatccagga cgtggaacgg  840
attctcgact actcgctgtg ccaggagacc tggtcgaaga tcagagcggg actgcccatc  900
tcaccggtgg acctgtccta cctggcgcca aagaatccgg gcactggacc ggcgttcacc  960
atcatcaacg gcaccctcaa atacttcgag acgcggtaca tccgggtgga catcgcagct  1020
```

-continued

```
ccgatcctct cccggatggt gggaatgatc tcggggacta ctaccgaacg cgagctctgg  1080
gacgactggg caccttacga ggatgtcgag atcggaccta acggagtgct ccggacctcc  1140
tccgggtaca agttccctct gtacatgatc ggccatggca tgctggactc ggatctgcat  1200
ctgtcgtcca aagcacaggt gtttgaacac ccacacattc aagacgccgc cagccagctg  1260
ccggacgatg agtcgctgtt cttcggagac acgggcttgt caaagaatcc catcgagctg  1320
gtggaaggat ggttttcatc ctggaaaagc agcatcgctt cattcttctt catcattggc  1380
ctgatcatcg gcctatttct agtcctgcgg gtgggaattc atctgtgcat caagctcaag  1440
cacactaaga agcggcaaat ctacactgat atcgagatga atcgcctggg caagtag     1497

SEQ ID NO: 101         moltype = AA  length = 498
FEATURE                Location/Qualifiers
REGION                 1..498
                       note = Trop-058 Mutated VSV-G
source                 1..498
                       mol_type = protein
                       organism = synthetic construct
SEQUENCE: 101
KFTIVFPHNQ KGNWKNVPSN YHYCPSSSDL NWHNDLIGTA LQVKMPGGSK SHKAIQADGW  60
MCHASKWVTT CDFRWYGPKY ITHSIRSFTP SVEQCKESIE QTKQGTWLNP GFPPQSCGYA  120
TVTDAEAVIV QVTPHHVLVD EYTGEWVDSQ FINGKCSNYI CPTVHNSTTW HSDYKVKGLC  180
DSNLISMDIT FFSEDGELSS LGKEGTGFRS NYFAYETGGK ACKMQYCKHW GVRLPSGVWF  240
EMADKDLFAA ARFPECPEGS SISAPSQTSV DVSLIQDVER ILDYSLCQET WSKIRAGLPI  300
SPVDLSYLAP KNPGTGPAFT IINGTLKYFE TRYIRVDIAA PILSRMVGMI SGTTTERELW  360
DDWAPYEDVE IGPNGVLRTS SGYKFPLYMI GHGMLDSDLH LSSKAQVFEH PHIQDAASQL  420
PDDESLFFGD TGLSKNPIEL VEGWFSSWKS SIASFFFIIG LIIGLFLVLR VGIHLCIKLK  480
HTKKRQIYTD IEMNRLGK                                                498

SEQ ID NO: 102         moltype = DNA  length = 1506
FEATURE                Location/Qualifiers
misc_feature           1..1506
                       note = Trop-061 Mutated VSV-G
source                 1..1506
                       mol_type = other DNA
                       organism = synthetic construct
SEQUENCE: 102
aagttcacta tcgtgtttcc gcacggcgga agcaacggcg ggagccaaaa gggcaactgg  60
aaaaacgtgc cttcaaatta ccattattgc cccagcagct cggacctgaa ctggcacaat  120
gacctcattg gaaccgcgct gcaggtgaag atgccaaaga gccacaaggc tatccaggct  180
gacggatgga tgtgccacgc gtcaaaatgg gtgactacct gcgatttccg ctggtacgga  240
ccaaaataca tcacgcacag catcagatca ttcaccccgt cagtggaaca atgcaaagaa  300
tccatcgaac agactaagca gggaacctgg ctgaaccctg gatttccgcc gcagtcgtgt  360
gggtacgcaa ccgtgaccga tgcagaggcc gtgatcgtgc aagtcacgcc gcatcacgtg  420
cttgtggacg agtacaccgg agaatgggtc gattcccagt tcatcaacgg caagtgctcc  480
aactacattt gcccaaccgt gcacaacagc actacttggc acagcgacta caaagtgaag  540
ggtctgtgtg attccaacct gatctccatg gatatcactt tcttctcgga agacggcgaa  600
ctgtcctcac tgggcaaaga aggaactggg tttcgctcaa attacttcgc ctacgaaact  660
ggaggaaaag cctgcaagat gcagtactgc aagcactggg gcgtgagact acccagcggt  720
gtctggttcg agatggccga taaggacctg tttgcagcag cgagattccc ggaatgccct  780
gagggatcga gcatctccgc tccaagccaa acttcagtgg acgtgagcct gatccaggac  840
gtggaacgga ttctcgacta ctcgctgtgc caggagacct ggtcgaagat cagagcggga  900
ctgcccatct caccggtgga cctgtcctac ctggcgccaa agaatccggg cactggaccg  960
gcgttcacca tcatcaacgg caccctcaaa tacttcgaga cgcggtacat ccgggtggac  1020
atcgcagctc cgatcctctc ccggatggtg ggaatgatct cggggactac taccgaacgc  1080
gagctctggg acgactgggc accttacgag gatgtcgaga tcggacctaa cggagtgctc  1140
cggacctcct ccgggtacaa gttccctctg tacatgatcg gccatggcat gctggactcg  1200
gatctgcatc tgtcgtccaa agcacaggtg tttgaacacc cacacattca agacgccgcc  1260
agccagctgc cggacgatga gtcgctgttc ttcggagaca cgggcttgtc aaagaatccc  1320
atcgagctgg tggaaggatg gttttcatcc tggaaaagca gcatcgcttc attcttcttc  1380
atcattggcc tgatcatcgg cctatttcta gtcctgcggg tgggaattca tctgtgcatc  1440
aagctcaagc acactaagaa gcggcaaatc tacactgata tcgagatgaa tcgcctgggc  1500
aagtag                                                             1506

SEQ ID NO: 103         moltype = AA  length = 501
FEATURE                Location/Qualifiers
REGION                 1..501
                       note = Trop-061 Mutated VSV-G
source                 1..501
                       mol_type = protein
                       organism = synthetic construct
SEQUENCE: 103
KFTIVFPHGG SNGGSQKGNW KNVPSNYHYC PSSSDLNWHN DLIGTALQVK MPKSHKAIQA  60
DGWMCHASKW VTTCDFRWYG PKYITHSIRS FTPSVEQCKE SIEQTKQGTW LNPGFPPQSC  120
GYATVTDAEA VIVQVTPHHV LVDEYTGEWV DSQFINGKCS NYICPTVHNS TTWHSDYKVK  180
GLCDSNLISM DITFFSEDGE LSSLGKEGTG FRSNYFAYET GGKACKMQYC KHWGVRLPSG  240
VWFEMADKDL FAAARFPECP EGSSISAPSQ TSVDVSLIQD VERILDYSLC QETWSKIRAG  300
LPISPVDLSY LAPKNPGTGP AFTIINGTLK YFETRYIRVD IAAPILSRMV GMISGTTTER  360
ELWDDWAPYE DVEIGPNGVL RTSSGYKFPL YMIGHGMLDS DLHLSSKAQV FEHPHIQDAA  420
SQLPDDESLF FGDTGLSKNP IELVEGWFSS WKSSIASFFF IIGLIIGLFL VLRVGIHLCI  480
KLKHTKKRQI YTDIEMNRLG K                                            501
```

```
SEQ ID NO: 104            moltype = AA   length = 19
FEATURE                   Location/Qualifiers
REGION                    1..19
                          note = PDGFR stalk
source                    1..19
                          mol_type = protein
                          organism = synthetic construct
SEQUENCE: 104
AVGQDTQEVI VVPHSLPFK                                                  19

SEQ ID NO: 105            moltype = AA   length = 49
FEATURE                   Location/Qualifiers
REGION                    1..49
                          note = PDGFR stalk
source                    1..49
                          mol_type = protein
                          organism = synthetic construct
SEQUENCE: 105
ASAKPTTTPA PRPPTPAPTI ASQPLSLRPE AARPAAGGAV HTRGLDFAK                 49

SEQ ID NO: 106            moltype = AA   length = 17
FEATURE                   Location/Qualifiers
REGION                    1..17
                          note = flexible linker
source                    1..17
                          mol_type = protein
                          organism = synthetic construct
SEQUENCE: 106
GAPGSGGGGS GGGGSAS                                                    17

SEQ ID NO: 107            moltype = AA   length = 31
FEATURE                   Location/Qualifiers
REGION                    1..31
                          note = IgG4 hinge domain
source                    1..31
                          mol_type = protein
                          organism = synthetic construct
SEQUENCE: 107
ESKYGPPCPP CPAVGQDTQE VIVVPHSLPF K                                    31

SEQ ID NO: 108            moltype = AA   length = 39
FEATURE                   Location/Qualifiers
REGION                    1..39
                          note = tetrameric coiled coil linker
source                    1..39
                          mol_type = protein
                          organism = synthetic construct
SEQUENCE: 108
ASGGGGSGEL AAIKQELAAI KKELAAIKWE LAAIKQGAG                            39

SEQ ID NO: 109            moltype = AA   length = 14
FEATURE                   Location/Qualifiers
REGION                    1..14
                          note = dimeric coiled coil linker
source                    1..14
                          mol_type = protein
                          organism = synthetic construct
SEQUENCE: 109
ASESKYGPPC PPCP                                                       14

SEQ ID NO: 110            moltype = AA   length = 20
FEATURE                   Location/Qualifiers
REGION                    1..20
                          note = Ig kappa leader sequence
source                    1..20
                          mol_type = protein
                          organism = synthetic construct
SEQUENCE: 110
METDTLLLWV LLLWVPGSTG                                                 20

SEQ ID NO: 111            moltype =    length =
SEQUENCE: 111
000

SEQ ID NO: 112            moltype = DNA   length = 357
FEATURE                   Location/Qualifiers
misc_feature              1..357
                          note = Anti-CD3 (12F6) heavy chain variable region
```

```
source                   1..357
                         mol_type = other DNA
                         organism = synthetic construct
SEQUENCE: 112
caagtgcagc tccagcagag cggcgctgag ctggcccggc ccggcgccag cgtgaagatg    60
agctgtaaag ccagcggcta tacatttacc agctacacca tgcactgggt caagcagcgg   120
cctggccagg gcctggaatg gattggatat atcaaccccag gcagcggcta caccaagtac   180
aaccagaaat tcaaggacaa ggccaccctg accgccgaca gagctcctc aacagctac     240
atgcaactga gcagcctgac cagcgaggat agcgccgtgt actactgcgc cagatggcag   300
gactacgacg tgtacttcga ctactggggc caaggcacaa cactgaccgt gtccagc      357

SEQ ID NO: 113           moltype = AA  length = 119
FEATURE                  Location/Qualifiers
REGION                   1..119
                         note = Anti-CD3 (12F6) heavy chain variable region
source                   1..119
                         mol_type = protein
                         organism = synthetic construct
SEQUENCE: 113
QVQLQQSGAE LARPGASVKM SCKASGYTFT SYTMHWVKQR PGQGLEWIGY INPSSGYTKY    60
NQKFKDKATL TADKSSSTAY MQLSSLTSED SAVYYCARWQ DYDVYFDYWG QGTTLTVSS    119

SEQ ID NO: 114           moltype = DNA  length = 321
FEATURE                  Location/Qualifiers
misc_feature             1..321
                         note = Anti-CD3 (12F6) light chain variable region
source                   1..321
                         mol_type = other DNA
                         organism = synthetic construct
SEQUENCE: 114
cagatcgtgc tgagccagtc cccagccatc ctgtctgcca gccctggcga gaaggtgacc    60
atgacctgca gagcctcttc ttctgtttcc tacatgcact ggtatcagca aaagcccggc   120
agctctccta agccttggat ctacgccaca agcaacctgg ctagcggcgt gcctgctcgc   180
ttcagcggca gcggcagcgg caccagctac agcctgacca tcagcagagt ggaagccgag   240
gacgccgcca cctactactg ccagcagtgg tcctctaatc tccaacatt cggcggcggc    300
accaagctgg aaaccaaaag a                                             321

SEQ ID NO: 115           moltype = AA  length = 107
FEATURE                  Location/Qualifiers
REGION                   1..107
                         note = Anti-CD3 (12F6) light chain variable region
source                   1..107
                         mol_type = protein
                         organism = synthetic construct
SEQUENCE: 115
QIVLSQSPAI LSASPGEKVT MTCRASSSVS YMHWYQQKPG SSPKPWIYAT SNLASGVPAR    60
FSGSGSGTSY SLTISRVEAE DAATYYCQQW SSNPPTFGGG TKLETKR                 107

SEQ ID NO: 116           moltype = DNA  length = 996
FEATURE                  Location/Qualifiers
misc_feature             1..996
                         note = Anti-CD3 (12F6) Full molecule
source                   1..996
                         mol_type = other DNA
                         organism = synthetic construct
SEQUENCE: 116
atggccttac cagtgaccgc cttgctcctg ccgctggcct tgctgctcca cgccgccagg    60
ccgcaagtgc agctccagca gagcggcgct gagctggccc ggcccggcgc cagcgtgaag   120
atgagctgta aagccagcgg ctatacattt accagctaca ccatgcactg ggtcaagcag   180
cggcctggcc agggcctgga atggattgga tatatcaacc ccagcagcgg ctacaccaag   240
tacaaccaga aattcaagga caaggccacc ctgaccgccg acaagagctc ctcaacagcc   300
tacatgcaac tgagcagcct gaccagcgag gatagcgccg tgtactactg cgccagatgg   360
caggactacg acgtgtactt cgactactgg ggccaaggca aacactgac cgtgtccagc    420
ggaggcggta gtggcggtgg atcaggtgga ggcagcggta gcggatctca gatcgtgctg   480
agccagtccc cagccatcct gtctgccagc cctggcgaga aggtgaccat gacctgcaga   540
gcctcttctt ctgtttccta catgcactgg tatcagcaaa agcccggcag ctctcctaag   600
ccttggatct acgccacaag caacctggct agcggcgtgc ctgctcgctt cagcggcagc   660
ggcagcggca ccagctacag cctgaccatc agcagagtgg aagccgaggacgccgccacc    720
tactactgcc agcagtggtc ctctaatcct ccaacattc ggcggcggca caagctggtc    780
accaaaagaa ccactacacc agcacctaga ccaccaacac tgcgccaac catcgcatcg    840
cagccactgt ctctgcgccc agaggcatgc cggccagcag ctgggggcgc agtgcacaca    900
agggggctgg acttcgcatg tgatatctac atctgggcac cattggcagg gacttgtggg    960
gtccttctcc tgtcactggt tatcaccctt tactgc                            996

SEQ ID NO: 117           moltype = AA  length = 332
FEATURE                  Location/Qualifiers
REGION                   1..332
                         note = Anti-CD3 (12F6) Full molecule
REGION                   1..21
```

```
                        note = MISC_FEATURE - signal peptide
source                  1..332
                        mol_type = protein
                        organism = synthetic construct
SEQUENCE: 117
MALPVTALLL PLALLLHAAR PQVQLQQSGA ELARPGASVK MSCKASGYTF TSYTMHWVKQ    60
RPGQGLEWIG YINPSSGYTK YNQKFKDKAT LTADKSSSTA YMQLSSLTSE DSAVYYCARW   120
QDYDVYFDYW GQGTTLTVSS GGGSGGGSGG GSGGGSQIVL SQSPAILSAS PGEKVTMTCR   180
ASSSVSYMHW YQQKPGSSPK PWIYATSNLA SGVPARFSGS GSGTSYSLTI SRVEAEDAAT   240
YYCQQWSSNP PTFGGGTKLE TKRTTTPAPR PPTPAPTIAS QPLSLRPEAC RPAAGGAVHT   300
RGLDFACDIY IWAPLAGTCG VLLLSLVITL YC                                332

SEQ ID NO: 118          moltype = AA  length = 12
FEATURE                 Location/Qualifiers
REGION                  1..12
                        note = IgG4 hinge region
source                  1..12
                        mol_type = protein
                        organism = synthetic construct
SEQUENCE: 118
ESKYGPPCPP CP                                                        12

SEQ ID NO: 119          moltype = DNA  length = 207
FEATURE                 Location/Qualifiers
misc_feature            1..207
                        note = CD8a Hinge and Transmembrane
source                  1..207
                        mol_type = other DNA
                        organism = synthetic construct
SEQUENCE: 119
accacaacac ctgctccaag gcccccccaca cccgctccaa ctatagccag ccaaccattg    60
agcctcagac ctgaagcttg caggcccgca gcaggaggcg ccgtccatac gcgaggcctg   120
gacttcgcgt gtgatattta tatttgggca cctttggccg gaacatgtgg ggtgttgctt   180
ctctcccttg tgatcactct gtattgt                                       207

SEQ ID NO: 120          moltype = DNA  length = 126
FEATURE                 Location/Qualifiers
misc_feature            1..126
                        note = 4-1BB costimulatory domain
source                  1..126
                        mol_type = other DNA
                        organism = synthetic construct
SEQUENCE: 120
aagcgcggga gaaagaagct cctgtacatc ttcaagcagc cttttatgcg acctgtgcaa    60
accactcagg aagaagatgg gtgttcatgc cgcttccccg aggaggaaga aggagggtgt   120
gaactg                                                              126

SEQ ID NO: 121          moltype = DNA  length = 336
FEATURE                 Location/Qualifiers
misc_feature            1..336
                        note = CD3 zeta effector domain no. 2
source                  1..336
                        mol_type = other DNA
                        organism = synthetic construct
SEQUENCE: 121
agggtgaaat tttctagaag cgccgatgct cccgcatatc agcagggtca gaatcagctc    60
tacaatgaat tgaatctcgg caggcgagaa gagtacgatg ttctggacaa gagacggggc   120
agggatcccg agatggggg aaagccccgg agaaaaaatc ctcaggaggg gttgtacaat    180
gagctgcaga aggacaagat ggctgaagcc tatagcgaga tcggaatgaa aggcgaaaga   240
cgcagaggca aggggcatga cggtctgtac cagggtctct ctacagccac caaggacact   300
tatgatgcgt tgcatatgca agccttgcca ccccgc                             336

SEQ ID NO: 122          moltype = AA  length = 112
FEATURE                 Location/Qualifiers
REGION                  1..112
                        note = CD3 zeta effector domain no. 2
source                  1..112
                        mol_type = protein
                        organism = synthetic construct
SEQUENCE: 122
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 123          moltype = AA  length = 20
FEATURE                 Location/Qualifiers
REGION                  1..20
                        note = B2M signal peptide
source                  1..20
                        mol_type = protein
```

```
                            organism = synthetic construct
SEQUENCE: 123
MSRSVALAVL ALLSLSGLEA                                              20
```